United States Patent
Mahoney et al.

(10) Patent No.: US 12,240,107 B2
(45) Date of Patent: Mar. 4, 2025

(54) EXOSUIT SYSTEMS AND METHODS

(71) Applicant: SEISMIC HOLDINGS, INC., Menlo Park, CA (US)

(72) Inventors: Richard Mahoney, Menlo Park, CA (US); Chris Gadway, San Francisco, CA (US); Mary Elizabeth Hogue, Menlo Park, CA (US); Nicole Ida Kernbaum, Sunnyvale, CA (US); Melinda Cromie Lear, San Jose, CA (US); Hayley Stolee-Smith, Redwood City, CA (US); Mallory L. Tayson-Frederick, Oakland, CA (US); Rayyan Toh, San Francisco, CA (US); Regis Vincent, San Mateo, CA (US); Trent Weber, San Francisco, CA (US); Katherine Goss Witherspoon, Menlo Park, CA (US)

(73) Assignee: Seismic Holdings, Inc., Menlo Park, CA (US)

( * ) Notice: Subject to any disclaimer, the term of this patent is extended or adjusted under 35 U.S.C. 154(b) by 318 days.

(21) Appl. No.: 17/541,047

(22) Filed: Dec. 2, 2021

(65) Prior Publication Data

US 2022/0250234 A1    Aug. 11, 2022

Related U.S. Application Data

(63) Continuation of application No. 16/203,081, filed on Nov. 28, 2018, now Pat. No. 11,192,237.
(Continued)

(51) Int. Cl.
*A61H 3/00* (2006.01)
*A61F 2/68* (2006.01)
(Continued)

(52) U.S. Cl.
CPC ............... *B25J 9/0006* (2013.01); *A61F 2/68* (2013.01); *A61H 3/00* (2013.01); *A61B 5/1114* (2013.01);
(Continued)

(58) Field of Classification Search
CPC .................... A61H 11/00; A61H 11/02; A61H 2201/01616; A61H 2201/01628;
(Continued)

(56) References Cited

U.S. PATENT DOCUMENTS

| | | |
|---|---|---|
| 9,089,173 B2 | 7/2015 | Krishnan |
| 9,351,900 B2 | 5/2016 | Walsh et al. |

(Continued)

FOREIGN PATENT DOCUMENTS

| | | |
|---|---|---|
| WO | 2016/138264 A1 | 9/2016 |
| WO | 2017/026943 A1 | 2/2017 |
| WO | 2017/160751 A1 | 9/2017 |

OTHER PUBLICATIONS

Home Brew Robotics Club Meeting—Feb. 2016—Talk2: SRI Robotics, published Mar. 2, 2016, https://www.youtube.com/watch?v=UzpisQq0I3U (2 pages).

*Primary Examiner* — Colin W Stuart
*Assistant Examiner* — Douglas Y Sul
(74) *Attorney, Agent, or Firm* — Van Court & Aldridge LLP

(57) ABSTRACT

Exosuit systems and methods according to various embodiments are described herein. The exosuit system can be a suit that is worn by a wearer on the outside of his or her body. It may be worn under the wearer's normal clothing, over their clothing, between layers of clothing, or may be the wearer's primary clothing itself. The exosuit may be assistive, as it physically assists the wearer in performing particular activities, or can provide other functionality such as
(Continued)

communication to the wearer through physical expressions to the body, engagement of the environment, or capturing of information from the wearer.

9 Claims, 111 Drawing Sheets

Related U.S. Application Data

(60) Provisional application No. 62/724,452, filed on Aug. 29, 2018, provisional application No. 62/644,301, filed on Mar. 16, 2018, provisional application No. 62/591,739, filed on Nov. 28, 2017.

(51) Int. Cl.
| | |
|---|---|
| *B25J 9/00* | (2006.01) |
| *A61B 5/11* | (2006.01) |
| *A63B 21/00* | (2006.01) |
| *B25J 9/10* | (2006.01) |
| *B25J 9/16* | (2006.01) |

(52) U.S. Cl.
CPC .............. *A61F 2002/6827* (2013.01); *A61H 2201/1616* (2013.01); *A61H 2201/1626* (2013.01); *A61H 2201/163* (2013.01); *A61H 2201/1642* (2013.01); *A61H 2201/165* (2013.01); *A61H 2201/1659* (2013.01); *A61H 2201/5023* (2013.01); *A61H 2201/5038* (2013.01); *A61H 2201/5061* (2013.01); *A61H 2201/5069* (2013.01); *A61H 2201/5079* (2013.01); *A63B 21/4039* (2015.10); *A63B 21/4043* (2015.10); *A63B 2209/10* (2013.01); *B25J 9/104* (2013.01); *B25J 9/1633* (2013.01); *G05B 2219/39345* (2013.01); *G05B 2219/40305* (2013.01)

(58) Field of Classification Search
CPC .. A61H 2201/0163; A61H 2201/01659; A61F 5/026; A61F 5/028; A61F 5/03
See application file for complete search history.

(56) References Cited

U.S. PATENT DOCUMENTS

| | | | |
|---|---|---|---|
| 9,510,968 B2* | 12/2016 | Berry | A61F 5/028 |
| 11,000,439 B2* | 5/2021 | Romo | A61H 1/0244 |
| 11,452,632 B2* | 9/2022 | Kramer | A61F 5/32 |
| 2004/0116260 A1 | 6/2004 | Drennan | |
| 2004/0230150 A1 | 11/2004 | West | |
| 2005/0130815 A1 | 6/2005 | Abdoli-Eramaki | |
| 2007/0004571 A1 | 1/2007 | Gonzalez | |
| 2007/0265140 A1 | 11/2007 | Kim et al. | |
| 2009/0036888 A1* | 2/2009 | Dunfee | A61F 5/026 606/54 |
| 2009/0112136 A1* | 4/2009 | Litton | A61H 11/00 601/48 |
| 2010/0217167 A1* | 8/2010 | Ingimundarson | A61F 5/028 602/19 |
| 2011/0077567 A1* | 3/2011 | Bledsoe | A61F 5/028 602/19 |
| 2013/0040783 A1 | 2/2013 | Duda | |
| 2013/0288863 A1 | 10/2013 | Yamamoto et al. | |
| 2013/0345612 A1* | 12/2013 | Bannister | A61F 5/02 602/19 |
| 2014/0135672 A1* | 5/2014 | Joseph | A61F 5/028 602/19 |
| 2014/0277739 A1 | 9/2014 | Kombluh et al. | |
| 2014/0316314 A1 | 10/2014 | Schubert | |
| 2015/0216756 A1 | 8/2015 | Yamamoto et al. | |
| 2016/0107309 A1 | 4/2016 | Walsh et al. | |
| 2016/0213548 A1 | 7/2016 | John | |
| 2016/0374886 A1* | 12/2016 | Wyatt | A61N 1/3603 601/18 |
| 2018/0008502 A1 | 1/2018 | Asbeck | |
| 2018/0049903 A1 | 2/2018 | Witherspoon | |
| 2018/0056104 A1 | 3/2018 | Cromie | |
| 2019/0070062 A1 | 3/2019 | O'Donnell | |
| 2019/0290466 A1 | 9/2019 | Nishi | |
| 2019/0343707 A1 | 11/2019 | Riener | |
| 2020/0268592 A1* | 8/2020 | Johnson | A61H 9/0057 |

* cited by examiner

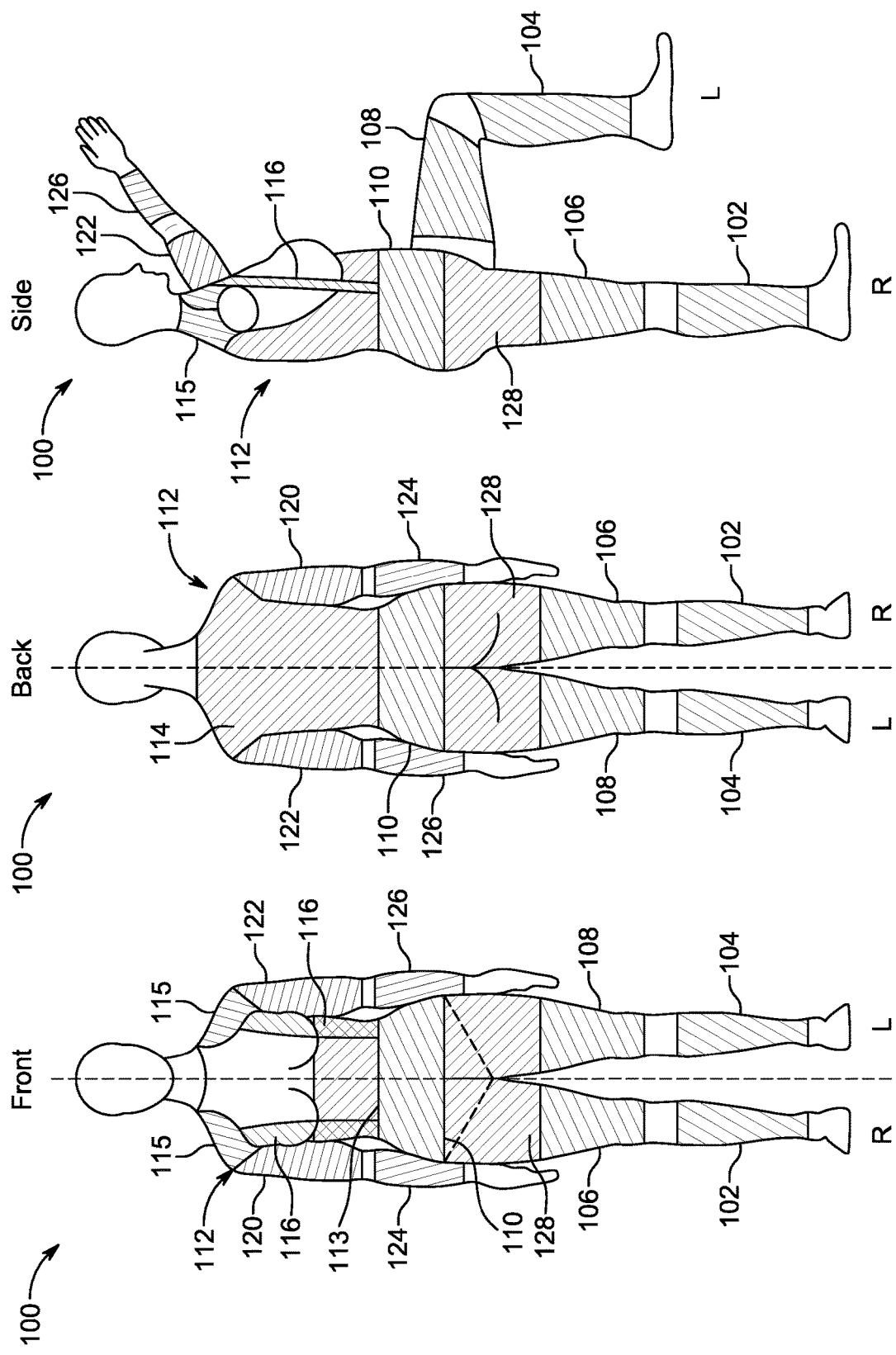

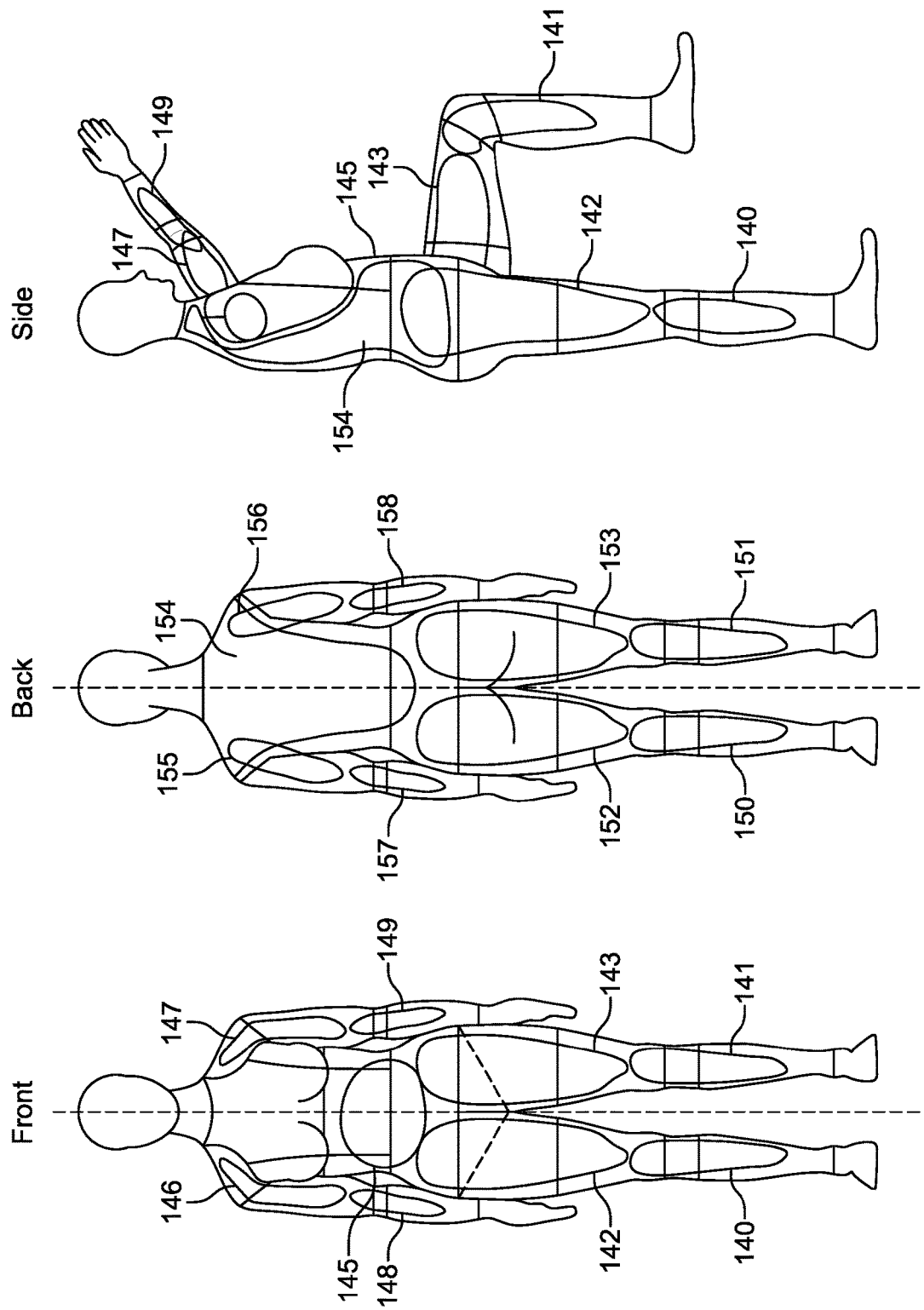

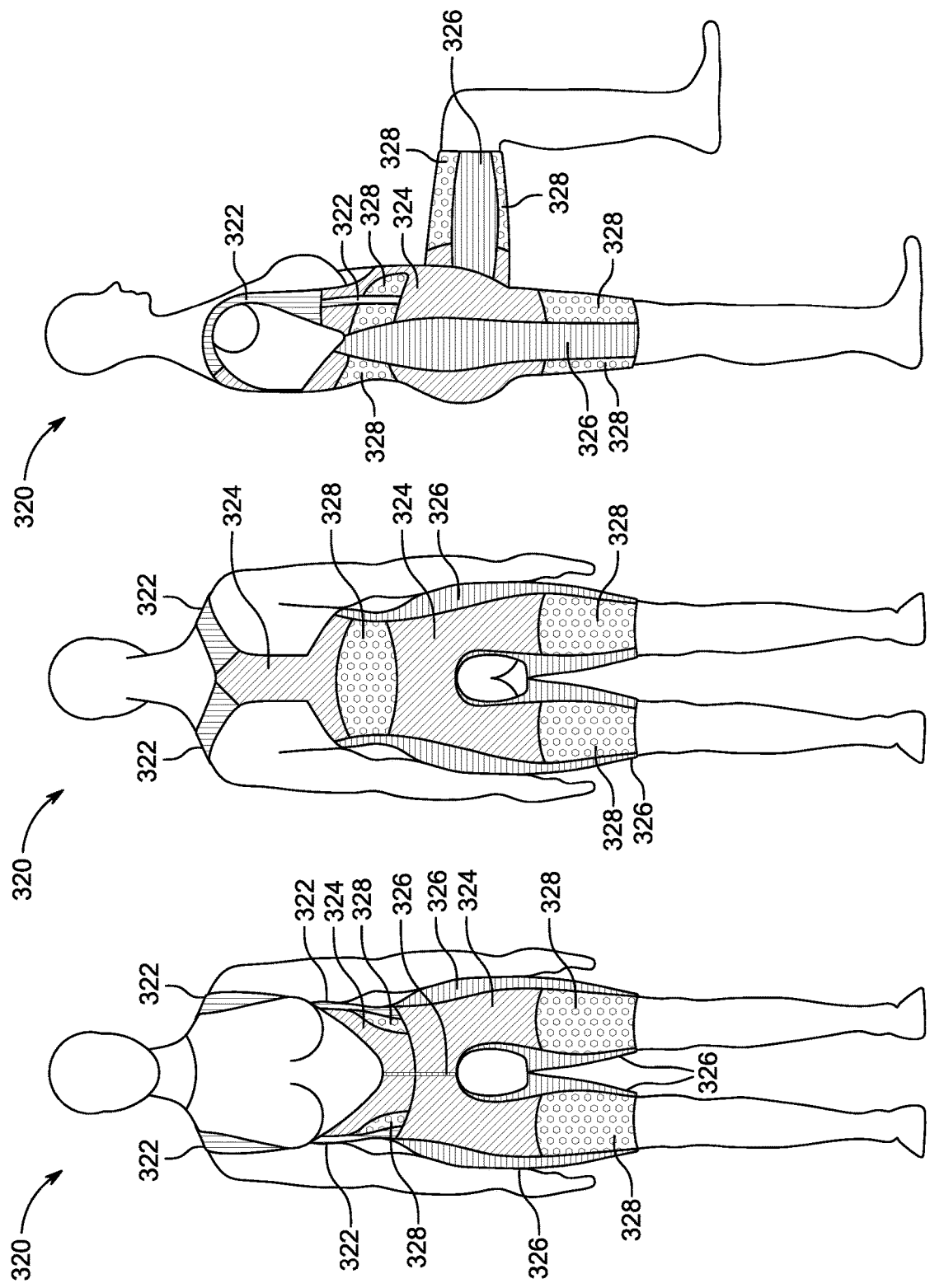

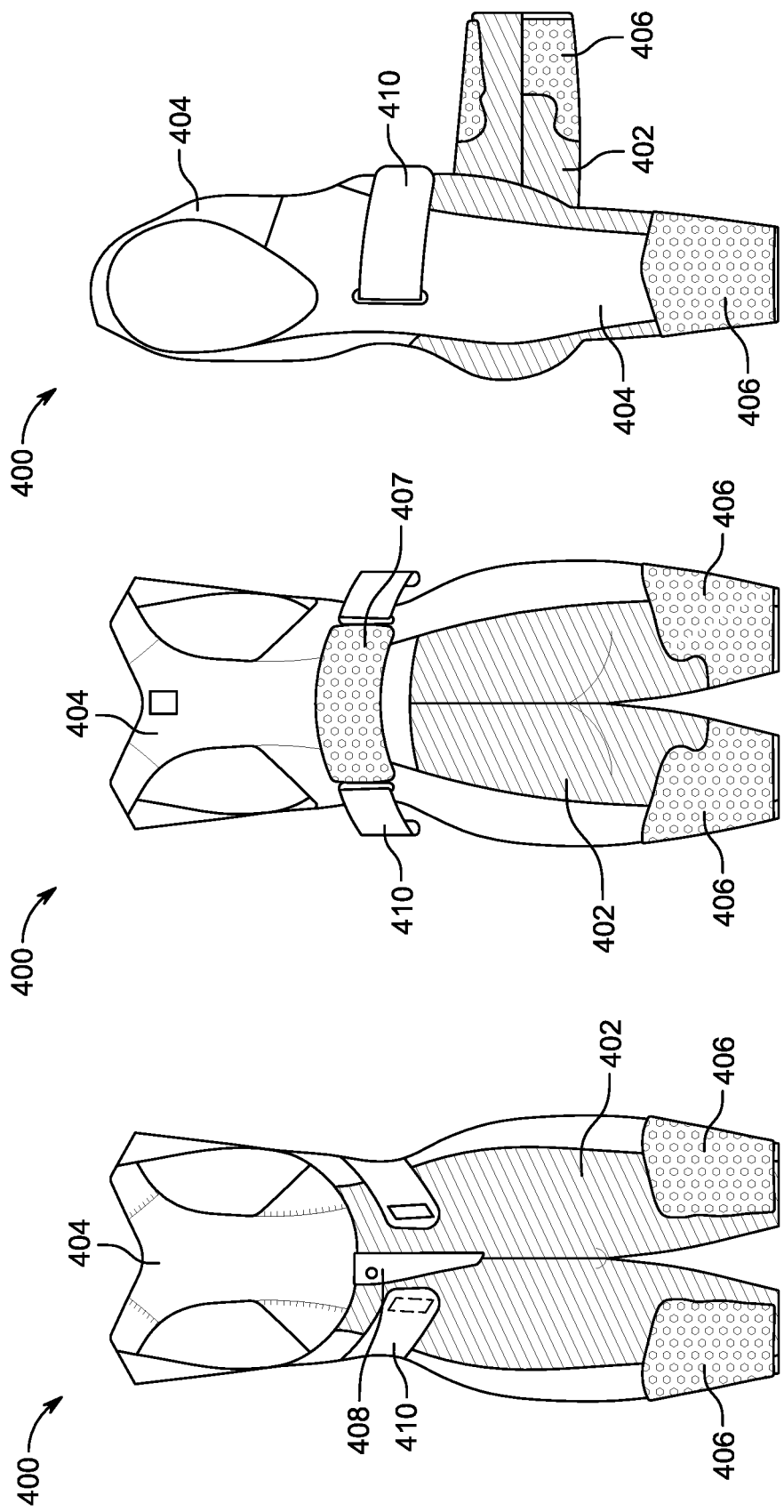

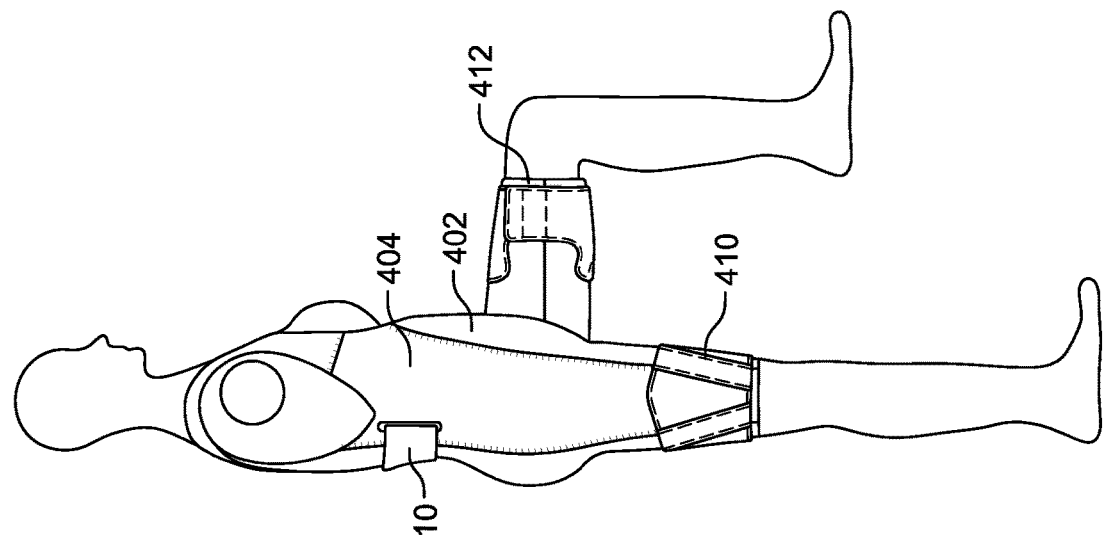
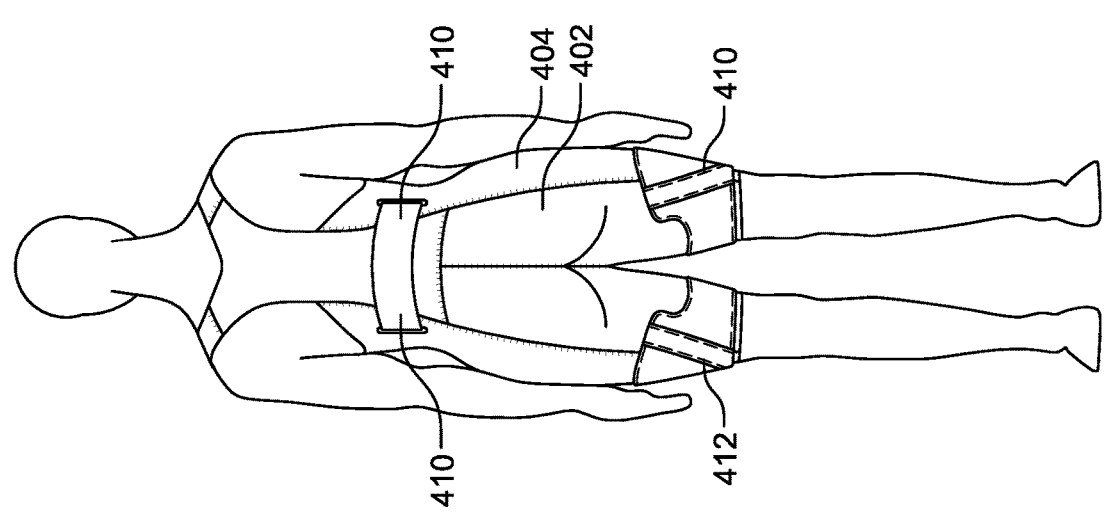
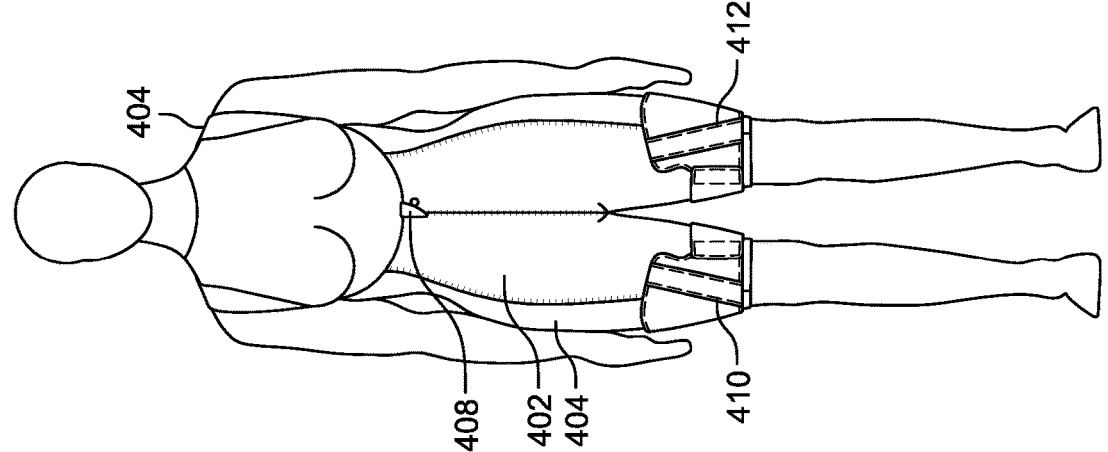
FIG. 4F
FIG. 4E
FIG. 4D

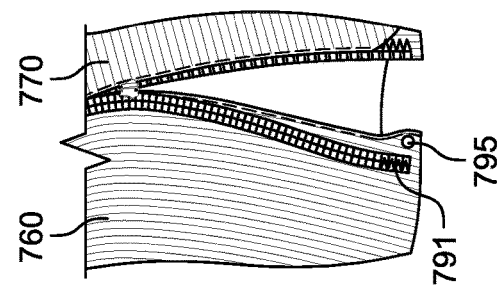
FIG. 7G
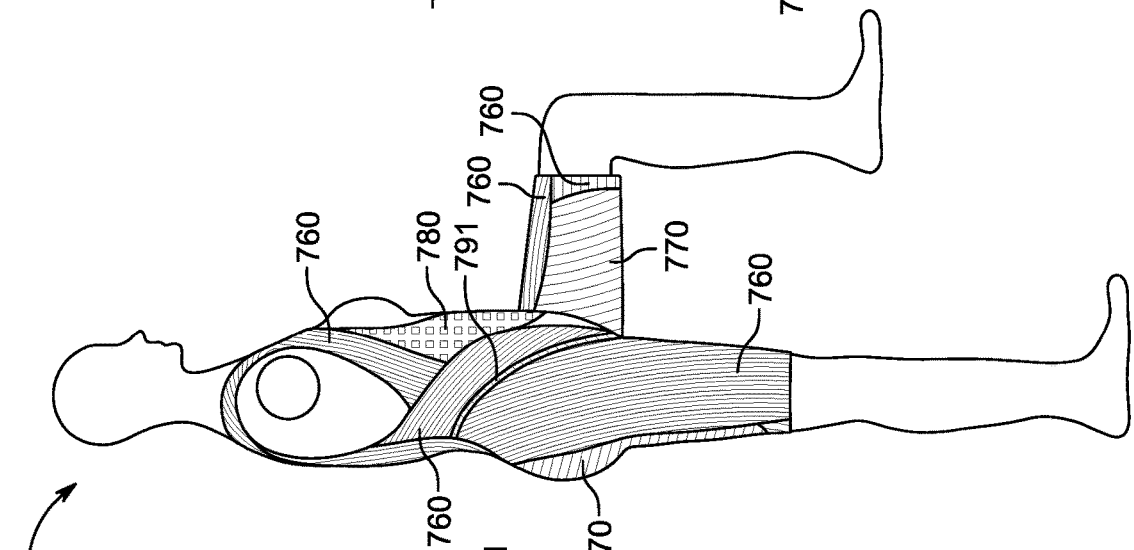
FIG. 7F
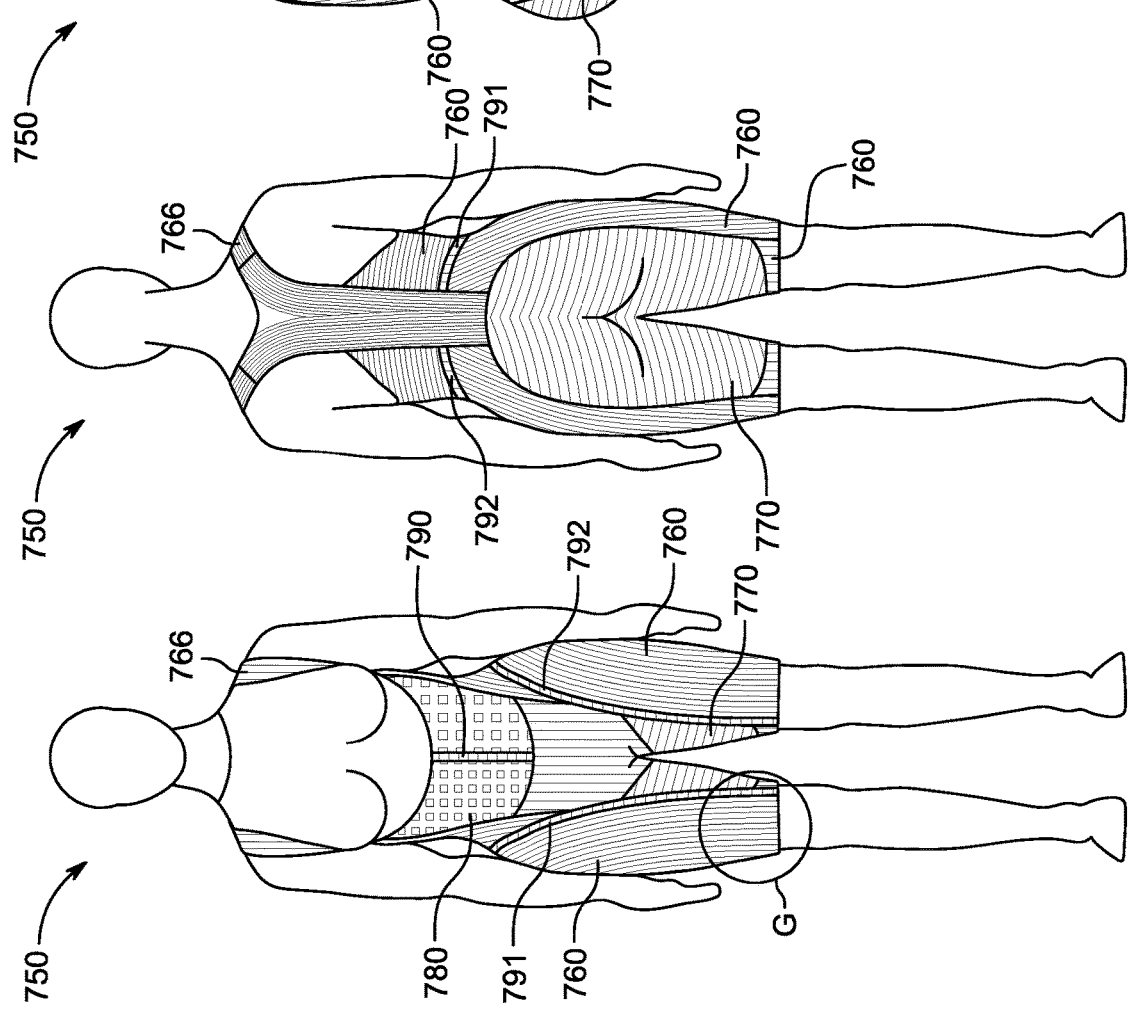
FIG. 7E
FIG. 7D

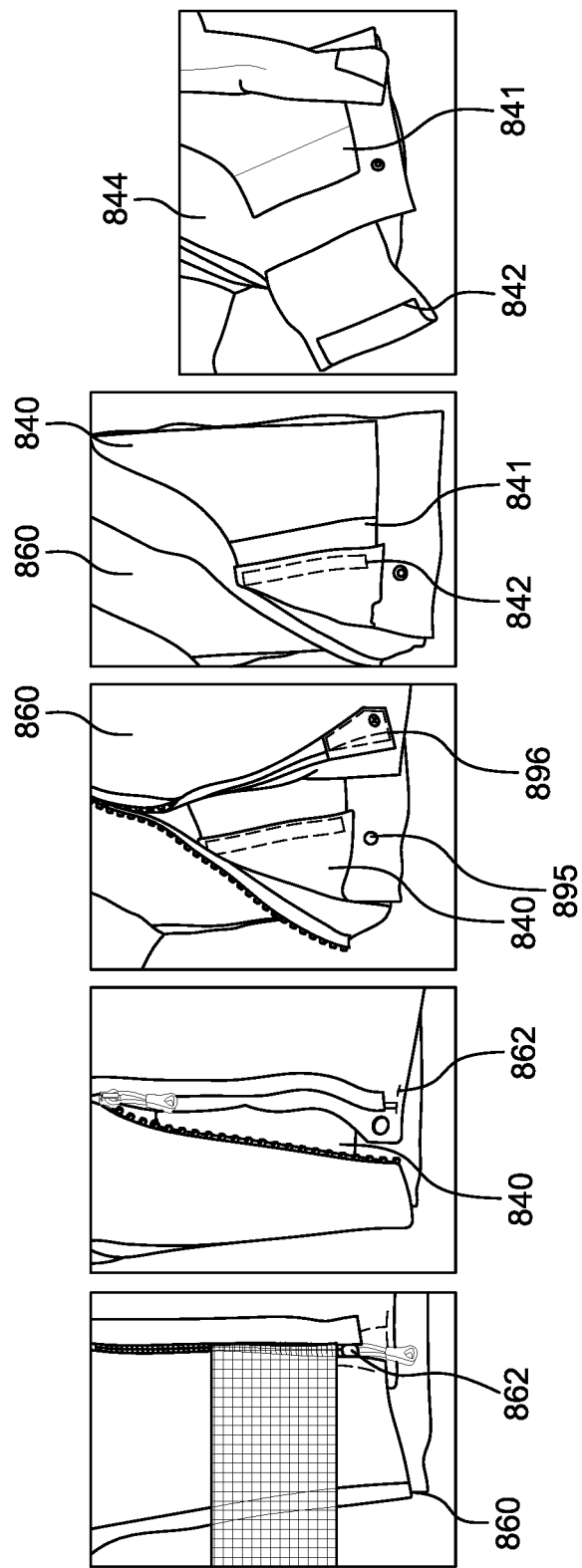

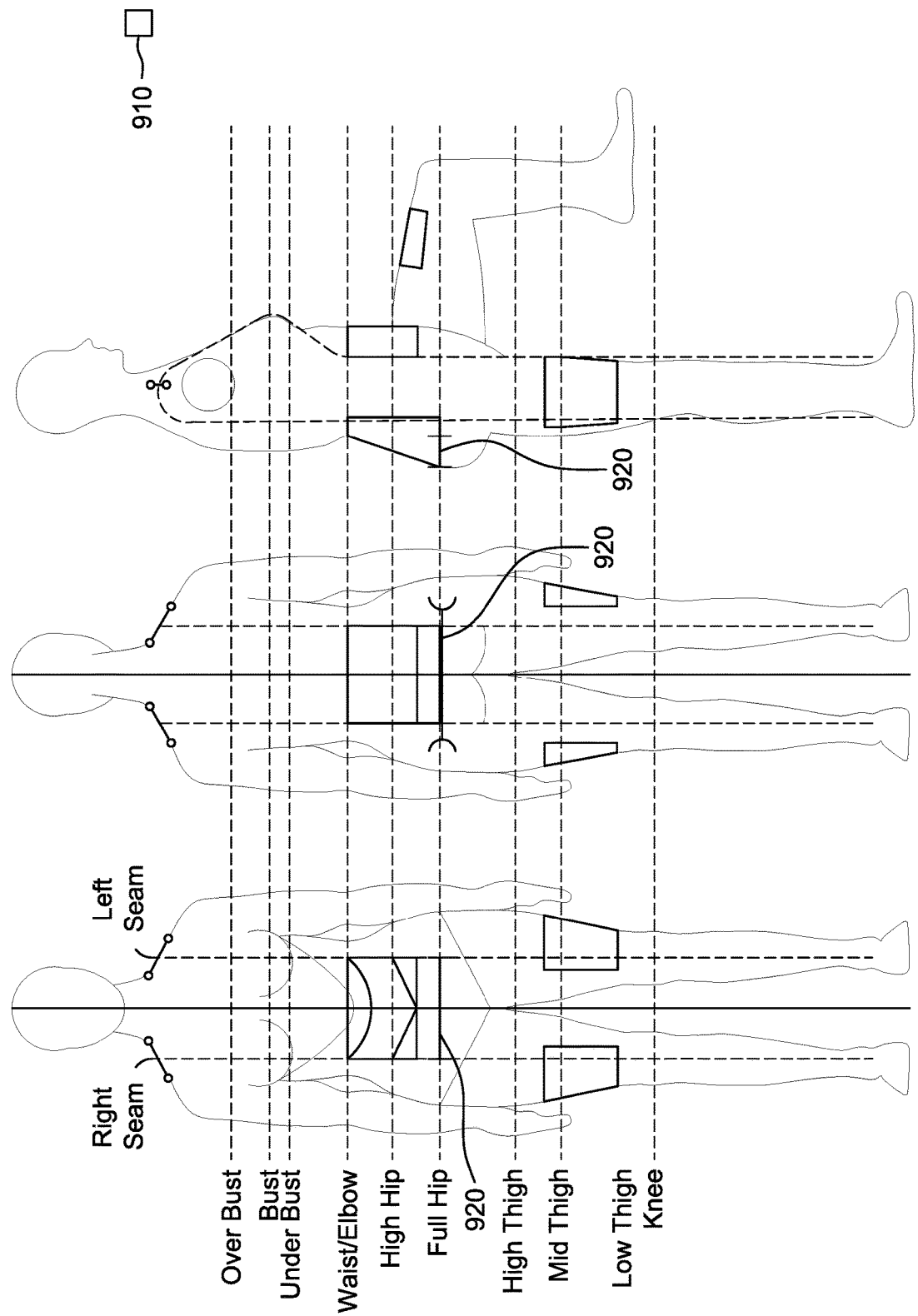

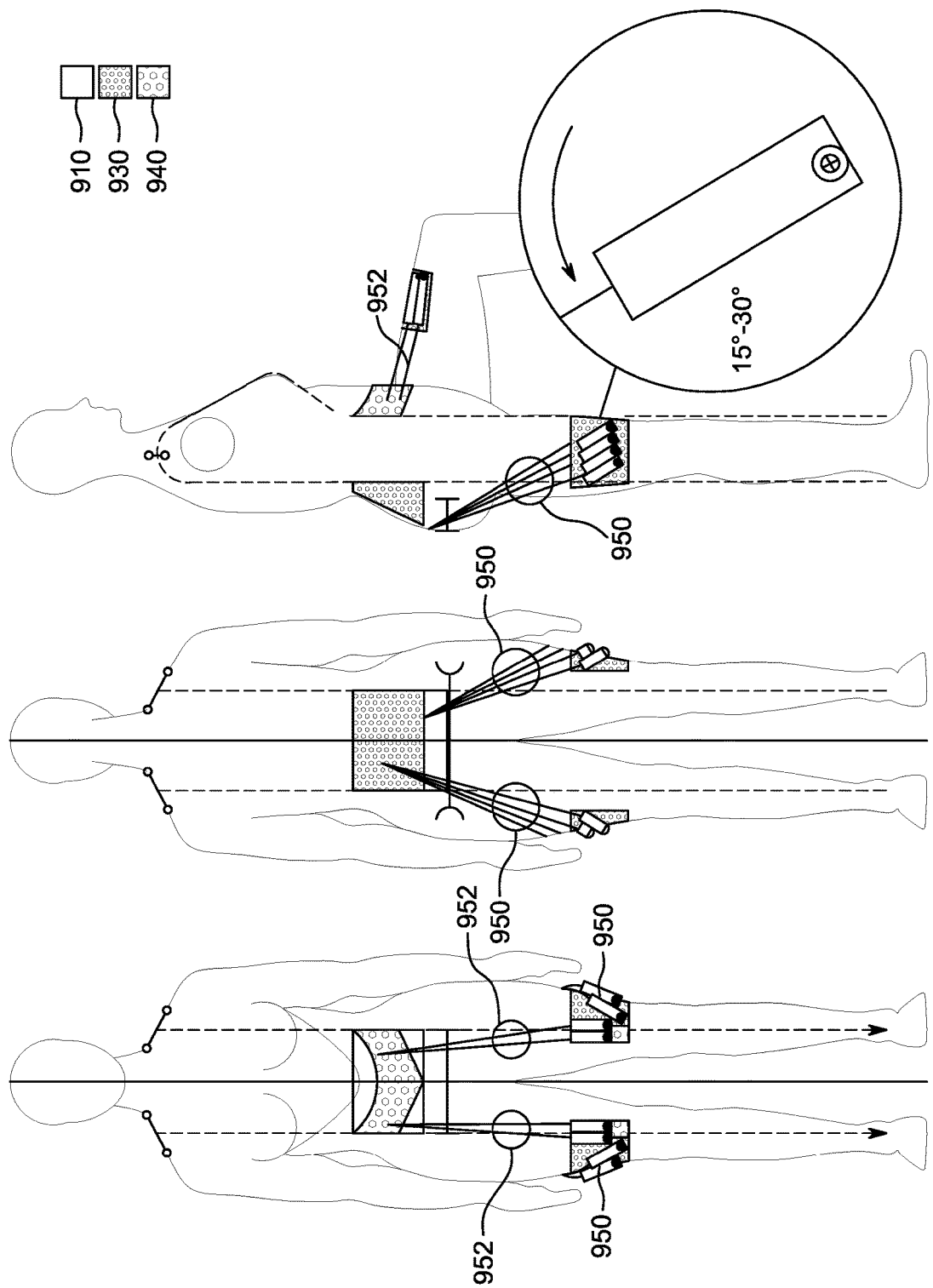

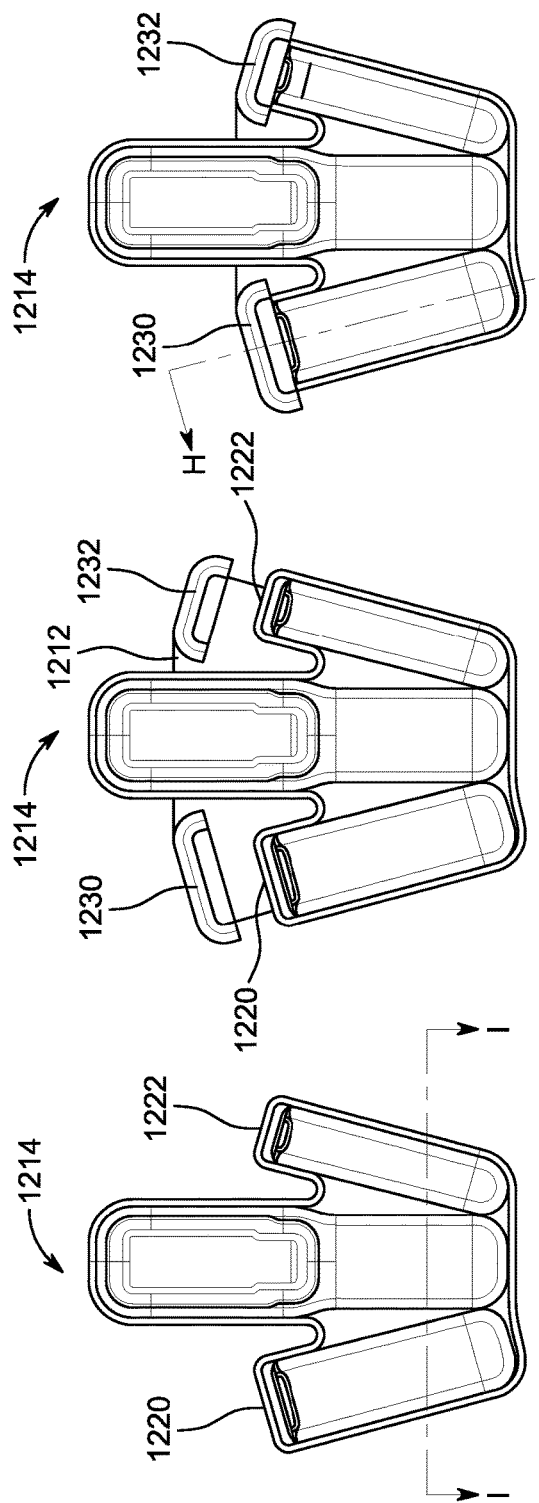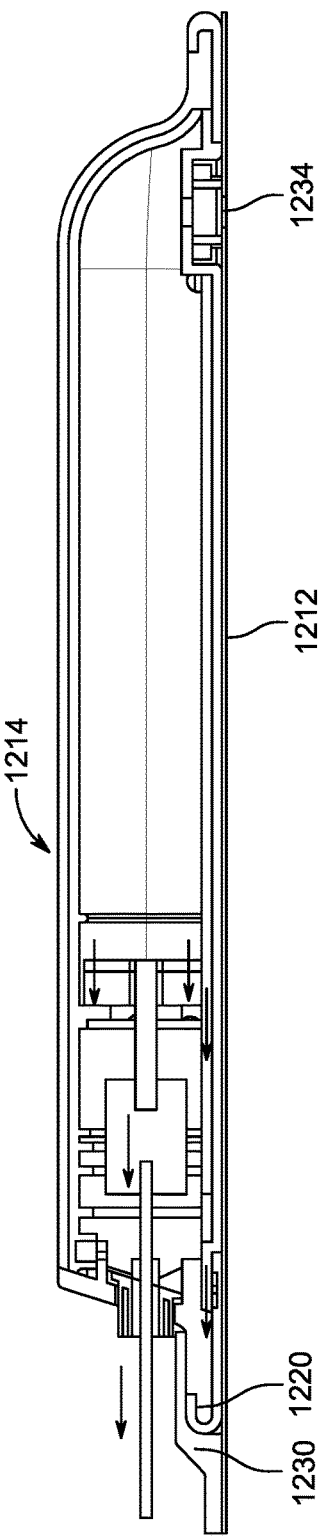
FIG. 12E  FIG. 12F  FIG. 12G  FIG. 12H

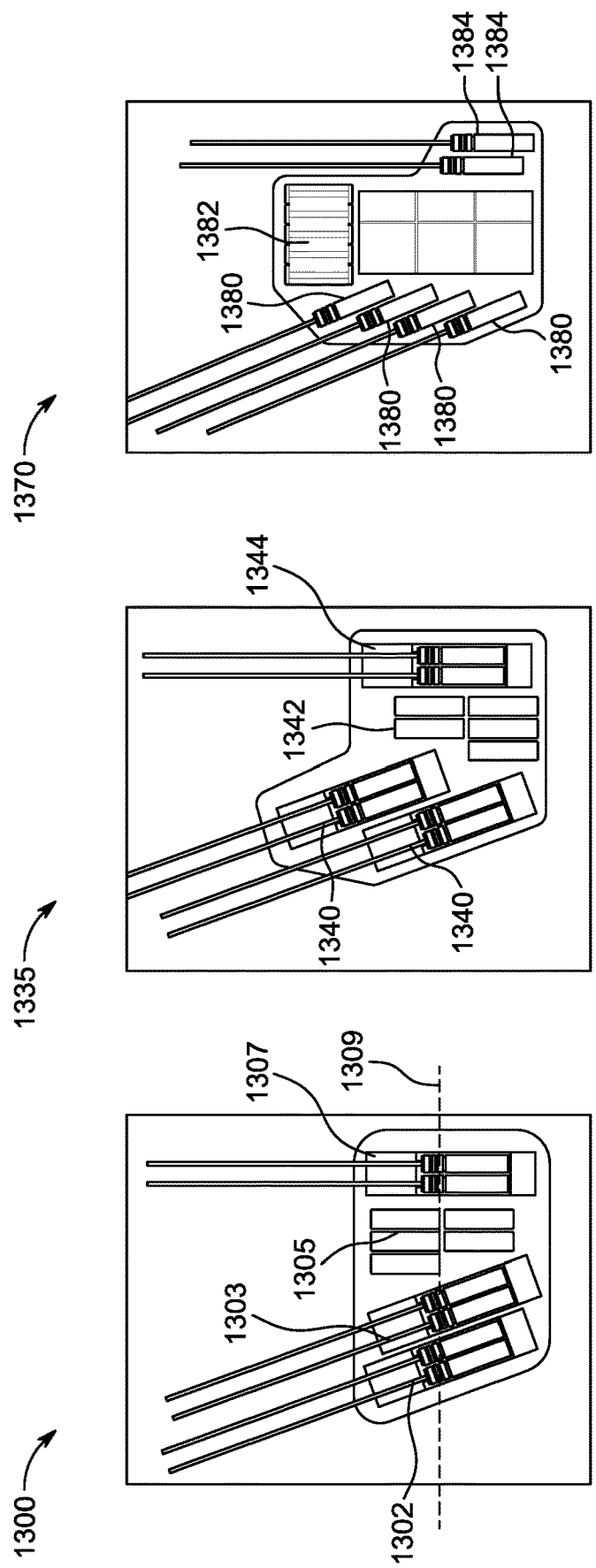

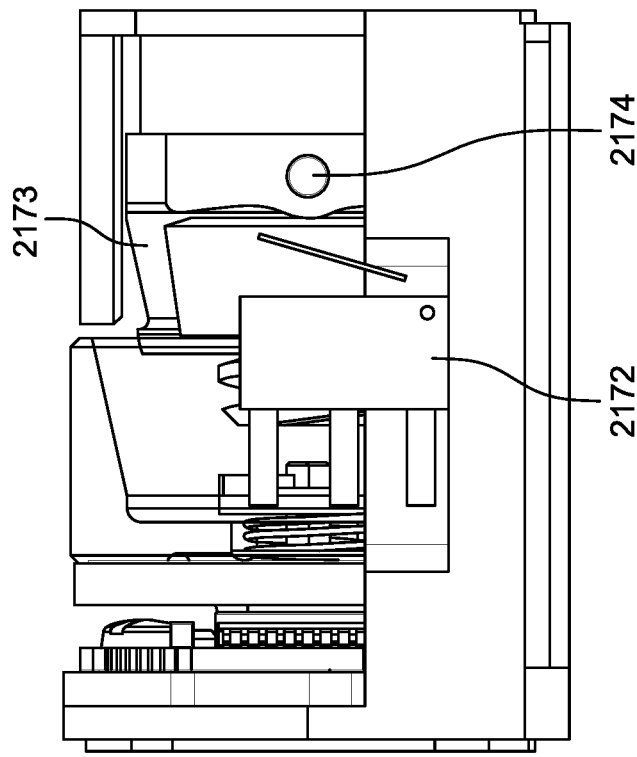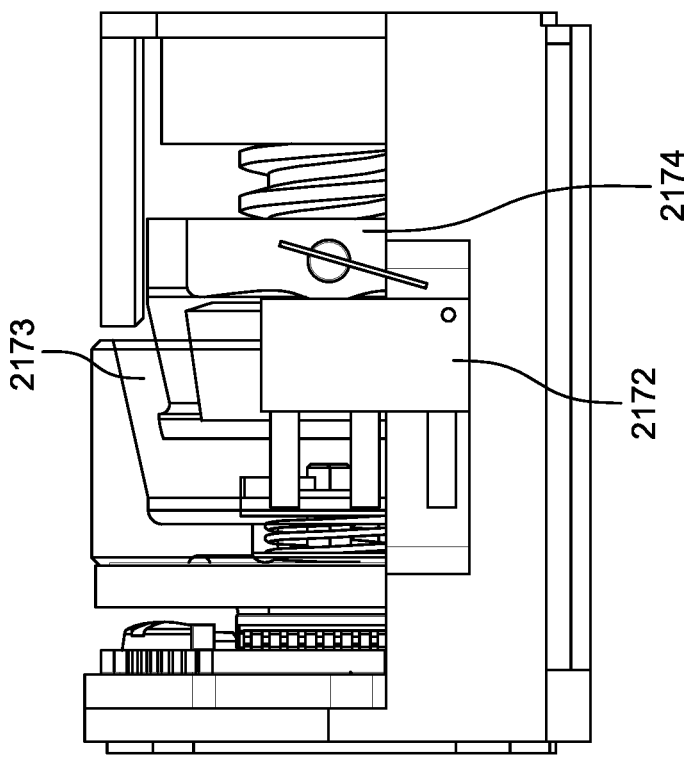
FIG. 21F

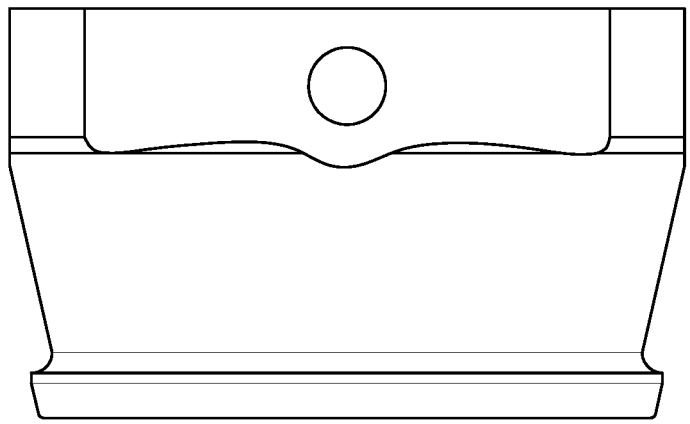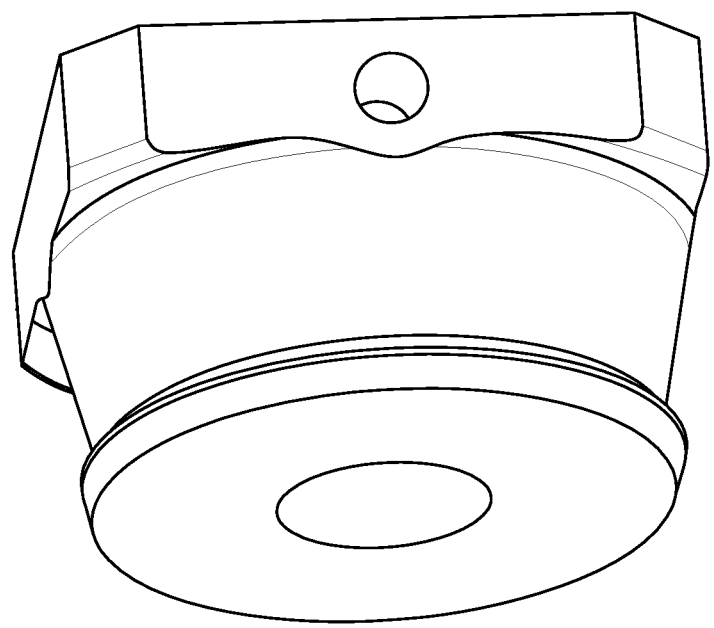
FIG. 21J

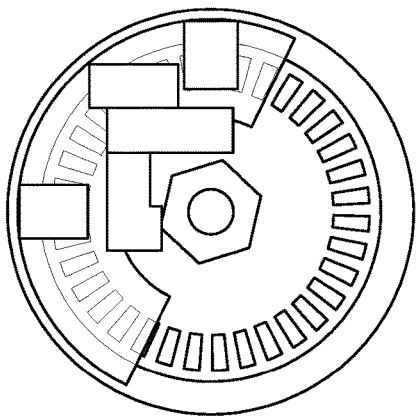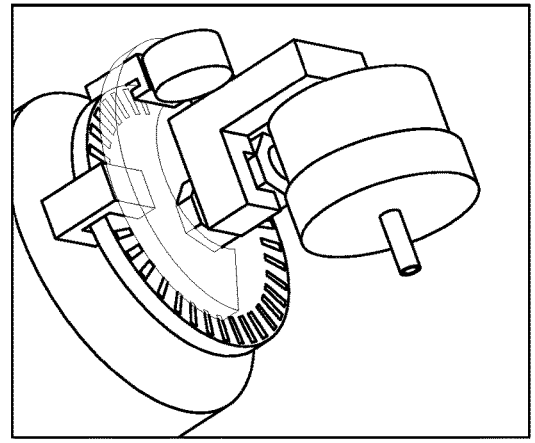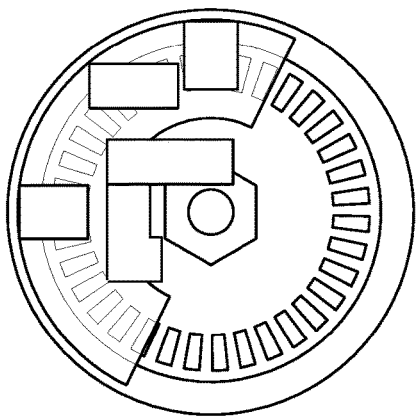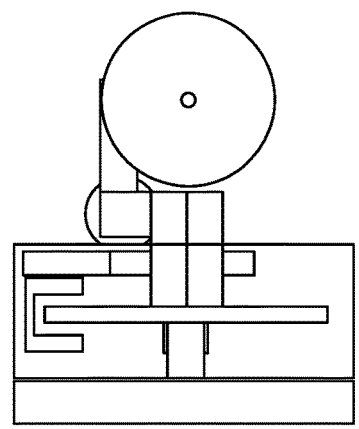
FIG. 26

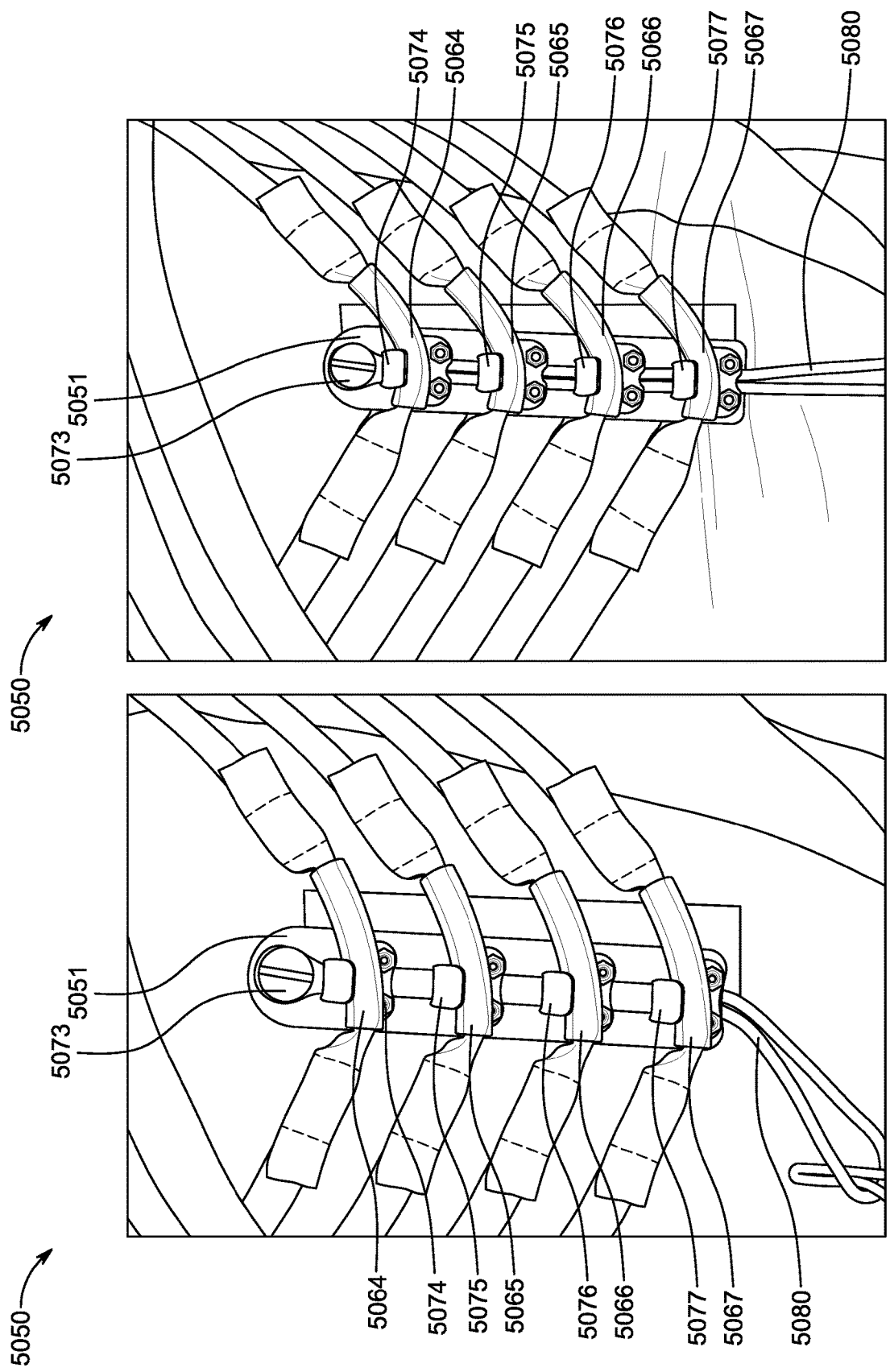

EXOSUIT SYSTEMS AND METHODS

CROSS-REFERENCE TO RELATED APPLICATIONS

This application is a continuation of U.S. patent application Ser. No. 16/203,081, filed Nov. 28, 2018 (now U.S. Patent No. 11, 192, 237), which claims priority to U.S. Provisional Patent Application No. 62/591,739, filed Nov. 28, 2017, U.S. Provisional Patent Application No. 62/644, 301, filed Mar. 16, 2018 and U.S. Provisional Patent Application No. 62/724,452, filed Aug. 29, 2018, the disclosures of which are incorporated by reference in their entireties.

BACKGROUND

Wearable robotic systems have been developed for augmentation of humans' natural capabilities, or to replace functionality lost due to injury or illness.

SUMMARY

In one embodiment, an exosuit is provided that includes a next-to-skin (N2S) layer configured to be in direct contact with a human body; a plurality of grip members that are integrated with the N2S layer. Each grip member includes an adjustment mechanism that enables a user to adjust fit, and a power segment connection interface operative to secure a power layer in place, wherein integration of the plurality of grip members with the N2S layer enables the user to don and doff without requiring that the plurality of grip members be separately attached or removed.

In one embodiment the plurality of grip members include a first thigh load distribution member, a second thigh load distribution member, and a waist load distribution member.

In one embodiment, each of the first and second load distribution members include a base material constructed to include an extension portion and a power layer portion, wherein the extension portion comprises a first hook and loop region and a second hook and loop region, and wherein the power layer portion comprises at least one loop member, wherein the extension portion wraps around a circumference of a thigh of the human and the first hook and loop region threads through the at least one loop member and interlocks with the second hook and loop region, and at least one reinforcement region positioned on the power layer portion.

In one embodiment, each of the first and second load distribution members includes a base material constructed to include an extension portion and a power layer portion, wherein the extension portion comprises a first hook and loop region, and wherein the power layer portion comprises a second hook and loop region, wherein the extension portion wraps around a circumference of a thigh of the human and the first hook and loop region interlocks with the second hook and loop region, and at least one reinforcement region positioned on the power layer portion.

In one embodiment, the N2S layer comprises an extensible fabric portion, and wherein the waist load distribution member includes first non-extensible fabric members secured to the extensible fabric portion and spanning between a front portion of the exosuit and a back portion of the exosuit, second non-extensible fabric members secured to the extensible fabric portion and spanning between the front portion and the back portion, a first power layer segment attached to the first non-extensible fabric members, and a second power layer segment attached to second first non-extensible fabric members.

In one embodiment, the first power layer segment is a hip extension attachment, and wherein the second power layer segment is a hip flexor attachment.

In one embodiment, the N2S layer comprises an extensible fabric portion, and wherein the waist load distribution member includes non-extensible fabric members secured to the extensible fabric portion and spanning between a front portion of the exosuit and a back portion of the exosuit, an interface segment attached to the non-extensible fabric members. The interface segment includes a terminal anchor point, plurality of fastener connection points, a plurality of hook members secured to the plurality of fastener connection points, and a tensioning member secured to the terminal anchor point and secured in place along the interface segment by the plurality of hook members. A plurality of retention members are secured to the non-extensible fabric members and the plurality of hook members.

In one embodiment, when the waist load distribution member is loaded, a combination of the plurality of hook members the plurality of retention members distribute a load evenly across the non-extensible fabric members.

In one embodiment, the tension member is a portion a flexible linear actuator that is coupled to one of the first thigh load distribution member and the second thigh load distribution member.

In one embodiment where each of the first and second thigh load distribution members includes an extension portion and a power layer portion, wherein the extension portion comprises a first hook and loop region and a second hook and loop region, and wherein the power layer portion comprises at least one loop member, wherein the extension portion wraps around a circumference of a thigh of the human and the first hook and loop region threads through the at least one loop member and interlocks with the second hook and loop region, a rigid member connected to the N2S layer in the power layer portion, a plurality of non-extensible fabric members secured to the N2S layer and the rigid member within the power layer portion, and at least one interface member coupled to the rigid member, wherein the at least one interface member is operative to support a power component.

In one embodiment, wherein the at least one interface member is aligned with a line of action.

In one embodiment, wherein the rigid member is triangular in shape or rectangular in shape.

In one embodiment, wherein the plurality of grip members are designed such that end point locations and lines of action are co-located with a bone structure of a user of the exosuit such a way that flexdrive placements on the exosuit system are aligned with a muscle structure of the user for comfort, and moment arms and forces generated by the flexdrive are aligned with the forces generated by the user's own muscles.

In one embodiment, wherein the first thigh load distribution member is connected to the waist load distribution member via at least one line of action, and wherein the second thigh load distribution member is connected to the waist load distribution member via at least a second line of action.

In one embodiment, wherein each of the lines of actions pass through a zone that is approximately located near a full hip demarcation of the user and left and right seams of the user.

In one embodiment, wherein the first thigh load distribution member is connected to the waist load distribution member via a first plurality of lines of action, and wherein the second thigh load distribution member is connected to the waist load distribution member via a second plurality of lines of action.

In one embodiment, a cover layer is constructed to fit over the N2S layer and the plurality of grip members, wherein the cover layer comprises at least one zipper.

In one embodiment, wherein a first of the least one zipper supports donning and doffing.

In one embodiment, wherein a second of the least one zipper provides access to the power layer.

In one embodiment, wherein the cover layer comprises at least one snap or a hook and loop region.

In one embodiment, a patch assembly for use with an exosuit is provided. The patch assembly is operative to interface with first and second load distribution members, and includes a housing, at least one attachment mechanism constructed to interface with the first load distribution member, at least one flexdrive each flexdrive comprising a motor and a tensioning member, wherein the tensioning member extends from the housing and is constructed to interface with the second load distribution member, and electronics coupled to at least one flexdrive and operative to control operation of the at least one flexdrive.

In one embodiment, the housing includes a battery cradle operative to receive a removable battery.

In one embodiment, a battery is installed in the battery cradle.

In one embodiment a sleeve member encapsulates the tensioning member.

In one embodiment, wherein the at least one attachment mechanism includes a plurality of anchors that interface with the first load distribution member.

In one embodiment, wherein the plurality of anchors are selected from the group consisting of hook and loop attachments, clip attachments, button attachments, zipper attachments, buckle attachments, cord attachments, self-arresting attachments, bungee cord attachments, tongue and groove attachments, clip attachments, magnetic attachments, connector attachments, or any combination thereof.

In one embodiment a patch assembly is provided for use with an exosuit. The patch assembly is operative to interface with first and second load distribution members, and includes a housing having at least one attachment mechanism constructed to interface with the first load distribution member, a plurality of flexdrives, wherein each of the flexdrives comprises a motor and a tensioning member, wherein the tensioning member extends from the housing, and electronics coupled to at least one flexdrive and operative to control operation of the at least one flexdrive. The patch assembly includes a tension anchor coupled to each tensioning member, wherein the tension anchor interfaces with the second load distribution member.

In one embodiment, wherein the plurality of flexdrives comprises first and second flexdrives, wherein the first flexdrive is arranged for hip flexor assistance movement, and wherein the second flexdrive is arranged for hip extensor assistance actions.

In one embodiment, wherein the housing further comprises a battery cradle positioned between the first and second flexdrives, wherein the battery cradle is operative to receive a removable battery.

In one embodiment, wherein the patch assembly comprises a central axis, wherein a first angle exists between alignment of the first flexdrive and the central axis, and wherein a second angle exists between alignment of the second flexdrive and the central axis, wherein the first and second angles are selected based on a size of a human for which the patch assembly is to be used.

In one embodiment, wherein the housing is operative to exert a counteractive force into the first load distribution member in response to an assistive force exerted by one of the flexdrives.

In one embodiment, wherein the counteractive force is tuned to provide a predetermined level of the counteractive force based on a construction profile of the housing and the plurality of flexdrives.

In one embodiment, wherein the assistive force is generated when flexdrive twists a string existing in the tensioning member, the twisting of which shortens the length of the tensioning member between the first and second load distribution members.

In one embodiment, wherein the tensioning member includes a data cable electrically coupled to the electronics, a twisted string conduit mechanically coupled to one of the flexdrives, and a sleeve member enshrouding the data cable and the twisted string conduit.

In one embodiment, wherein the first load distribution member comprises a pocket and a flap, and wherein the housing sits in the pocket and the flap is operative to secure the housing in the pocket when it is secured to the at least one attachment mechanism.

In one embodiment, wherein the first load distribution member comprises a cord that is threaded through a plurality of holes in a continuous loop and a cord hook, wherein the housing is secured in place by the cord when it is pulled tight and secured to the cord hook, wherein the cord interfaces with the at least one attachment mechanism and a portion of the housing.

In one embodiment, wherein the first load distribution member comprises a plurality of bottom tabs and a plurality of top tabs, wherein the at least one attachment mechanism comprises a plurality of retention holes, and wherein the housing is secured to the first load distribution member when the plurality of retention holes are in contact with respective ones of the plurality of bottom tabs and the plurality of top tabs.

In one embodiment, wherein the first load distribution member comprises a plurality of hook tabs, a male strap, and a female strap, wherein the at least one attachment member comprises a plurality of retention holes, and wherein the housing is secured to the first load distribution member when the plurality of hook tabs are interfacing the retention holes and the male and female straps are connected together around a portion of the housing.

In one embodiment, a lumbar tensioning system for use with an exosuit worn by human being having a core region is provided. The lumbar tensioning system includes a belt comprising first and second belt segments, a buckle coupled to the first and second belt segments, a first pouch coupled to the first felt belt segment, wherein the first pouch includes a motor, a second pouch coupled to the second belt segment, a tensioning member coupled to the first and second pouches, wherein the lumbar tensioning system increase pressure applied to the core region when the motor causes the tensioning member to tighten, wherein tightening of the tensioning member causes the first and second pouches to be pulled together.

In one embodiment, wherein the first pouch comprises control electronics for controlling operation of the motor.

In one embodiment, wherein the second pouch comprises a battery that supplies power to the motor via the tensioning member.

In one embodiment, a lumbar tensioning system for use with an exosuit worn by human being having a core region is provided. The lumbar tensioning system includes first and second belt segments, a buckle coupled to the first and second belt segments, a pouch system coupled to the first and second belt segments. The pouch system including a motor, a slide track, a slide member coupled to the first belt segment and operative to move back and forth along the slide track, and a tensioning member coupled to the motor and the slide member, wherein the lumbar tensioning system increase pressure applied to the core region when the motor causes the tensioning member to tighten, wherein tightening of the tensioning member causes the first belt segment, via the slide member, to be pulled towards the second belt segment In one embodiment, wherein the pouch system comprises a battery and control electronics.

In one embodiment, wherein the slide member is the only slide member in the pouch system.

In one embodiment, a lumbar system for use with an exosuit worn by human being having a core region is provided. The lumbar system includes first and second belt segments, a buckle coupled to the first and second belt segments, a pouch system coupled to the first and second belt segments. The pouch system includes a motor, a slide rail, a first slide member coupled to the first belt segment and operative to move back and forth along the slide rail, a second slide member coupled to the second belt segment and operative to move back and forth along the slide rail, and a tensioning system coupled to the motor and the first and second slide members, wherein the tensioning system is operative to increase pressure applied to the core region by pulling the first and second slide members together.

In one embodiment, wherein the pouch system includes a battery and control electronics.

In one embodiment, wherein the first and second slide members pull respective first and second belt segments together when the tensioning system is operative to increase pressure applied to the core region.

In one embodiment, wherein the tensioning system is operative to decrease pressure applied to the core region by enabling the first and second slide members to pulled apart.

In one embodiment, wherein the tensioning system includes the motor being mounted to the second sliding member such that motor slides along the track rail in conjunction with the second sliding member, and a tensioning member coupled to the motor and the first sliding member.

In one embodiment, wherein the tensioning system comprises a pulley tensioning system comprising a plurality of pullies and a plurality of pulley lines, wherein the plurality of pulley lines move in response to operation of the motor.

In one embodiment, a flexdrive system for use with an exosuit, the flexdrive system includes a motor, a string rotation assembly coupled to the motor, a lock mechanism operative to lock at least the string rotation assembly in a fixed position independent of operation of the motor, and control circuitry. The control circuitry is operative to control rotation of the motor to control rotation of the string rotation assembly, and control operation of the lock mechanism.

In one embodiment, includes an axis, and wherein the motor and the string rotation assembly are arranged co-axially along the axis.

In one embodiment, wherein the lock mechanism is arranged co-axially along the axis.

In one embodiment, wherein the motor comprise first and second ends, wherein the first end of the motor is coupled to the string rotation assembly, and wherein the second end of the motor is coupled to the lock mechanism.

In one embodiment, an encoder is coupled to the motor and operative to monitor speed and/or position of a shaft of the motor.

In one embodiment, wherein the string rotation assembly includes a gearbox coupled to the motor, a first coupler coupled to the gearbox, and a second coupler coupled to the first coupler.

In one embodiment, a sensor operative to monitor rotation of the string rotation assembly is provided.

In one embodiment, wherein the string rotation assembly includes a first coupler coupled to the motor, and a second coupler coupled to the first coupler.

In one embodiment a sensor operative to monitor rotation of the string rotation assembly is provided.

In one embodiment, wherein the motor includes a shaft, and the first coupler is coupled to the shaft, and wherein the first coupler comprises a string drive coupler that is secured to the second coupler.

In one embodiment, wherein the second coupler includes a first dowel that couples the string drive coupler to the second coupler, and a second dowel constructed to secure a twisted string to the second coupler.

In one embodiment, wherein the string rotation assembly is coupled to a twisted string, wherein rotation of the motor in a first direction causes the twisted string to shorten, and wherein rotation of the motor in a second direction causes the twisted string to lengthen.

In one embodiment, wherein the lock mechanism is operative to lock the motor in a fixed position after the motor has caused the twisted string to shorten.

In one embodiment, wherein the motor comprises a shaft that is coupled to string rotation assembly and the lock mechanism, wherein when the lock mechanism is in a locked position, the shaft is not permitted to rotate, and when the lock mechanism is in an unlocked position, the shaft is permitted to rotate.

In one embodiment, wherein the lock mechanism includes a female lock cone secured to the shaft, a lock motor, a lock screw coupled to the lock motor, and a male lock cone coupled to the lock screw, wherein in the locked position, the lock motor rotates the lock screw such that it causes the male lock cone to engage with and lock the female lock cone in a fixed position, and wherein in the unlocked position, the lock motor rotates the lock screw such that it causes the male lock cone to disengage with and unlock the female lock cone so that the shaft is free to rotate.

In one embodiment, wherein the lock mechanism further comprises a switch that indicates whether the lock mechanism is in the locked position or the unlocked position.

In one embodiment, wherein the male lock cone comprises an extension component that is operative to engage with the switch when in the locked position.

In one embodiment, wherein the lock mechanism comprises a push pull solenoid.

In one embodiment, wherein the lock mechanism includes a lock wheel coupled to the shaft, a push pull solenoid, and an engagement member coupled to the push pull solenoid, wherein in the locked position, the push pull solenoid pushes the engagement member to interface with the lock wheel, and wherein in the unlocked position, the push pull solenoid pulls the engagement member away from the lock wheel.

In one embodiment, wherein the lock mechanism is lead screw locking mechanism, a worm drive locking mechanism, a nitinol actuated push pull mechanism, a solenoid lock mechanism, or a non-backdrivable lock mechanism.

In one embodiment, an exosuit is provided that includes a next-to-skin (N2S) layer configured to be in direct contact with a human body and that serves as a foundation for a power layer to provide assistance to a user of the exosuit. The N2S layer includes a plurality of stretch profiles, wherein each stretch profile is configured to impart a particular functional performance as applied to a particular location on the user, wherein the particular functional performance for each stretch profile is based on an amount of stretching, a direction of the stretching, and a coefficient of friction.

In one embodiment, wherein each stretch profile is based on a particular material type.

In one embodiment, wherein a first material type is characterized as having a near zero or minimal amount of stretching.

In one embodiment, wherein a second material type is characterized as having a stretch direction in a first direction.

In one embodiment, wherein a third material type is characterized as having a stretch direction in a second direction, which is different than the first direction.

In one embodiment, wherein a fourth material type is characterized as having a stretch direction that allows for expansion around circumference of hips or thighs.

In one embodiment, wherein the particular material type permits one of no stretching, stretching along a length of the user, stretching along a width of the user, and stretching along a circumference of the user.

In one embodiment, wherein the N2S layer further comprises a toileting access portion.

In one embodiment, wherein the plurality of stretch profiles are interfacing with each other such that each stretch portion is aligned with a particular location on the user.

In one embodiment, the exosuit includes a plurality of load distribution members positioned on top of the N2S layer, a plurality of power layer segments coupled to the plurality of load distribution members, and a cover layer that covers the N2S layer, the plurality of load distribution members, and the plurality of load distribution members.

In one embodiment, wherein the N2S layer comprises a plurality of friction patches that serve as interface regions with a respective load distribution member. The exosuit includes a plurality of load distribution members, each of the plurality of load distribution members associated with a respective one of the plurality of friction patches, wherein the user can self-adjust a tensioning system to control how tight a particular one of the load distribution members is wrapped around a particular body part.

In one embodiment, wherein the N2S layer comprises a load distribution member that is integrated with one of the plurality of stretch profiles, wherein the user can self-adjust a tensioning system to control how tight the load distribution member is wrapped around a particular body part.

In one embodiment, a thigh load distribution member for use with an exosuit that is worn by a human, includes a base material constructed to include an extension portion and a power layer portion, wherein the extension portion comprises a first hook and loop region, and wherein the power layer portion comprises a second hook and loop region, wherein the extension portion wraps around a circumference of a thigh of the human and the first hook and loop region interlocks with the second hook and loop region; and at least one reinforcement region positioned on the power layer portion.

In one embodiment, the thigh load distribution member includes at least power layer attachment mechanism positioned on the power layer portion for securing a power layer component to the thigh load distribution member.

In one embodiment, wherein the at least one reinforcement region spans an entire length of the power layer portion.

In one embodiment, a thigh load distribution member for use with an exosuit that is worn by a human is provided that includes a base material constructed to include an extension portion and a power layer portion, wherein the extension portion comprises a first hook and loop region and a second hook and loop region, and wherein the power layer portion comprises at least one loop member, wherein the extension portion wraps around a circumference of a thigh of the human and the first hook and loop region threads through the at least one loop member and interlocks with the second hook and loop region; and at least one reinforcement region positioned on the power layer portion.

In one embodiment, the thigh load distribution member includes at least one stability layer positioned on the power layer portion.

In one embodiment, the thigh load distribution member includes at least one stability layer positioned on the extension portion.

In one embodiment, wherein the first hook and loop region comprises first and second sub-regions, and wherein the power layer comprise two loop members, wherein the first sub-region threads through a first loop member and wherein the second sub-region threads through a second loop member.

In one embodiment, the thigh load distribution member includes at least power layer attachment mechanism positioned on the power layer portion for securing a power layer component to the thigh load distribution member.

In one embodiment, wherein the at least one reinforcement region is positioned on a body facing side of the thigh load distribution member, and wherein the first and second hook and loop regions are positioned on an outside facing side of the load distribution member.

In one embodiment, a thigh load distribution member is provided that includes a base material constructed to include an extension portion and a power layer portion, wherein the extension portion comprises a first hook and loop region and a second hook and loop region, and wherein the power layer portion comprises at least one loop member, wherein the extension portion wraps around a circumference of a thigh of the human and the first hook and loop region threads through the at least one loop member and interlocks with the second hook and loop region; a rigid member connected to the base material in the power layer portion; a plurality of non-extensible fabric members secured to the base material and the rigid member within the power layer portion; and at least one interface member coupled to the rigid member, wherein the at least one interface member is operative to support a power component.

In one embodiment, wherein the at least one interface member is aligned with a line of action.

In one embodiment, wherein the rigid member is triangular in shape.

In one embodiment, wherein the rigid member is rectangular in shape.

In one embodiment, an exosuit includes a next-to-skin (N2S) layer configured to be in direct contact with a human body and that serves as a foundation for a power layer to provide assistance to a user of the exosuit. The N2S layer includes toileting access located at groin and buttocks regions of the human body having at least one cutout that provides access to the groin and buttocks.

In one embodiment, wherein the at least one cutout includes a first hole; a second hole; and a channel connecting the first and second holes.

In one embodiment, wherein the first hole is larger than the second hole, wherein the first hole is positioned near the buttocks, and wherein the second hole is positioned near the groin.

In one embodiment, the exosuit includes front attachment region; rear attachment region; and a removable flap operable to attach to the first and second attachment regions to cover the toileting access.

In one embodiment, wherein the removable flap and the front and second attachment regions comprise magnets.

In one embodiment, wherein the removable flap and the front and second attachment regions comprise hook and loop regions.

In one embodiment, wherein the removable flap and the front and second attachment regions comprise button snaps.

In one embodiment, wherein the removable flap comprises a waterproof membrane.

In one embodiment, a method for donning an exosuit is provided for opening a plurality of access ports of the exosuit; preparing a plurality of patch assemblies; inserting the plurality of patch assemblies into respective ones of the plurality of open access ports; donning the exosuit after the plurality of patch assemblies are inserted; adjusting at least one load distribution member after the exosuit is donned; and closing the plurality of access ports.

In one embodiment, a method for donning an exosuit is provided for opening a plurality of access ports of the exosuit; preparing a plurality of patch assemblies, the plurality of patch assemblies comprising a core patch and first and second thigh patches; inserting the core patch into its respective one of the plurality of open access ports; partially donning the exosuit; adjusting at least one load distribution member after the exosuit is partially donned; inserting the first and second thigh patch through their respective ones of the plurality of open access ports; attaching a plurality of string members; complete donning the exosuit; and closing the plurality of access ports.

In one embodiment, a method for donning an exosuit is provided for opening a plurality of access ports of the exosuit; donning the exosuit; preparing a plurality of patch assemblies, the plurality of patch assemblies comprising a belt core patch and first and second thigh patches; and after the exosuit is donned: inserting the belt core patch; adjusting at least one load distribution member after the exosuit is partially donned; inserting the first and second thigh patch through their respective ones of the plurality of open access ports; attaching a plurality of string members; and closing the plurality of access ports.

In one embodiment, an exosuit system is provided that includes an exosuit comprising a next-2-skin layer, a power layer, and a plurality of sensors, wherein the exosuit is operative provide a plurality of assistive movements; control circuitry coupled to the power layer and the plurality of sensors, the control circuitry operative to: execute a body physiology estimator that estimates physiological conditions of a user of the exosuit; execute a suit control module based, at least in part, on the estimated physiological conditions to autonomously control the plurality of assistive movements.

In one embodiment, wherein the autonomous control of the plurality of assistive movements is fully autonomous control.

In one embodiment, wherein the autonomous control of the plurality of assistive movements is intermediate autonomous control.

In one embodiment, wherein the autonomous control of the plurality of assistive movements is performed without requiring any user input manipulation of a user interface.

In one embodiment, the exosuit includes a user interface coupled to the control circuitry, wherein the control circuitry is operative to process inputs received via the user interface.

In one embodiment, wherein the control circuitry is operative to: execute a learning module that improves operation of the body physiology estimator and the suit control module.

In one embodiment, wherein the control circuitry is operative to transmit signals to the power layer to control the plurality of assistive movements.

In one embodiment, wherein the body physiology estimator is operative to apply data analytics and statistics to data obtained from the plurality of sensors.

In one embodiment, wherein the control module comprises a plurality of state machines and a plurality of timers.

In one embodiment, wherein the control module comprises a master state machine and a plurality of slave state machines, wherein the master state machine controls a comprehensive operation of the exosuit system and wherein the slave state machines control specific ones of the plurality of assistive movements.

In one embodiment, wherein the plurality of slave state machines the control the plurality of assistive movements selected from a sit-to-stand assistance movement, a stand-to sit movement, a stretch movement, a standing movement, a walking movement, a running movement, a jumping movement, a crouch movement, a specific exercise movement.

In one embodiment, a symbiosis exosuit system is provided that includes an exosuit comprising a next-2-skin layer, a power layer, and a plurality of sensors, wherein the exosuit is operative provide a plurality of assistive movements; and control circuitry coupled to the power layer and the plurality of sensors, the control circuitry operative to: track body physiology of a user wearing the exosuit; and automatically control any one or more of the plurality of assistive movements to provide anticipated or required support or assistance to the user.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIGS. 1A-1C show front, back, and side views of a base layer of an exosuit according to an embodiment;

FIGS. 1D-1F show front, back, and side views, respectively, of a power layer according to an embodiment;

FIGS. 3D-3F show illustrative front, back, and side views of next-to-skin (N2S) layer according to an embodiment;

FIGS. 4A-4C show illustrative front, back, and side views of a next-to-skin (N2S) layer according to an embodiment;

FIGS. 4D-4F show additional illustrative front, back, and side views of a N2S layer according to an embodiment;

FIGS. 7D-7F show illustrative front, back, and side views of cover layer according to an embodiment;

FIG. 7G shows a close up of circle portion G of cover layer according to an embodiment;

FIGS. 8A-8E show a leg portion of an exosuit in various states according to an embodiment;

FIGS. 9A-9L show illustrative front, back, and side views of a human, with emphasis on different power layer segment anchoring locations, preferred anchoring locations, projected string transmission paths, and load distribution members, according to various embodiments;

FIGS. 12A-12L show different views of a leg patch assembly according to various embodiments;

FIGS. 13A-13C show schematic views of different leg patch assemblies according to various embodiments;

FIGS. 21C-21J show views of an alternative flexdrive module according to an embodiment;

FIG. 26 shows a solenoid lock mechanism assembly according to an embodiment;

FIGS. 50F and 50G show an illustrative waist grip member in respective unloaded and loaded usage with additional components added thereto according to an embodiment;

DETAILED DESCRIPTION

Figures 1G, 1H, 1I, 1J:
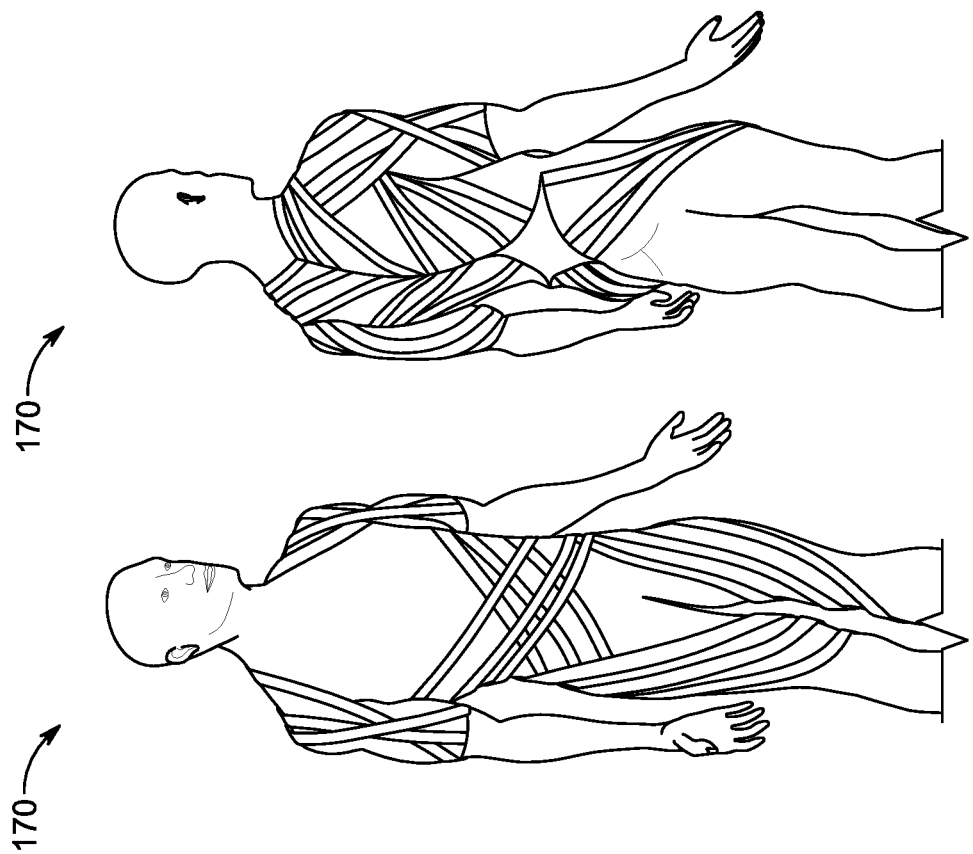
FIGS. 1G and 1H show respective front and back views of a human male's musculature anatomy, according to an embodiment.
FIGS. 1I and 1J show front and side views of an illustrative exosuit having several power layer segments that approximate many of the muscles shown in FIGS. 1G and 1H, according to various embodiments.

In the following description, numerous specific details are set forth regarding the systems, methods and media of the disclosed subject matter and the environment in which such systems, methods and media may operate, etc., in order to provide a thorough understanding of the disclosed subject matter. It can be apparent to one skilled in the art, however, that the disclosed subject matter may be practiced without such specific details, and that certain features, which are well known in the art, are not described in detail in order to avoid complication of the disclosed subject matter. In addition, it can be understood that the examples provided below are exemplary, and that it is contemplated that there are other systems, methods and media that are within the scope of the disclosed subject matter.

In the descriptions that follow, an exosuit or assistive exosuit is a suit that is worn by a wearer on the outside of his or her body. It may be worn under the wearer's normal clothing, over their clothing, between layers of clothing, or may be the wearer's primary clothing itself. The exosuit may be supportive and/or assistive, as it physically supports or assists the wearer in performing particular activities, or can provide other functionality such as communication to the wearer through physical expressions to the body, engagement of the environment, or capturing of information from the wearer. In some embodiments, a powered exosuit system can include several subsystems, or layers. In some embodiments, the powered exosuit system can include more or less subsystems or layers. The subsystems or layers can include the base layer, stability layer, power layer, sensor and controls layer, a covering layer, and user interface/user experience (UI/UX) layer.

The base layer provides the interfaces between the exosuit system and the wearer's body. The base layer may be adapted to be worn directly against the wearer's skin, between undergarments and outer layers of clothing, over outer layers of clothing or a combination thereof, or the base layer may be designed to be worn as primary clothing itself. In some embodiments, the base layer can be adapted to be both comfortable and unobtrusive, as well as to comfortably and efficiently transmit loads from the stability layer and power layer to the wearer's body in order to provide the desired assistance. The base layer can typically comprise several different material types to achieve these purposes. Elastic materials may provide compliance to conform to the wearer's body and allow for ranges of movement. The innermost layer is typically adapted to grip the wearer's skin, undergarments or clothing so that the base layer does not slip as loads are applied. Substantially inextensible materials may be used to transfer loads from the stability layer and power layer to the wearer's body. These materials may be substantially inextensible in one axis, yet flexible or extensible in other axes such that the load transmission is along preferred paths. The load transmission paths may be optimized to distribute the loads across regions of the wearer's body to minimize the forces felt by the wearer, while providing efficient load transfer with minimal loss and not causing the base layer to slip. Collectively, this load transmission configuration within the base layer may be referred to as a load distribution member. Load distribution members refer to flexible elements that distribute loads across a region of the wearer's body. Examples of load distribution members can be found in International Application PCT/US16/19565, titled "Flexgrip," the contents of which are incorporated herein by reference.

The load distribution members may incorporate one or more catenary curves to distribute loads across the wearer's body. Multiple load distribution members or catenary curves may be joined with pivot points, such that as loads are applied to the structure, the arrangement of the load distribution members pivots tightens or constricts on the body to increase the gripping strength. Compressive elements such as battens, rods, or stays may be used to transfer loads to different areas of the base layer for comfort or structural purposes. For example, a power layer component may terminate in the middle back due to its size and orientation requirements, however the load distribution members that anchor the power layer component may reside on the lower back. In this case, one or more compressive elements may transfer the load from the power layer component at the middle back to the load distribution member at the lower back.

The load distribution members may be constructed using multiple fabrication and textile application techniques. For example, the load distribution member can be constructed from a layered woven 45°/90° with bonded edge, spandex tooth, organza (poly) woven 45°/90° with bonded edge, organza (cotton/silk) woven 45°/90°, and Tyvek (non-woven). The load distribution member may be constructed using knit and lacing or horse hair and spandex tooth. The load distribution member may be constructed using channels and/or laces.

The base layer may include a flexible underlayer that is constructed to compress against a portion of the wearer's body, either directly to the skin, or to a clothing layer, and also provides a relatively high grip surface for one or more load distribution members to attach thereto. The load distribution members can be coupled to the underlayer to facilitate transmission of shears or other forces from the members, via the flexible underlayer, to skin of a body segment or to clothing worn over the body segment, to maintain the trajectories of the members relative to such a body segment, or to provide some other functionality. Such a flexible underlayer could have a flexibility and/or compliance that differs from that of the member (e.g., that is less than that of the members, at least in a direction along the members), such that the member can transmit forces along their length and evenly distribute shear forces and/or pressures, via the flexible underlayer, to skin of a body segment to which a flexible body harness is mounted.

Further, such a flexible underlayer can be configured to provide additional functionality. The material of the flexible underlayer could include anti-bacterial, anti-fungal, or other agents (e.g., silver nanoparticles) to prevent the growth of microorganisms. The flexible underlayer can be configured to manage the transport of heat and/or moisture (e.g., sweat) from a wearer to improve the comfort and efficiency of activity of the wearer. The flexible underlayer can include straps, seams, hook-and-loop fasteners, clasps, zippers, or other elements configured to maintain a specified relationship between elements of the load distribution members and aspects of a wearer's anatomy. The underlayer can additionally increase the ease with which a wearer can don and/or doff the flexible body harness and/or a system (e.g., a flexible exosuit system) or garment that includes the flexible body harness. The underlayer can additionally be configured to protect the wearer from ballistic weapons, sharp edges, shrapnel, or other environmental hazards (by including, e.g., panels or flexible elements of para-aramid or other high-strength materials).

The base layer can additionally include features such as size adjustments, openings and electro-mechanical integration features to improve ease of use and comfort for the wearer.

Size adjustment features permit the exosuit to be adjusted to the wearer's body. The size adjustments may allow the suit to be tightened or loosened about the length or circumference of the torso or limbs. The adjustments may comprise lacing, the Boa system, webbing, elastic, hook-and-loop or other fasteners. Size adjustment may be accomplished by the load distribution members themselves, as they constrict onto the wearer when loaded. In one example, the torso circumference may be tightened with corset-style lacing, the legs tightened with hook-and-loop in a double-back configuration, and the length and shoulder height adjusted with webbing and tension-lock fasteners such as cam-locks, D-rings or the like. The size adjustment features in the base layer may be actuated by the power layer to dynamically adjust the base layer to the wearer's body in different positions, in order to maintain consistent pressure and comfort for the wearer. For example, the base layer may be required to tighten on the thighs when standing, and loosen when sitting such that the base layer does not excessively constrict the thighs when seated. The dynamic size adjustment may be controlled by the sensor and controls layer, for example by detecting pressures or forces in the base layer and actuating the power layer to consistently attain the desired force or pressure. This feature does not necessarily cause the suit to provide physical assistance, but can create a more comfortable experience for the wearer, or allow the physical assistance elements of the suit to perform better or differently depending on the purpose of the movement assistance.

Opening features in the base layer may be provided to facilitate donning (putting the exosuit on) and doffing (taking the exosuit off) for the wearer. Opening features may comprise zippers, hook-and-loop, snaps, buttons or other textile fasteners. In one example, a front, central zipper provides an opening feature for the torso, while hook-and-loop fasteners provide opening features for the legs and shoulders. In this case, the hook-and-loop fasteners provide both opening and adjustment features. In other examples, the exosuit may simply have large openings, for example around the arms or neck, and elastic panels that allow the suit to be donned and doffed without specific closure mechanisms. A truncated load distribution member may be simply extended to tighten on the wearer's body. Openings may be provided to facilitate toileting so the user can keep the exosuit on, but only have to remove or open a relatively small portion to use the bathroom.

Electro-mechanical integration features attach components of the stability layer, power layer and sensor and controls layer into the base layer for integration into the exosuit. The integration features may be for mechanical, structural, comfort, protective or cosmetic purposes. Structural integration features anchor components of the other layers to the base layer. For the stability and power layers, the structural integration features provide for load-transmission to the base layer and load distribution members, and may accommodate specific degrees of freedom at the attachment point. For example, a snap or rivet anchoring a stability or power layer element may provide both load transmission to the base layer, as well as a pivoting degree of freedom.

Stitched, adhesive, or bonded anchors may provide load transmission with or without the pivoting degree of freedom. A sliding anchor, for example along a sleeve or rail, may provide a translational degree of freedom. Anchors may be separable, such as with snaps, buckles, clasps or hooks; or may be inseparable, such as with stitching, adhesives or other bonding. Size adjustment features as described above may allow adjustment and customization of the stability and power layers, for example to adjust the tension of spring or elastic elements in the passive layer, or to adjust the length of actuators in the power layer.

Other integration features such as loops, pockets, and mounting hardware may simply provide attachment to components that do not have significant load transmission requirements, such as batteries, circuit boards, sensors, or cables. In some cases, components may be directly integrated into textile components of the base layer. For example, cables or connectors may include conductive elements that are directly woven, bonded or otherwise integrated into the base layer.

Electromechanical integration features may also protect or cosmetically hide components of the stability, power or sensor and controls layers. Elements of the stability layer (e.g. elastic bands or springs), power layer (e.g. flexible linear actuators or twisted string actuators) or sensor and controls layer (e.g. cables) may travel through sleeves, tubes, or channels integrated into the base layer, which can both conceal and protect these components. The sleeves, tubes, or channels may also permit motion of the component, for example during actuation of a power layer element. The sleeves, channels, or tubes may comprise resistance to collapse, ensuring that the component remains free and uninhibited within.

Enclosures, padding, fabric coverings, or the like may be used to further integrate components of other layers into the base layer for cosmetic, comfort, or protective purposes. For example, components such as motors, batteries, cables, or circuit boards may be housed within an enclosure, fully or partially covered or surrounded in padded material such that the components do not cause discomfort to the wearer, are visually unobtrusive and integrated into the exosuit, and are protected from the environment. Opening and closing features may additionally provide access to these components for service, removal, or replacement.

In some cases—particularly for exosuits configurable for either provisional use or testing—a tether may allow for some electronic and mechanical components to be housed off the suit. In one example, electronics such as circuit boards and batteries may be over-sized, to allow for added configurability or data capture. If the large size of these components makes it undesirable to mount them on the exosuit, they could be located separately from the suit and connected via a physical or wireless tether. Larger, over-powered motors may be attached to the suit via flexible drive linkages that allow actuation of the power layer without requiring large motors to be attached to the suit. Such over-powered configurations allow optimization of exosuit parameters without constraints requiring all components to be attached or integrated into the exosuit.

Electro-mechanical integration features may also include wireless communication. For example, one or more power layer components may be placed at different locations on the exosuit. Rather than utilizing physical electrical connections to the sensors and controls layer, the sensor and controls layer may communicate with the one or more power layer components via wireless communication protocols such as Bluetooth, ZigBee, ultrawide band, or any other suitable communication protocol. This may reduce the electrical interconnections required within the suit. Each of the one or more power layer components may additionally incorporate a local battery such that each power layer component or group of power layer components are independently powered units that do not require direct electrical interconnections to other areas of the exosuit.

The stability layer provides passive mechanical stability and assistance to the wearer. The stability layer comprises one or more passive (non-powered) spring or elastic elements that generate forces or store energy to provide stability or assistance to the wearer. An elastic element can have an un-deformed, least-energy state. Deformation, e.g. elongation, of the elastic element stores energy and generates a force oriented to return the elastic element toward its least-energy state. For example, elastic elements approximating hip flexors and hip extensors may provide stability to the wearer in a standing position. As the wearer deviates from the standing position, the elastic elements are deformed, generating forces that stabilize the wearer and assist maintaining the standing position. In another example, as a wearer moves from a standing to seated posture, energy is stored in one or more elastic elements, generating a restorative force to assist the wearer when moving from the seated to standing position. Similar passive, elastic elements may be adapted to the torso or other areas of the limbs to provide positional stability or assistance moving to a position where the elastic elements are in their least-energy state.

Elastic elements of the stability layer may be integrated to parts of the base layer or be an integral part of the base layer. For example elastic fabrics containing spandex or similar materials may serve as a combination base/stability layer. Elastic elements may also include discrete components such as springs or segments of elastic material such as silicone or elastic webbing, anchored to the base layer for load transmission at discrete points, as described above.

The stability layer may be adjusted as described above, both to adapt to the wearer's size and individual anatomy, as well as to achieve a desired amount of pre-tension or slack in components of the stability layer in specific positions. For example, some wearers may prefer more pre-tension to provide additional stability in the standing posture, while others may prefer more slack, so that the passive layer does not interfere with other activities such as ambulation.

The stability layer may interface with the power layer to engage, disengage, or adjust the tension or slack in one or more elastic elements. In one example, when the wearer is in a standing position, the power layer may pre-tension one or more elastic elements of the stability layer to a desired amount for maintaining stability in that position. The pre-tension may be further adjusted by the power layer for different positions or activities. In some embodiments, the elastic elements of the stability layer should be able to generate at least 5 lbs force; preferably at least 50 lbs force when elongated.

The power layer can provide active, powered assistance to the wearer, as well as electromechanical clutching to maintain components of the power or stability layers in a desired position or tension. The power layer can include one or more flexible linear actuators (FLA). An FLA is a powered actuator capable of generating a tensile force between two attachment points, over a give stroke length. An FLA is flexible, such that it can follow a contour, for example around a body surface, and therefore the forces at the attachment points are not necessarily aligned. In some embodiments, one or more FLAs can include one or more twisted string actuators. In the descriptions that follow, FLA refers to a flexible linear actuator that exerts a tensile force, contracts or shortens when actuated. The FLA may be used in conjunction with a mechanical clutch that locks the tension force generated by the FLA in place so that the FLA motor does not have to consume power to maintain the desired tension force. Examples of such mechanical clutches are discussed below. In some embodiments, FLAs can include one or more twisted string actuators or flexdrives, as described in further detail in U.S. Pat. No. 9,266,233, titled "Exosuit System," the contents of which are incorporated herein by reference. FLAs may also be used in connection with electrolaminate clutches, which are also described in the U.S. Pat. No. 9,266,233. The electrolaminate clutch (e.g., clutches configured to use electrostatic attraction to generate controllable forces between clutching elements) may provide power savings by locking a tension force without requiring the FLA to maintain the same force.

The powered actuators, or FLAs, are arranged on the base layer, connecting different points on the body, to generate forces for assistance with various activities. The arrangement can often approximate the wearer's muscles, in order to naturally mimic and assist the wearer's own capabilities. For example, one or more FLAs may connect the back of the torso to the back of the legs, thus approximating the wearer's hip extensor muscles. Actuators approximating the hip extensors may assist with activities such as standing from a seated position, sitting from a standing position, walking, or lifting. Similarly, one or more actuators may be arranged approximating other muscle groups, such as the hip flexors, spinal extensors, abdominal muscles or muscles of the arms or legs.

The one or more FLAs approximating a group of muscles are capable of generating at least 10 lbs over at least a ½ inch stroke length within 4 seconds. In some embodiments, one or more FLAs approximating a group of muscles may be capable of generating at least 250 lbs over a 6-inch stroke within ½ second. Multiple FLAs, arranged in series or parallel, may be used to approximate a single group of muscles, with the size, length, power, and strength of the FLAs optimized for the group of muscles and activities for which they are utilized.

The sensor and controls layer captures data from the suit and wearer, utilizes the sensor data and other commands to control the power layer based on the activity being performed, and provides suit and wearer data to the UX/UI layer for control and informational purposes.

Sensors such as encoders or potentiometers may measure the length and rotation of the FLAs, while force sensors measure the forces applied by the FLAs. Inertial measurement units (IMUs) measure and enable computation of kinematic data (positions, velocities and accelerations) of points on the suit and wearer. These data enable inverse dynamics calculations of kinetic information (forces, torques) of the suit and wearer. Electromyographic (EMG) sensors may detect the wearer's muscle activity in specific muscle groups. Electronic control systems (ECSs) on the suit may use parameters measured by the sensor layer to control the power layer. Data from the IMUs may indicate both the activity being performed, as well as the speed and intensity. For example, a pattern of IMU or EMG data may enable the ECS to detect that the wearer is walking at a specific pace. This information then enables the ECS, utilizing the sensor data, to control the power layer in order to provide the appropriate assistance to the wearer. Stretchable sensors may be used as a strain gauge to measure the strain of the elements in the stability layer, and thereby predict the forces in the elastic elements of the stability layer. Stretchable sensors may be embedded in the base layer or grip layer and used to measure the motion of the fabrics in the base layer and the motion of the body.

Data from the sensor layer may be further provided to the UX/UI layer, for feedback and information to the wearer, caregivers or service providers.

The UX/UI layer comprises the wearer's and others' interaction and experience with the exosuit system. This layer includes controls of the suit itself such as initiation of activities, as well as feedback to the wearer and caregivers. A retail or service experience may include steps of fitting, calibration, training and maintenance of the exosuit system. Other UX/UI features may include additional lifestyle features such as electronic security, identity protection and health status monitoring.

The assistive exosuit can have a user interface for the wearer to instruct the suit which activity is to be performed, as well as the timing of the activity. In one example, a user may manually instruct the exosuit to enter an activity mode via one or more buttons, a keypad, or a tethered device such as a mobile phone. In another example, the exosuit may detect initiation of an activity from the sensor and controls layer, as described previously. In yet another example, the user may speak a desired activity mode to the suit, which can interpret the spoken request to set the desired mode. The suit may be pre-programmed to perform the activity for a specific duration, until another command is received from the wearer, or until the suit detects that the wearer has ceased the activity. The suit may include cease activity features that, when activated, cause the suit to cease all activity. The cease activity features can take into account the motion being performed, and can disengage in a way that takes into account the user's position and motion, and safely returns the user to an unloaded state in a safe posture.

The exosuit may have a UX/UI controller that is defined as a node on another user device, such as a computer or mobile smart phone. The exosuit may also be the base for other accessories. For example, the exosuit may include a cell phone chip so that the suit may be capable of receiving both data and voice commands directly similar to a cell phone, and can communicate information and voice signals through such a node. The exosuit control architecture can be configured to allow for other devices to be added as accessories to the exosuit. For example, a video screen may be connected to the exosuit to show images that are related to the use of the suit. The exosuit may be used to interact with smart household devices such as door locks or can be used to turn on smart televisions and adjust channels and other settings. In these modes, the physical assist of the suit can be used to augment or create physical or haptic experiences for the wearer that are related to communication with these devices. For instance, an email could have a pat on the back as a form of physical emoji that when inserted in the email causes the suit to physically tap the wearer or perform some other type of physical expression to the user that adds emphasis to the written email.

The exosuit may provide visual, audio, or haptic feedback or cues to inform the user of various exosuit operations. For example, the exosuit may include vibration motors to provide haptic feedback. As a specific example, two haptic motors may be positioned near the front hip bones to inform the user of suit activity when performing a sit-to-stand assistive movement. In addition, two haptic motors may be positioned near the back hip bones to inform the user of suit activity when performing a stand-to-sit assistive movement. The exosuit may include one or more light emitting diodes (LEDs) to provide visual feedback or cues. For example, LEDS may be placed near the left and/or right shoulders within the peripheral vision of the user. The exosuit may include a speaker or buzzer to provide audio feedback or cues.

In other instances, the interaction of the FLA's with the body through the body harness and otherwise can be used as a form of haptic feedback to the wearer, where changes in the timing of the contraction of the FLA's can indicate certain information to the wearer. For instance, the number or strength of tugs of the FLA on the waist could indicate the amount of battery life remaining or that the suit has entered a ready state for an impending motion.

The control of the exosuit may also be linked to the sensors that are measuring the movement of the wearer, or other sensors, for instance on the suit of another person, or sensors in the environment. The motor commands described herein may all be activated or modified by this sensor information. In this example, the suit can exhibit its own reflexes such that the wearer, through intentional or unintentional motions, cues the motion profile of the suit. When sitting, for further example, the physical movement of leaning forward in the chair, as if to indicate an intention to stand up, can be sensed by the suit IMU's and be used to trigger the sit to stand motion profile. In one embodiment, the exosuit may include sensors (e.g., electroencephalograph (EEG) sensor) that are able to monitor brain activity may be used to detect a user's desire to perform a particular movement. For example, if the user is sitting down, the EEG sensor may sense the user's desire to stand up and cause the exosuit to prime itself to assist the user in a sit-to-stand assistive movement.

The suit may make sounds or provide other feedback, for instance through quick movements of the motors, as information to the user that the suit has received a command or to describe to the user that a particular motion profile can be applied. In the above reflex control example, the suit may provide a high pitch sound and/or a vibration to the wearer to indicate that it is about to start the movement. This information can help the user to be ready for the suit movements, improving performance and safety. Many types of cues are possible for all movements of the suit.

Control of the suit includes the use of machine learning techniques to measure movement performance across many instances of one or of many wearers of suits connected via the internet, where the calculation of the best control motion for optimizing performance and improving safety for any one user is based on the aggregate information in all or a subset of the wearers of the suit. The machine learning techniques can be used to provide user specific customization for exosuit assistive movements. For example, a particular user may have an abnormal gait (e.g., due to a car accident) and thus is unable to take even strides. The machine learning may detect this abnormal gait and compensate accordingly for it.

FIGS. 1A-1C show front, back, and side views of a base layer 100 of an exosuit according to an embodiment. Base layer 100 may be worn as a single piece or as multiple pieces. As shown, base layer 100 is shown to represent multiple pieces that can serve as load distribution members (LDMs) for the power layer (shown in FIGS. 1D-1F). Base layer 100 and any LDMs thereof can cover or occupy any part of the human body as desired. The LDMs shown in FIGS. 1A-1C are merely illustrative of a few potential locations and it should be appreciated that additional LDMs may be added or certain LDMs may be omitted.

Base layer 100 can include calf LDMs 102 and 104 that are secured around the calf region or lower leg portion of the human. Calf LDMs 102 and 104 are shown to be positioned between the knees and the ankles, but this is merely illustrative. If desired, calf LDM 102 and 104 can also cover the foot and ankle and/or the knee.

Base layer 100 can include thigh LDMs 106 and 108 that are secured around the thigh region of the human. Thigh LDMs 106 and 108 are shown to be positioned between the knees and an upper region of the thighs. In some embodiments, thigh LDMs 106 and 108 and calf LDMs 102 and 104, respectively, may be merged together to form leg LDMs that cover the entirety of the legs and/or feet.

Base layer 100 can include hip LDM 110 that is secured around a hip region of the human. LDM 110 may be bounded such that it remains positioned above the toileting regions of the human. Such bounding may make toileting relatively easy for the human as he or she would be not be required to remove base layer 100 to use the bathroom. In some embodiments, LDM 110 may be attached to thigh LDMs 106 and 108, but the toileting regions may remain uncovered. In another embodiment, a removable base layer portion may exist between LDM 100 and thigh LDMS 106 and 108.

Base layer 100 can include upper torso LDM 112 that is secured around an upper torso region of the human. Upper torso LDM 112 may include waist LDM 113, back LDM 114, shoulder LDM 115, and shoulder strap LDMs 116. Waist LDM 113, back LDM 114, shoulder LDM 115, and shoulder strap LDMs 116 may be integrally formed to yield upper torso LDM 112. In some embodiments, a chest LDM (not shown) may also be integrated into upper torso LDM 112. Female specific exosuits may have built in bust support for the chest LDM.

Base layer 100 can include upper arm LDMs 120 and 122 and lower arm LDMs 124 and 126. Upper arm LDMs 120 and 122 may be secured around bicep/triceps region of the arm and can occupy space between the shoulder and the elbow. Lower arm LDMs 124 and 126 may be secured around the forearm region of the arm and can occupy the space between the elbow and the wrist. If desired, upper arm LDM 120 and lower arm LDM 124 may be integrated to form an arm LDM, and upper arm LDM 122 and lower arm LDM 126 may be integrated to form another arm LDM. In some embodiments, arm LDMS 120, 122, 124, and 126 may form part of upper torso LDM 112.

Base layer 100 can include gluteal/pelvic LDM 128 that is secured the gluteal and pelvic region of the human. LDM 128 may be positioned between thigh LDMs 106 and 108 and hip LDM 110. LDM 128 may have removable portions such as buttoned or zippered flaps that permit toileting.

Although not shown in FIGS. 1A-1C, LDMs may exist for the feet, toes, neck, head, hands, fingers, elbows, or any other suitable body part.

As explained above, the LDMs may serve as attachment points for components of the power layer. In particular, the components that provide muscle assistance movements typically need to be secured in at least two locations on the body. This way, when the flexible linear actuators are engaged, the contraction of the actuator can apply a force between the at least two locations on the body. With LDMs strategically placed around the body, the power layer can also be strategically placed thereon to provide any number of muscle assistance movements. For example, the power layer may be distributed across different LDMs or within different regions of the same LDM to approximate any number of different muscles or muscle groups. The power layer may approximate muscle groups such as the abdominals, adductors, dorsal muscles, shoulders, arm extensors, wrist extensors, gluteals, arm flexors, wrist flexors, scapulae fixers, thigh flexors, lumbar muscles, surae, pectorals, quadriceps, and trapezii.

FIGS. 1D-1F show front, back, and side views, respectively, of a power layer according to an embodiment. The power layer is shown as multiple segments distributed across and within the various LDMs. As shown, the power layer can include power layer segments 140-158. Each of power layer segments can include any number of flexible linear actuators.

Some of the power layer segments may exist solely on the anterior side of the body, exist solely on the posterior side, start on the anterior side and wrap around to the posterior side, start on the posterior side and wrap around to the anterior side, or wrap completely around a portion of the body. Power layer segment (PLS) 140 may be secured to LDM 102 and LDM 106, and PLS 141 may be secured to LDM 104 and LDM 108. PLS 142 may be secured to LDM 106 and LDM 110 and/or LDM 114, and PLS 143 may be secured to LDM 108 and LDM 110 and/or LDM 114. PLS 145 may be secured to LDM 110 and LDM 113 and/or to LDM 114 or LDM 128. PLS 146 may be secured to LDM 115 and LDM 120, and PLS 147 may be secured to LDM 115 and LDM 122. PLS 148 may be secured to LDM 120 and LDM 124, and PLS 149 may be secured to LDM 122 and LDM 126.

PLS 150 may be secured to LDM 104 and LDM 108, and PLS 151 may be secured to LDM 102 and LDM 106. PLS 152 may be secured to LDM 106 and LDM 110 and/or to LDM 113, and PLS 153 may be secured to LDM 108 and LDM 110 and/or LDM 113. PLS 154 may be secured to LDM 112 and LDM 110. PLS 155 may be secured to LDM 112 and LDM 120, and PLS 156 may be secured to LDM 112 and LDM 122. PLS 157 may be secured to LDM 120 and LDM 124, and PLS 158 may be secured to LDM 122 and LDM 126.

It should be appreciated that the power layer segments are merely illustrative and that additional power layer segments may be added or that some segments may be omitted. In addition, the attachment points for the power layer segments are merely illustrative and that other attachment points may be used.

The human body has many muscles, including large and small muscles that are arranged in all sorts of different configuration. For example, FIGS. 1G and 1H show respective front and back views of a human male's musculature anatomy, which shows many muscles. In particular, the abdominals, adductors, dorsal muscles, shoulders, arm extensors, wrist extensors, gluteals, arm flexors, wrist flexors, scapulae fixers, thigh flexors, lumbar muscles, pectorals, quadriceps, and trapezii are all shown.

The LDMs may be designed so that they can accommodate different sizes of individuals who don the exosuit. For example, the LDMs may be adjusted to achieve the best fit. In addition the LDMs are designed such that the location of the end points and the lines of action are co-located with the bone structure of the user in such a way that the flexdrive placement on the exosuit system are aligned with the actual muscle structure of the wearer for comfort, and the moment arms and forces generated by the flexdrive/exosuit system feel aligned with the forces generated by the wearer's own muscles.

FIGS. 1I and 1J show front and side views of illustrative exosuit 170 having several power layer segments that approximate many of the muscles shown in FIGS. 1G and 1H. The power layer segments are represented by the individual lines that span different parts of the body.

These lines may represent specific flexible linear actuators or groups thereof that work together to form the power layer segments that are secured to the LDMs (not shown). As shown, the FLAs may be arrayed to replicate at least a portion of each of the abdominal muscles, dorsal muscles, shoulder muscles, arm extensor and flexor muscles, gluteal muscles, quadriceps muscles, thigh flexor muscles, and trapezii muscles. Thus, exosuit 170 exemplifies one of many possible different power layer segment arrangements that may be used in exosuits in accordance with embodiments discussed herein. These power layer segments are arranged so that the moment arms and forces generated feel like forces being generated by the user's own muscles, tendons, and skeletal structure. Other possible power layer segment arrangements are illustrated and discussed below.

The power layer segments may be arranged such that they include opposing pairs or groups, similar to the way human muscles are arranged in opposing pairs or groups of muscles. That is, for a particular movement, the opposing pairs or groups can include protagonist and antagonist muscles. While performing the movement, protagonist muscles may perform the work, whereas the antagonist muscles provide stabilization and resistance to the movement. As a specific example, when a user is performing a curl, the biceps muscles may serve as the protagonist muscles and the triceps muscles may serve as the antagonist muscles. In this example, the power layer segments of an exosuit may emulate the biceps and triceps. When the biceps human muscle is pulling to bend the elbow, the exosuit triceps power layer segment can pull on the other side of the joint to resist bending of the elbow by attempting to extend it. The power layer segment can be, for example, either be a FLA operating alone to apply the force and motion, or a FLA in series with an elastic element. In the latter case, the human biceps would be working against the elastic element, with the FLA adjusting the length and thereby the resistive force of the elastic element.

Thus, by arranging the power layer segments in protagonist and antagonist pairs, the power layers segments can mimic or emulate any protagonist and antagonist pairs of the human anatomy musculature system. This can be used to enable exosuits to provide assistive movements, alignment movements, and resistive movements. For example, for any exercise movement requires activation of protagonist muscles, a subset of the power layer segments can emulate activation of antagonist muscles associated with that exercise movement to provide resistance.

The design flexibility of the LDMs and PLSs can enable exosuits to be constructed in accordance with embodiments discussed herein. Using exosuits, the power layer segments can be used to resist motion, assist motion, or align the user's form.

Figure 2A:
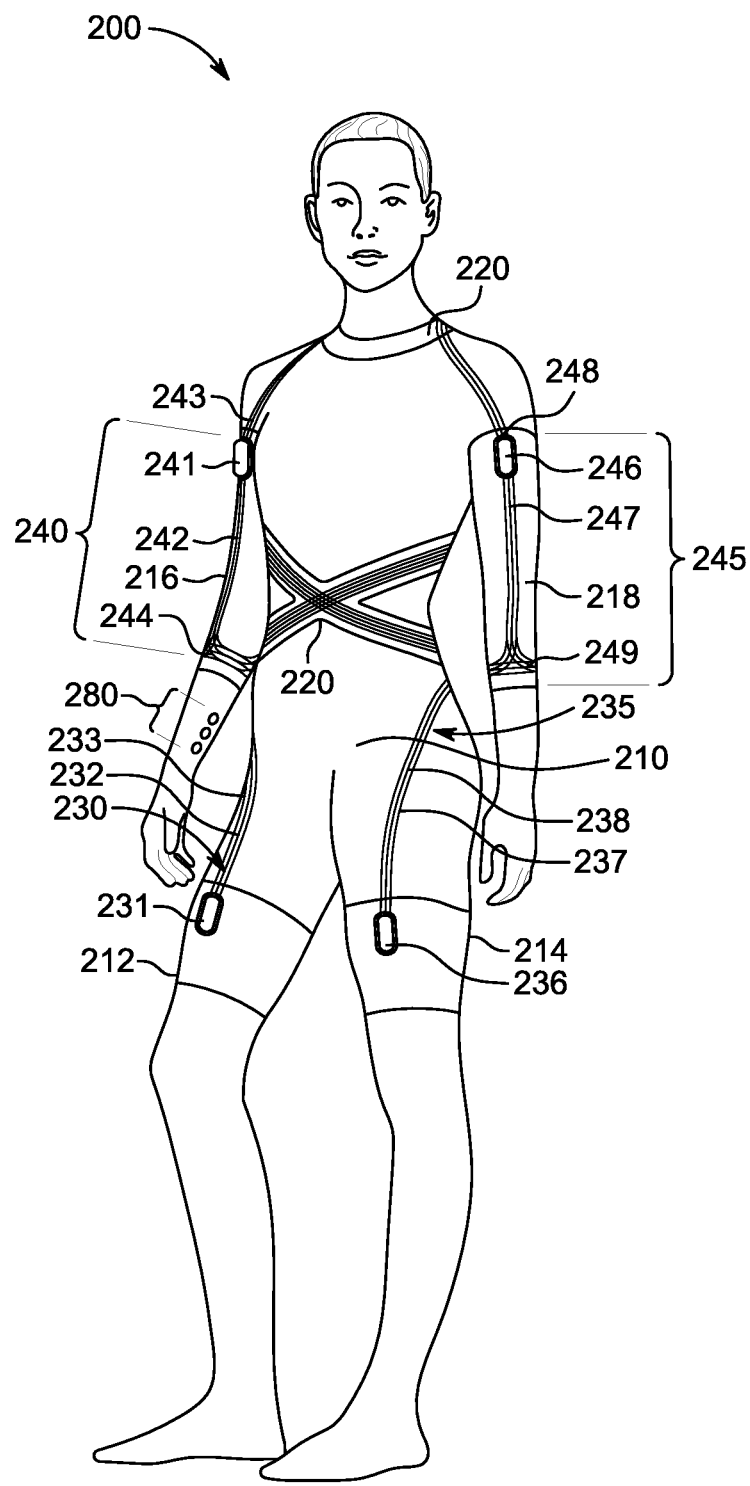
FIGS. 2A and 2B show front and back view of illustrative exosuit according to an embodiment.
Figure 2B:
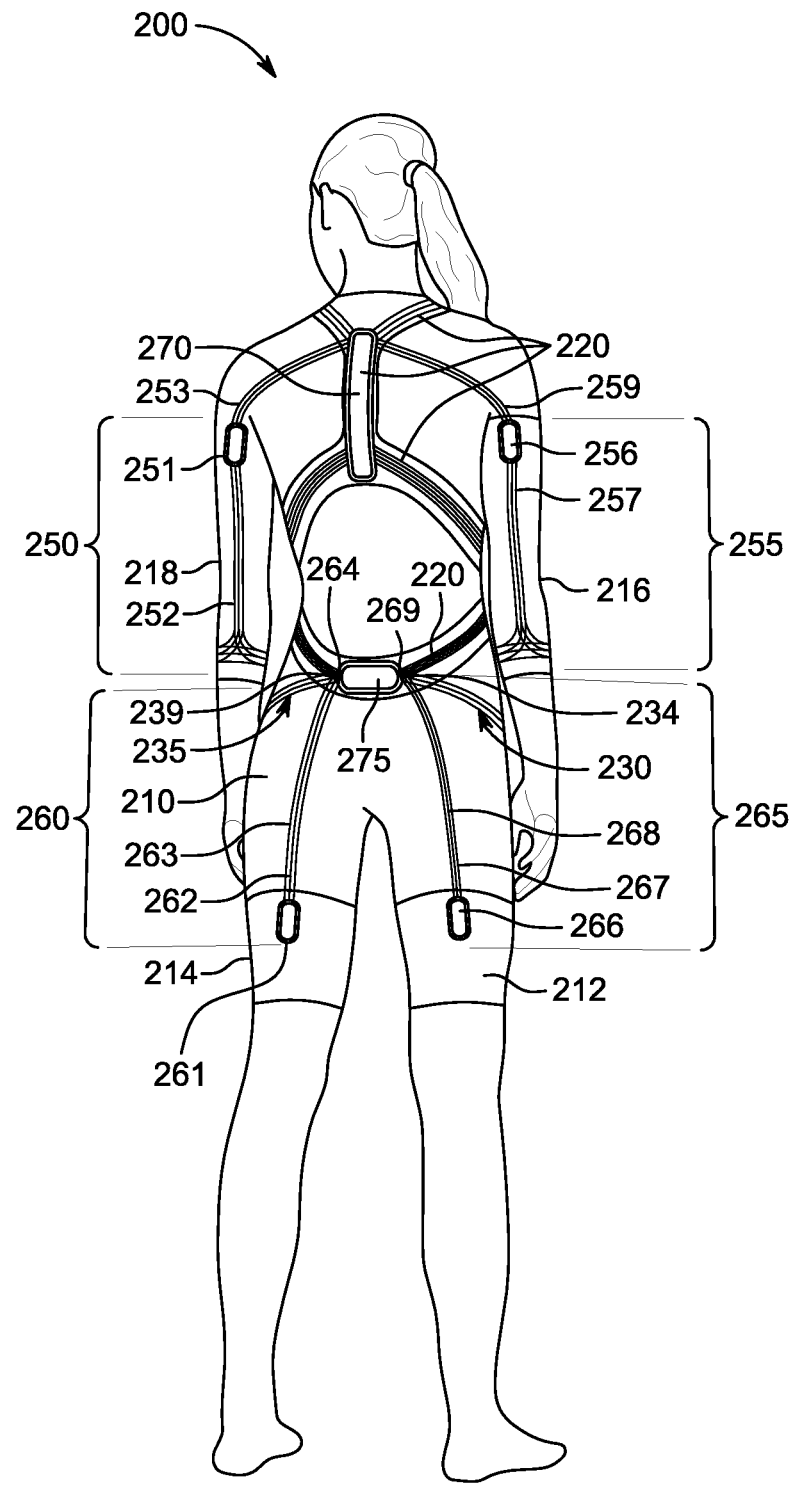

FIGS. 2A and 2B show front and back view of illustrative exosuit 200 according to an embodiment. Exosuit 200 may embody some or all of the base layer, stability layer, power layer, sensor and controls layer, a covering layer, and user interface/user experience (UI/UX) layer, as discussed above. In addition, exosuit 200 may represent one of many different specification implementations of the exosuit shown in FIGS. 1A-1F. Exosuit 200 can include base layer 210 with thigh LDMs 212 and 214, arm LDMs 216 and 218, and upper torso LDM 202. Thigh LDMs 212 and 214 may wrap around the thigh region of the human, and arm LDMs 216 and 218 may wrap around arm region (including the elbow) of the human. Upper torso LDM 220 may wrap around the torso and neck of the human as shown. In particular, LDM 220 may cross near the abdomen, abut the sacrum, cover a portion of the back, and extend around the neck.

Exosuit 200 can include extensor PLSs 230 and 235 secured to thigh LDM 212 and 214 and upper torso LDM 220. Extensor PLSs 230 and 235 may provide leg muscle extensor movements. Extensor PLS 230 may include flexdrive subsystem 231, twisted string 232, and power/communication lines 233. Flexdrive subsystem 231 may include a motor, sensors, a battery, communications circuitry, and/or control circuitry. Twisted string 232 may be attached to flexdrive subsystem 231 and an attachment point 234 on LDM 220. Power/communications lines 233 may convey control signals and/or power to flexdrive subsystem 231. Extensor PLS 235 may include flexdrive subsystem 236, twisted string 237, and power/communication lines 238. Twisted string 237 may be attached to flexdrive subsystem 236 and attachment point 239.

Exosuit 200 can include flexor PLSs 240 and 245 and extensor PLSs 250 and 255 that are secured to LDMs 216, 218, and 220 (as shown). Flexor PLSs 240 and 245 may provide arm muscle flexor movements, and extensor PLSs 250 and 255 may provide arm muscle extensor movements. Flexor PLS 240 may include flexdrive subsystem 241, twisted string 242, and power/communication lines 243. Twisted string 242 may be attached to flexdrive subsystem 241 and attachment point 244. Power/communication lines 243 may be coupled to power and communications module 270. Flexor PLS 245 may include flexdrive subsystem 246, twisted string 247, and power/communication lines 248. Twisted string 247 may be attached to flexdrive subsystem 246 and attachment point 249. Power/communication lines 248 may be coupled to power and communications module 270. Extensor PLS 250 may include flexdrive subsystem 251, twisted string 252, and power/communication lines 253. Twisted string 252 may be attached to flexdrive subsystem 251 and attachment point 254. Power/communication lines 253 may be coupled to power and communications module 270. Extensor PLS 250 may include flexdrive subsystem 256, twisted string 257, and power/communication lines 258. Twisted string 256 may be attached to flexdrive subsystem 256 and attachment point 259.

Power/communication lines 258 may be coupled to power and communications module 270.

Exosuit 200 can include flexor PLS 260 and 265 that are secured to thigh LDMs 212 and 214 and LDM 220. Flexor PLSs 260 and 265 may provide leg muscle flexor ARA movements. Flexor PLS 260 may include flexdrive subsystem 261, twisted string 262, and power/communication lines 263. Twisted string 262 may be attached to flexdrive subsystem 261 and attachment point 264. Power/communication lines 263 may be coupled to power and communications module 275. Flexor PLS 266 may include flexdrive subsystem 266, twisted string 267, and power/communication lines 268. Twisted string 267 may be attached to flexdrive subsystem 266 and attachment point 269. Power/communication lines 263 may be coupled to power and communications module 275

Exosuit 200 is designed to assist, resist, and align movements being performed by the user of the suit. Exosuit 200 may include many sensors in various locations to provide data required by control circuitry to provide such movements. These sensors may be located anywhere on base layer 210 and be electrically coupled to power and communications lines (e.g., 233, 237, 243, 247, 253, 257, 263, 267, or other lines). The sensors may provide absolute position data, relative position data, accelerometer data, gyroscopic data, inertial moment data, strain gauge data, resistance data, or any other suitable data.

Exosuit 200 may include user interface 280 that enables the user to control the exosuit. For example, user interface 280 can include several buttons or a touch screen interface. User interface 280 may also include a microphone to receive user spoken commands. User interface 280 may also include a speaker that can be used to playback voice recordings. Other user interface element such as buzzers (e.g., vibrating elements) may be strategically positioned around exosuit 200.

Exosuit 200 can include communications circuitry such as that contained in power and communications module 270 or 275 to communicate directly with a user device (e.g., a smartphone) or with the user device via a central sever. The user may use the user device to select one or more movements he or she would like to perform, and upon selection of the one or more movements, exosuit 200 can the assist, resist, or align movement. The user device or exosuit 200 may provide real-time alignment guidance as to the user's performance of the movement, and exosuit 200 may provide resistance, alignment, or assistance to the movement.

Figure 3C:
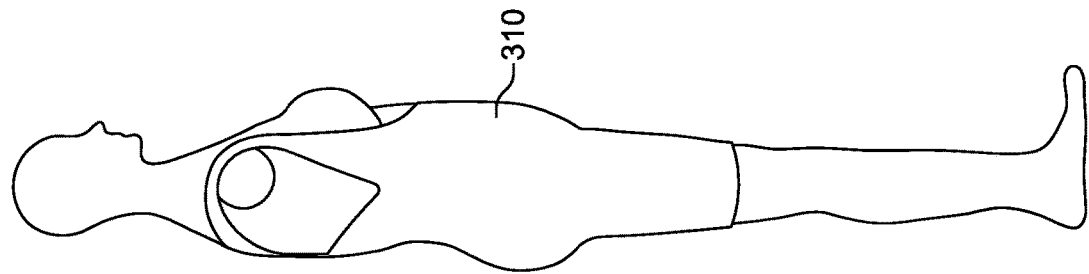
FIGS. 3A-3C show illustrative front, back, and side views of next-to-skin (N2S) layer according to an embodiment.
Figure 3B:
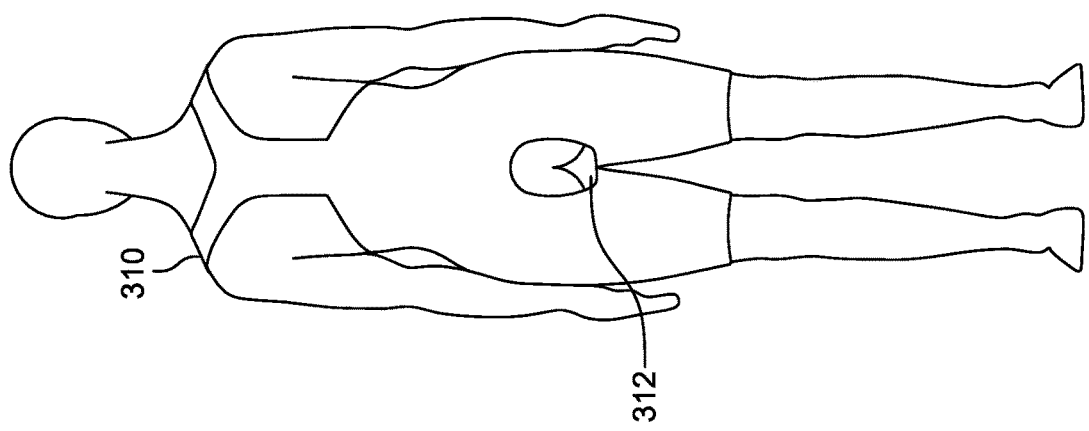
Figure 3A:
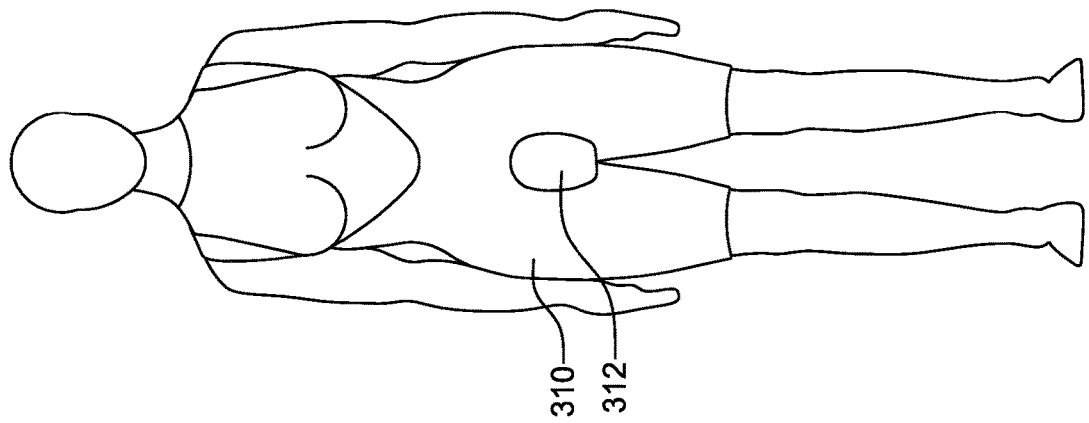

FIGS. 3A-3C show illustrative front, back, and side views of next-to-skin (N2S) layer 310 according to an embodiment. N2S layer 310 may be the inner most layer of an exosuit that makes contact with the user's body. N2S layer 310 may be constructed to cover different parts of the user and leave certain parts uncovered. For example, as shown, the arms, part of the shoulders, the lower part of the legs, chest region, and neck are not covered. In addition, toileting region 312 may also be uncovered or may include a removable material.

N2S 310 may be constructed from any suitable material. N2S 310 may be constructed from only one material type or from a combination of different material types. For example, the material types can be polyester or nylon. In some embodiments, even if N2S 310 is constructed from only one material type, that material type may be woven to exhibit different stretch profiles. For example, the stretch profiles can include little or no stretch, stretch in first, second, third, or any other desired directions, where each stretch direction is different relative to another stretch direction. N2S 310 may be constructed to have a combination of different stretch profiles. For example, a first portion of N2S 310 may include minimal stretch material, a second portion may include material that stretches in a first direction, and third portion may include material that stretches in a second direction. The material types can also exhibit different friction coefficients. Some materials may have a relatively high friction coefficient relative to human skin (to increase adherence thereto) or a relatively low friction coefficient relative to human skin (to permit relative ease in stretching against the skin and/or donning and doffing). Some portions of N2S 310 may be constructed to have a relatively high coefficient of friction with respect to load distribution members and/or power layer segments.

FIGS. 3D-3F show illustrative front, back, and side views of next-to-skin (N2S) layer 320 according to an embodiment. N2S layer 320 may be constructed to include different functional performance aspects as applied to different parts of the user. For example, functional performance can be achieved with different amounts and directional orientations of stretch, as well as adding different amounts of friction surfaces. Illustrated in FIGS. 1D-1F is N2S layer 320 having four different material types. These different materials are illustrated with cross-hatchings, dots, or solid patterns. First material 322 may be a polyester or nylon woven that has little or no stretch. First material 322 may have a relatively low profile to hide beneath clothing. Second material 324 may be a polyester or nylon stretch woven that is constructed to stretch along a first direction. Second material 324 may distribute load from the lower extremities upwards while allowing some stretch for movement and fit. Third material 326 may be another polyester or nylon woven that is constructed to stretch along a second direction. Third material 326 may be sized to allow for expansion around the circumference of the thighs and hips. Fourth material 328 may be relatively high coefficient woven or knit material that may or may not stretch. Fourth material 328 may have a relatively high amount of friction on both sides, and may be intended support a load distribution member or a power layer segment. Zipper 325 may exist as shown.

N2S 310 is constructed such that different material types or stretch profiles are arranged such that each material type of stretching profile is aligned with a particular portion of the user. That is, even though N2S 310 exhibits a one piece construction, the multiplicity of different stretching profiles is such that each portion of the user's body is specifically addressed to maximize comfort of fit, suitability for load distribution members, suitability for power layer support, and/or exosuit functionality. For example, as shown in FIGS. 3D-3F, third material 326 is shown to run along the sides of the body (e.g., legs, hips, and abdomen), whereas fourth material 328 is shown to be positioned adjacent to the third material 326 (e.g., in the abdomen, back, and thighs), and second material 324 occupies a remainder of the space not covered by third and fourth materials 326 and 328. First material 322 is shown to wrap around the shoulders.

Figure 3I:
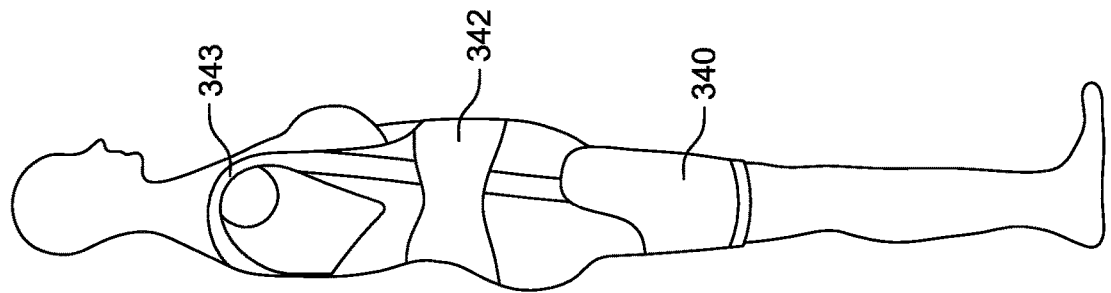
FIGS. 3G-3I show illustrative front, back, and side views of load distribution members according to an embodiment.
Figure 3H:
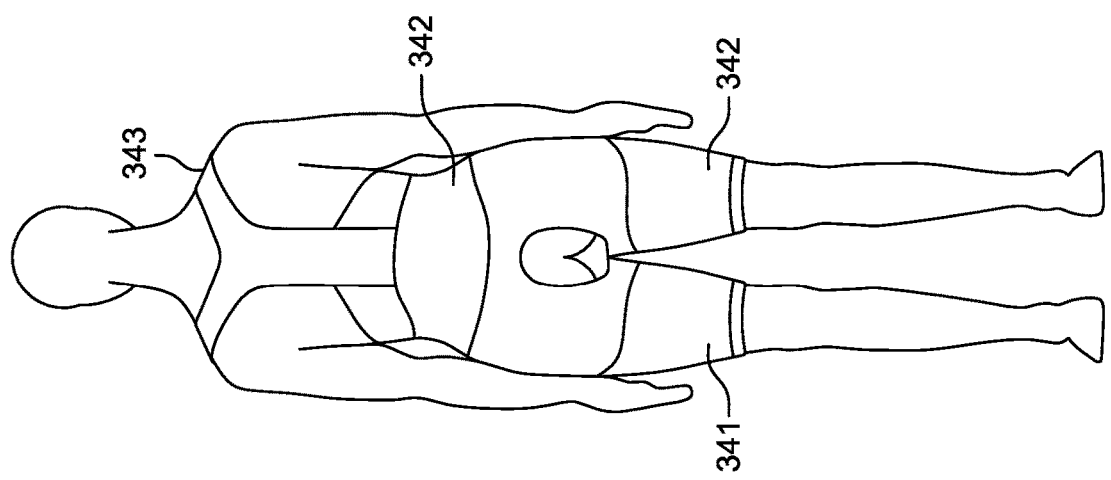
Figure 3G:
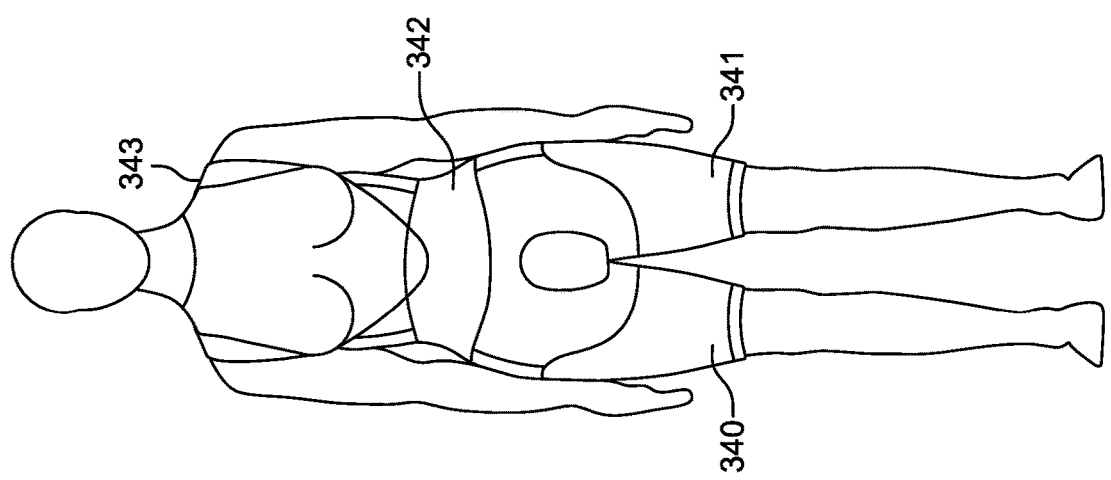

FIGS. 3G-3I show illustrative front, back, and side views of load distribution members according to an embodiment. FIGS. 3G-3I shows LDMs 340, 341, 342, and 343 positioned on top of the base layer. LMDs 340 and 341 may be associated with the thighs, LDM 342 may be associated with the core, and LDM 343 may be associated with the shoulders and back. In some embodiments, LDM 342 may be connected to LDMs 340 and 341 via a coupling member.

Figure 3L:
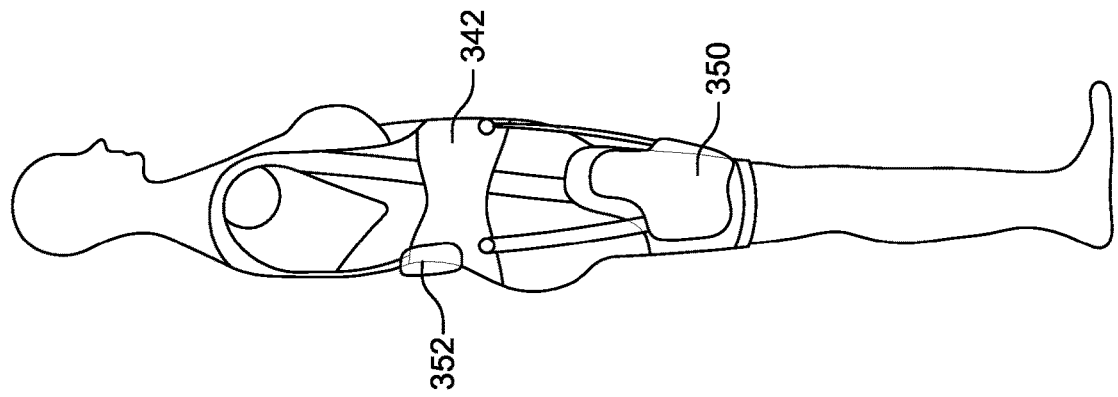
FIGS. 3J-3L show illustrative front, back, and side views of power layer segments according to an embodiment.
Figure 3K:
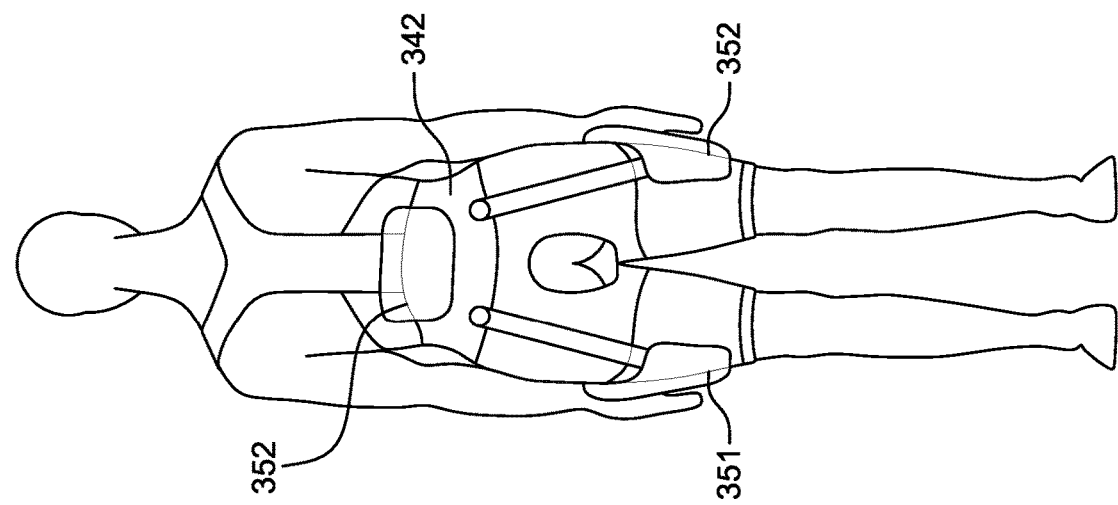
Figure 3J:
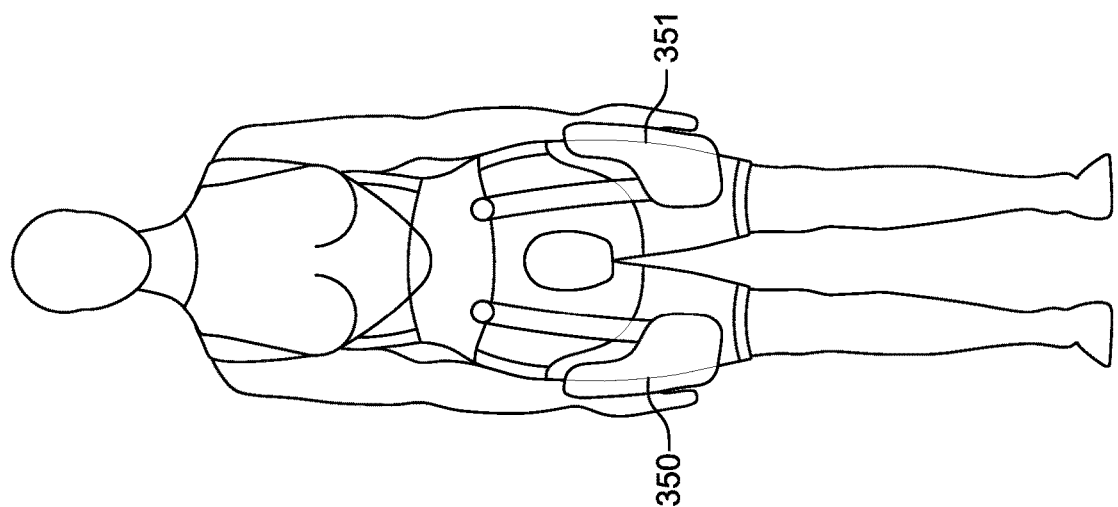

FIGS. 3J-3L show illustrative front, back, and side views of power layer segments according to an embodiment. FIGS. 3J-3L can include PLSs 350, 351, and 352 that are positioned on top of LDMs. PLSs 350 and 351 may be associated the thighs and are coupled to LDMS 340, 341, and 342. PLS 352 may be coupled to LDM 342.

Figure 3O:
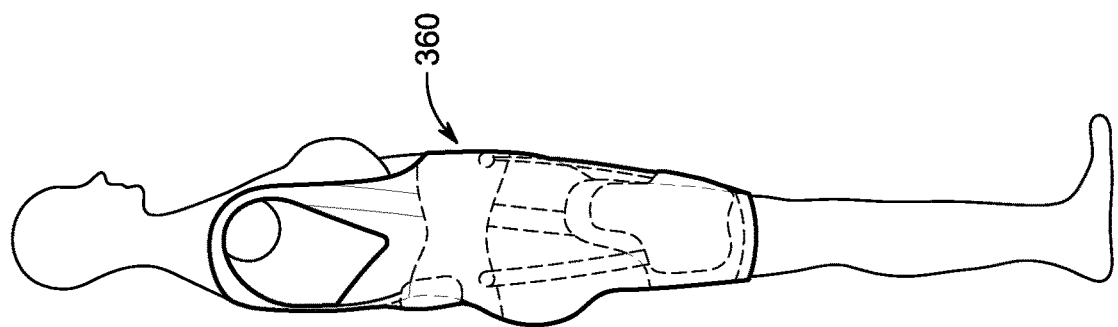
FIGS. 3M-3O show illustrative front, back, and side views of cover layer according to an embodiment.
Figure 3N:
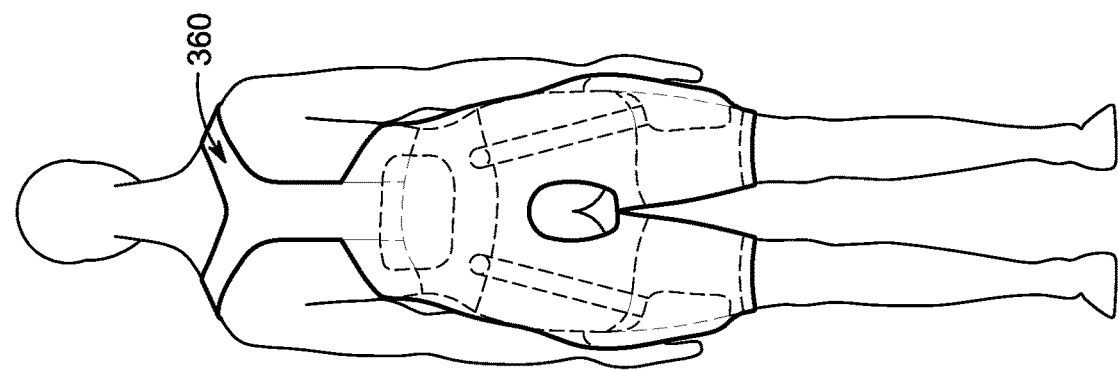
Figure 3M:
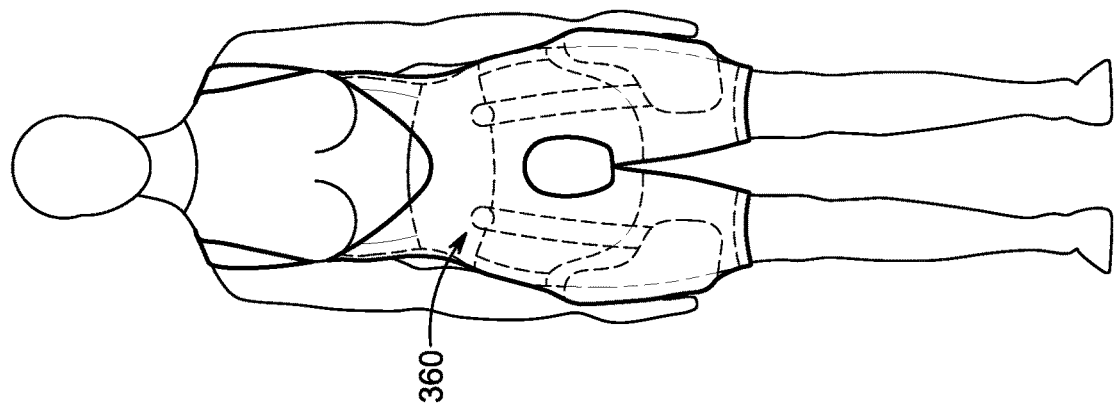

FIGS. 3M-3O show illustrative front, back, and side views of cover layer 360 according to an embodiment. Cover layer 360 may be a top layer that overlays the base layer, load distribution members, and power layer segments. Cover layer 360 may provide an aesthetic look that tastefully covers the load distribution members and power layer segments. In some embodiments, cover layer 360 may be constructed to have ribbing or knit patterns that emulate muscles of the human body.

Figure 3P:
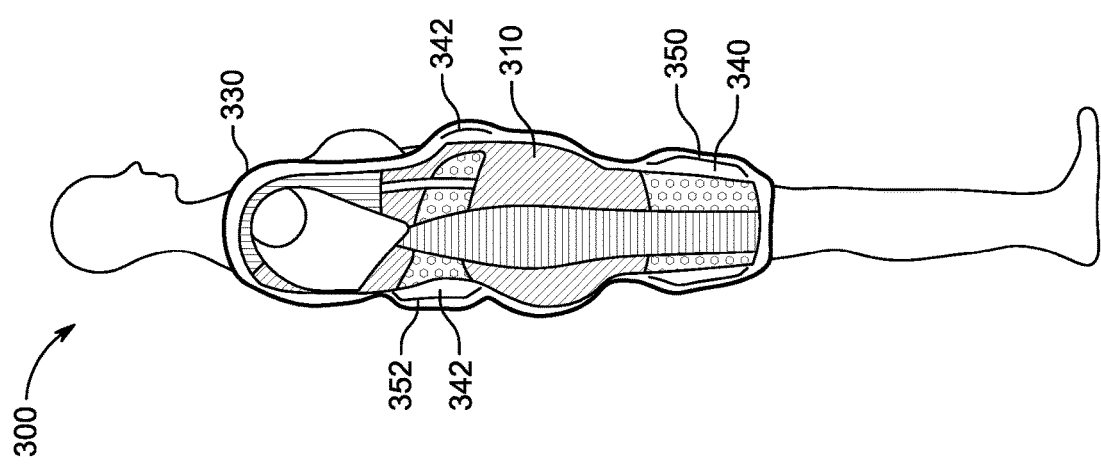
FIG. 3P shows an illustrative cross-sectional view of an exosuit according to an embodiment.

FIG. 3P shows an illustrative cross-sectional view of exosuit 300 according to an embodiment. In particular, FIG. 3P shows N2S layer 320, load distribution members 740 and 742, power layers segments 350 and 352, and cover layer 370.

FIGS. 4A-4C show illustrative front, back, and side views of next-to-skin (N2S) layer 400 according to an embodiment. N2S layer 400 may embody some of the general concepts of NS2 layer 320 (discussed above). N2S layer 400 may be constructed with first material type 402 (which is shown by the cross-hatchings), second material type 404 (which is shown by the solid texture), and friction patches 406 and 407 (which is shown by a dotted pattern). As explained in connection NS2 layer 320, the different material types may exhibit different weave patterns, material properties, friction coefficients, etc. Friction patches 406 are associated with the thighs and friction patch 407 is associated with a portion of the back. Load distribution members (not shown) may be constructed and sized to adhere to friction patches 406 and 407. N2S layer 400 may also include flap 408 and core support belt 410. Flap 408 may be button/zipper combination to promote donning and doffing. Core support belt 410 may loop around the torso region of the user and can be connected together on the front side of the wearer. Core support belt 410 may pass behind friction pad 407.

FIGS. 4D-4F show illustrative front, back, and side views of next-to-skin (N2S) layer 400 of FIGS. 4A-4C, but with the addition of load distribution members 410 and 412 according to an embodiment. Load distribution members 410 and 412 may be removable items that can wrap around friction patches 406 (not shown). LDMs 410 and 412 may be user adjustable in that the user can adjust how tightly the LDMs are wrapped around the thighs. For example, LDMs 410 and 412 may have a tensioning system the enable the user to control how tight the LDM is wrapped around the thigh. Different tensioning systems for a thigh LDM are discussed below in connection with FIGS. 5A-5C and 6A-6D. It should be appreciated that in some embodiments, friction patches may not exist and that LDMs 410 and 412 may be integrally formed components of layer 400 or may reside on top of layer 400.

Figure 5A:
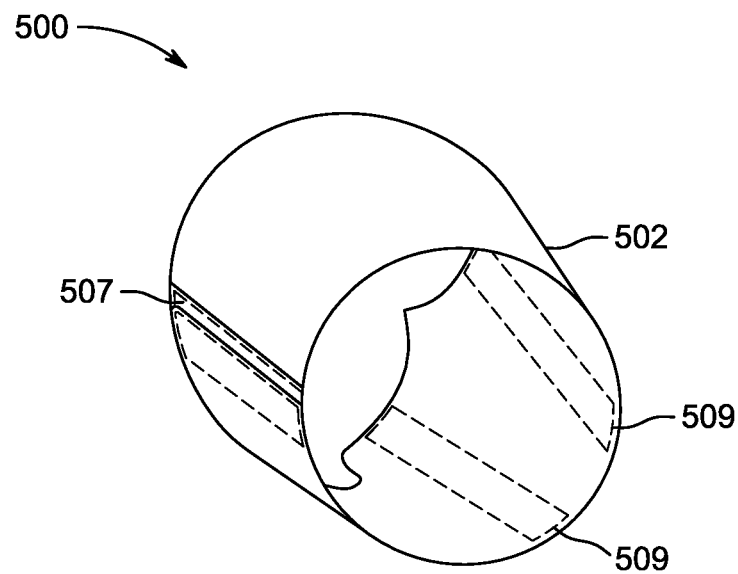
FIGS. 5A-5C show different views a thigh load distribution member according to an embodiment.
Figure 5B:
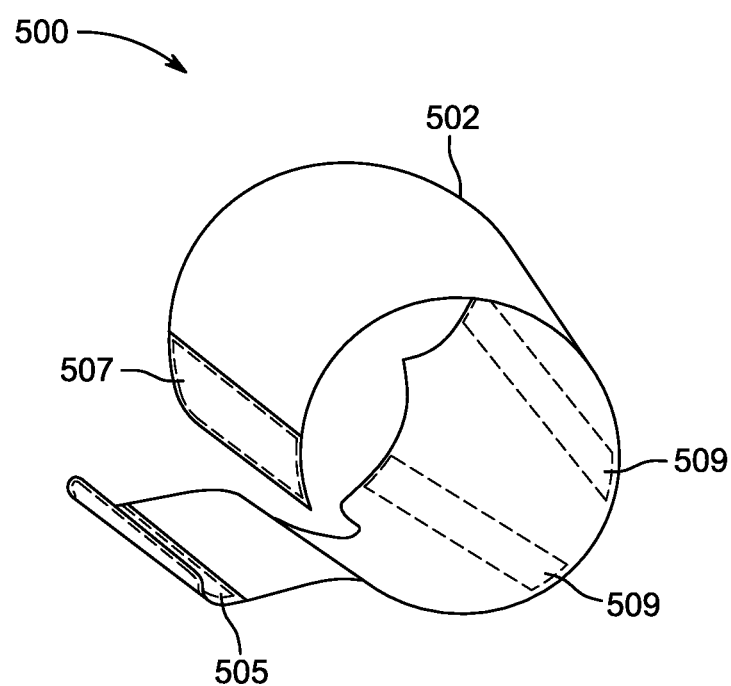
Figure 5C:
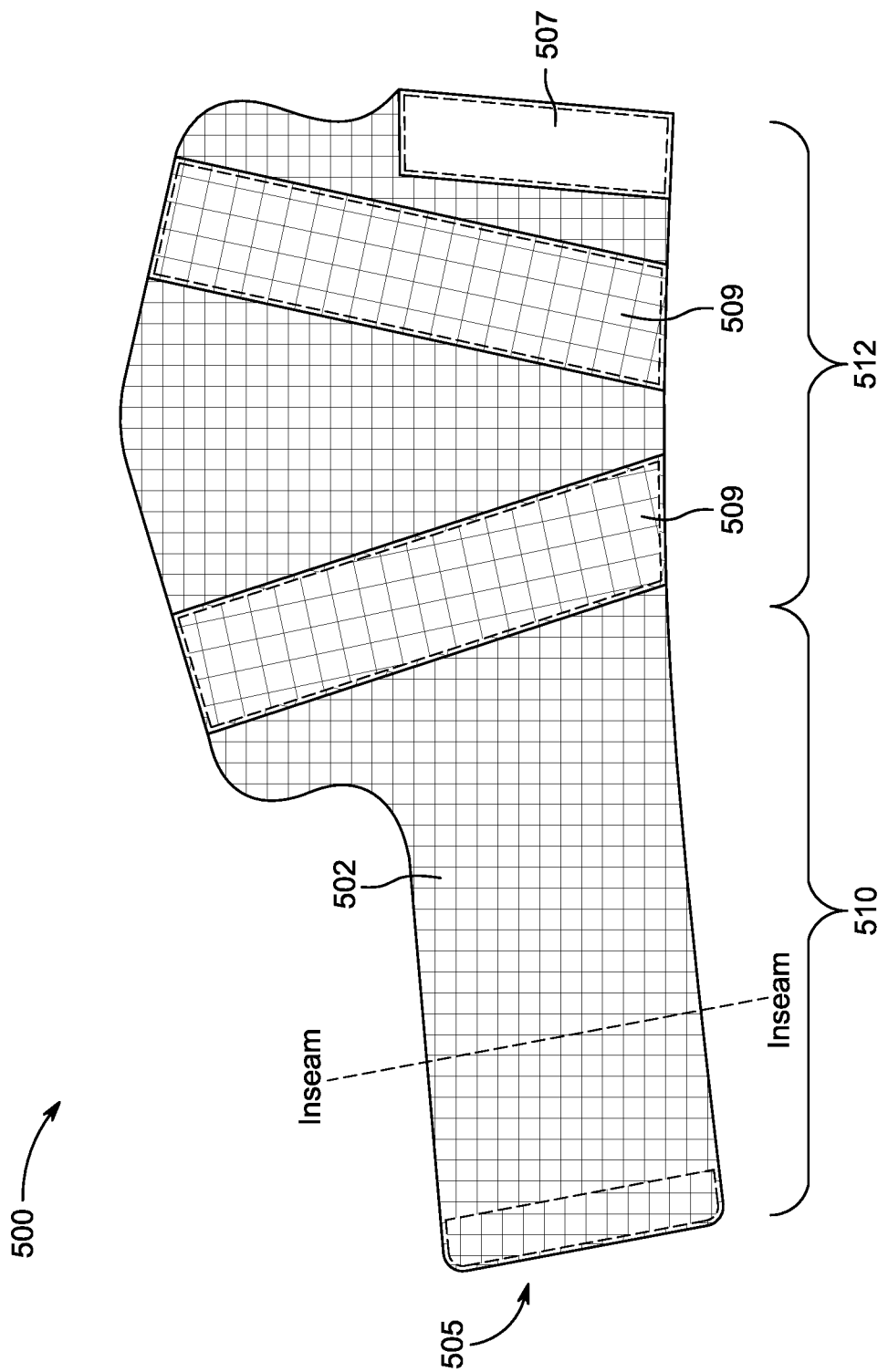

FIGS. 5A-5C show different views a thigh load distribution member 500 according to an embodiment. In particular, FIG. 5A shows LDM 500 in a closed position, FIG. 5B shows LDM 500 in an open position, and FIG. 5C shows a plan view of LDM 500. LDM 500 may be used in place of LDM 410, for example. LDM 500 can include extension portion 510 and power layer portion 512. Extension portion 510 may align with the inseam of the user wearing LDM 500. Power layer portion 512 may represent the portion of LDM 500 that can support a power layer segment (not shown). LDM 500 can include hook region 505 and loop region 507. Hook and loop regions 505 and 507 may couple together to secure LDM 500 around the thigh. LDM 500 can include a base material 502 that forms the general shape of LDM 500 and may also have loop and hook regions 505 and 507 incorporated therein. In addition, reinforcement regions 509 may be overlaid on top of base material 502. Reinforcement regions 509 may add structural support to LDM 500 and may be used to buttress power layer segments (not shown) that can be attached to LDM 500.

Figure 6A:
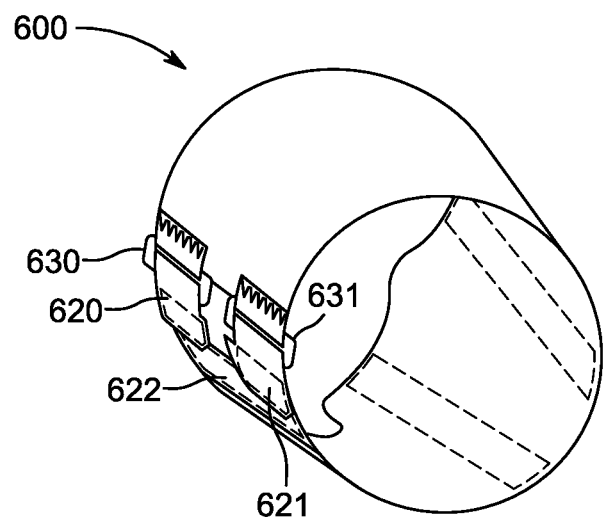
FIGS. 6A-6D show different views of a thigh load distribution member according to an embodiment.
Figure 6B:
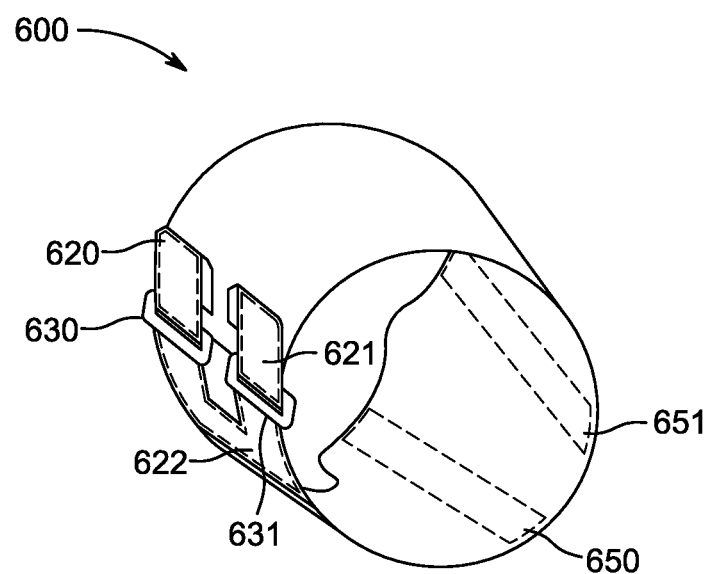
Figure 6C:
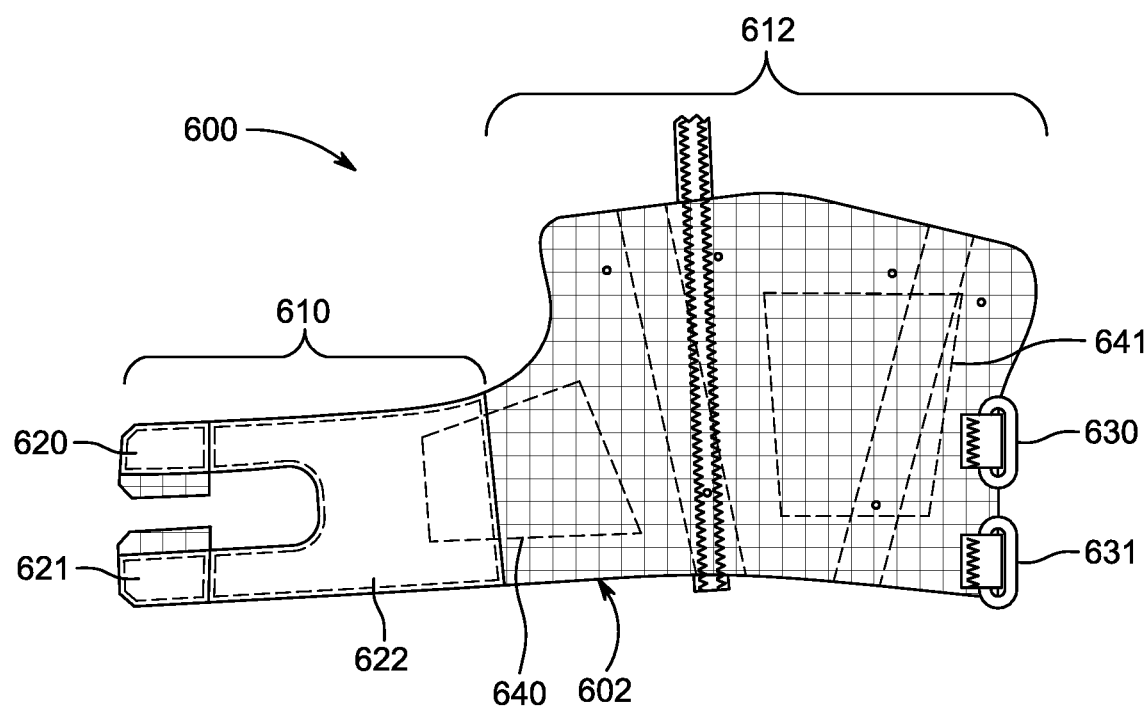
Figure 6D:
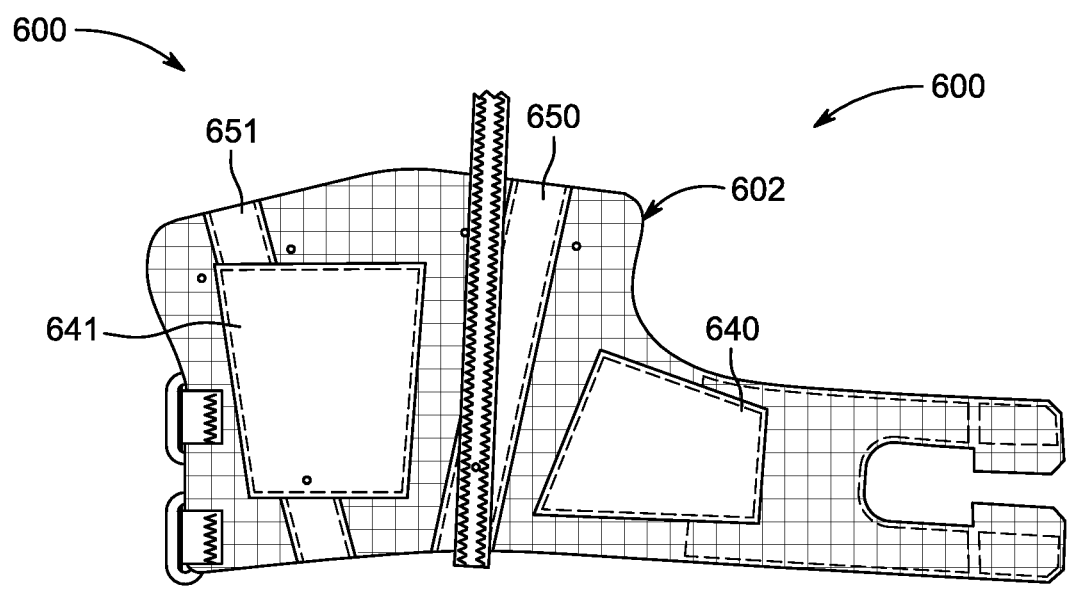

FIGS. 6A-6D show different views of a thigh load distribution member 600 according to an embodiment. In particular, FIG. 6A shows LDM 600 in a closed position, FIG. 6B shows LDM 600 in an open position, FIG. 6C shows a first plan view of LDM 600, and FIG. 6D shows a second plan view of LDM 600. LDM 600 may be used in place of LDM 410, for example. LDM 600 can include base material 602 that can logically be divided into extension portion 610 and power layer portion 612. Extension portion 610 may align with the inseam of the user wearing LDM 600. Power layer portion 612 may represent the portion of LDM 500 that can support a power layer segment (not shown).

Extension portion 610 can include hook regions 620 and 621 and loop region 622. Hook regions 620 and 621 may each be inserted through loop members 630 and 631, which are both part of power layer portion 612, and be releasably coupled to loop region 622. That is, when a user dons LDM 600, he or she may string hook regions 620 and 621 through loop members 630 and 631 and fold hook regions 620 and 621 back on top of loop region 622 to secure them place, thereby fixing LDM 600 around the thigh. LDM 600 may include stability patches 640 and 641 and reinforcement ribs 650 and 651. Stability patches 640 and 641 and reinforcement ribs 650 and 651 may provide enhanced structural stability to base material 602.

Figure 49A:
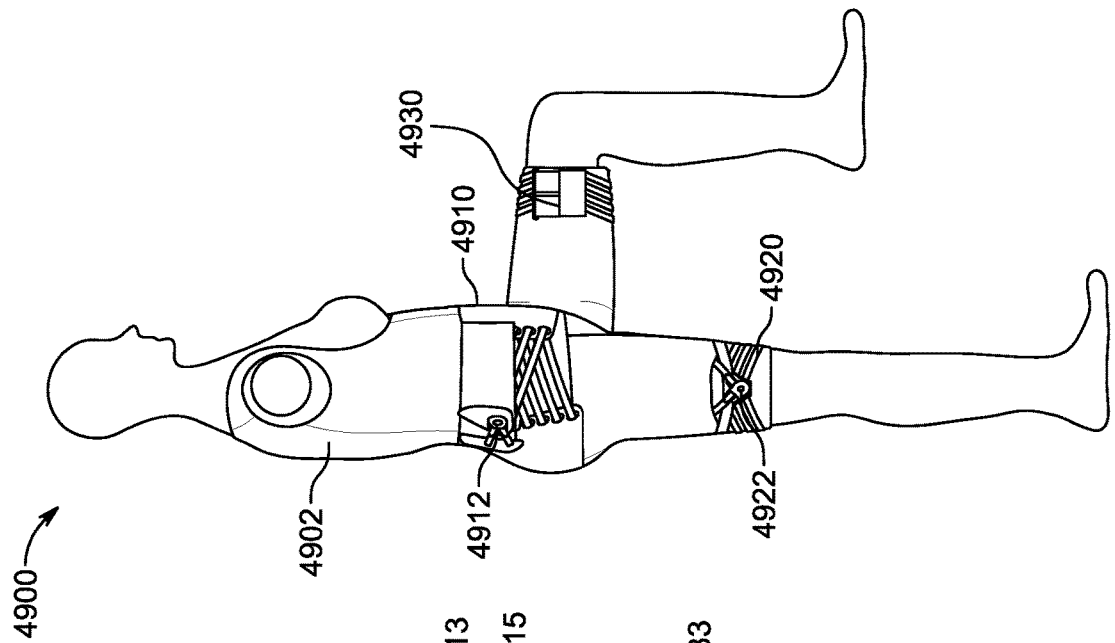
FIGS. 49A-49C show illustrative front, back, and side views of an exosuit with integrated N2S and grip members, according to an embodiment.
Figure 49B:
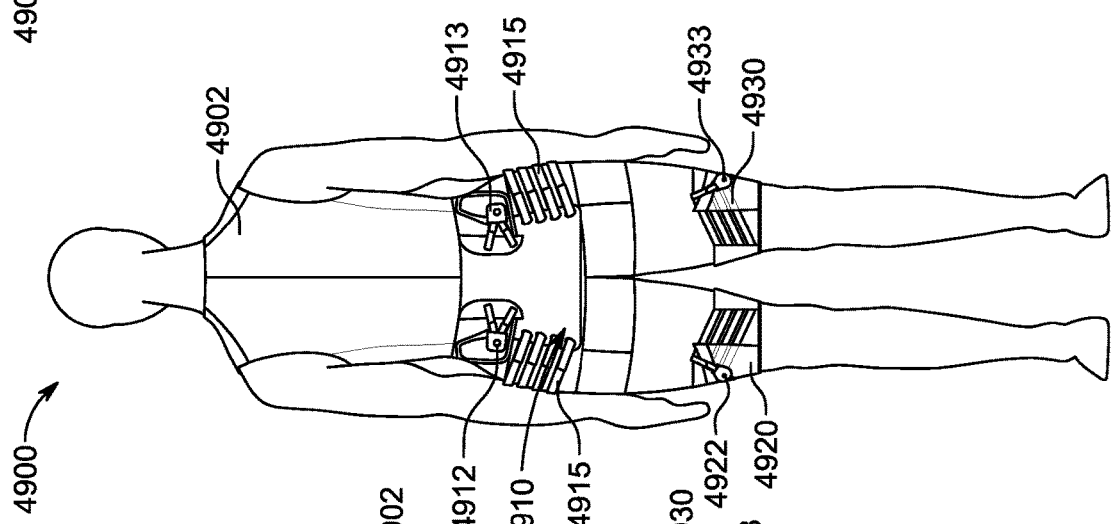
Figure 49C:
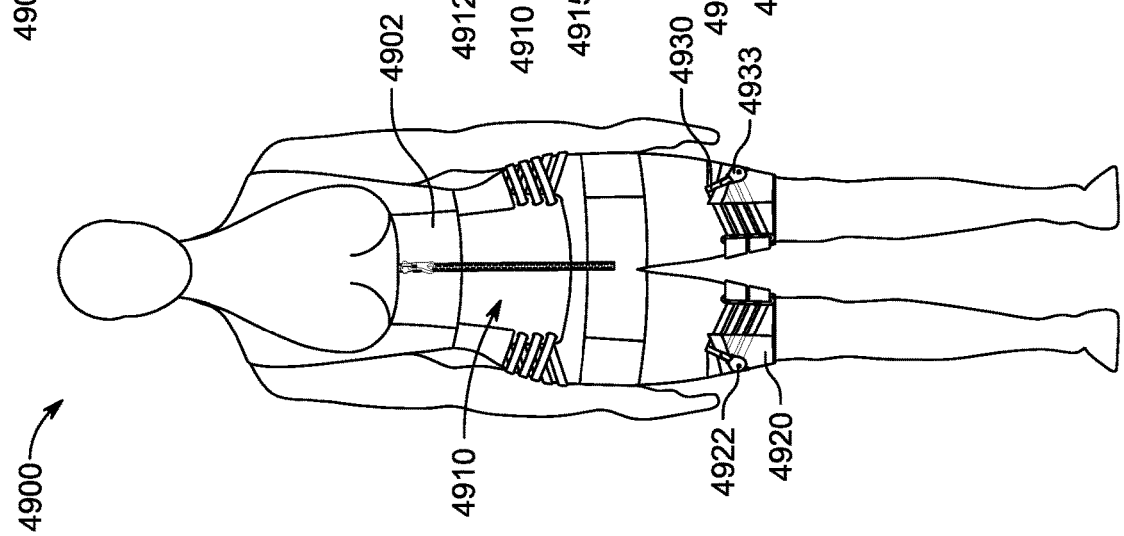

FIGS. 49A-49C show illustrative front, back, and side views of exosuit 4900 with integrated N2S and grip members, according to an embodiment. Exosuit 4900 may include N2S layer 4902 that has grip members 4910, 4920, and 4930 integrated into N2S layer 4902. It should be understood that grip members may perform the same or similar functions a load distribution member. By integrating grip members 4910, 4920, and 4930 with the N2S layer 4902, the user is able to don the N2S layer 4902 with members 4910, 4920, and 4930 already attached, and once N2S layer 4902 is on, the user can make adjustments to each of members 4910, 4920, and 4930 as required to provide the appropriate support for the power layer segments. Grip member 4910 is a waist grip member with power segment connection interfaces 4912 and 4913 for hip extensor attachment. No back or hip flexor power segment connection interfaces are shown. The user can adjust straps 4915 to tighten grip 4910 to a desired grip level.

Grip members 4920 and 4930 are thigh grip members that include power layer segment connection interfaces 4922 and 4933 for hip extensor attachment. A power layer (not shown) may be attached to interfaces 4912 and 4922, and another power layer may be attached to interfaces 4913 and 4933. Grip members 4920 and 4930 may include adjustable straps 4925 and 4935 to enable the user to adjust a tightness fit.

Figure 50A:
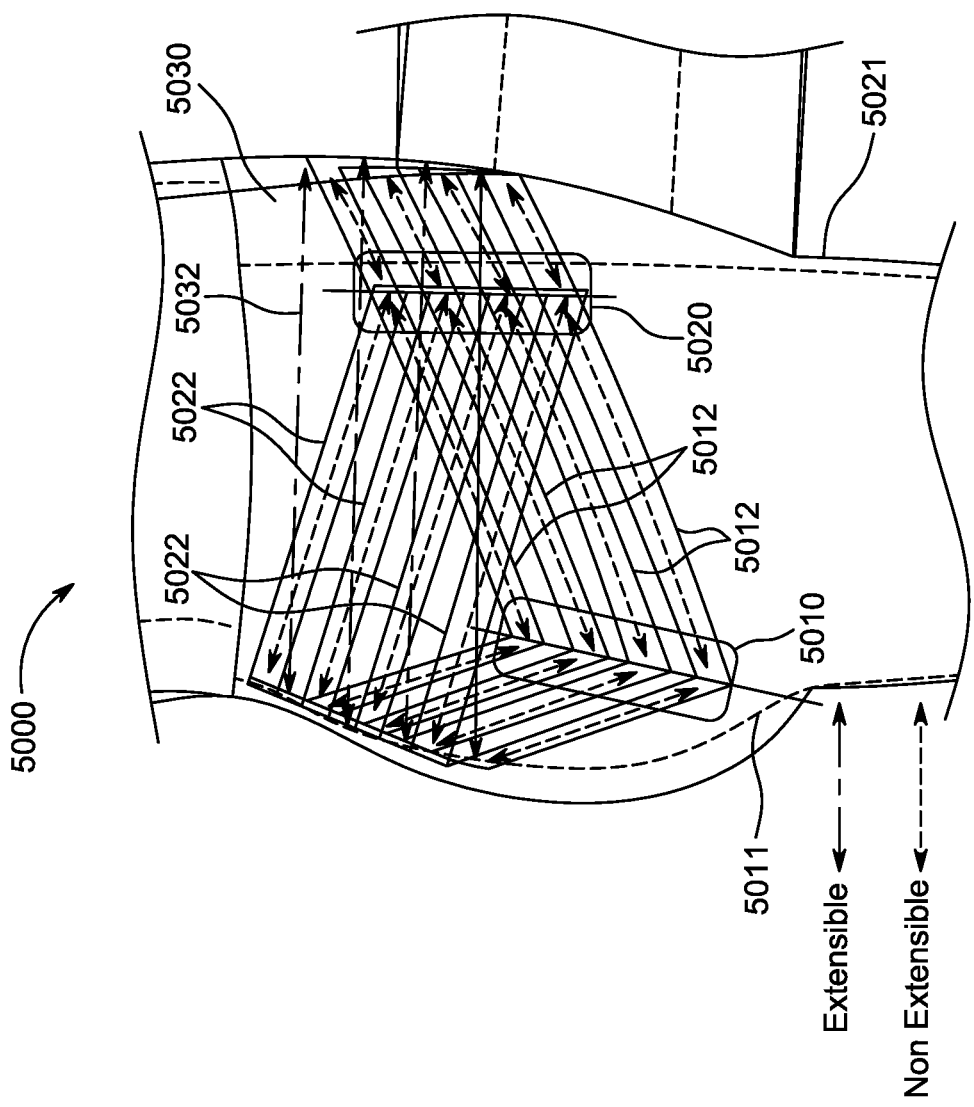
FIG. 50A shows an illustrative and more detailed view of a waist grip according to an embodiment.

FIG. 50A shows an illustrative and more detailed view of a waist grip according to an embodiment. Waist grip 5000 includes first power layer segment 5010 (e.g., for hip extensor attachment) and second power layer segment 5020 (e.g., for hip flexor attachment). First power layer segment 5010 is attached to non-extensible fabric members 5012 as shown, and second power layer segment 5020 is attached to non-extensible fabric members 5022. Power layer segments 5010 and 5020 may be solid construction of plastic or fabric. One or both of non-extensible fabric members 5012 and 5022 may be secured to a N2S layer 5030, which includes extensible fabric member 5032 (illustrated by the dashed lines). The extensible fabric member may be part of the N2S layer. That N2S layer may include different materials or stretch profiles which enable extension fabric member to stretch, for example, in a lateral direction (e.g., front to back) across the body. Non-extension fabric members 5012 and 5022 may span from a front portion of the exosuit to a back portion of the exosuit. Non-extensible fabric members 5012 and 5022 provide non-extensibility in areas where force is applied (shown by dotted lines), while providing extensibility horizontally (shown by dashed lines) to provide comfort and compliance to body shape. In some embodiments, some portions of non-extension fabric members 5012 and 5022 may be shared.

Power layer segments 5010 and 5020 can exist at along on a line of pivot points locations at the lines of non-extensibility and extensibility (shown where the arrowheads point towards each other). Force line 5011 represents a line of force (towards the ground) that may be applied to power layer segment 5010 when a power component is attached thereto and used in exosuit operation. Non-extension fabric members 5012 resist the force pulling power segment 5010 down. Force line 5021 represents a line of force that may be applied to power layer segment 5020 when a power component is attached thereto and used in exosuit operation. Non-extension fabric members 5022 resist the force pulling power segment 5020 down. It should be appreciated that construction of grip member 5000 enables force transactions to occur on only one of power layer segments 5010 and 5020 or simultaneously on both of power layer segments 5010 and 5020.

Figure 50C:
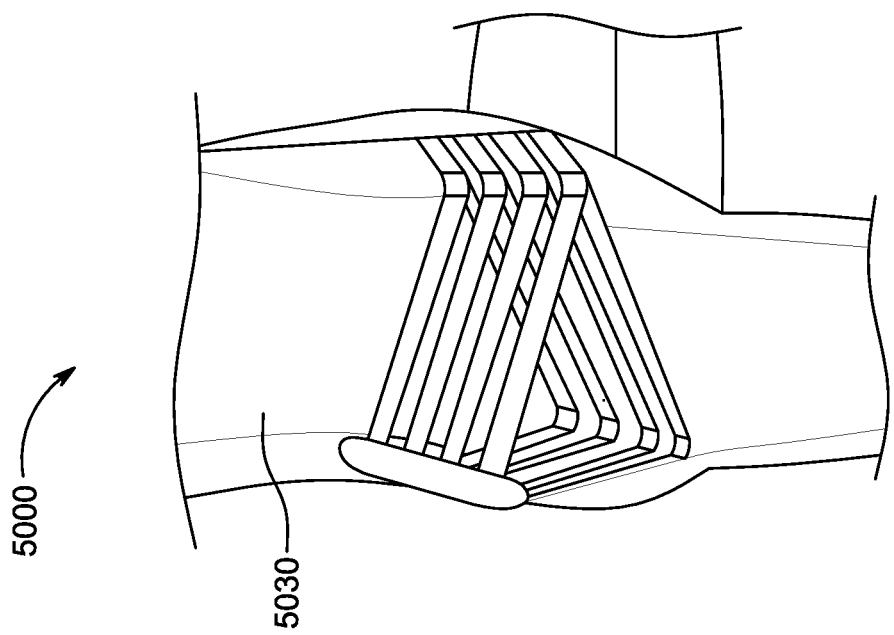
FIGS. 50B and 50C show alternative views of a waist member according to various embodiments.
Figure 50B:
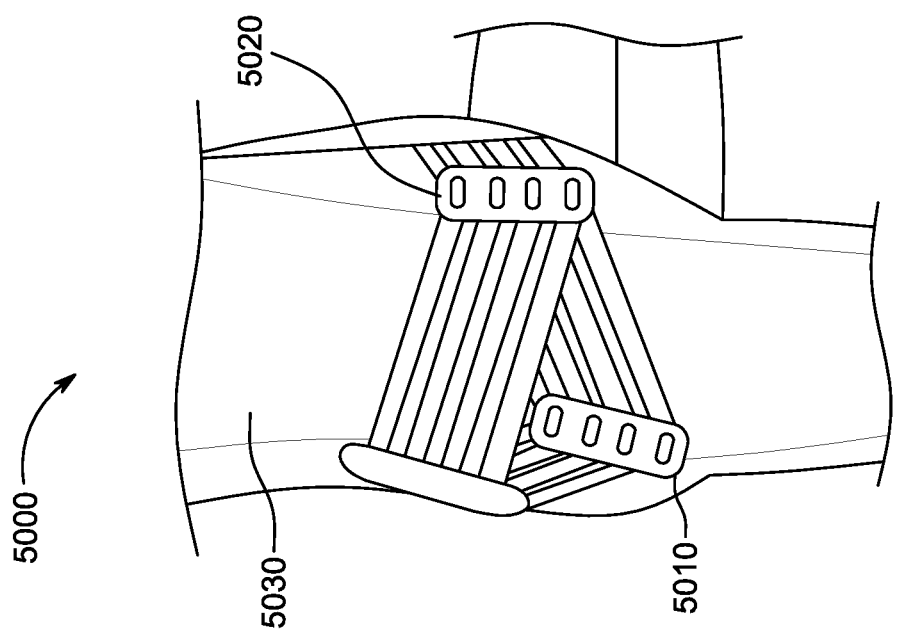

FIG. 50B shows an alternative view of waist member 5000 and FIG. 50C shows yet another alternative view of waist member 5000 with power segments 5010 and 5020 removed. It should be understood that FIGS. 50A-50C only show one half of the power layer segments and non-extensible members, as the other side of the exosuit includes other power layer segments.

Figure 50E:
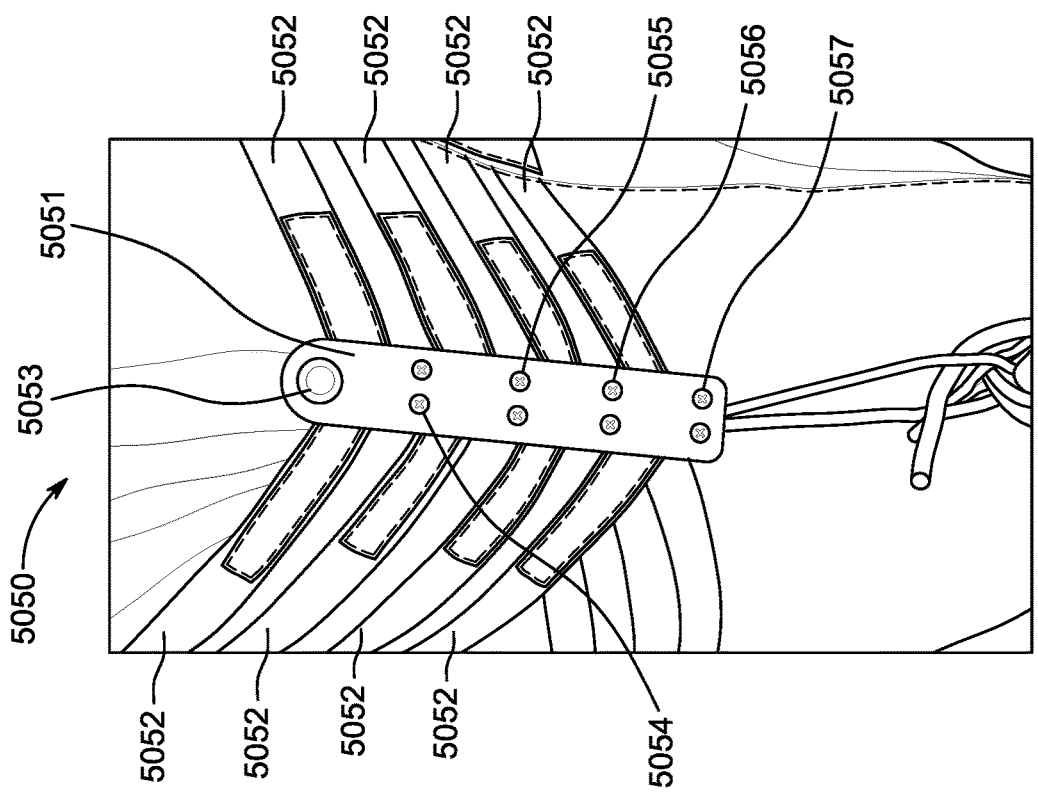
FIGS. 50D and 50E show an illustrative waist grip member in respective unloaded and loaded usage.
Figure 50D:
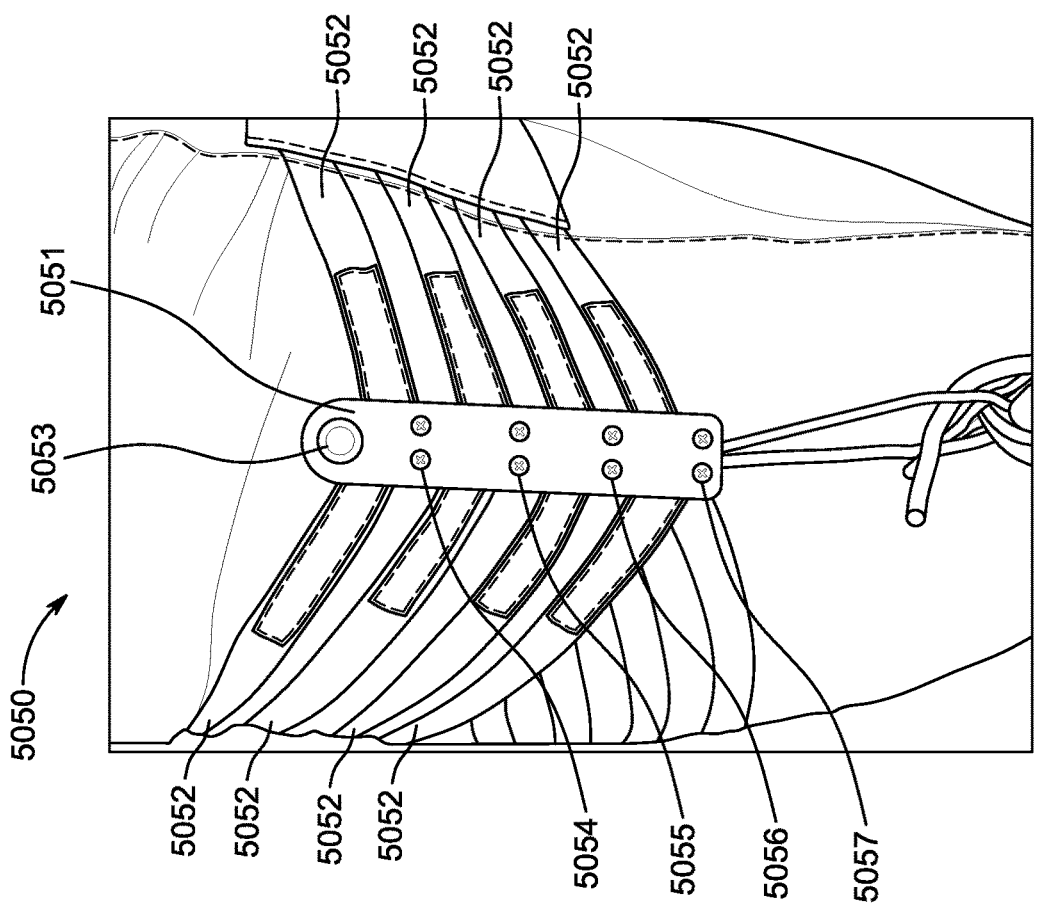

FIGS. 50D and 50E show illustrative waist grip member 5050 in respective unloaded and loaded usage. Waist grip member 5050 includes interface segment 5051, which is connected to each of non-extension lines 5052. The construction of waist grip 5050 shows that loading is evenly distributed across all non-extension lines 5052, when loaded and unloaded. Interface segment 5051 can include fastener connection points 5053-5057 that can be used as anchor points for a power layer component (e.g., a twisting string connected to a FLA).

FIGS. 50F and 50G show illustrative waist grip member 5050 in respective unloaded and loaded usage with additional components added thereto. Retention members 5064-5067 have been added. As shown, each retention member 5064-5067 is attached to respective non-extension lines 5052 and includes an interface element designed to interface with one of hook members 5074-5077. Waist grip member 5050 includes tensioning member 5080 that is secured to connection point 5053 via fastener 5073 and member 5080 may be further fastened to interface segment 5051 via hook members 5074-5077, which are also secured to interface segment 5051. Connection point 5053 and fastener 5073 may serve as the terminal anchor point for tensioning member 5080. Hook members 5074-5077 may guide or hold tensioning member 5080 in place along interface member 5051. Hook members 5074-5077 are designed to interface with retention members 5064-5067, respectively, so that when a load is applied, the combination of hook members and retention members distribute the load across waist grip member 5050.

Figure 51A:
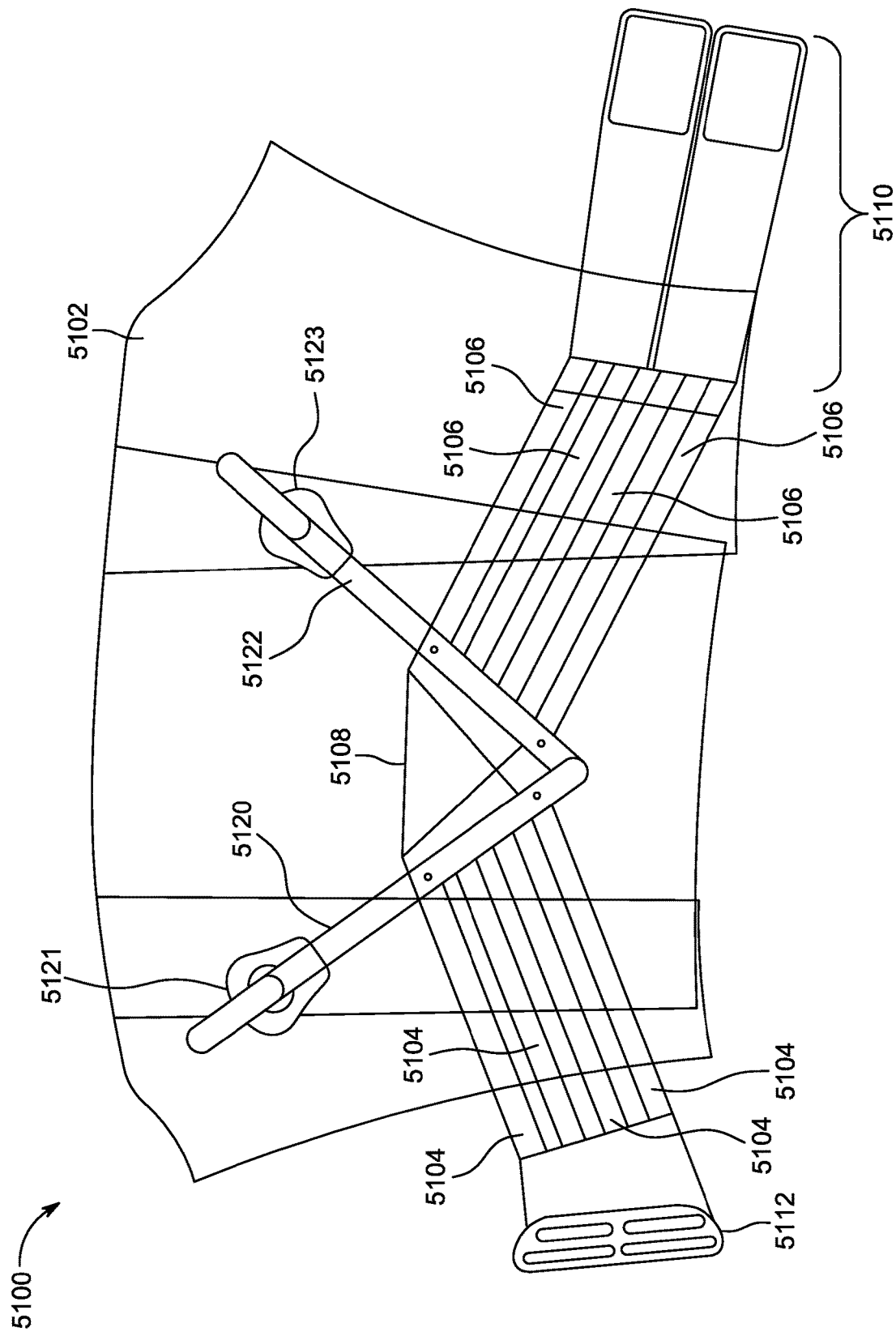
FIG. 51A shows an illustrative thigh grip member according to an embodiment.

FIG. 51A shows illustrative thigh grip member 5100 according to an embodiment. Thigh grip member 5100 can include N2S layer 5102, which may be an extensible fabric, non-extensible fabric members 5104 and 5106, rigid member 5108, extension portion 5110, loop member 5112, interface member 5120, eyelet 5121, interface member 5122, and eyelet 5123. Non-extensible fabric members 5104 may be secured to N2s layer 5102, rigid member 5108, and loop member 5112. Non-extensible fabric member 5106 may be secured to N2s layer 5102, rigid member 5108, and extension portion 5110. Extension portion 5110 may include multiple hook and loop regions (e.g., two hook regions and one relatively large loop region) so that the extension portion 5110 slides through loop member 5112 and double backs onto itself to self-lock via the hook and loop regions. Interface member 5120 may be secured to non-extensible fabric member 5104 and/or rigid member 5108, and passes through eyelet 5121. Interface member 5122 may be secured to non-extensible fabric member 5106 and/or rigid member 5108, and passes through eyelet 5123. Interface members 5120 and 5122 may serve as platforms for securing power components (e.g., FLAs, batteries, etc.). Interface members 5120 and 5122 are arranged such that they are oriented along selected lines of action. A selected line of action refers to the exosuit assistance movement (e.g., hip flexor assistance movement or hip extensor assistance movement). The angle of a particular line of action may vary depending on the size and physiology of the user. This is discussed in more detail below.

Figure 51B:
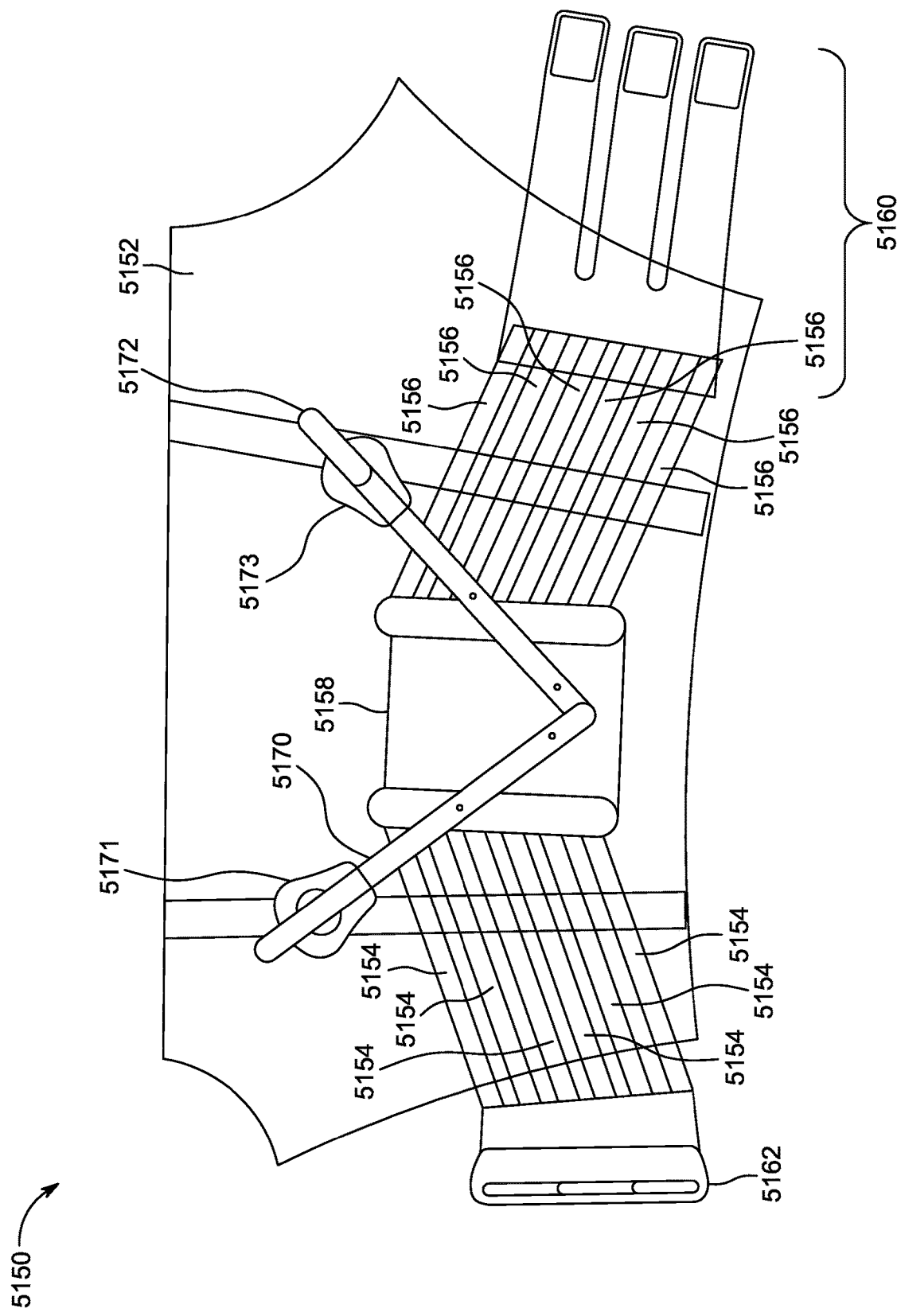
FIG. 51B shows another illustrative thigh grip member according to an embodiment.

FIG. 51B shows another thigh grip member 5150 according to an embodiment. Thigh grip member 5150 can include N2S layer 5152, which may be an extensible fabric, non-extensible fabric members 5154 and 5156, rigid member 5158, extension portion 5160, loop member 5162, interface member 5170, eyelet 5171, interface member 5172, and eyelet 5173. Non-extensible fabric members 5154 may be secured to N2s layer 5152, rigid member 5158, and loop member 5162. Rigid member 5158 is substantially larger than rigid member 5108. Non-extensible fabric member 5156 may be secured to N2s layer 5152, rigid member 5158, and extension portion 5160. Extension portion 5160 may include multiple hook and loop regions (e.g., two hook regions and one relatively large loop region) so that the extension portion 5160 slides through loop member 5162 and double backs onto itself to self-lock via the hook and loop regions. Interface member 5170 may be secured to rigid member 5158 and passes through eyelet 5171. Interface member 5172 may be secured to rigid member 5158 and passes through eyelet 5173. Interface members 5170 and 5172 may serve as platforms for securing power components (e.g., FLAs, batteries, etc.). Interface members 5170 and 5172 are arranged such that they are oriented along selected lines of action.

Figure 7C:
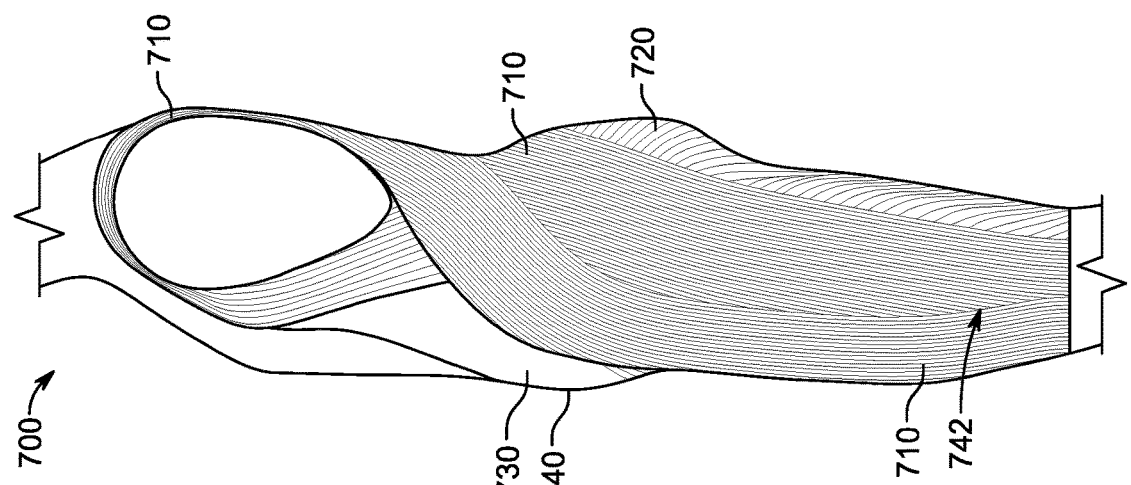
FIGS. 7A-7C show illustrative front, back, and side views of a cover layer according to an embodiment.
Figure 7B:
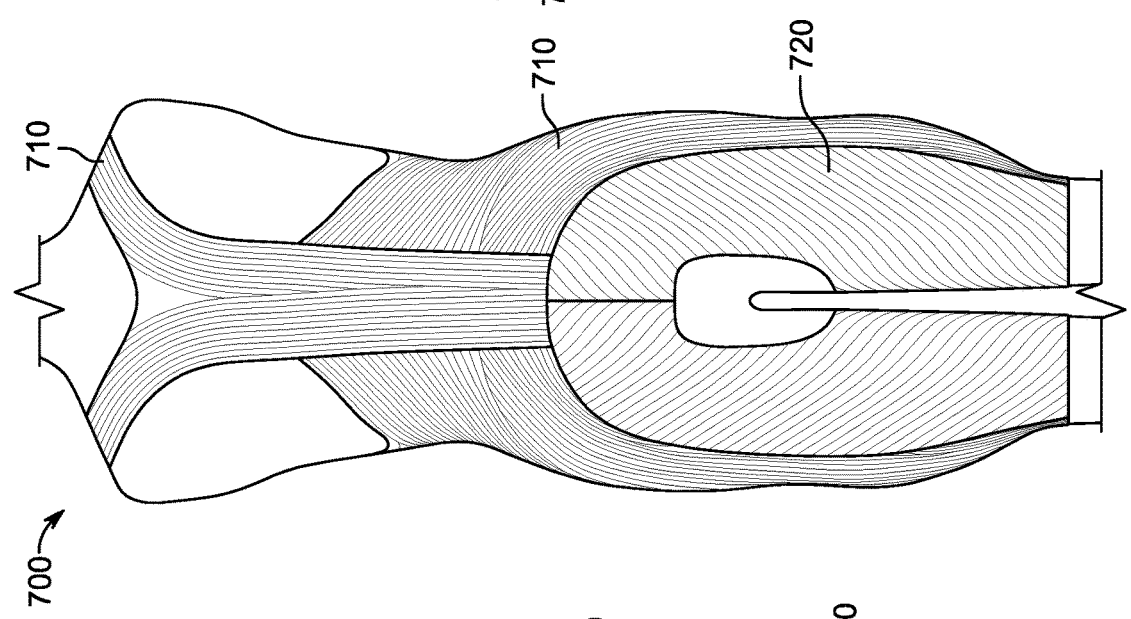
Figure 7A:
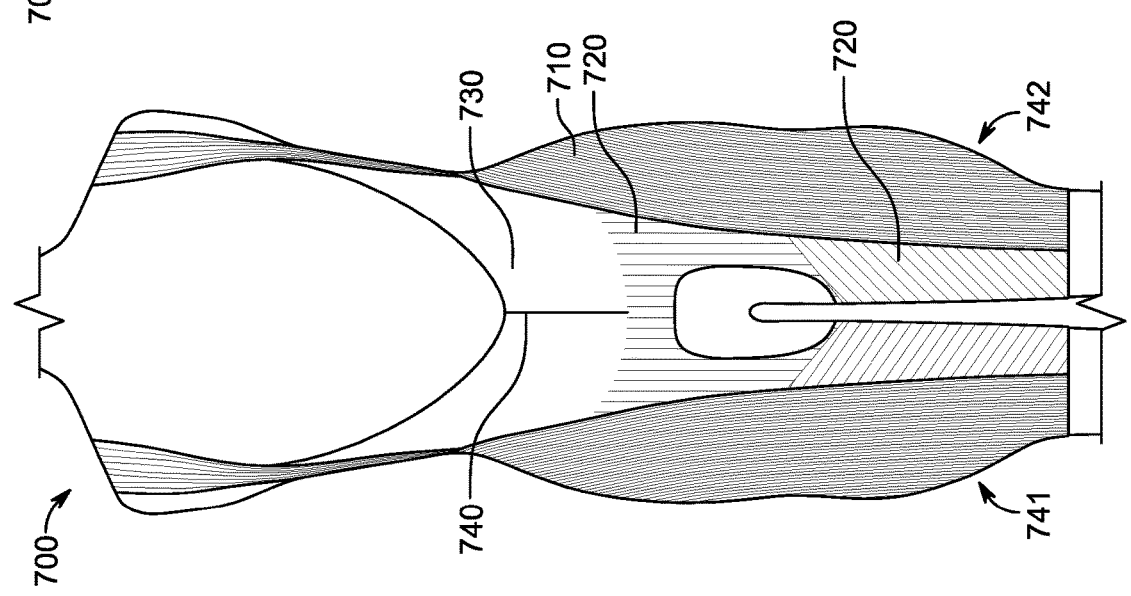

FIGS. 7A-7C show illustrative front, back, and side views of cover layer 700 according to an embodiment. Cover layer 700 may include a multi-piece construction of different structures that are designed to comfortably cover the power layer segments and next to skin layer. For example, cover layer 700 can include ribbed structures 710, knit structures 720, and mesh/perforation panels 730. Ribbed structures 710 can include array of columns stacked next to each other such that valleys exist between any two columns. The columns and valleys may be color coded to enhance visual appeal of cover layer. For example, the columns may be a first color and the valleys may be a second color. Knit structures 720 may be a plain knit material that is knitted to have, for example, a jacquard striped appearance. In some embodiments, the cover layer can be ordinary clothing such a shirt, blouse, pants, or a dress.

Cover layer 700 can also include zippers 740, 741, and 742. Zipper 740 may promote donning and doffing. Zippers 741 and 742 may be partially hidden (e.g., by fabric) and may provide access to power layer segments contained beneath cover layer 700.

FIGS. 7D-7F show illustrative front, back, and side views of cover layer 750 according to an embodiment. Cover layer 750 may include a multi-piece construction of different structures that are designed to comfortably cover the power layer segments and next to skin layer. For example, cover layer 750 can include ribbed structures 760, stripped structures 770, and mesh structures 780. Cover layer 750 can include zippers 790, 791, and 792. Zipper 790 may promote donning and doffing. Zippers 791 and 792 may provide access to power layers contained beneath cover layer 750. FIG. 7G shows a close up of circle portion G of cover layer 750. Snap 795 may attach to a reciprocal snap of a next to skin layer (e.g., N2S 310).

FIGS. 8A-8E show a leg portion of an exosuit in various states according to an embodiment. FIG. 8A shows a cover layer 860 having zipper 862 in a closed position. FIG. 8B shows zipper 862 partially open to show load distribution member 840. FIG. 8C shows snap features 895 and 896 to secure cover layer 860 to LDM 840. FIG. 8D shows hook region 841 and loop region 842 of LDM 840. FIG. 8E shows hook region 841 decoupled from loop region 842. Also shown in FIG. 8E is power layer portion 844.

FIGS. 9A-9L show illustrative front, back, and side views of a human, with emphasis on different power layer segment anchoring locations, preferred anchoring locations, projected string transmission paths, and load distribution members. Moreover, FIGS. 9A-9L may represent a more specific illustration of power layer segments and load distribution members of FIGS. 1A-1F. Starting with FIGS. 9A-9C, a human female is shown with anatomical demarcations such as over bust, bust, under bust, waist/elbow, high hip, full hip, high thigh, mid thigh, low thigh, knee, left side seam, and right side seam. Left and right side seams originate at the half way point between the neck and the shoulder bone and extend to heel when the feet are placed shoulder width apart. These anatomical demarcations provide guidepost to illustrate where different anchor locations 910 can be on the human body. Anchor locations 910 may represent locations where the power layer segment (e.g., flexible linear actuator) can be secured. Anchor locations 910 are shown by shaded areas. String zones 920 different regions through which the twisted strings associated with power layer segments should pass. The string zone in on the front of the human can exist at the full hip demarcation and in between the left and right seams. The string on the back of the human may exist at the full hip demarcation and extends slightly beyond the left and right seams. Abdomen and back based anchor locations can exist in the region bounded by the left and right seams and the waist and full hip demarcations. Thigh based anchor locations can exist between the knee and high thigh demarcations.

The combination of the anchor locations 910 and string zones 920 define lines of action. Each line of action can represent a power layer path that originates a first load distribution member, passes through a string zone, and terminates at a second load distribution member. The power layer provides an exosuit assistance movement, such as, for example, hip flexor or hip extensor movement. The actual lines of action may vary from one person to the next, such as length and angles, but the general principles remain the same.

Figure 9F:
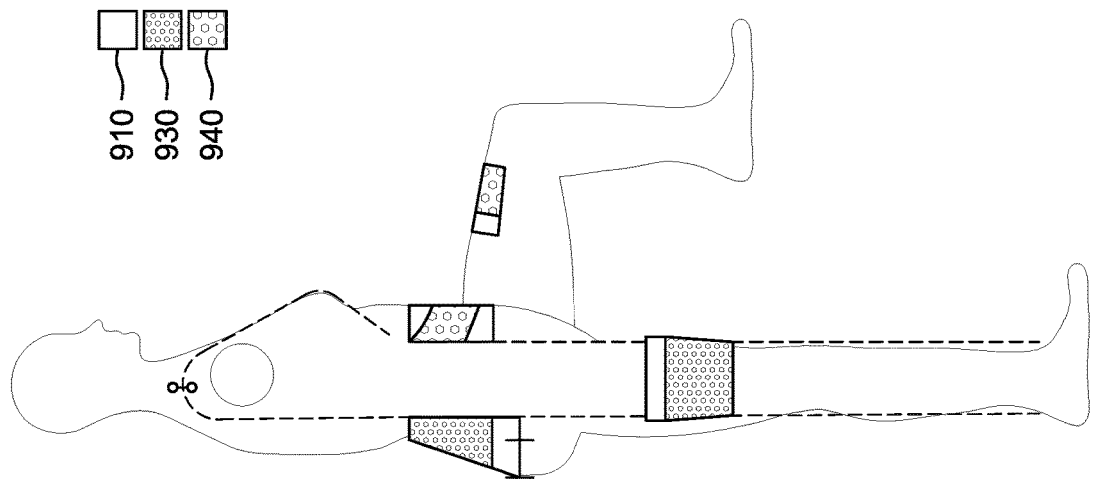
Figure 9E:
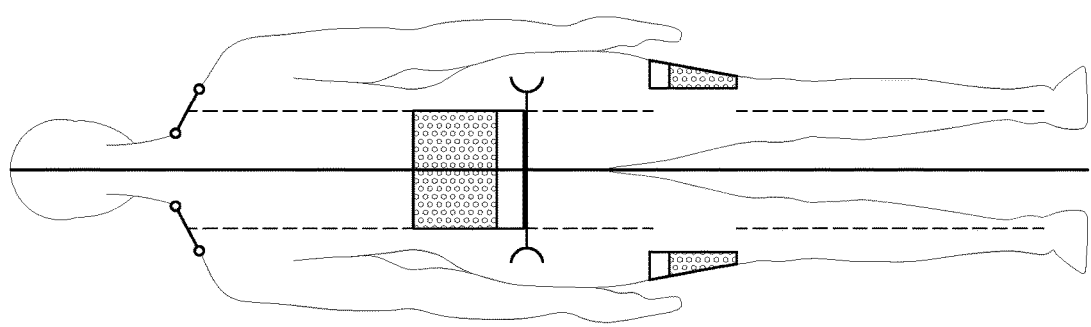
Figure 9D:
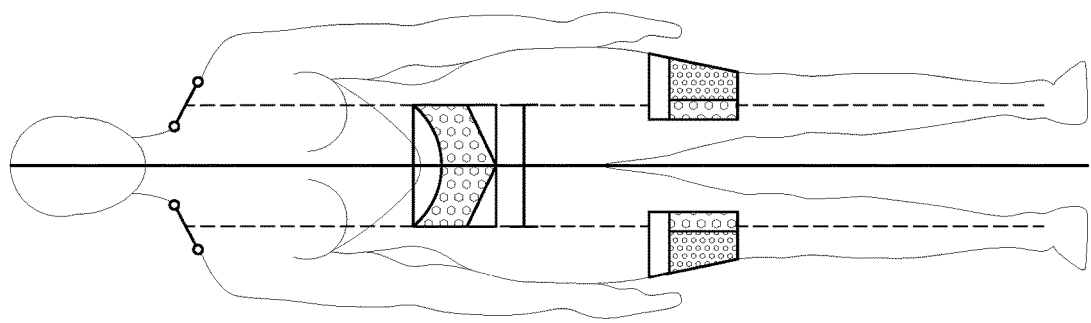

FIGS. 9D-9F show extensor anchor points 930 and flexor anchor points 940. Extensor anchor points 930 are represented by small dots, and flexor anchor points 940 are represented by big dots. Note that anchor points 930 and 940 are overlaid over anchor point locations 910.

FIGS. 9G-9I show power segments and their respective twisted strings 950 and 952. Twisted strings 950 may be associated with extensor power layer segments and twisted strings 952 may be associated with flexor power layer segments. Note that each of twisted strings 950 and 952 can serve as a line of action.

Figure 9L:
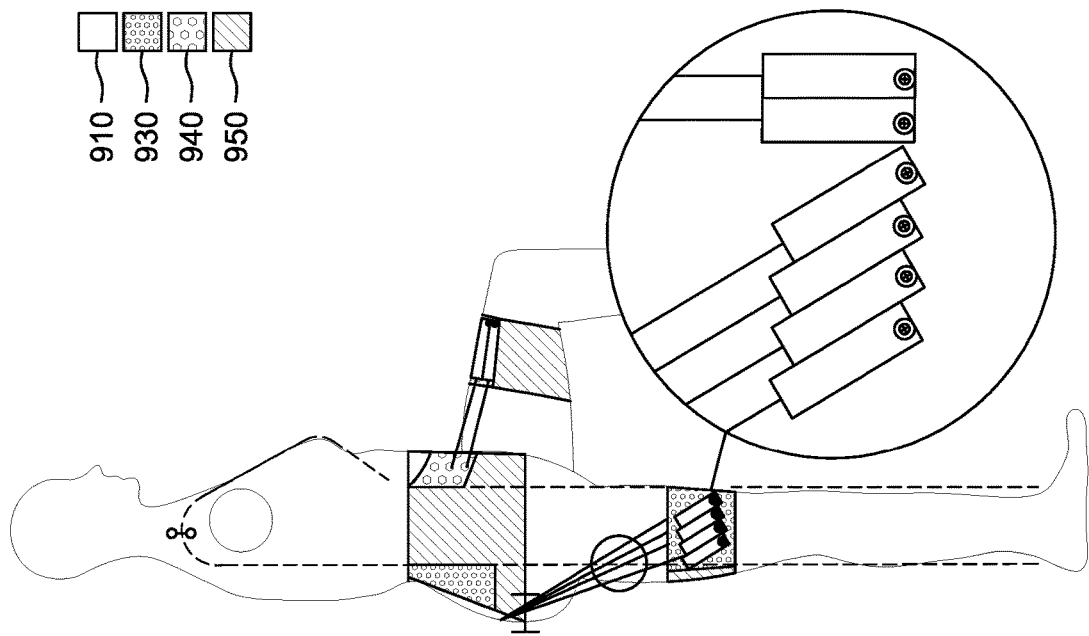
Figure 9K:
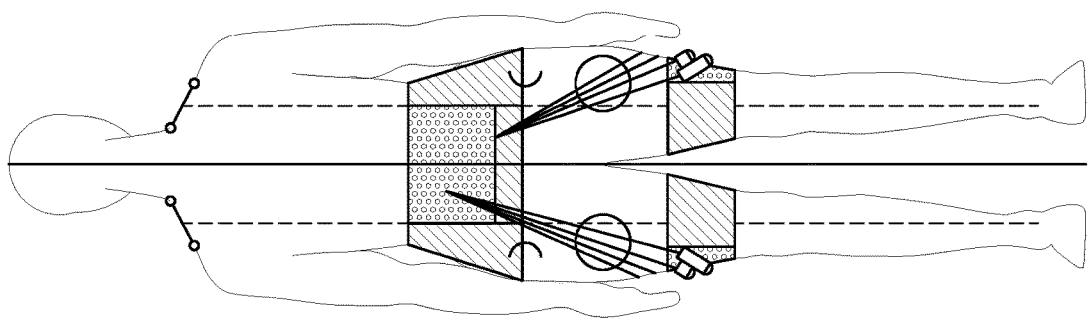
Figure 9J:
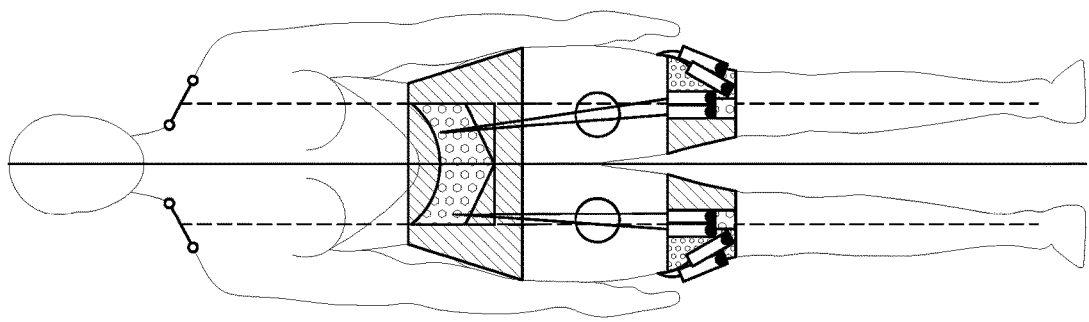
Figure 10A:
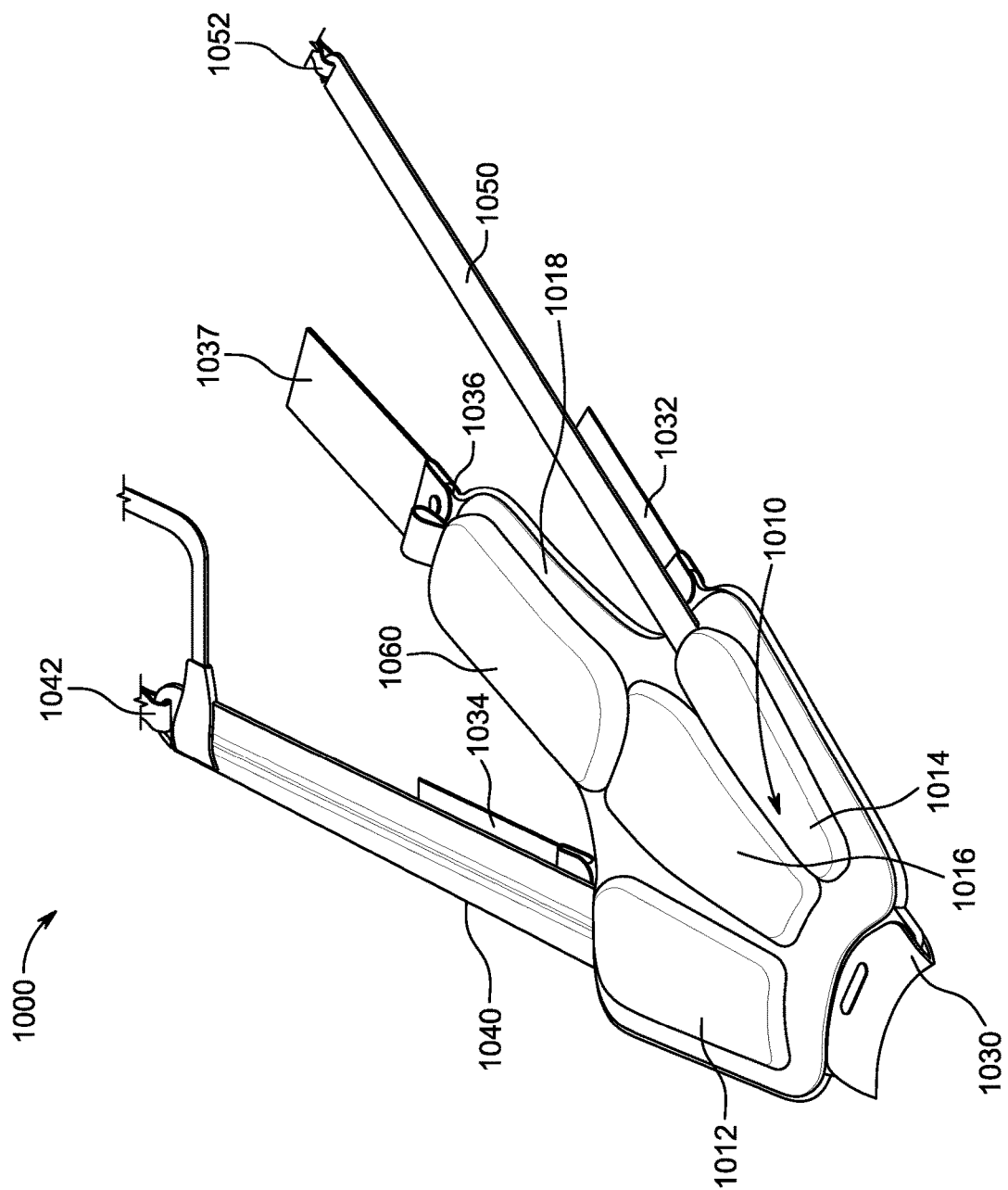
FIG. 10A-10D show an illustrative leg patch assembly according to an embodiment.
Figure 10B:
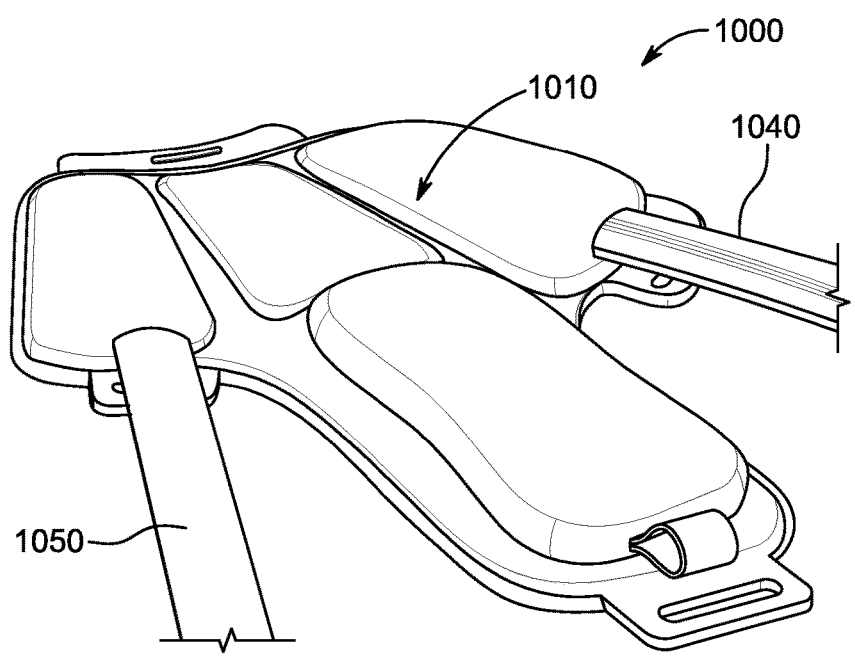
Figure 10C:
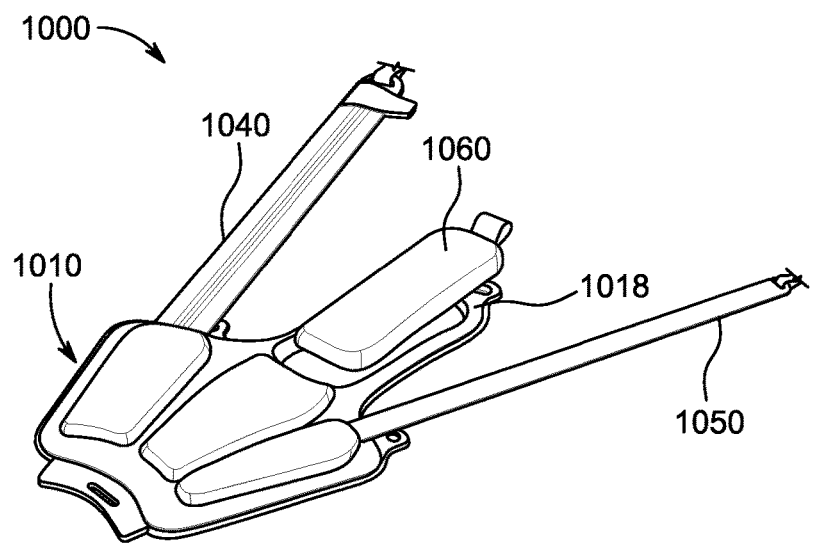
Figure 10D:
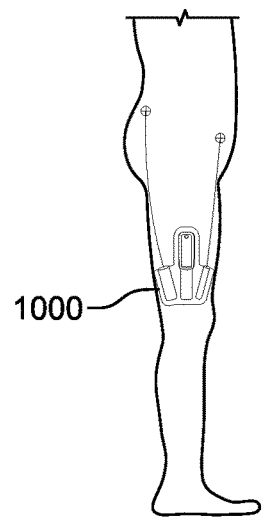

FIGS. 9J-9L show load distribution members 950 (as illustrated by shading), which are overlaid by extensor anchor points 930, flexor anchor points 940, and the twisted strings.

Figure 35:
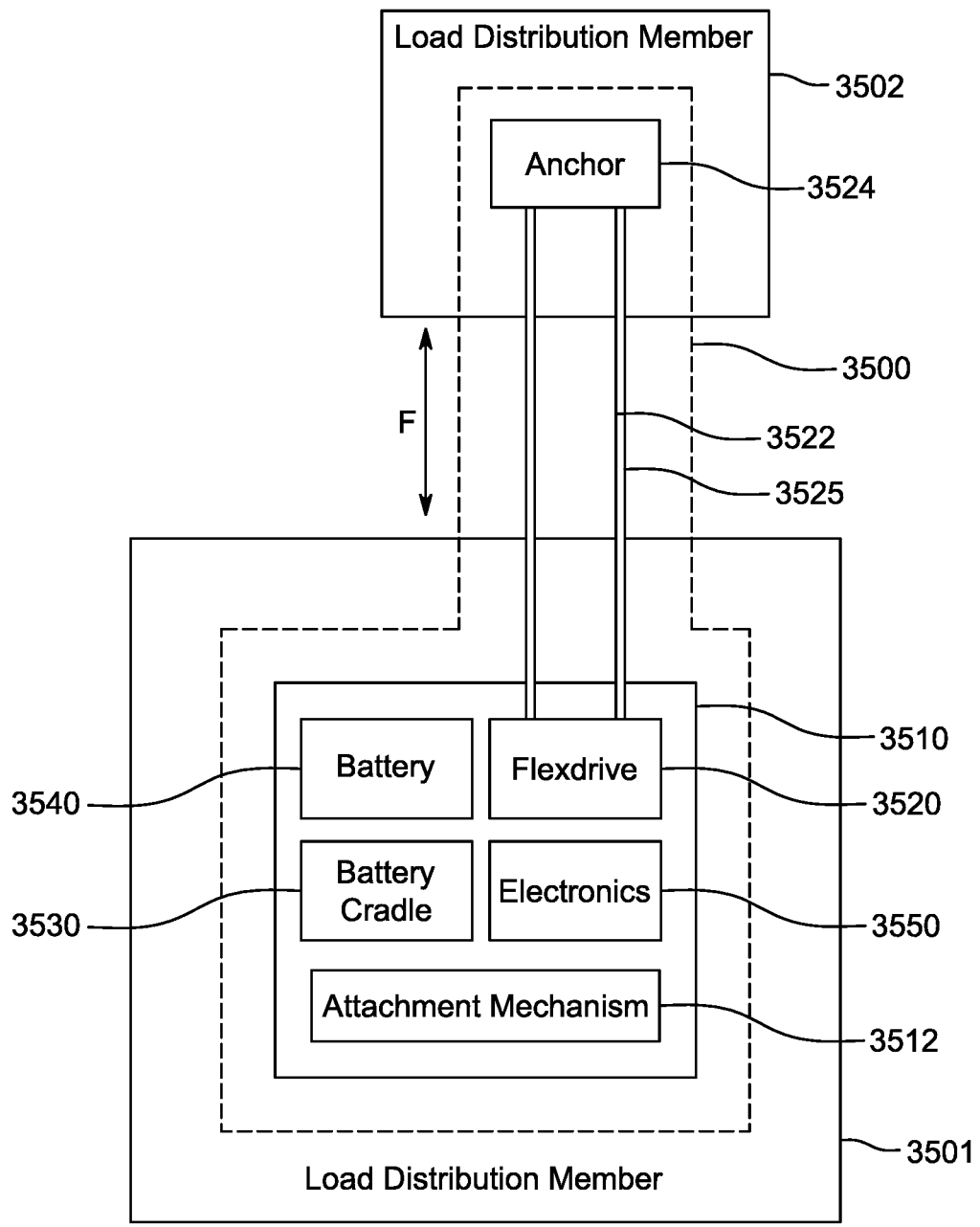
FIG. 35 shows an illustrative patch assembly according to an embodiment.
Figure 36B:
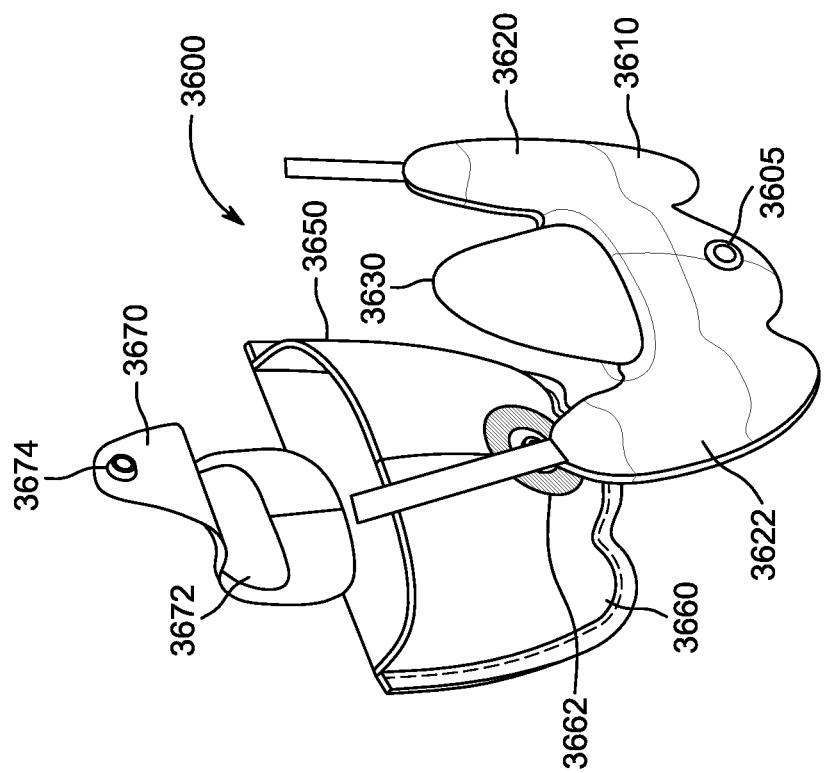
FIGS. 36A-36D show different illustrative views of a pocket patch assembly and how it interfaces with a load distribution member, according to an embodiment.
Figure 36A:
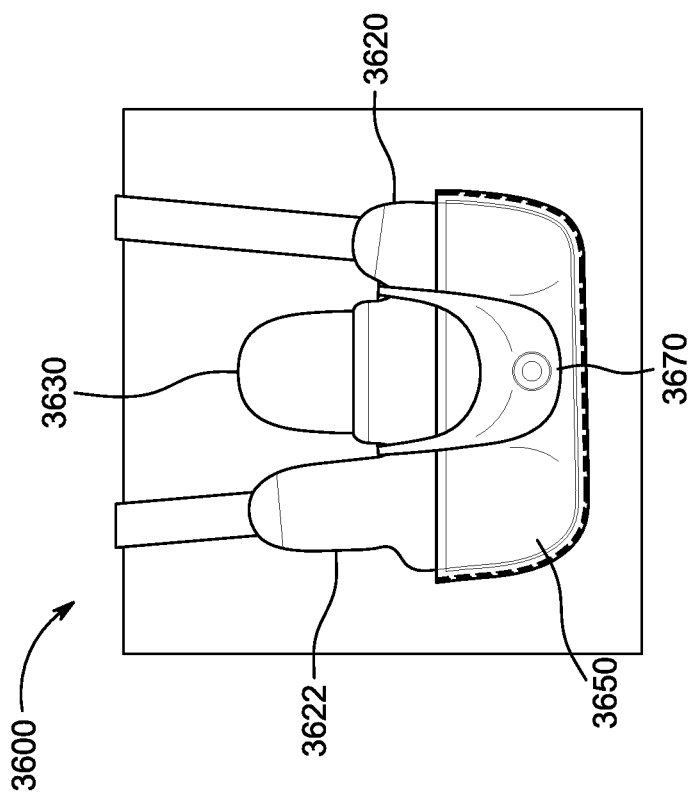
Figure 36D:
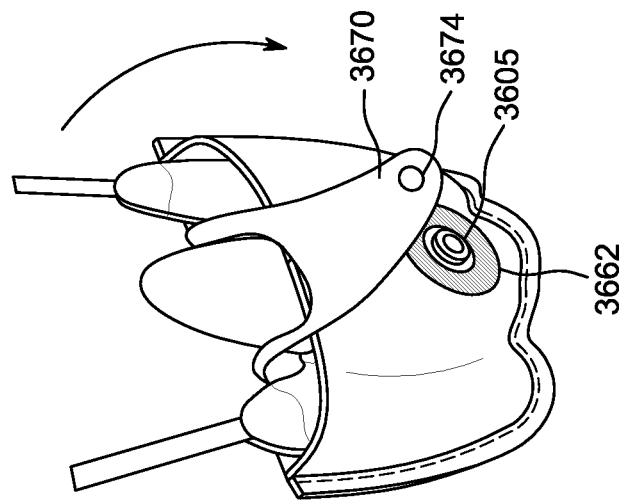
Figure 36C:
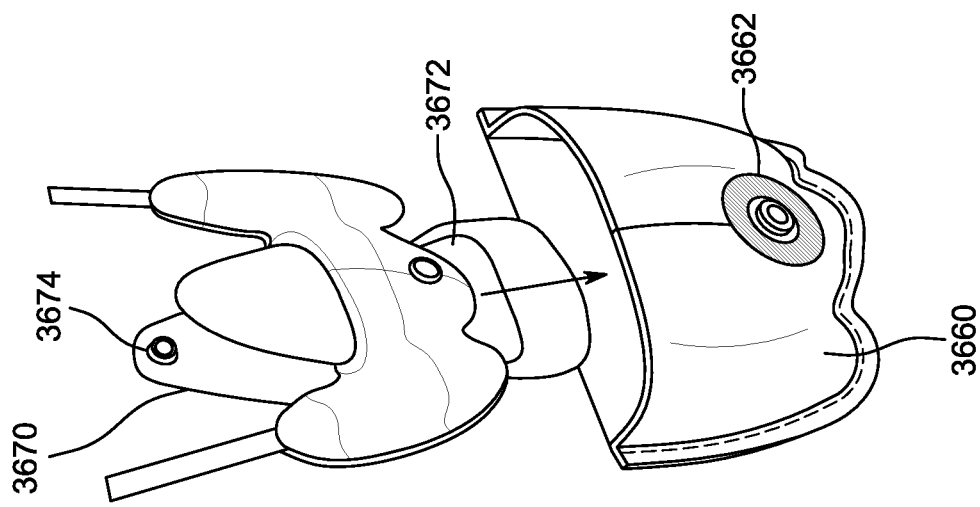
Figure 37A:
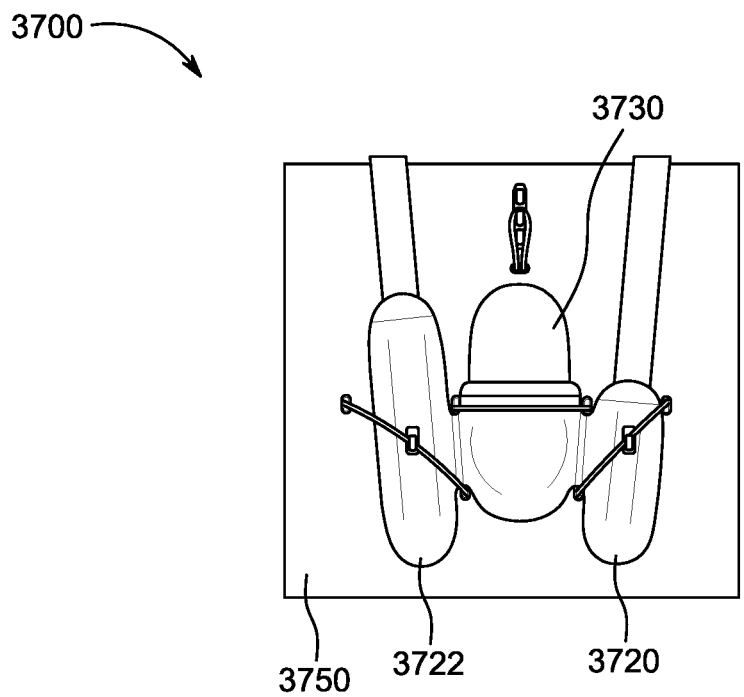
FIGS. 37A-37F show different illustrative views of cord patch assembly and how it interfaces with load a distribution member, according to an embodiment.
Figure 37B:
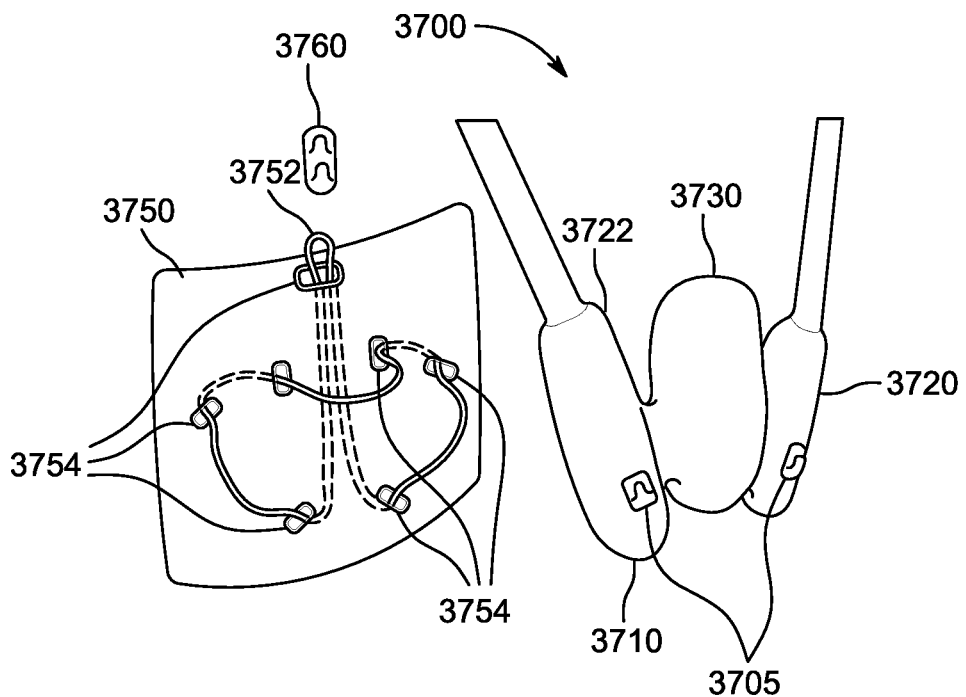
Figure 37C:
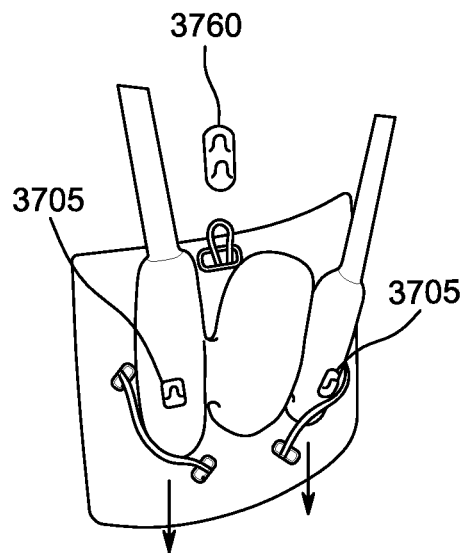
Figure 37D:
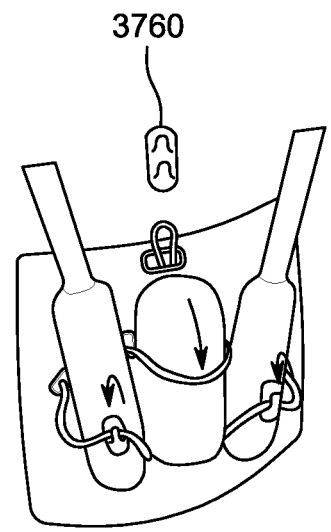
Figure 37E:
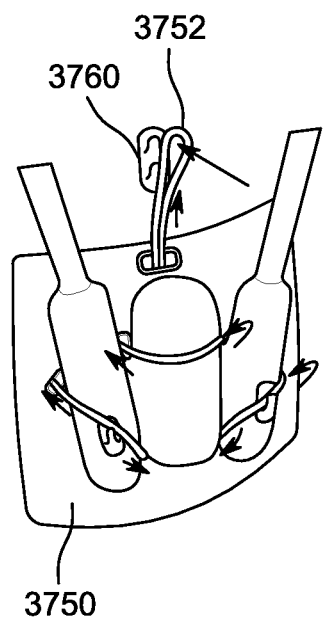
Figure 37F:
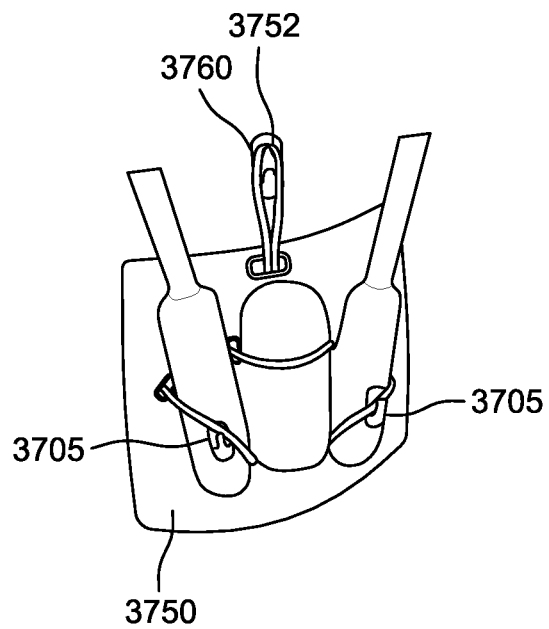
Figure 38A:
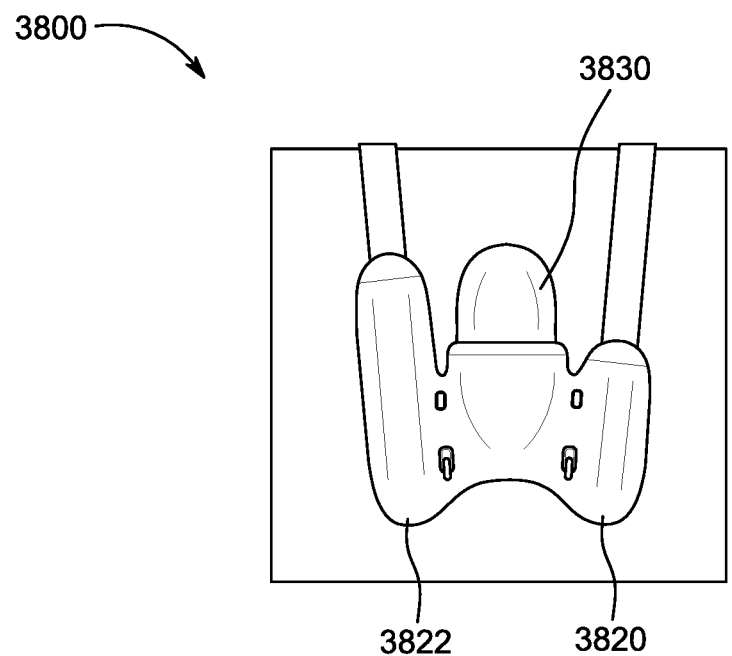
FIGS. 38A-38D show different illustrative views of press fit patch assembly and how it interfaces with a load distribution member, according to an embodiment.
Figure 38B:
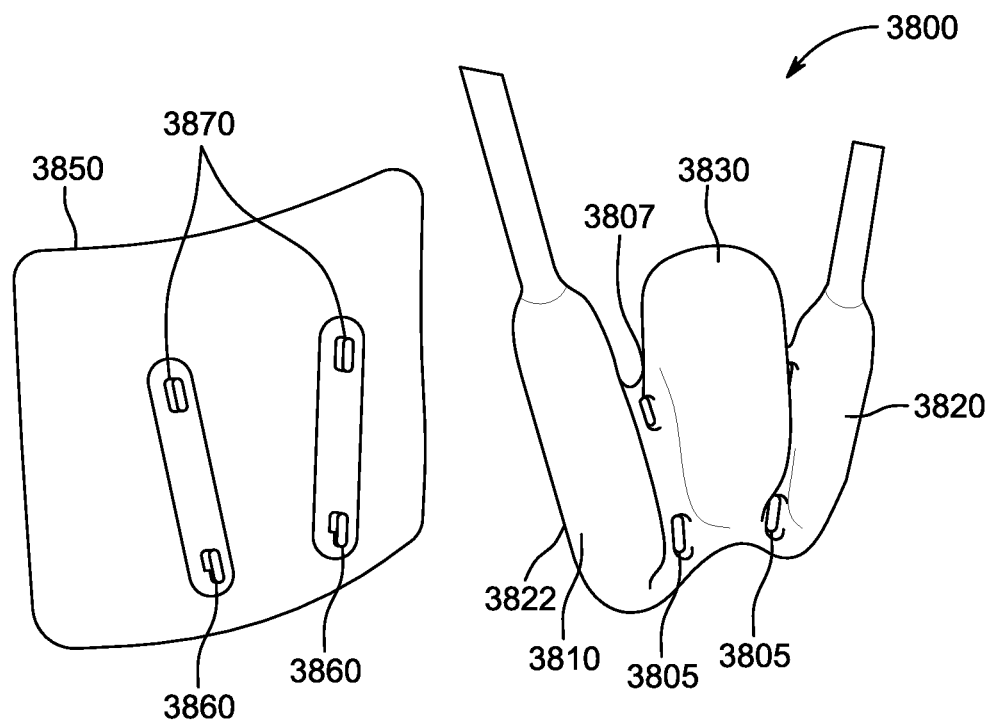
Figure 38C:
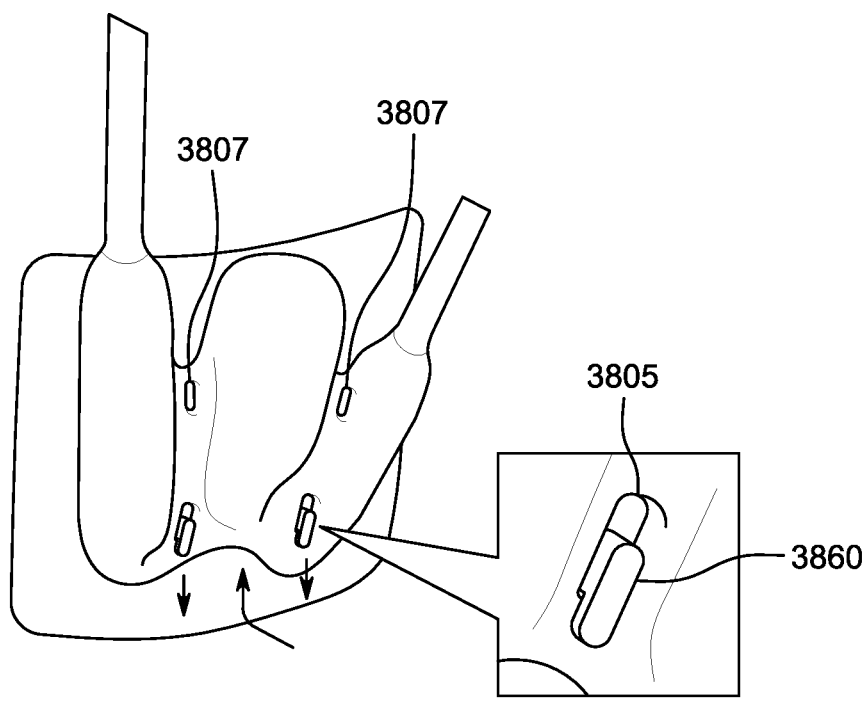
Figure 38D:
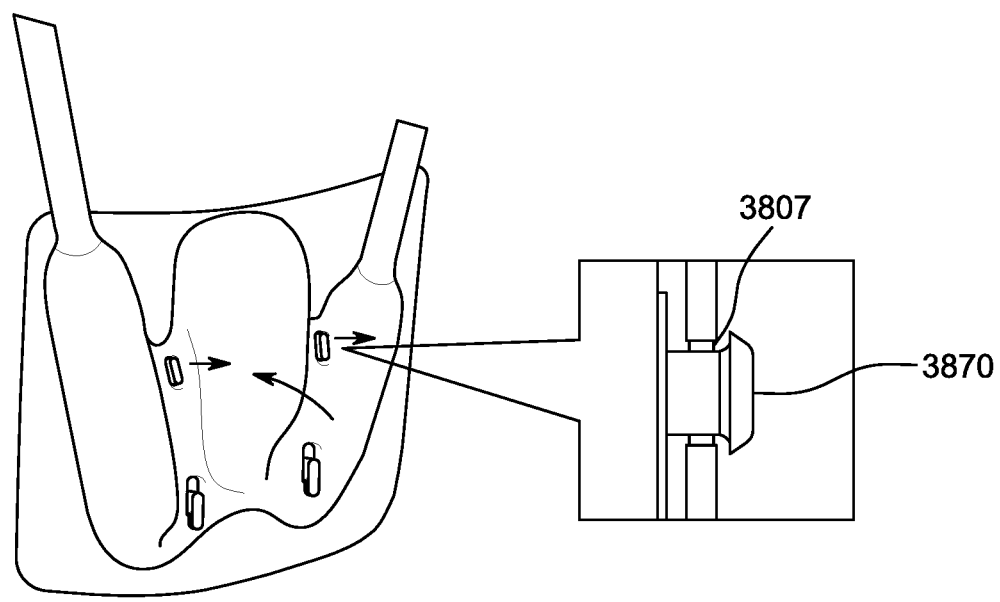
Figure 39A:
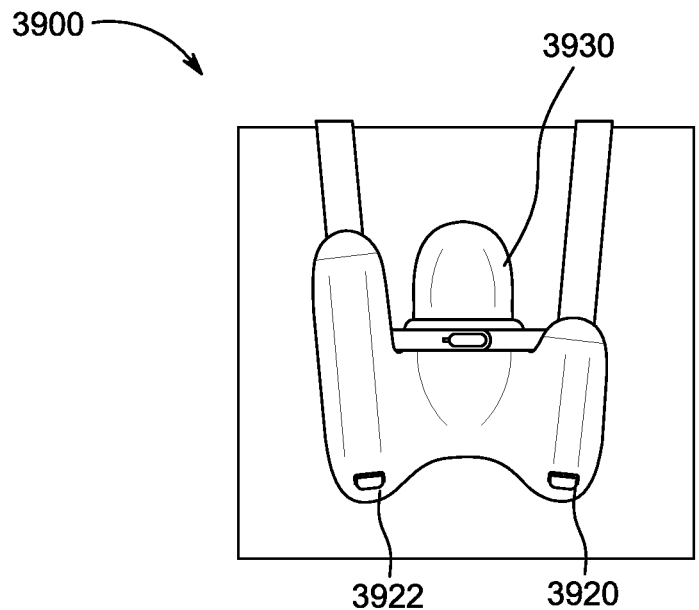
FIGS. 39A-39D show different illustrative views of hook and strap assembly and how it interfaces with a load distribution member, according to an embodiment.
Figure 39B:
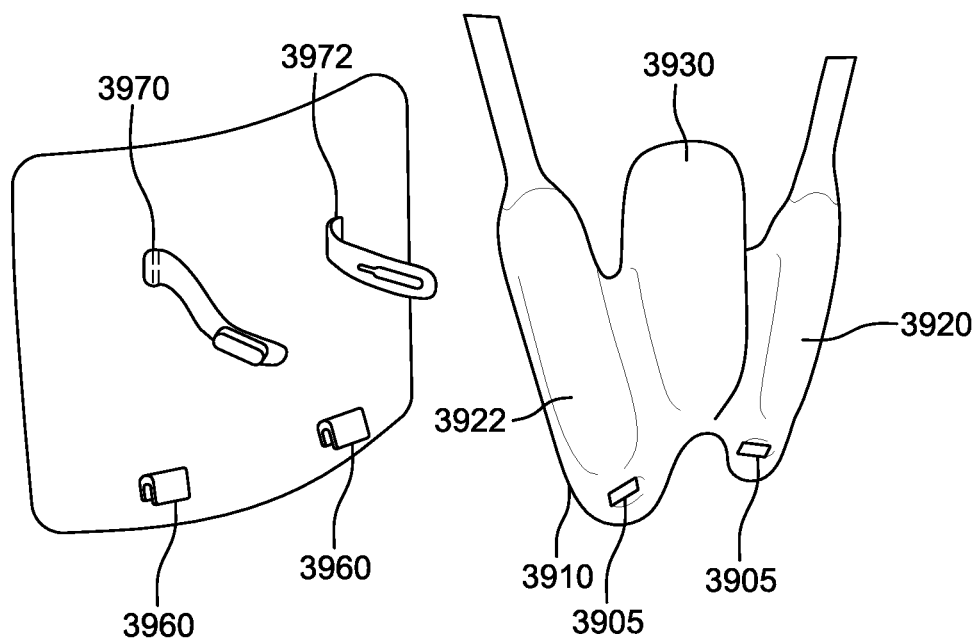
Figure 39C:
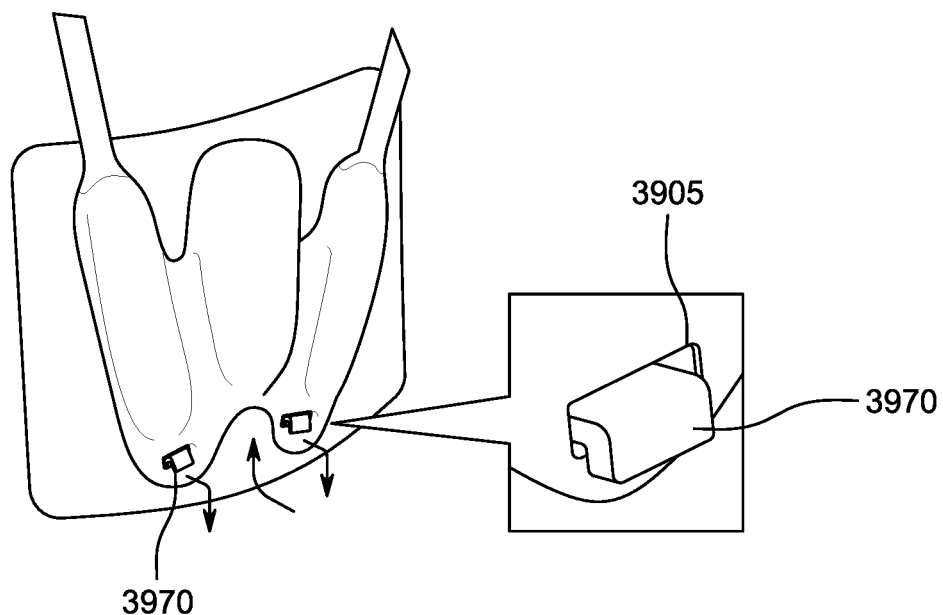
Figure 39D:
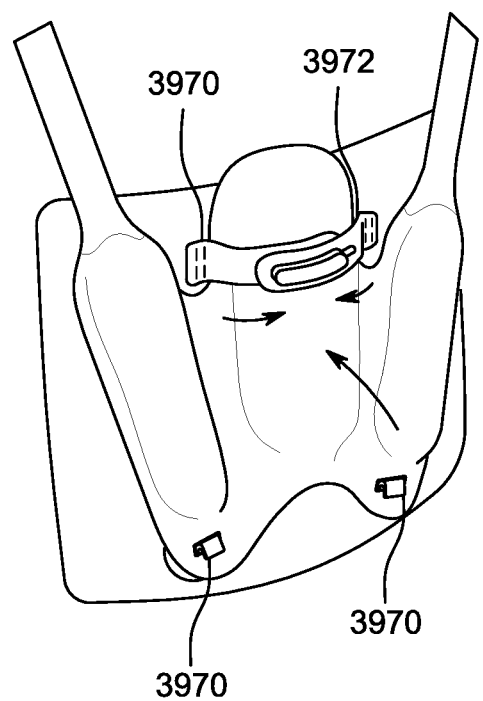

FIG. 35 shows an illustrative patch assembly 3500 according to an embodiment. Patch assembly 35000 may represent a power layer segment that is attached to a load distribution member 3501 associated with a first location (e.g., a thigh) and at least one other load distribution member 3501 associated with a second location (e.g., the core region or hips). Patch assembly 3500 is designed to be easily secured to and removed from the load distribution members, and is comfortable to the user. In addition, sub-components within assembly 3500 such as, for example, a battery pack may be removed from assembly 3500 and replaced with a fully charged battery pack. Patch assembly 3500 can include housing 3510, one or more flexdrives 3520 that are integrated within housing 3510, battery cradle 3530, battery 3540, and control electronics 3550. Housing 3510 may include one or more attachment mechanisms 3512 that are used to secure patch assembly 3500 to a load distribution member. Only one flexdrive is shown in FIG. 35 to avoid overcrowding the drawing. Details of different attachment mechanisms are discussed below. Each flexdrive 3520 may include tensioning member 3522 that is secured to a respective anchor 3524. Anchor 3524 is fixed to load distribution member 3502 and enables the flexdrive to shorten tensioning member 3522 to controllably increase force contraction between patch assembly 3500's location on its load distribution member and the load distribution member holding anchor 3524 in place. The flexdrive can also lengthen tensioning member 3522 to controllably decrease force contraction between the two load distribution members. In some embodiments, a sleeve member 3525 may encapsulate tensioning member 3522 and span a distance between flexdrive 3520 and anchor 3524. In some embodiments, patch assemblies may include one or more flexdrives that serve as hip extensors, and one or more flexdrives that serve as hip flexors. In some embodiments, patch assemblies may only have one or more flexdrives that serve as hip extensors, or that only have one or more flexdrives that serve as hip extensors. In yet other another embodiment, patch assemblies may include one or more flexdrives that serve as back extensors or lumbar support.

The attachment of patch assembly 3500 to its load distribution members is such that it allows for relatively easy donning and doffing. That is, users need to be able to readily attach and detach the patch assembly to and from the suit in a manner that is intuitive and trouble free. In addition, because loads are being transferred from the patch assembly to the load distribution members, maintaining comfort during its use while simultaneously providing desired load transfer is another important consideration that is taken into account. Attachment mechanisms 3512 and anchor 3524 are designed and constructed with these criteria in mind.

FIG. 10A-10D show an illustrative leg patch assembly 1000 according to an embodiment. Leg patch assembly 1000 may represent a power layer segment that is attached to a load distribution member associated with a thigh and at least one other load distribution member associated with the core region or hips. Leg patch assembly 1000 is designed to be easily secured to and removed from the load distribution members. In addition, sub-components within assembly 1000 such as, for example, a battery pack may be removed from assembly 1000 and replaced with a fully charged battery pack. Leg patch assembly 1000 can include housing 1010, base anchor 1030, first anchor 1032, second anchor 1034, suspension anchor 1036, extensor sleeve 1040, extensor anchor 1044, flexor sleeve 1050, and flexor anchor 1054. Base anchor 1030, first anchor 1032, second anchor 1034, suspension anchor 1036, extensor sleeve 1040, extensor anchor 1044, flexor sleeve 1050, and flexor anchor 1054 may take any suitable configuration for interfacing with a load distribution member. For example, in some embodiments, the anchors can be hook and loop attachments, clip attachments, button attachments, zipper attachments, buckle attachments, cord attachments, self-arresting attachments, bungee cord attachments, tongue and groove attachments, clip attachments, magnetic attachments, connector attachments, or any combination thereof. Several specific examples of anchors are discussed herein.

Housing 1010 can include extensor flexdrive portion 1012, flexor flexdrive portion 1014, electronics portion 1016, and battery portion 1018. Extensor flexdrive portion 1012 may include one or more flexdrives that are secured within housing 1010 and each have twisted strings that are contained within extensor sleeve 1040. Flexor flexdrive portion 1014 may include one or more flexdrives that are secured within housing 1010 and each have twisted strings that are contained within flexor sleeve 1050. Electronics portion 1016 may contain various electronics, circuit boards, sensors, etc., and battery portion 1018 may be constructed to receive battery pack 1060. Battery pack 1060 may be a removable and rechargeable battery pack that is designed to be retained in battery portion 1018.

When a user secures leg patch assembly 1000 to his or her exosuit, base anchor 1030, first anchor 1032, and second anchor 1034 may be secured to a thigh LDM. Securing housing 1010 to the thigh LDM via base anchor 1030, first anchor 1032, and second anchor 1034 provides a stable platform for the flexdrives to operate. Suspension anchor 1036 may be coupled to a thigh LDM or to another LDM via strap 1037. Extensor anchor 1044 may be secured to a LDM other than the thigh LDM. Flexor anchor 1054 may be secured to a LDM other than the thigh LDM. When anchors 1044 and 1054 are secured, sleeves 1040 and 1050 are positioned to enable the flexdrives to active the twisted strings contained within the sleeves to engage in assistive movement.

Figure 11:
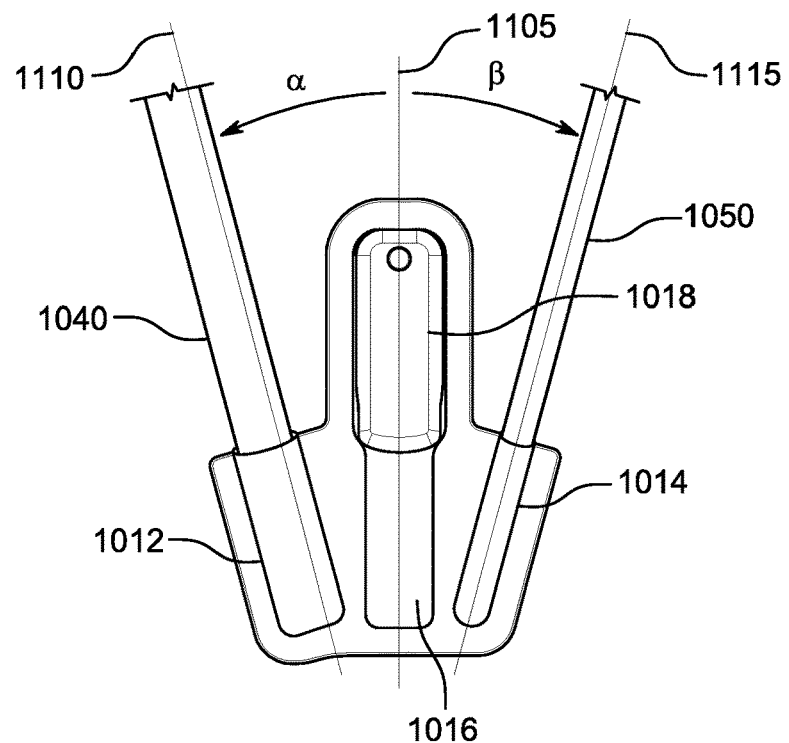
FIG. 11 shows an illustrative top view of leg patch assembly 1000 according to an embodiment.

FIG. 11 shows an illustrative top view of leg patch assembly 1000 according to an embodiment. In particular, FIG. 11 shows center axis 1105 passing through battery portion 1018 and electronics portion 1016. FIG. 11 also show extensor axis 1110 aligned with the orientation of extensor flexdrive portion 1012 and extensor sleeve 1040. FIG. 11 further shows flexor axis 1115 aligned with the orientation of flexor flexdrive portion 1014 and flexor sleeve 1050. The angle between center axis 1105 and extensor axis 1110 may be referred to as alpha, $\alpha$, and the angle between center axis 1105 and flexor axis 1115 may be referred to beta, $\beta$. In some embodiments, alpha and beta may be the same. In other embodiments, alpha may be greater than beta. In yet other embodiments, alpha may be less than beta.

FIGS. 12A-12J show different views of a leg patch assembly 1200 according to various embodiments. Leg patch assembly 1200 can include LDM engagement housing 1210.

Leg patch assembly 1200 can include housing 1210, first anchor 1230, second anchor 1232, extensor sleeve 1240, extensor anchor 1244, flexor sleeve 1250, and flexor anchor 1254. Housing 1210 may include plate member 1212 that can serve as a foundation for flexdives, electronics, and batteries. Housing 1210 may include extensor portion 1202, flexor portion 1204, and electronics portion 1206. First and second anchors 1230 and 1232 may be integrally formed with or attached to plate member 1212 and are designed to hold flexdrives in place by preventing them from moving up along the direction of their respective sleeves when activated. For example, in one embodiment, anchors 1230 and 1232 may adhesively bonded and sewn to plate member 1212. First and second anchors 1230 and 1232 may be constructed from a plastic material such as polyurethane. Plate member 1212 may be constructed from a fabric or rubber material. For example, the material may be a chlorosulfonated polyethylene synthetic rubber, sometimes referred to as Hypalon. Snaps 1234 may be secured to plate member 1212 and provide a retention mechanism for securing cover plate 1214 to plate member 1212. Cover plate 1214 may be secured on top of plate member 1212 to cover the flexdives and electronics. Battery 1260 may be inserted into battery region 1218 and removed as desired. Extensor anchor 1244 and flexor anchor 1254 may both have G-shaped hooks to interface with a load distribution member.

FIG. 12E shows cover plate 1214 without plate member 1212 and also shows extensor faceplate 1220 and flexor faceplate 1222. Faceplates 1220 and 1222 may be rigid members that transfer load into anchors 1230 and 1232. FIG. 12F shows cover plate 1214 positioned on top of plate member 1212, but positioned such that faceplates 1220 and 1222 are positioned below anchors 1230 and 1232. FIG. 12F shows cover plate 1214 positioned on top of plate member 1212, and positioned such that faceplates 1220 and 1222 are nestled in anchors 1230 and 1232. Thus, in FIG. 12G, anchors 1230 and 1232 interface with faceplates 1220 and 1222. FIG. 12H shows an illustrative cross-sectional view of a portion of leg patch assembly 1200 taken along line H-H of FIG. 12G. In particular, FIG. 12H shows anchor 1230 covering faceplate 1220 and how cover plate 1214 is secured to plate member 1212 via snap 1234.

Figure 12A:
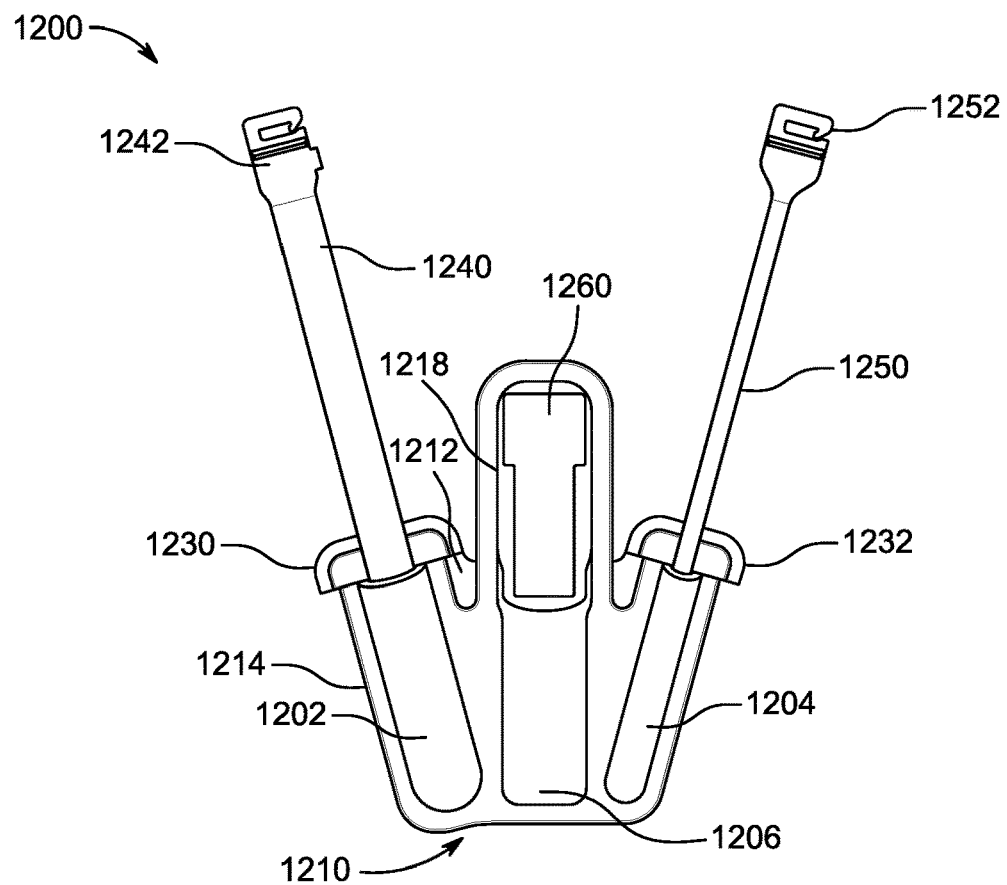
Figure 12B:
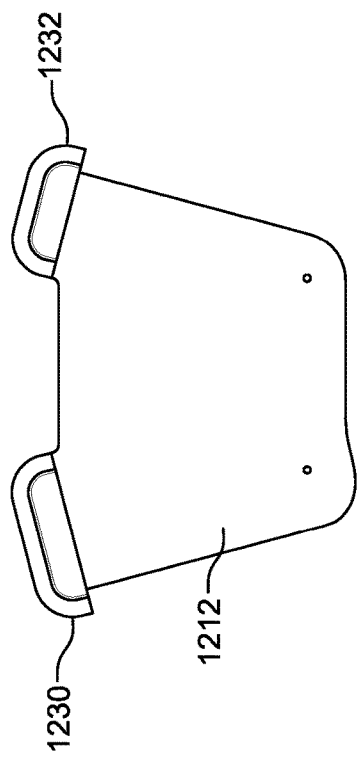
Figure 12D:
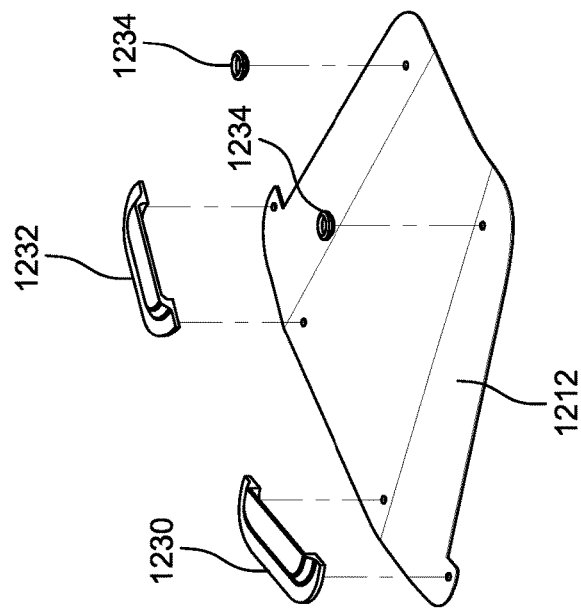
Figure 12C:
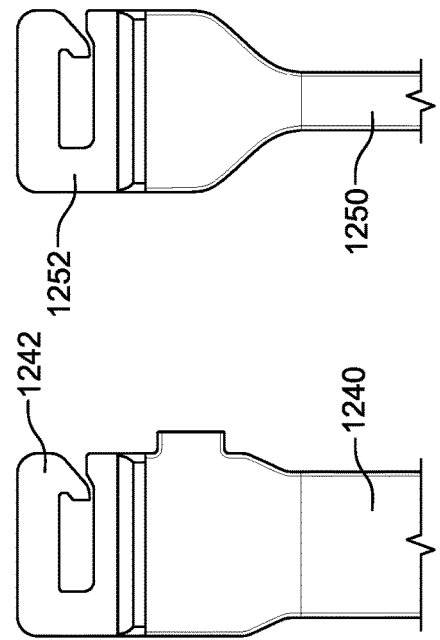
Figure 12I:
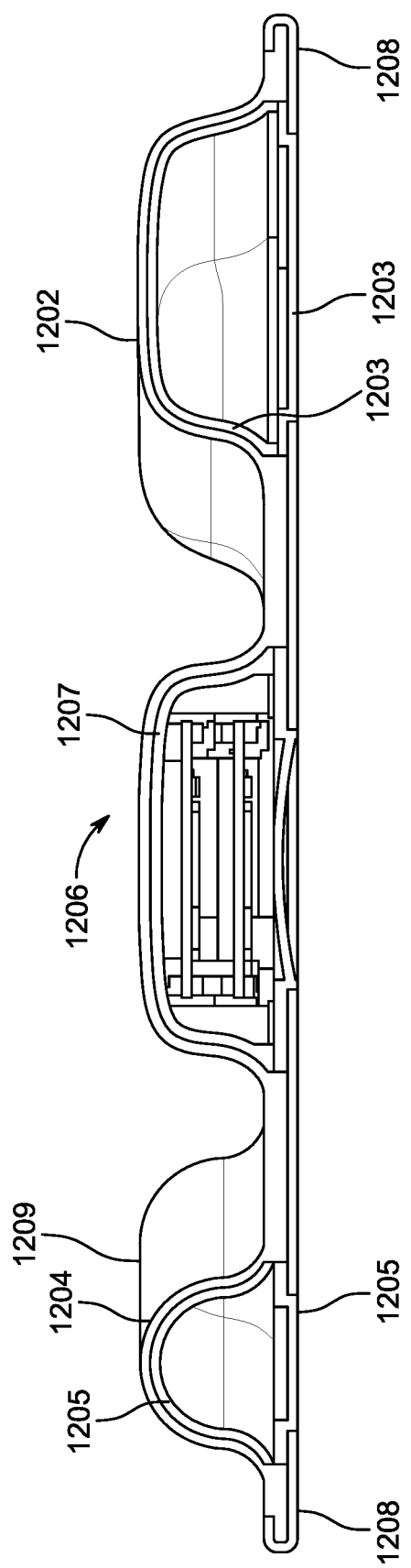

FIG. 12I shows an illustrative cross-sectional view of leg patch assembly 1200 taken along line I-I of FIG. 12E. Extensor portion 1202 can include rigid member 1203. Flexor portion 1204 can include rigid members 1205. Electronic portion 1206 can include rigid members 1207. Flexible foot member 1208 may wrap around the edge of cover layer 1212 and plate member 1212. Foam member 1209 may represent a top layer of cover layer 1214. Foam member 1209 may be a foam material that may emulate a fabric façade.

Figure 12J:
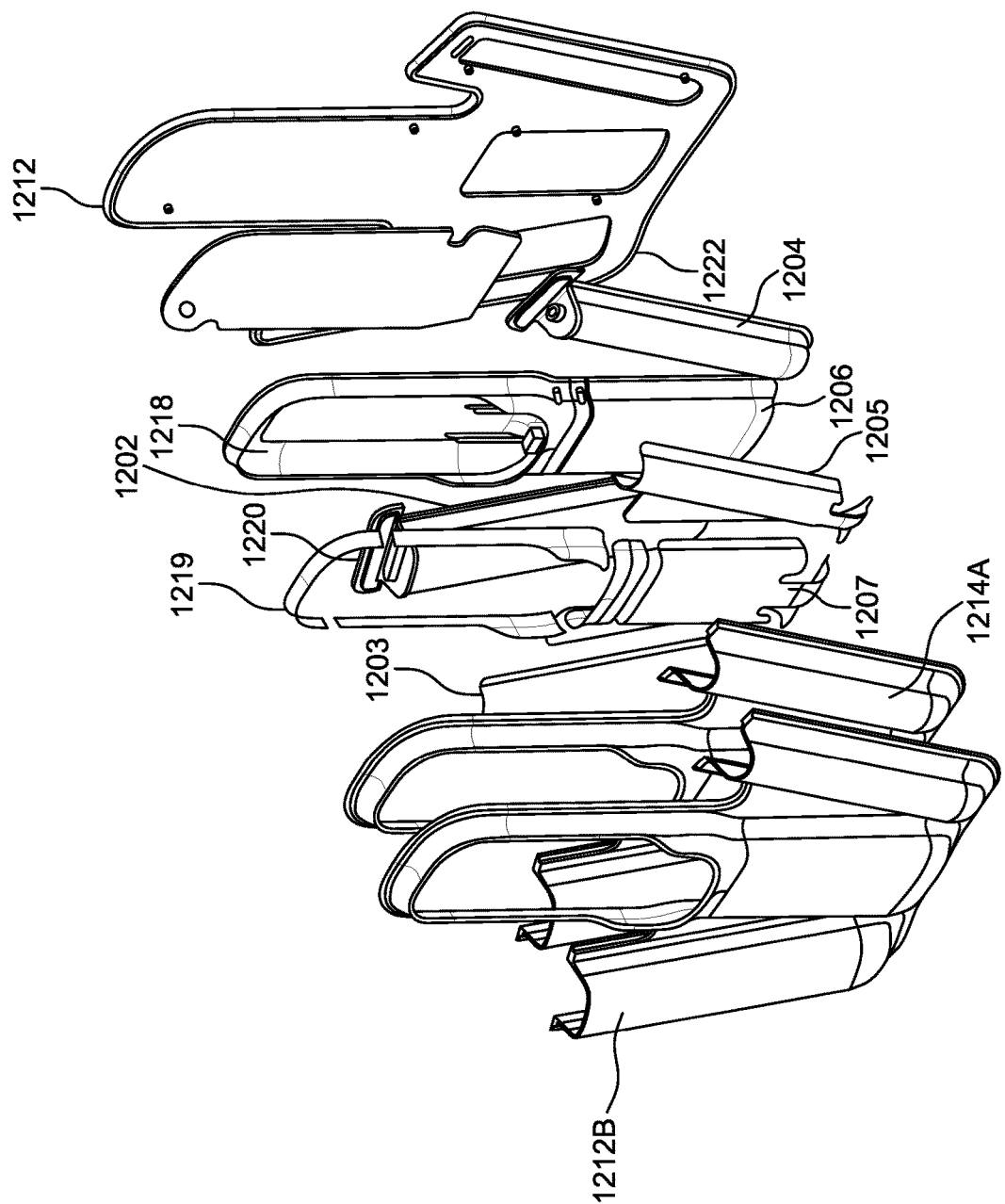

FIG. 12J shows an illustrative exploded view of leg patch assembly 1200. FIG. 12 shows two alternative cover plates 1214A and 1214B. Cover plate 1214A may be a foam cover plate and cover plate 1214B may be a fabric cover.

Figure 12K:
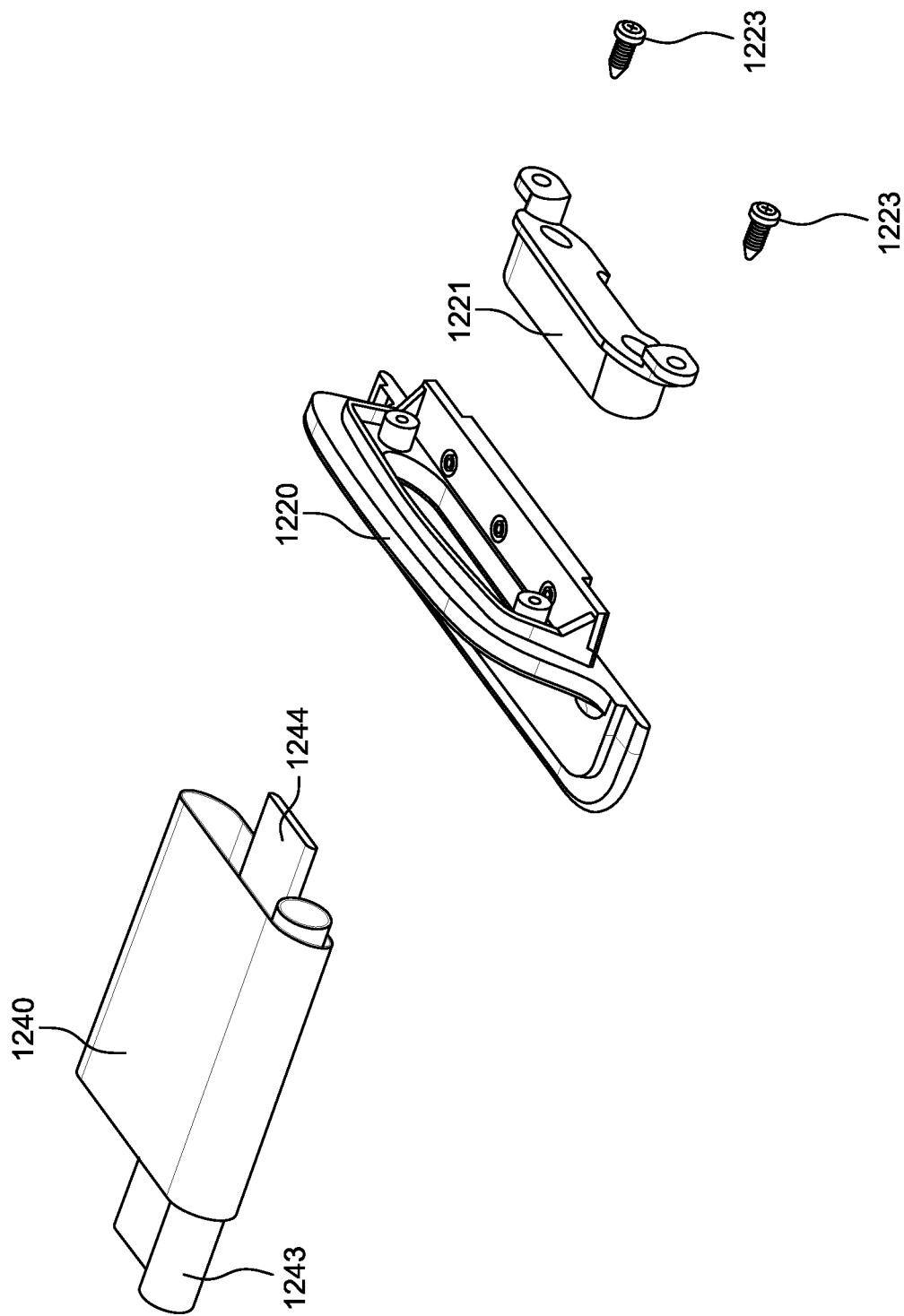

FIG. 12K shows an illustrative exploded view of faceplate 1220 and sleeve 1240. Faceplate 1220 may be secured to twisted string termination member 1221 via screws 1223. Twisted strings (not shown) may originate from one or more flexdives and pass through through-holes in member 1221 and be threaded through string conduits 1243 and secured to anchor 1242. Also shown in FIG. 12K is data cable 1244 that passes inside sleeve 1240.

Figure 12L:
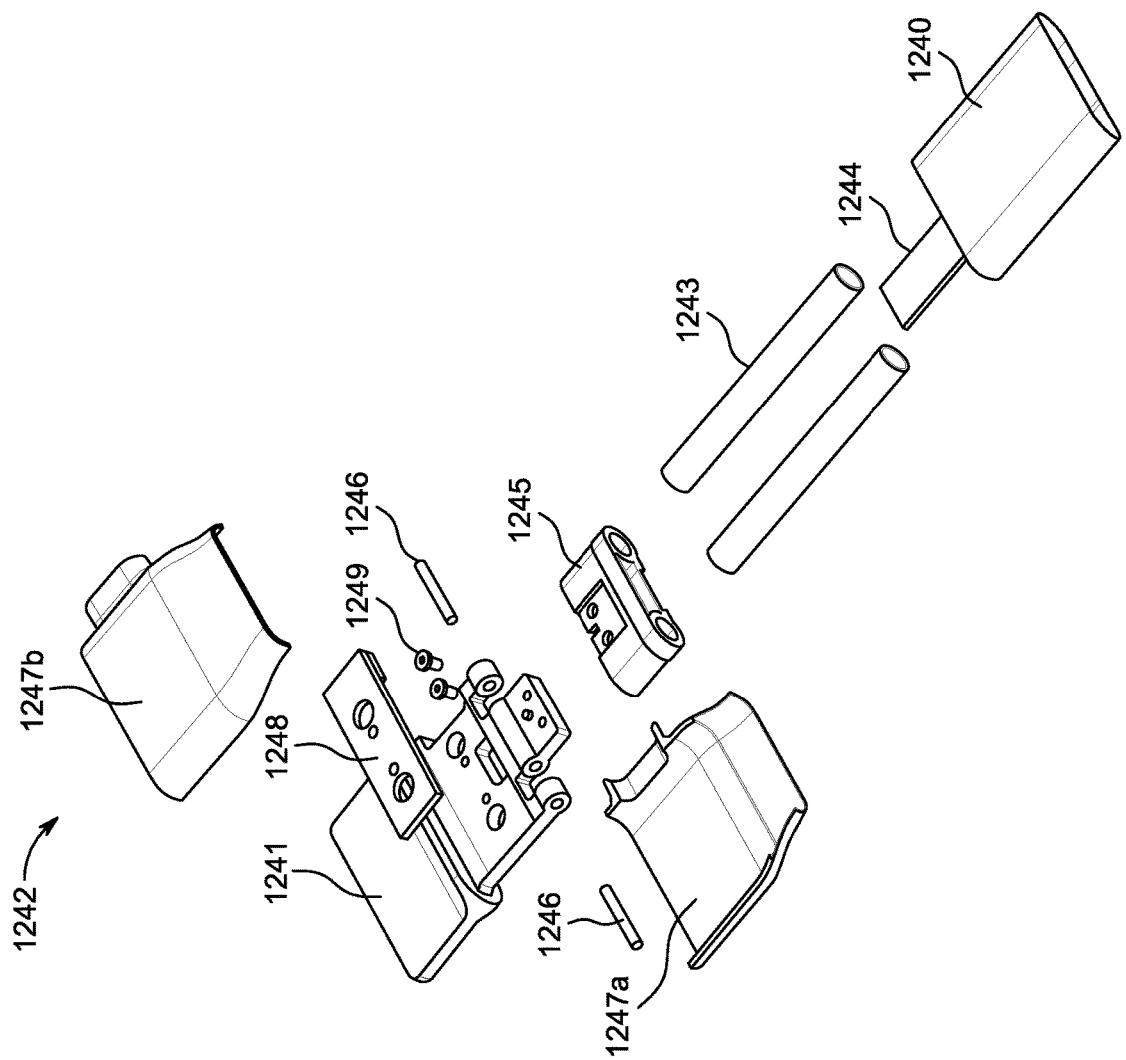

FIG. 12L shows an exploded view of anchor 1242. Anchor 1242 can include hook member 1241, bottom enclosure 1247a, top enclosure 1247b, PCB connector 1248, dowels 1246, conduit 1246, string conduits 1243, and sleeve 1240. A twisted string (not shown) may pass through each string conduit 1243 and through a through-hole in conduit 1245 and be attached to hook member 1241 via dowels 1246. Conduit 1245 may be secured to hook member 1241 via screws 1249. Data cable 1244 may be secured to PCB connector 1248, which can also be secured to hook member 1241. Bottom and top enclosures 1247a and 1247b serve as a cover for anchor 1242.

Sleeve 1240 may be secured to termination member 1221 and conduit 1245. Sleeve 1240 may be constructed from a material that can collapse onto itself when the twisted string is activated by a flexdrive. For example, in some embodiments, the material may be fabric. String conduits 1243 and data cable 1244 may be secured to sleeve 1240.

FIGS. 13A-13C show schematic views of leg patch assemblies 1300, 1335, and 1370 according to various embodiments. Each of leg patch assemblies 1300, 1335, and 1370 has their respective flexdrives and batteries arranged in different configurations. Leg patch assembly 1300 of FIG. 13A has a horizontally biased configuration in that extensor flexdrives 1302 and 1303, batteries 1305, and flexor flexdrives 1307 are aligned with respect to horizontal axis 1309. Leg patch assembly 1335 has a vertically biased configuration in that extensor flexdrives 1340 are positioned vertically with respect to batteries 1342 and flexor flexdrive 1344. Leg patch assembly 1370 has a vertically biased configuration in that extensor flexdrives 1380 are positioned vertically with respect to batteries 1382 and flexor flexdrive 1384.

Figure 14C:
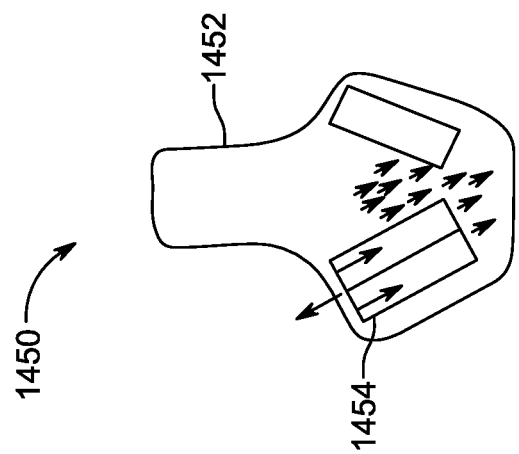
FIGS. 14A-14C show different force loading diagrams for various leg patch assemblies.
Figure 14B:
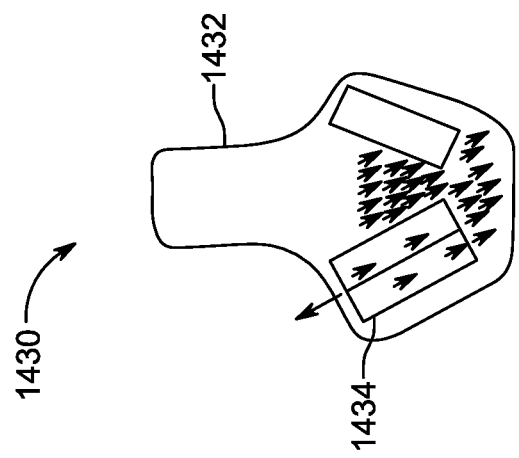
Figure 14A:
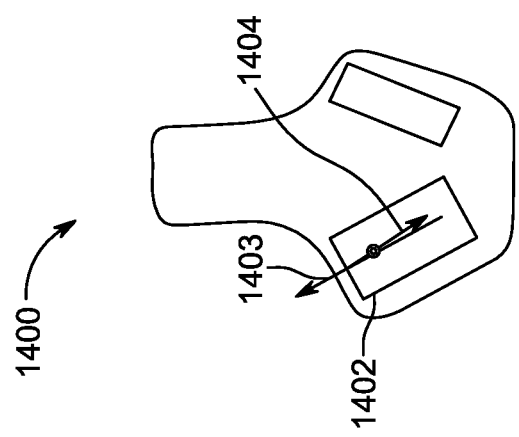

FIGS. 14A-14C show different force loading diagrams for various leg patch assemblies. In each of the force loading diagrams, the leg patch assembly applies a counteractive force to the force applied by one or more of the flexdrives. The leg patch assemblies can be designed and constructed to tune the degree of counteractive force applied by the leg patch. FIG. 14A shows leg patch assembly 1400 in which load is transmitted directly from flexdrive enclosure 1402 into a load distribution member (not shown). In this configuration, force applied by the flexdrive (shown by arrow 1403) is opposed only by flexdrive enclosure 1402. The opposing force is shown by arrow 1404. Leg patch assembly 1400 may provide predictable and quantifiable loading. The patch construction may include hardgood/softgood transitions that do not require structural leading. Leg patch assembly 1400 may require that the load distribution member include stiffener to assist in transmitting force across a larger than that which can be provide by flexdrive enclosure 1402.

FIG. 14B shows leg patch assembly 1430 in which load is transmitted in to base layer 1432 when flexdrive 1434 is activated. The load transmission force is shown by the small arrows pointing downwards and to the right. The flexdrive force is shown by the large arrow pointing upwards and to the left. In this embodiment, the entirety of base layer 1432 is distributing force across a load distribution member (not shown). This embodiment further enables flexibility in adjusting the angle of flexdrive 1434 of orientation with respect to base layer 1432. In addition, this embodiment may be used in conjunction with a load distribution member that does not require a stiffener.

FIG. 14C shows leg patch assembly 1450 in which load is transmitted in to base layer 1452 and flexdrive enclosure 1454 when the flexdrive is activated. In this embodiment, both base layer 1452 and flexdrive 1454 transmit the load exerted by the flexdrive. Base layer loads are shown by the small arrows pointed in the downwards direction. Flexdrive enclosure loads are shown by the large arrows pointed in the downwards direction. This embodiment represents a hybrid of patch assemblies 1400 and 1430 and thus benefits from the advantages provided by the other patch assemblies.

Figure 15A:
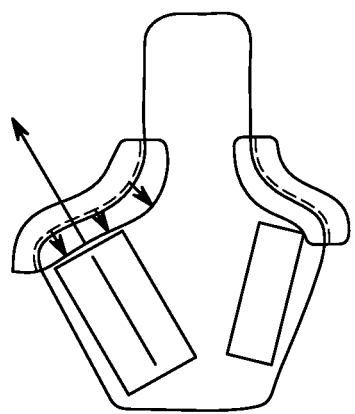
FIGS. 15A-15H shows different load distributions for a leg patch assembly according to various embodiments.
Figure 15B:
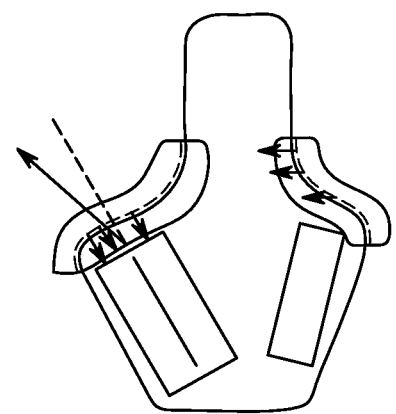
Figure 15C:
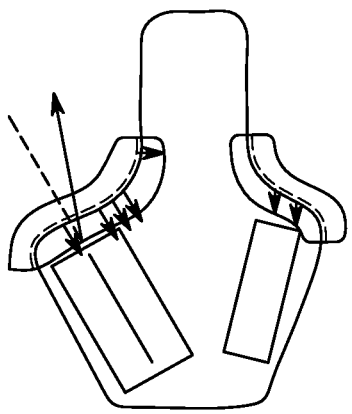
Figure 15D:
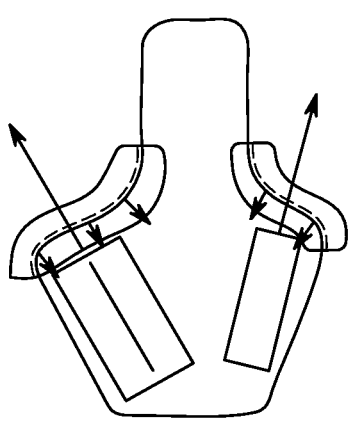

FIGS. 15A-15H shows different load distributions for a leg patch assembly according to various embodiments. Each FIG shows the force applied by the flexdrives and counteractive (or reactive) force applied by the patch. The FIGS shows different force angles for both flexdrive force and patch counteractive force. FIGS. 15A-15D show illustrative leading edge counteractive forces. In FIG. 15A, for example, the flexdrive force is parallel to the orientation of the flexdrive and the counteractive forces directly oppose that flexdrive force. In FIG. 15B, for example, the flexdrive force is directed at an angle (e.g., left of center) that is not parallel to the orientation of the flexdrive. As a result, the counteractive forces are shown to being exerted on both sides of the patch, thereby creating a moment. In FIG. 15C, the flexdrive force is directed at an angle (e.g., right of center) that is not parallel to the orientation of the flexdrive. The counteractive forces are shown to being exerted on both sides of the patch. In FIG. 15D, flexdrive forces for both flexdrives are parallel to their respective flexdrive orientation. The counteractive forces are shown to being exerted on both sides of the patch.

Figure 15E:
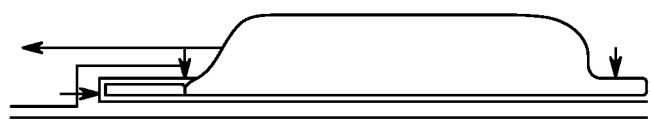
Figure 15F:
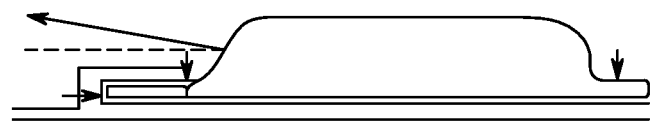
Figure 15G:
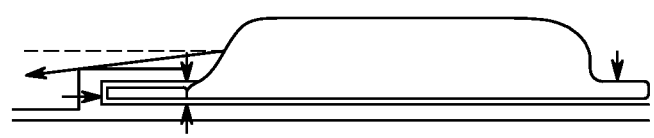
Figure 15H:
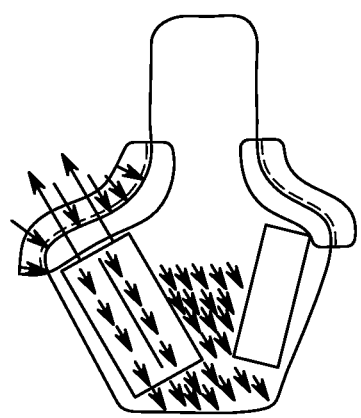

FIGS. 15E-15G illustrate examples of counteractive loads at the bottom or rear of the patch. The flexdrive forces and counteractive forces are self-explanatory. FIG. 15H shows a dual flexdrive forces being applied in parallel with the orientation of the flexdrives. In addition, FIG. 15H shows counteractive forces being applied by the leading edge and face of the patch.

Figure 16A:
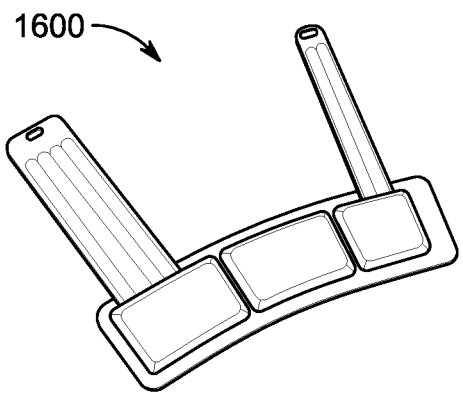
FIGS. 16A-16C show a leg patch assembly according to an embodiment.
Figure 16B:
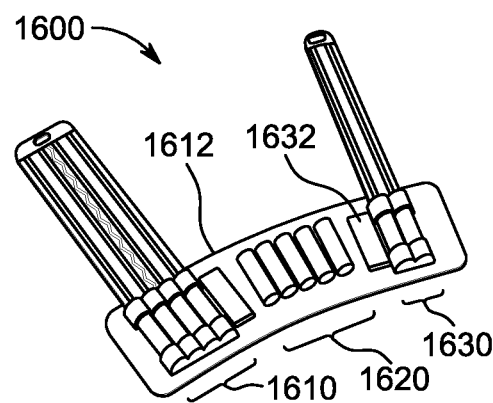
Figure 16C:
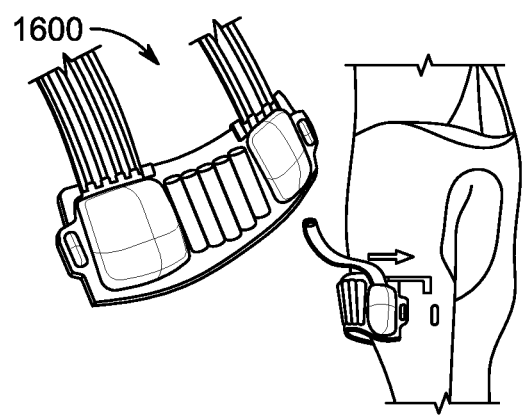

FIGS. 16A-16C show leg patch assembly 1600 according to an embodiment. Leg patch assembly 1600 can include flex drive group 1610, PCB 1612, batteries 1620, flexdrive group 1630, and PCB 1632. PCB 1612 may contain electronics needed to operate flex drive group 1610, and PCB 1632 may contain electronics needed to operate flex drive group 1630.

Figure 17:
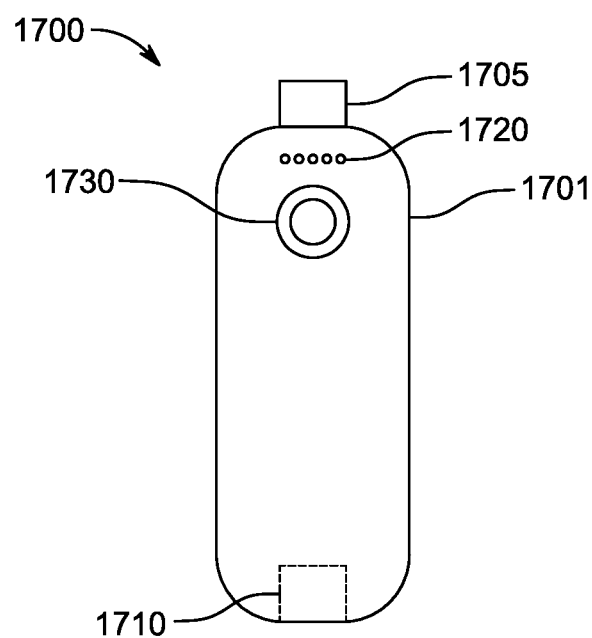
FIG. 17 shows an illustrative battery pack according to various embodiments.

FIG. 17 shows illustrative battery pack 1700 according to various embodiments. Battery pack 1700 may include housing 1701, pull tab 1705, connector 1710, LEDs 1720, and button 1730. Battery pack 1700 may also include electronics, sensors, and vibrator mechanism. Battery pack 1700 is designed to be inserted in and removed from the exosuit (e.g., a leg patch assembly). A user may pull on pull tab 1705 to remove battery pack 1700. Battery pack 1700 may be constructed in a variety of different shapes and sizes, but in general, it may be designed to maintain a relatively slim profile that does not protrude too far away from the body of the wearer. Connector 1710 may connect to a charger to charge the battery(ies) contained therein, and to interface with an electrical connection on the exosuit. LEDs 1720 may provide feedback as visual confirmation as to the charge status of battery pack 1700 and to provide other status indicators. The other status indicators can include, for example, an error indicator, a busy indicator, and a ready indicator. The user may press button 1730 to obtain feedback.

Battery pack 1700 may provide feedback to the user by activating a vibration unit (not shown). Battery pack 1700 may vibrate to communicate information to the user without requiring the user to visually access the battery. In addition, battery pack 1700 may be used to provide feedback in lieu of other exosuit feedback mechanisms (e.g., flexdrives, speakers, other LEDs). For example, the vibration mechanism may be used to indicate which region of the exosuit is performing assistive movements.

Figure 18:
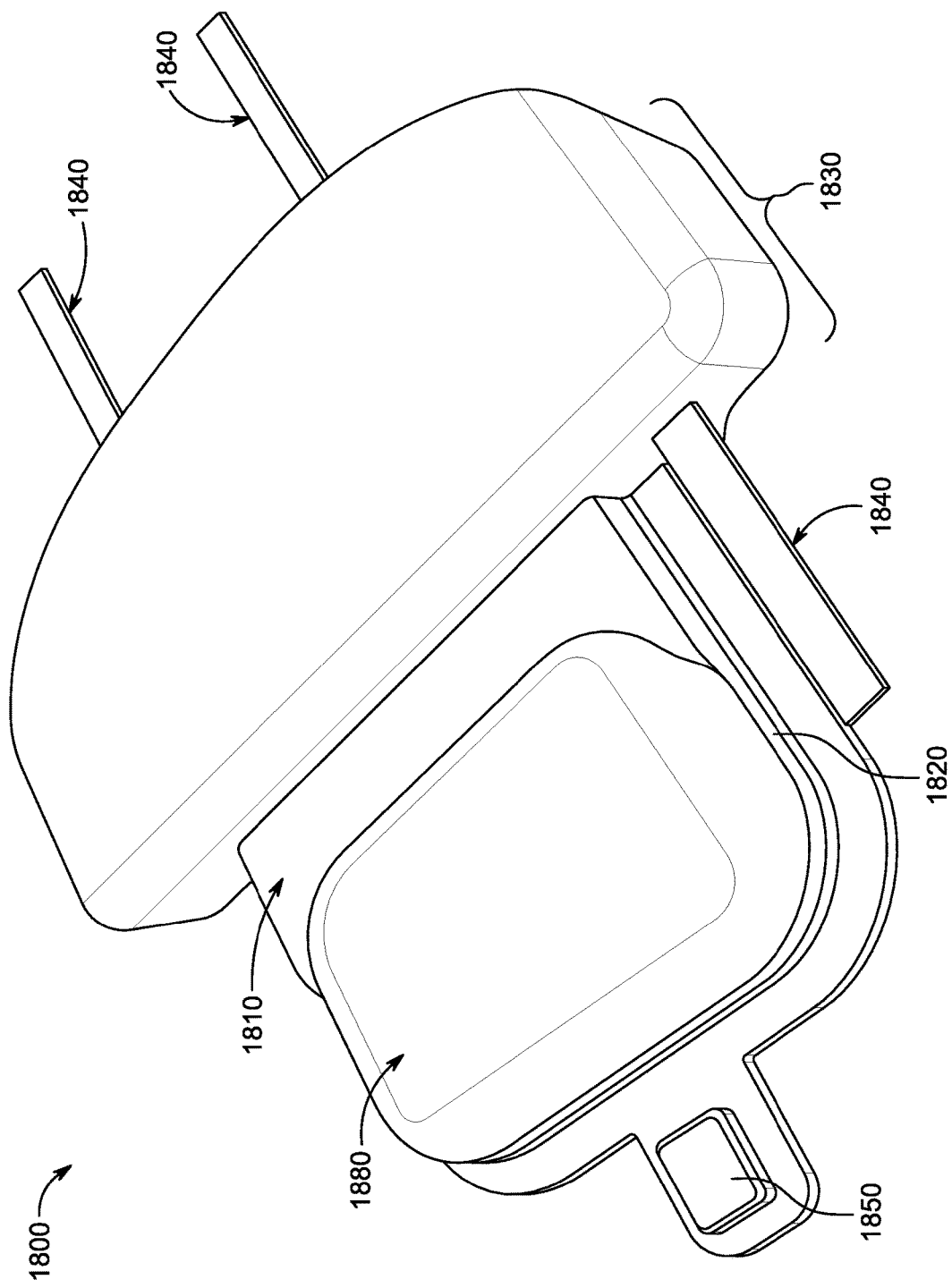
FIG. 18 shows an illustrative view of a core patch assembly according to an embodiment.

FIG. 18 shows an illustrative view of core patch assembly 1800 according to an embodiment. Core patch assembly 1800 may be a power layer segment that can be secured to a load distribution member associated with a back of a user. Core patch assembly 1800 may serve as a communications/processing center of the exosuit. Assembly 1800 may include housing 1810, battery portion 1820, electronics portion 1830, cables 1840, IMU portion 1850, and battery pack 1880. Housing 1810 may include anchors (not shown) that secure assembly 1800 to the load distribution member. Battery pack 1880 may be retained in battery portion 1820. Electronics portion 1830 may contain electronics such as a processor, communications circuitry, and power management circuitry to control operation of the exosuit.

Figure 55C:
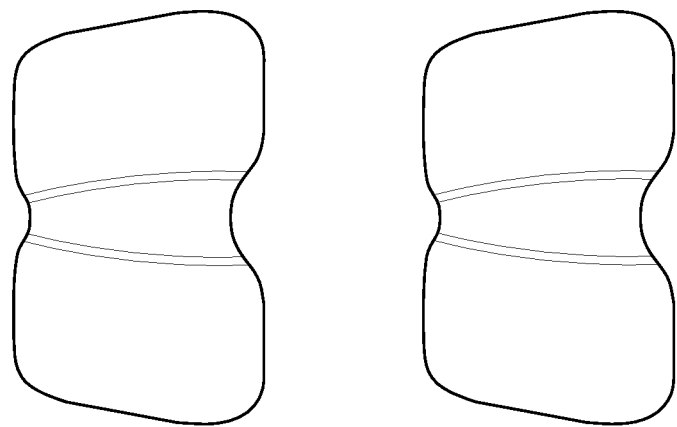
FIG. 55C shows illustrative front and back views of a lumbar power layer segment, according to an embodiment.
Figure 55B:
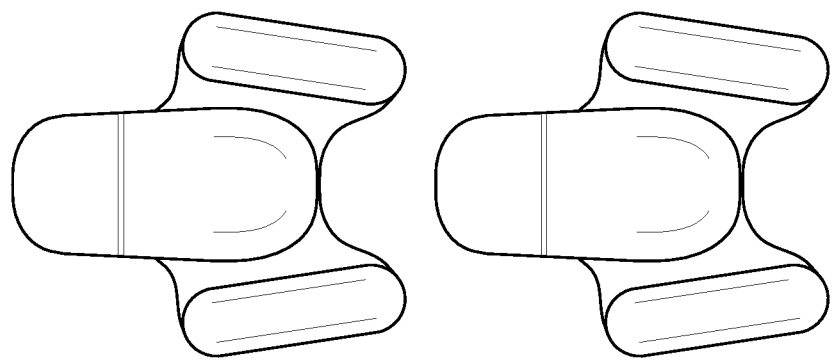
FIG. 55B shows illustrative front and back views of a thigh power layer segment according to an embodiment.
Figure 55A:
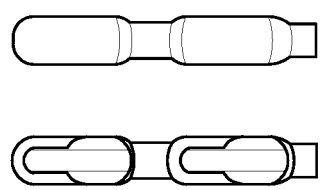
FIG. 55A shows illustrative front and back views of a tensioning member according to an embodiment.

FIG. 55A shows illustrative front and back views of a tensioning member. FIG. 55B shows illustrative front and back views of a thigh power layer segment. FIG. 55C shows illustrative front and back views of a lumbar power layer segment.

FIGS. 36A-36D show different illustrative views of pocket patch assembly 3600 and how it interfaces with load distribution member 3650, according to an embodiment. Pocket patch assembly 3600 can include locking mechanism 3605 and other features such as housing 3610, flexdrives 3620 and 3622, battery 3630, and other components that are not shown. Load distribution member 3650 include pocket 3660 and flap 3670, which is attached to the backside of pocket 3660. Pocket 3660 may be sized to accommodate housing 3610 and can include hole 3656. Flap 3670 may include hole 3672 and locking mechanism 3674. Patch assembly 3600 is inserted into pocket 3660, and flap 3670 can fold down over battery 3630 and over a portion of housing 3610 so that locking mechanism 3674 can be fastened to locking mechanism 3605. Locking mechanism 3605 may be accessible via hole 3662. When flap 3670 is secured to patch assembly 3600, patch assembly 3600 is secured in place to load distribution member 3650.

FIGS. 37A-37F show different illustrative views of cord patch assembly 3700 and how it interfaces with load distribution member 3750, according to an embodiment. Cord patch assembly 3700 can include cord hooks 3705 and other features such as housing 3710, flexdrives 3720 and 3722, battery 3730, and other components that are not shown. Load distribution member 3750 can include cord 3752 that is threaded a continuous loop through holes 3754. Cord 3752 is threaded such that portions are behind and in front of a surface of load distribution member 3750. In some embodiments, cord 3752 may be an elastic cord. In the specific example shown, seven holes 3754 are shown. Holes 3754 may be arranged such that cord 3752 can wrap around different portions of assembly 3700, including cord hooks 3705, to secure assembly 3700 in place to load distribution member 3750. Member 3750 can also include cord hooks 3760 that serve as a cord cinch point. A user can attach assembly 3700 to member 3750 by placing assembly 3700 in proximity of member 3750, and then by placing cord 3752 over hooks 3705. Then the user can pull cord 3752 taught up towards hooks 3760 and securing the cinched cord to one or more of hooks 3760.

FIGS. 38A-38D show different illustrative views of press fit patch assembly 3800 and how it interfaces with load distribution member 3850, according to an embodiment. Press fit patch assembly 3800 can include retention holes 3805 and 3807, and other features such as housing 3810, flexdrives 3820 and 3822, battery 3830, and other components that are not shown.

Load distribution member 3850 can include bottom tabs 3860 and top tabs 3870. During installation, a user may orient bottom tabs 3860 to fit through holes 3805 and then press assembly 3800 towards member 3850 so that top tabs 3870 are press fit through retention holes 3707. Retention holes 3505 can serve as an anchor onto which bottom tabs 3860 can rest, and retention holes 3507 can also serve as the anchors for securing top tabs 3870.

FIGS. 39A-39D show different illustrative views of hook and strap assembly 3900 and how it interfaces with load distribution member 3950, according to an embodiment. Press fit patch assembly 3900 can include retention holes 3905, and other features such as housing 3910, flexdrives 3820 and 3822, battery 3830, and other components that are not shown. Load distribution member 3950 can include hook tabs 3960, male strap 3970, and female strap 3972. During installation, a user may orient hook tabs 3960 to fit through holes 3705 and then connect male and female straps 3970 and 3972 together over body 3910.

Figure 40D:
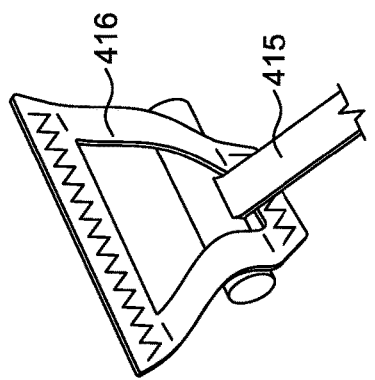
FIGS. 40A-40G show several different examples of load bearing anchors according to various embodiments.
Figure 40C:
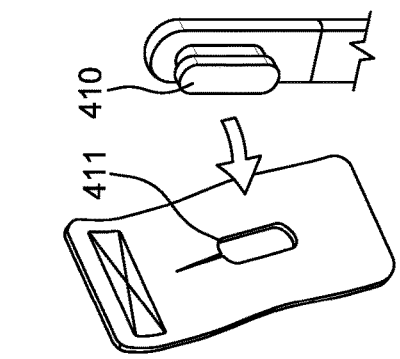
Figure 40B:
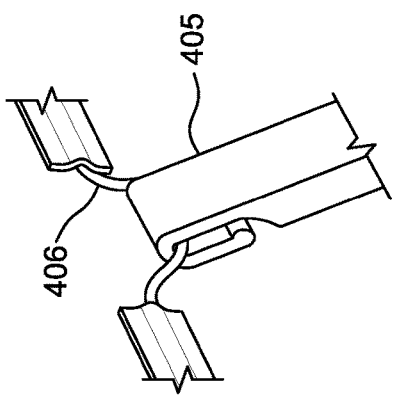
Figure 40A:
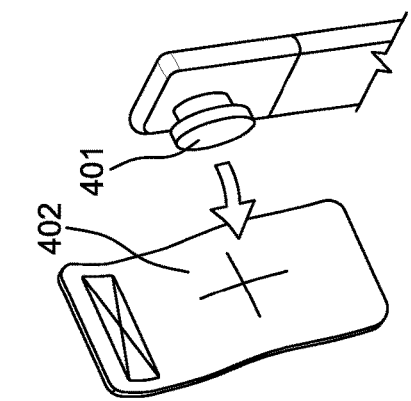
Figure 40G:
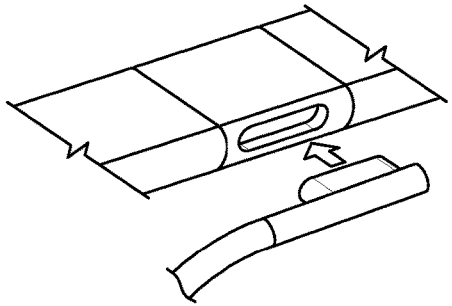
Figure 40F:
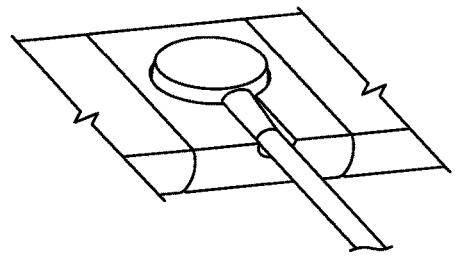
Figure 40E:
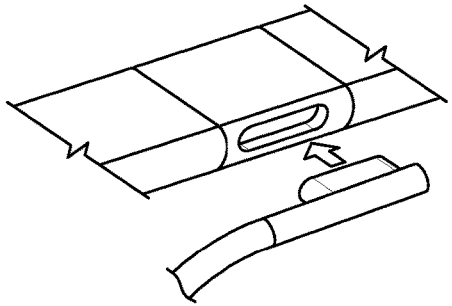

FIGS. 40A-40G show several different examples of load bearing anchors (e.g., anchor 3524) that can used to attach a tensioning member (e.g., tensioning member 3522) to a load distribution member. FIG. 40A shows a push tab anchor 401 that presses through a resistance hole 402 to be secured in place. FIG. 40B shows a hook tab 405 that clasps onto cord 406. FIG. 40C shows another push tab anchor 410 that slots into hole 411. FIG. 40D shows t-bar anchor 415 interfacing with loop 416. FIGS. 40E-40F show different male and female magnetic anchor configurations.

Figure 41:
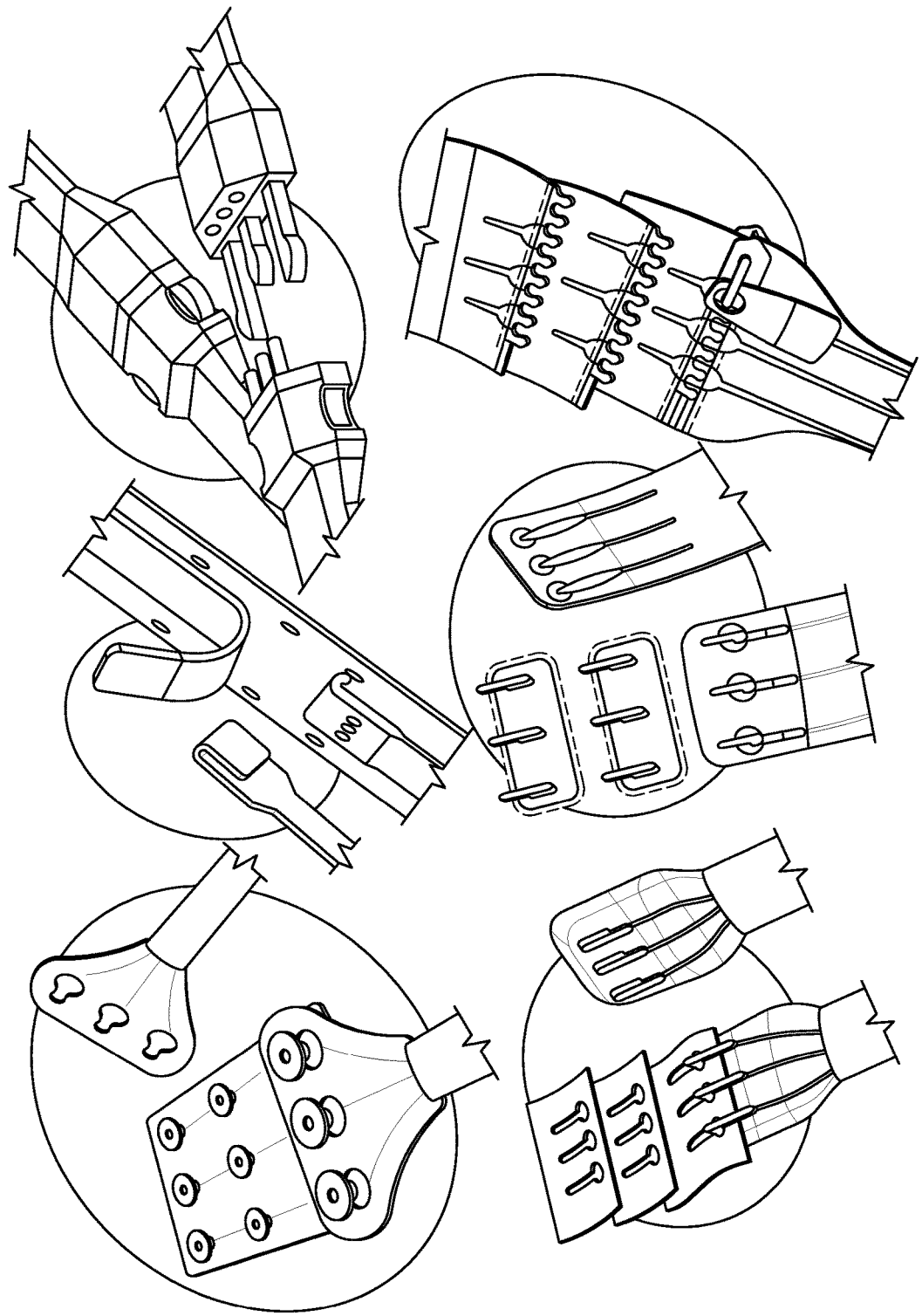
FIG. 41 shows examples of hybrid load bearing and electrical connection anchors according to various embodiments.

The examples shown in FIGS. 40A-40G may be designed primarily for load bearing applications. In other embodiments, anchors can serve as both load bearing instruments and electrical connections. The electrical connections may enable transfer of data and/or power through the tensioning member. Examples of hybrid load bearing and electrical connection anchors are shown in FIG. 41.

Figure 42A:
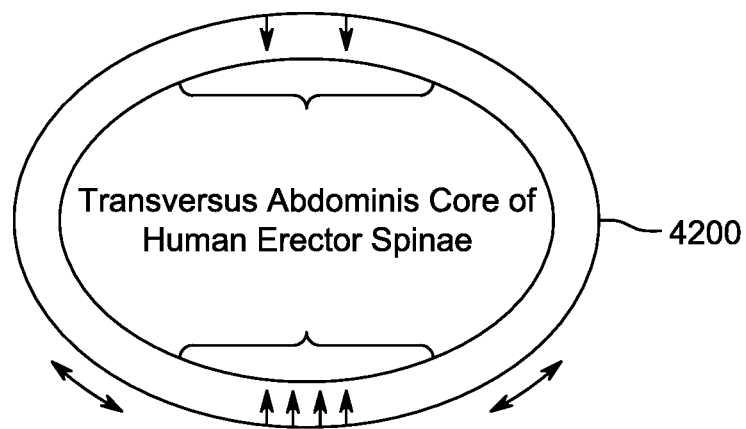
FIG. 42A shows illustrative cross-section of a core region of a human being according to an embodiment.
Figure 42B:
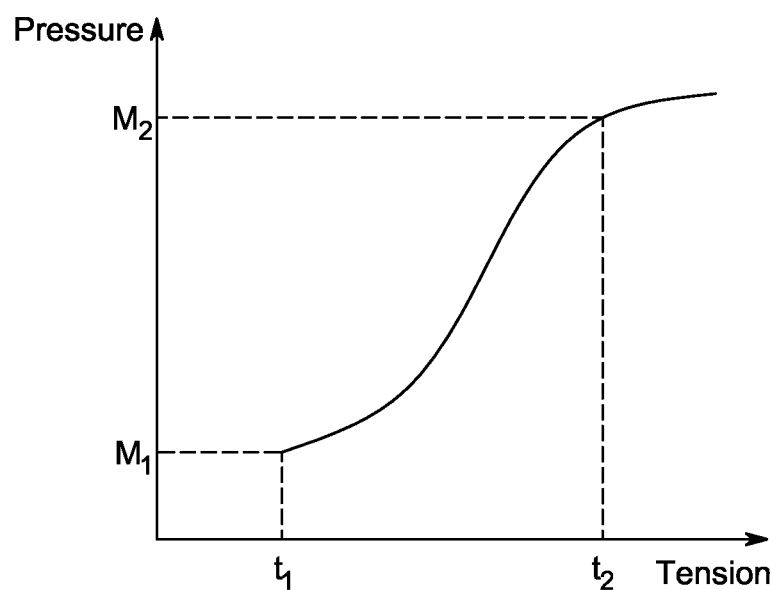
FIG. 42B shows an illustrative graph showing pressure exerted onto the core of a human in response to a tension applied by an adjustable lumbar tensioning member.

FIG. 42A shows illustrative cross-section of a core region of a human being, with emphasis showing the transversus abdominis (e.g., ab muscles) and erector spinae (e.g., back extension muscles), and also showing an adjustable lumbar tensioning member 4200 that is situated around the core region. FIG. 42B shows an illustrative graph showing pressure exerted onto the core of a human in response to a tension applied by adjustable lumbar tensioning member 4200. Lumbar tensioning member 4200 can exert pressure to a person's lower back and/or abs in response to an increase of tension or decrease said pressure in response to a decrease in tension. That is, as lumbar tensioning member 4200 tightens it grip around the core of the person, it is able to exert more and more pressure to the lower back and/or abs. Depending on the design of lumbar tensioning member, more pressure may be applied to the lower back than the abs, or vice versa, or the application of pressure may be approximately equal. Several different lumbar tensioning system embodiments are discussed below, and the operating principles discussed above apply to those embodiments.

Figure 43:
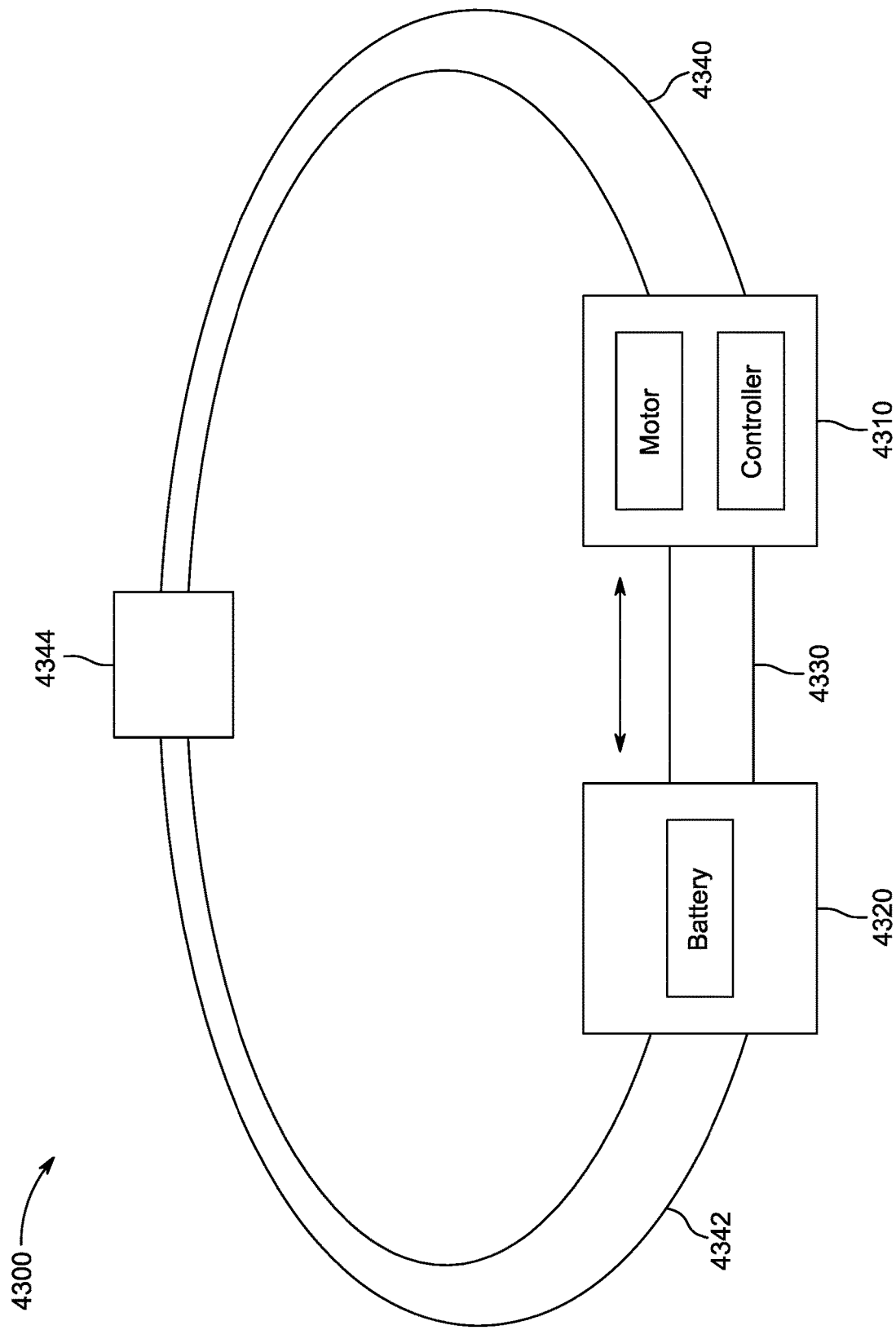
FIG. 43 shows dual pouch lumbar support system according to an embodiment.

FIG. 43 shows dual pouch lumbar support system 4300 according to an embodiment. Lumbar support system 4300 can include first pouch 4310, second pouch 4320, tensioning member 4330, which is connected between pouches 4310 and 4320, belt segments 4340 and 4342, and buckle 4346. Belt segment 4340 may be connected to pouch 4310 and buckle 4346, and belt segment 4342 may be connected to pouch 4320 and buckle 4346. Pouches 4320 and 4330 may include various components such as a motor, a controller, a battery, and other components needed for operating system 4300. To increase applied pressure to the human core, tensioning member 4330 can be tightened together by the motor. The tightening or shortening of tensioning member 4330 draws pouches 4310 and 4320 closer together to thereby increase pressure applied to the user's core.

Figure 44:
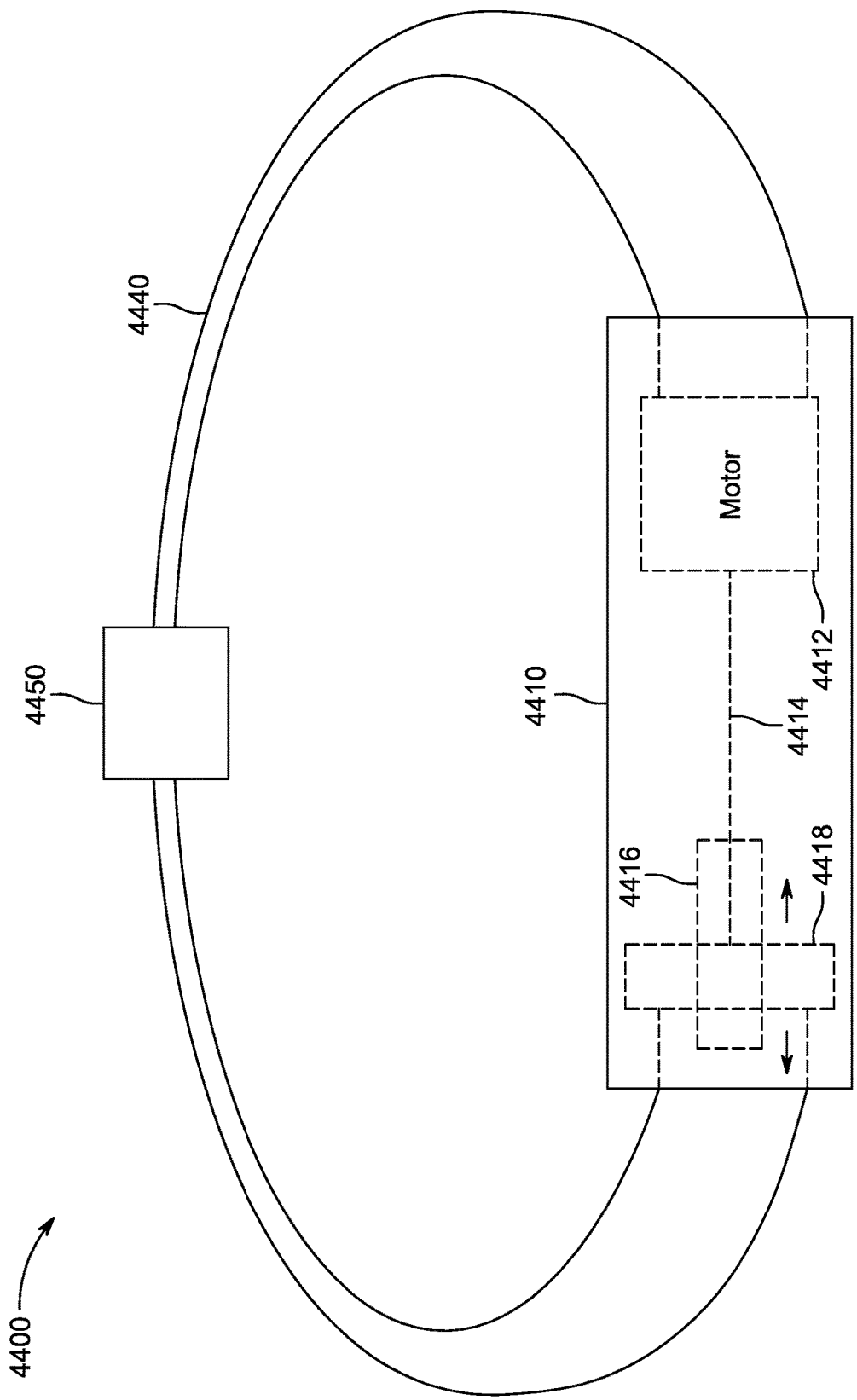
FIG. 44 shows single pouch lumbar support system according to an embodiment.

FIG. 44 shows single pouch lumbar support system 4400 according to an embodiment. Single pouch lumbar support system 4400 differs from system 4300 in that a single pouch is used to contain the moving parts, electronics, and other components needed to operate system 4400. System 4400 includes pouch 4410, belt 4440, and buckle 4450. Located within pouch 4410 are motor 4412, tensioning member 4414, slide track 4416, and sliding member 4418. Sliding member 4418 is operative to slide along slide track 4416 (in the direction of the arrows as shown). In addition, sliding member 4418 may be coupled to belt 4440, such that sliding member 4418 is pulled toward motor 4412, belt 4440 is pulled tighter around the user's body. System 4400 operates using a single slider system, whereas systems 4500 and 4600 use a dual slider system.

Figure 45:
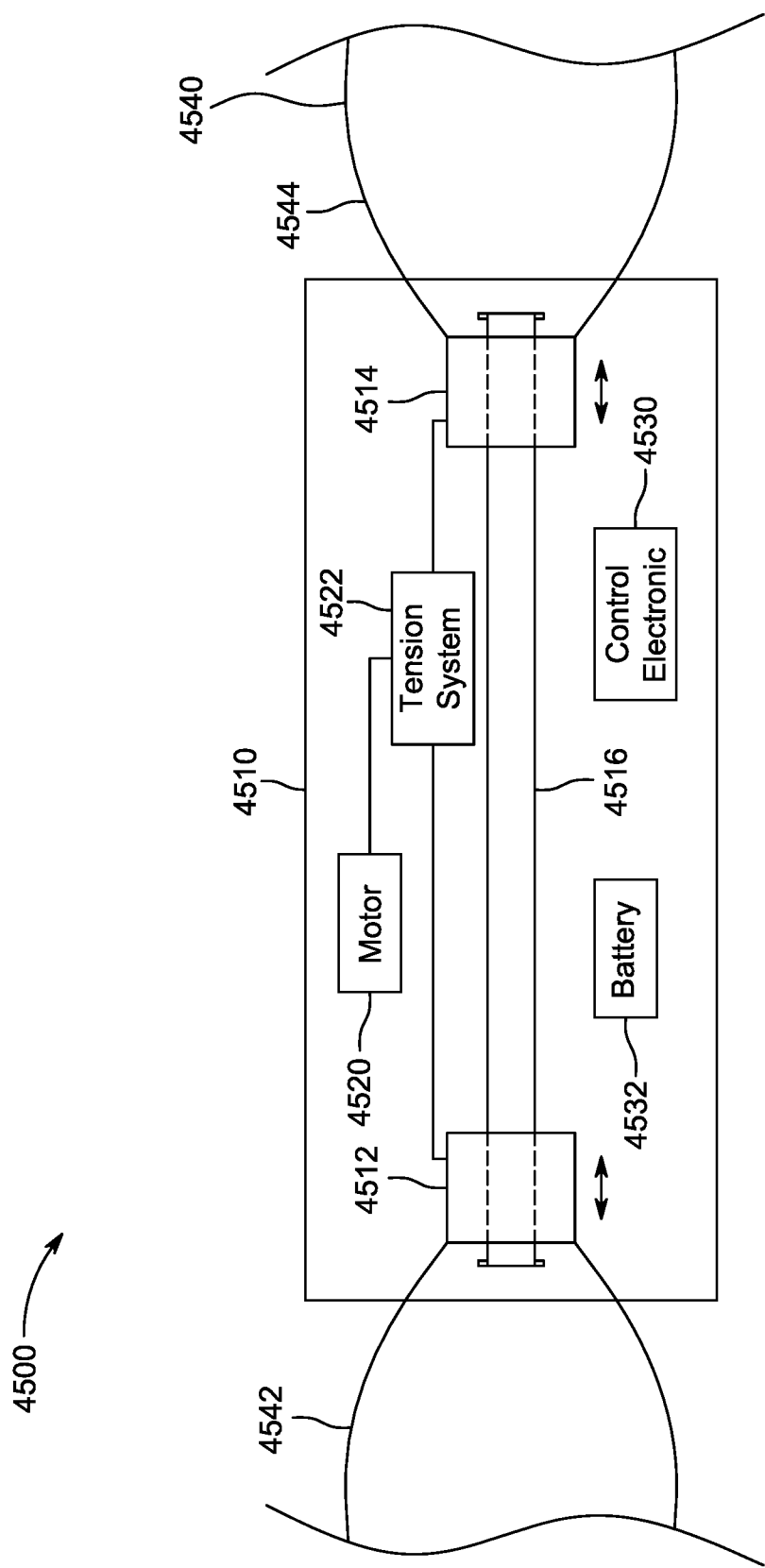
FIG. 45 shows dual slider lumbar support system according to an embodiment.

FIG. 45 shows dual slider lumbar support system 4500 according to an embodiment. System 4500 can include pouch 4510, belt 4540, and buckle (not shown). Pouch 4510 can include slider members 4512 and 4514, slide rail 4516, motor 4520, tension system 4522, control electronics 4530, and battery 4532 among other components (not shown). System 4500 uses a dual slider system that is able to apply equal loading to both attached segments of belt 4540. Belt segment 4542 is coupled to slider member 4512, and belt segment 4544 is coupled to slider member 4514. Slider members 4512 and 4514 may slide axially along slide rail 4516 in response to forces being applied thereto by motor 4520 and tension system 4522. Motor 4520 may drive tension 4522 so that it is able to pull slider members 4512 and 4514 together or enable them to be pulled apart.

Figure 46:
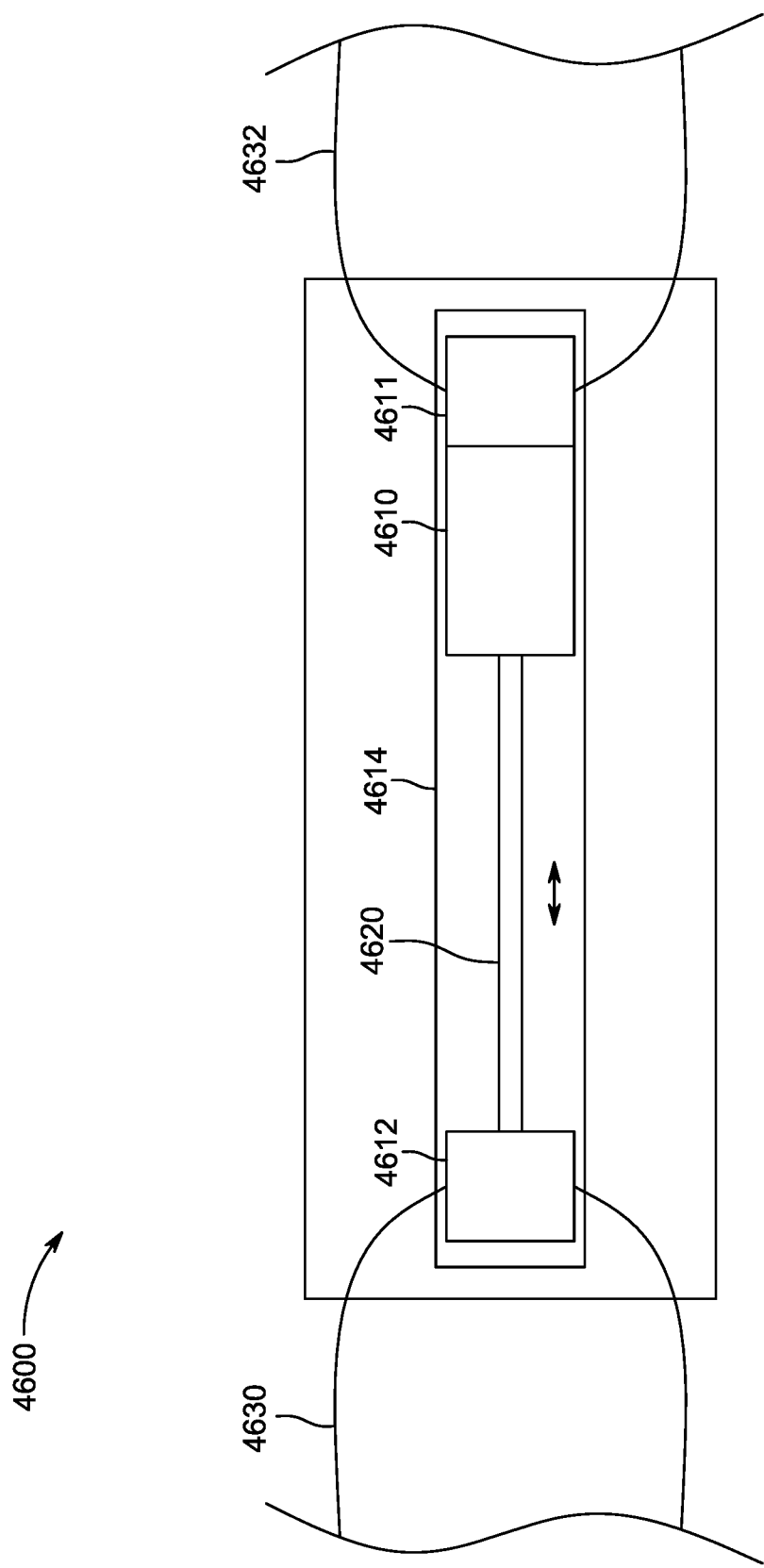
FIG. 46 shows a lumbar system with an in-line tensioning system according to an embodiment.
Figure 47A:
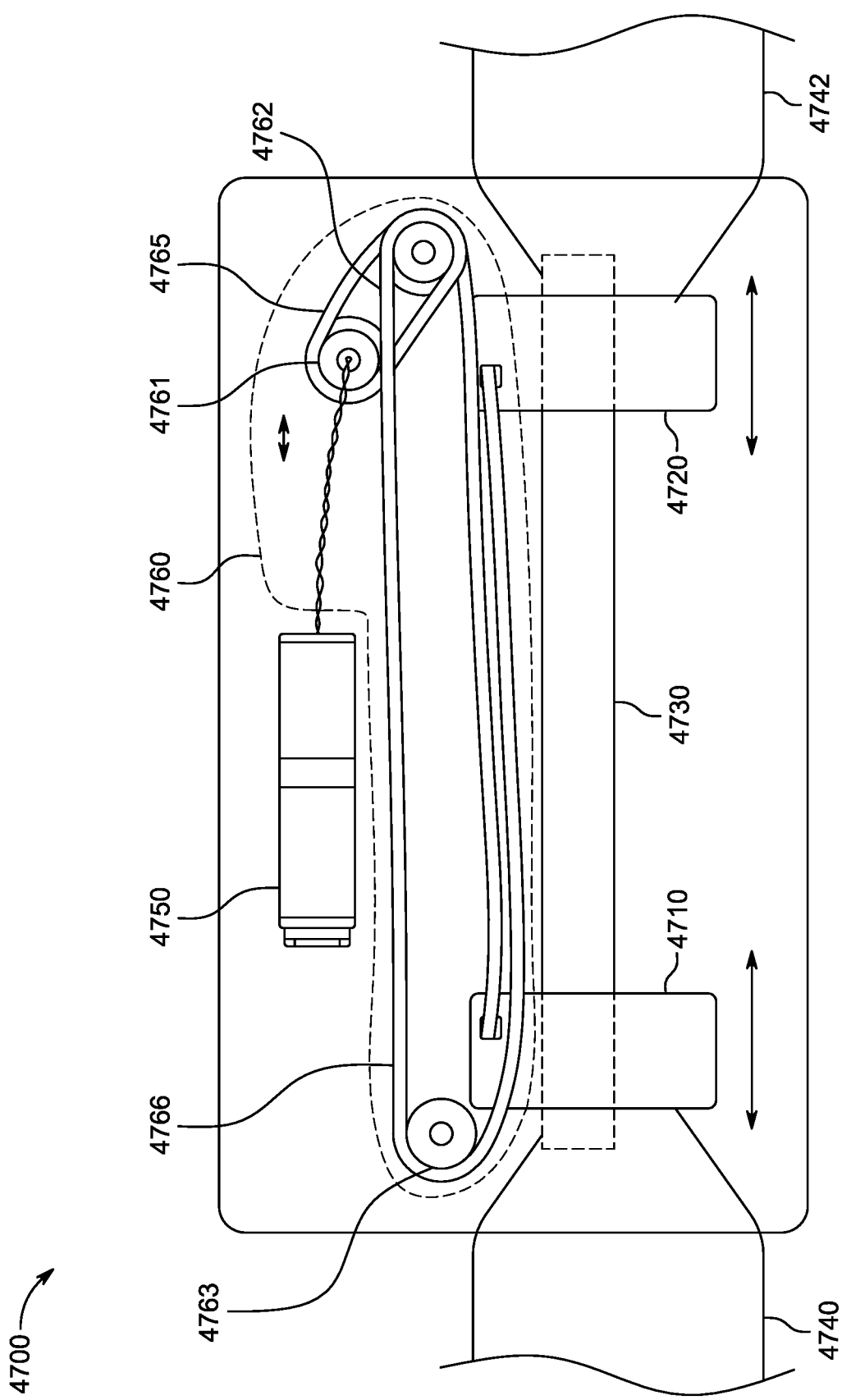
FIG. 47A shows a lumbar system 4700 with a pulley tensioning system according to an embodiment.

Different tensioning systems may be employed in the dual slider lumbar support system embodiments. For example, FIG. 46 shows a lumbar system 4600 with an in-line tensioning system and FIG. 47A shows a lumbar system 4700 with a pulley tensioning system. Referring now to FIG. 46, lumbar system 4600 shows motor 4610 and slide member 4612 positioned to slide axially along slide rail 4614 in response to motor 4610 increasing and decreasing tension of tensioning member 4620. Motor 4610 may be mounted in a motor carriage member 4611, which enables motor 4610 to slide along rail 4614. Belt segment 4630 is attached to sliding member 4612 and belt segment 4632 is attached to motor carriage member 4611. When motor 4610 operates to increase tension of tensioning member 4620, both sliding member 4612 and motor carriage member 4611 are pulled together, thereby increasing the pressure exerted by belt segments 4630 and 4632 being applied to the user.

Figure 47B:
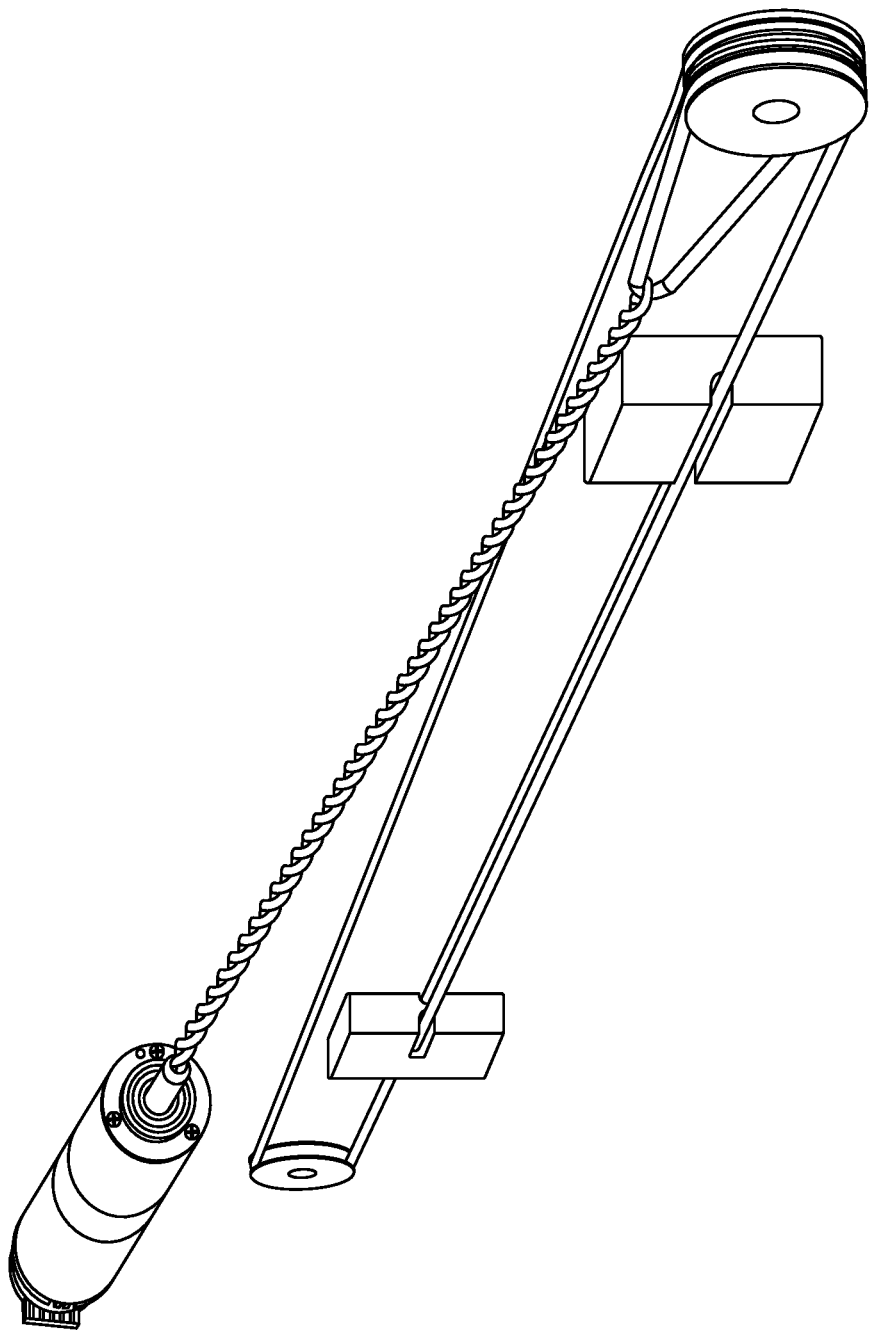
FIGS. 47B and 47C show different pulley tensioning system arrangements according to various embodiments.
Figure 47C:
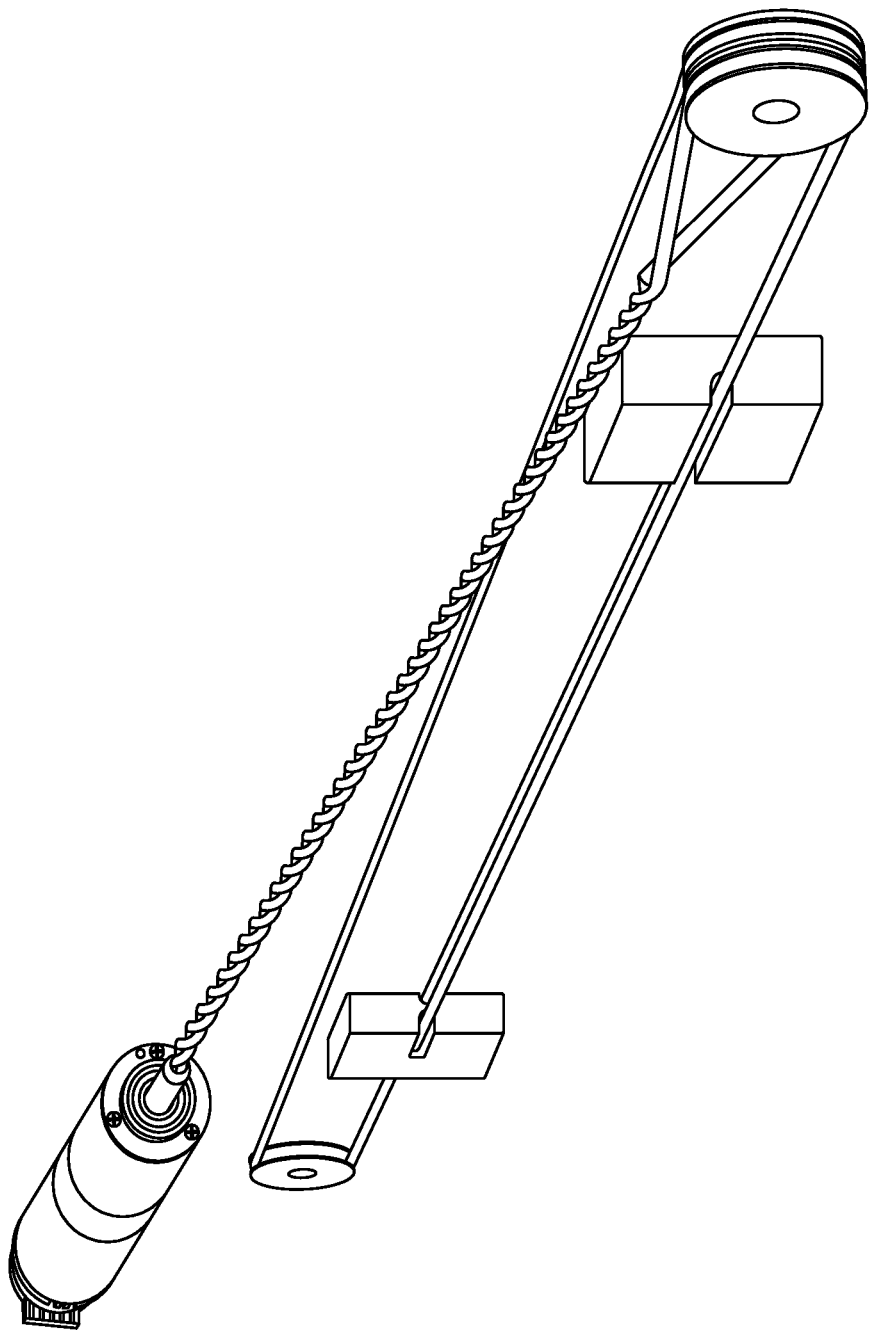

Referring now to FIG. 47A, lumbar system 4700 includes first and second sliding members 4710 and 4720 mounted to slide rail 4730. First sliding member 4710 is connected to belt segment 4740 and second sliding member 4720 is connected to belt segment 4742. Motor 4750 is connected to pulley tensioning system 4760, which together are operative to increase tension of lumbar system 4700 by pulling sliding members 4710 and 4720 together. Pulley tensioning system 4760 can include pulley 4671, pulley 4672, and pulley 4673. Pullies 4672 and 4673 may be held in place, whereas pulley 4671 may move in response to motor 4750 operation. First pulley line 4765 may be looped around pullies 4761 and 4762. Second pulley line 4766 may be looped around pullies 4762 and 4763 and secured to sliding members 4710 and 4720 as shown. FIGS. 47B and 47C show different pulley tensioning system arrangements.

Figure 48:
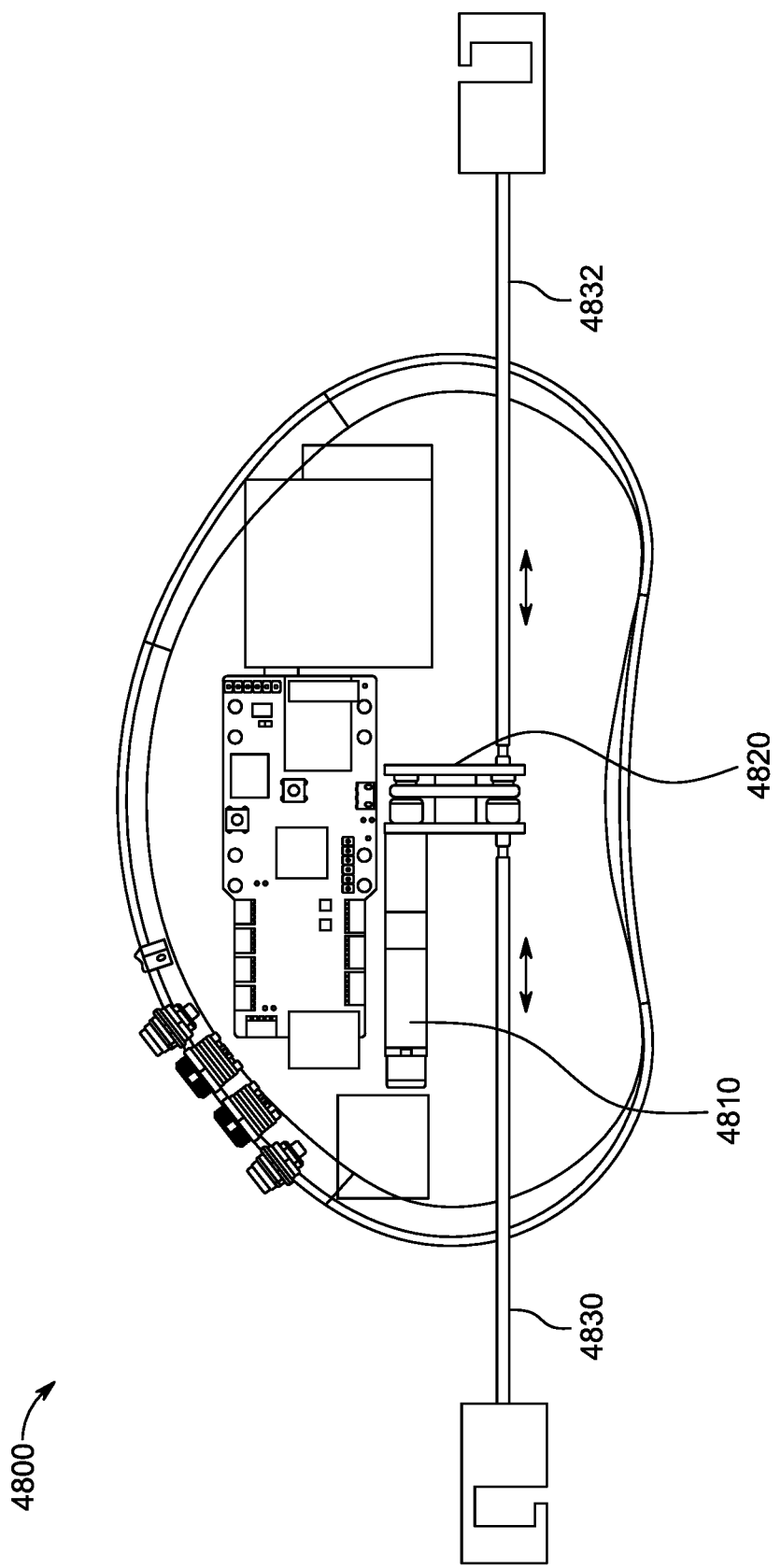
FIG. 48 shows lumbar system that uses a direct drive system to adjust tension, according to an embodiment.

FIG. 48 shows lumbar system 4800 that uses a direct drive system to adjust tension, according to an embodiment. Lumbar system 4800 can include motor 4810, drive system 4820, and tension segments 4830 and 4832, among other components. During operation, motor 4810 drives drive system 4820 to pull tension segments 4830 and 4832 together or to allow them to be pulled apart.

Figure 56:
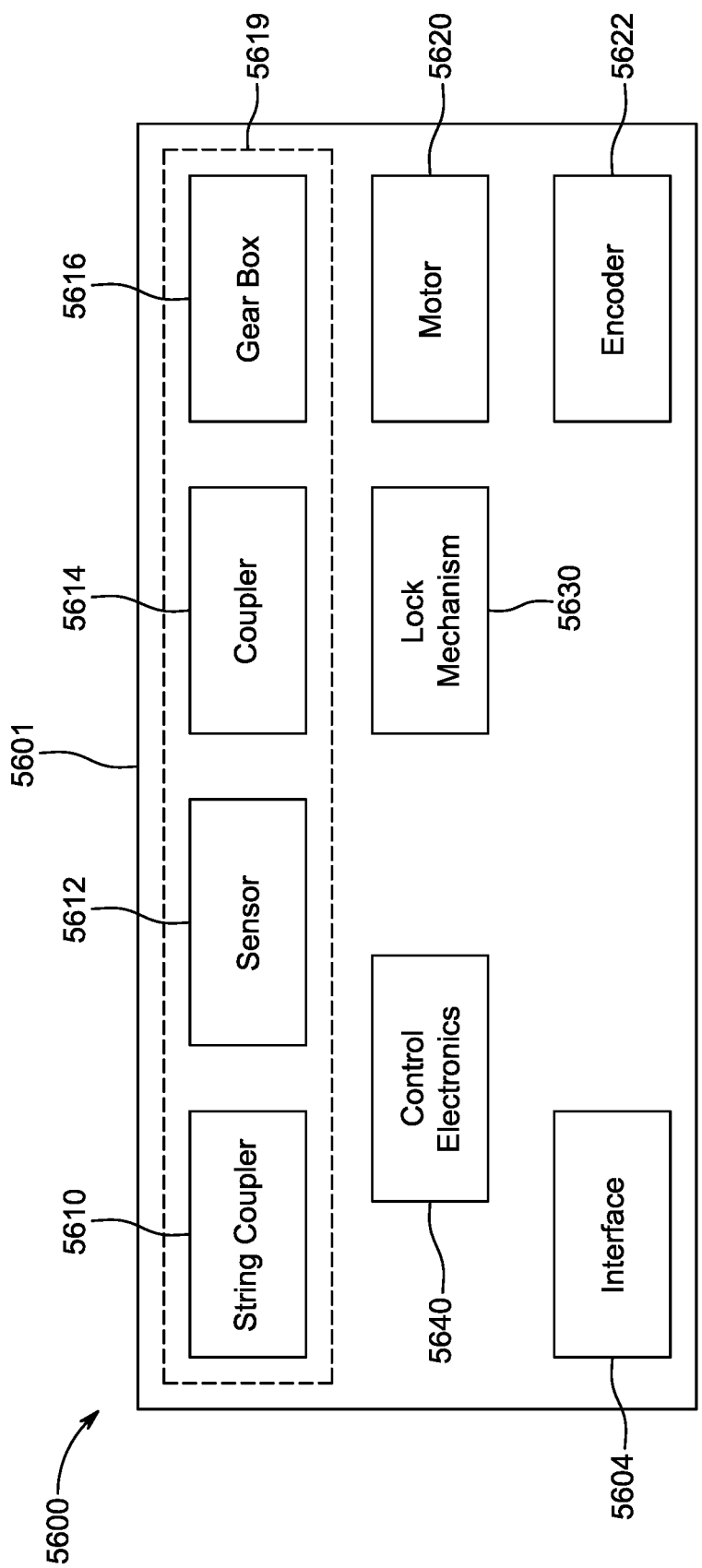
FIG. 56 shows illustrative flexdrive system according to an embodiment.

FIG. 56 shows illustrative flexdrive system 5600 according to an embodiment. Flexdrive system 5600 may be a power segment that is attached to a load distribution member or integrated into a patch assembly. Flexdrive system 5600 is responsible for actuating exosuit assistance movements by controlling a length of a tensioning member coupled between load distribution members (e.g., thigh and waist load distribution members). Flexdrive 5600 is connected to a tensioning member such as a twisted string that is twisted to shorten the length of the tension member or unwound to increase the length of the tension member. Flexdrive 5600 is designed to control tensioning with a desired amount of speed and power, while conserving power consumption and minimizing its footprint within the exosuit.

Flexdrive 5600 can include housing 5601, interface 5604, string coupler 5610, sensor 5612, coupler 5614, gearbox 5616, motor 5620, encoder 5622, lock mechanism 5630, control electronics 5640. Housing 5601 may be any suitable structure for containing the various components of flexdrive 5600. In some embodiments, housing may be a hard, non-flexible material or a relatively soft, partially compliant material. Interface 5604 may include attachment mechanisms necessary for securing flexdrive 5600 to the exosuit or a patch assembly.

String coupler 5610, sensor 5612, coupler 5614, and/or gearbox 5616 may be collectively referred to as string rotation assembly 5619. String rotation assembly 5619 is connected to a tensioning member (not shown) and translates rotation of motor 5020 to the tensioning member. In addition, when lock mechanism 5630 is in the locked position, string rotation assembly 5619 is also locked in position and does not rotate. Gearbox 5616 may be coupled to motor 5620 and is operative to translate revolutions of motor 5620 to string rotation revolutions (e.g., which may be faster or slower than the motors, or increase or decrease torque as required). Coupler 5614 may be coupled to gearbox 5616 and string coupler 5610 and is operative to rotate string coupler 5610. String coupler 5610 may be coupled to a tensioning member (e.g., twisted string). Sensor 5612 may be positioned between coupler 5616 and string coupler 5610 and is operative to monitor rotation of string coupler 5610. In some embodiments, string coupler 5610 can be directly coupled to motor 5620. In other embodiments, coupler 5616 may be coupled directly to motor 5020.

Motor 5620 may be any suitable motor for driving string rotation assembly 5619. Motor 5620 may have a shaft that extends from both ends of motor 5620 such that a first end interfaces with string rotation assembly 5619 and a second end interfaces with lock mechanism 5630. Such an arrangement may enable lock mechanism 5630 to lock shaft rotation in place without requiring motor 5020 to expend energy to hold string rotation assembly 5619 in place.

Encoder 5622 may be operative to monitor speed and/or position of a shaft of motor 5620. Control electronics 5640 may control operation of flexdrive 5600 by, for example, controlling operation of motor 5620, lock mechanism 5630, and monitoring data received from sensor 5612 and encoder 5622.

Figures 19A, 19B:
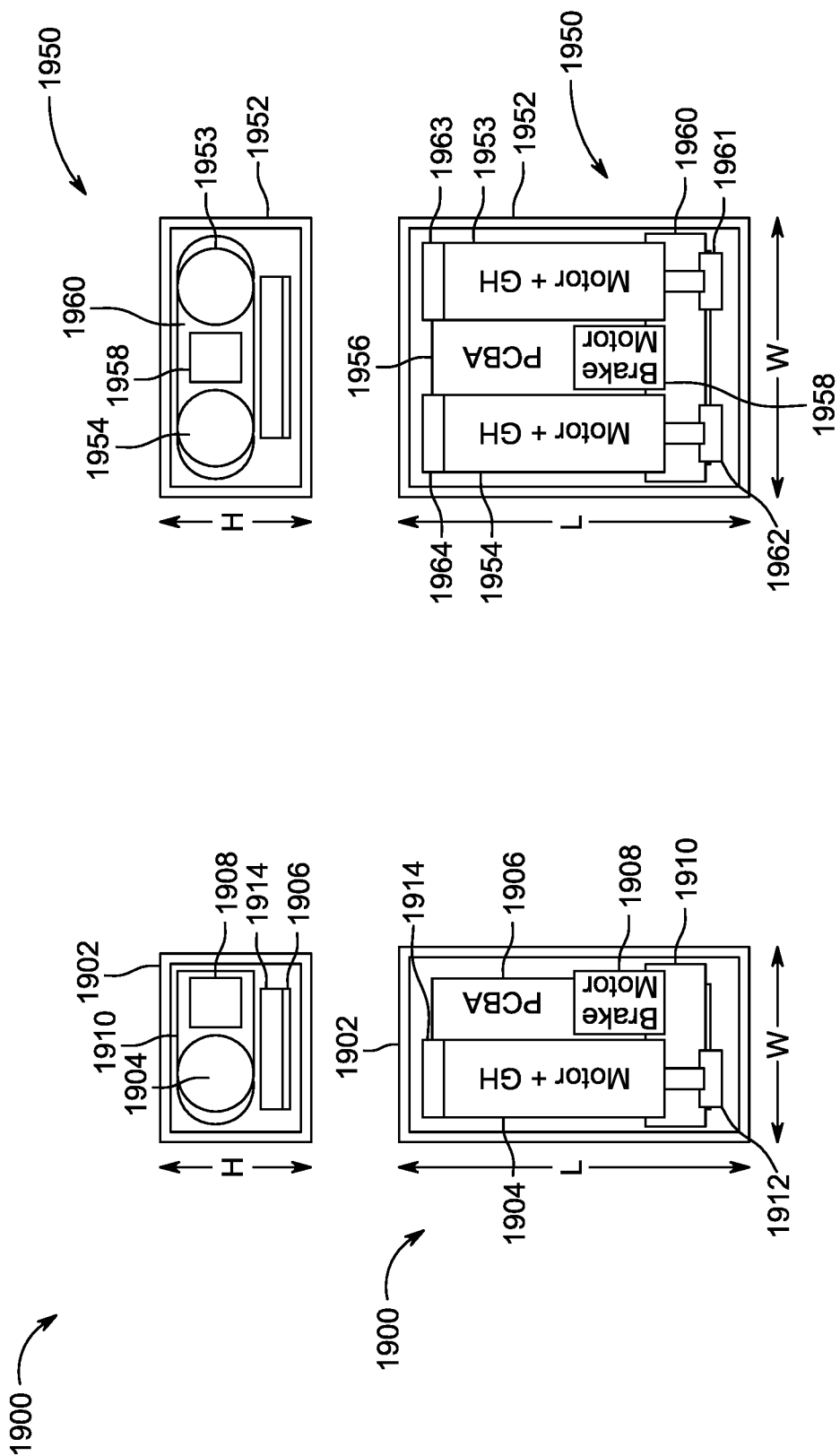
FIGS. 19A-19B show different flexdrive modules according to various embodiments.

FIGS. 19A-19B show different flexdrive modules according to various embodiments. FIG. 19A shows single motor flexdrive module 1900 and FIG. 19 shows dual motor flexdrive module 1950. Both FIGS. 19A and 19B show plan and top views of modules 1900 and 1950. Referring now specifically to FIG. 19A, module 1900 can include housing 1902, motor 1904, printed circuit board (PCB) 1906, brake motor 1908, brake mechanism 1910, sensor/string coupler 1912, encoder 1914. Referring now to FIG. 19B, module 1950 may include housing 1952, motors 1953 and 1954, printed circuit board (PCB) 1956, brake motor 1958, brake mechanism 1960, sensor/string couplers 1961 and 1962, and encoders 1963 and 1964. The arrangements of the components within modules 1900 and 1950 can be rearranged to accommodate different footprint sizing. By combining two motors into a single package (as shown in module 1950), space savings can be realized by having the two motors share components.

Figure 20A:
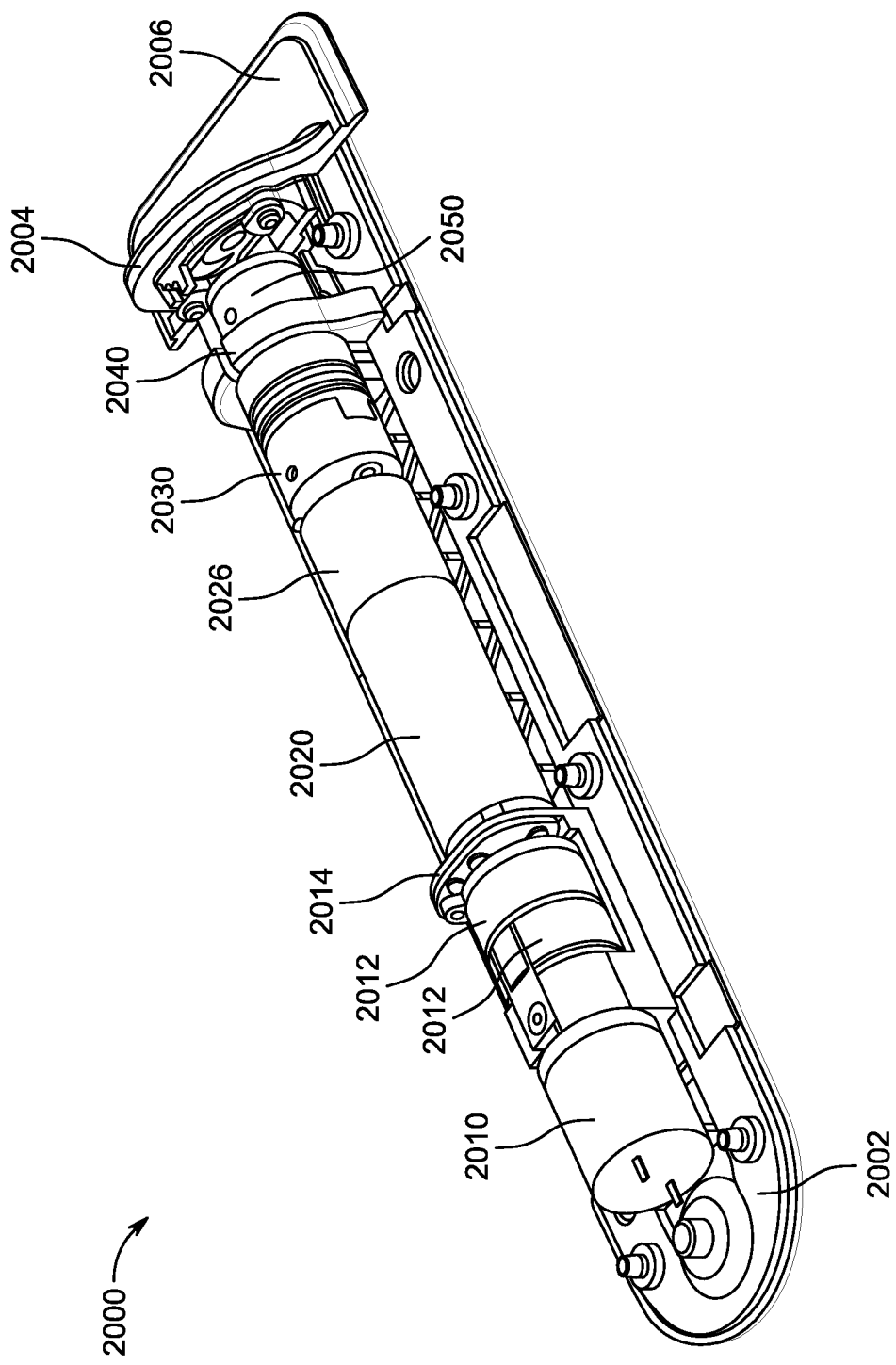
FIG. 20A shows a flexdrive module according to an embodiment.

FIG. 20A shows flexdrive module 2000 according to an embodiment. FIGS. 20B-20J shows different views of module 2000 or portions thereof. The following discussion will collectively reference FIGS. 20A-20J. Flexdrive module 2000 may be incorporated into a leg patch assembly as discussed above, and in particular, may be secured within a flexdrive enclosure. Module 2000 can include base 2002, faceplate 2004, patch interface 2006, lock motor 2010, lock mechanism 2012, encoder 2014, drive motor 2020, gearbox 2026, coupler 2030, sensor 2040, and string coupler 2050.

Figure 20B:
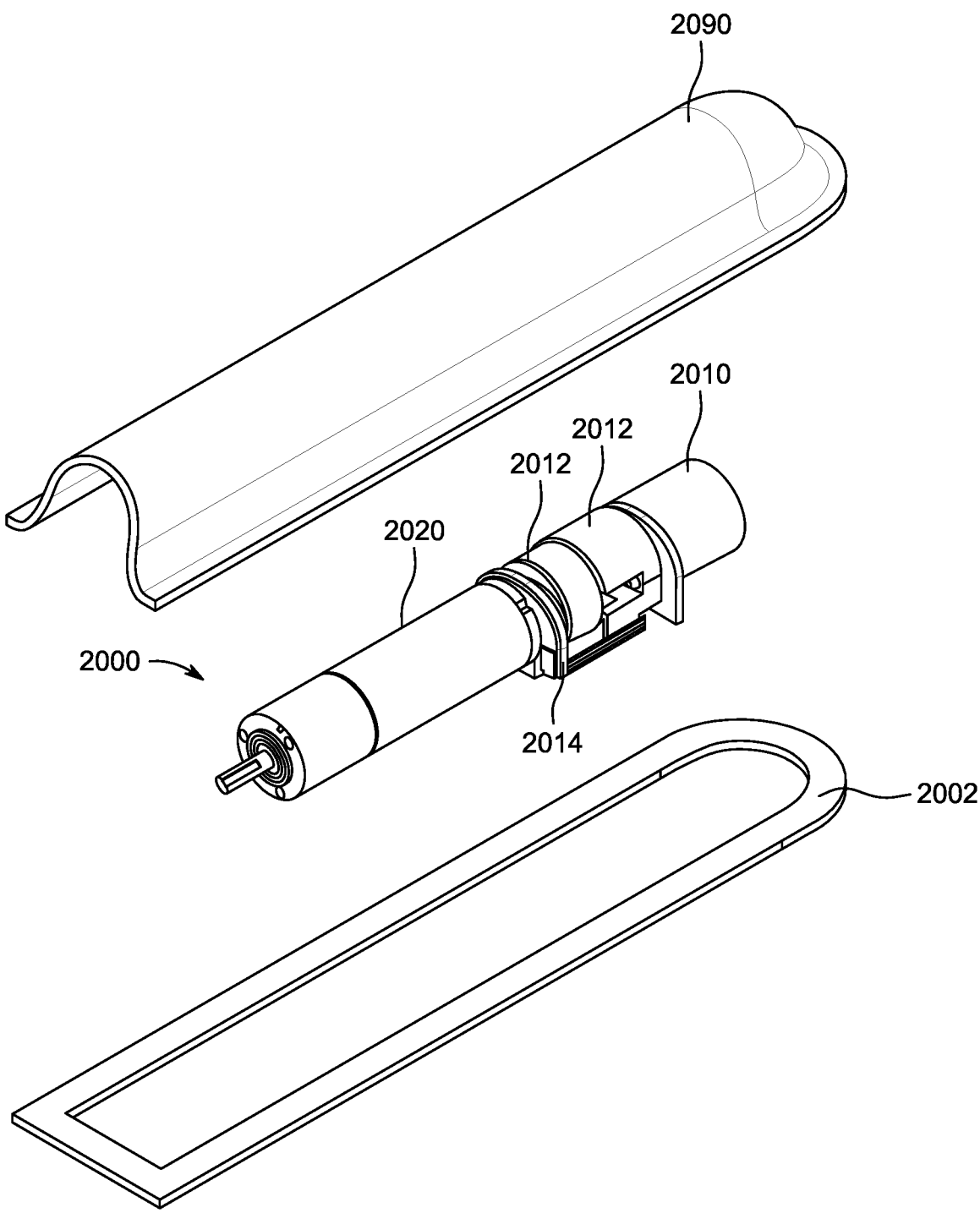
FIGS. 20B-20K shows different views of the module of FIG. 20A or portions thereof according to various embodiments.
Figure 20C:
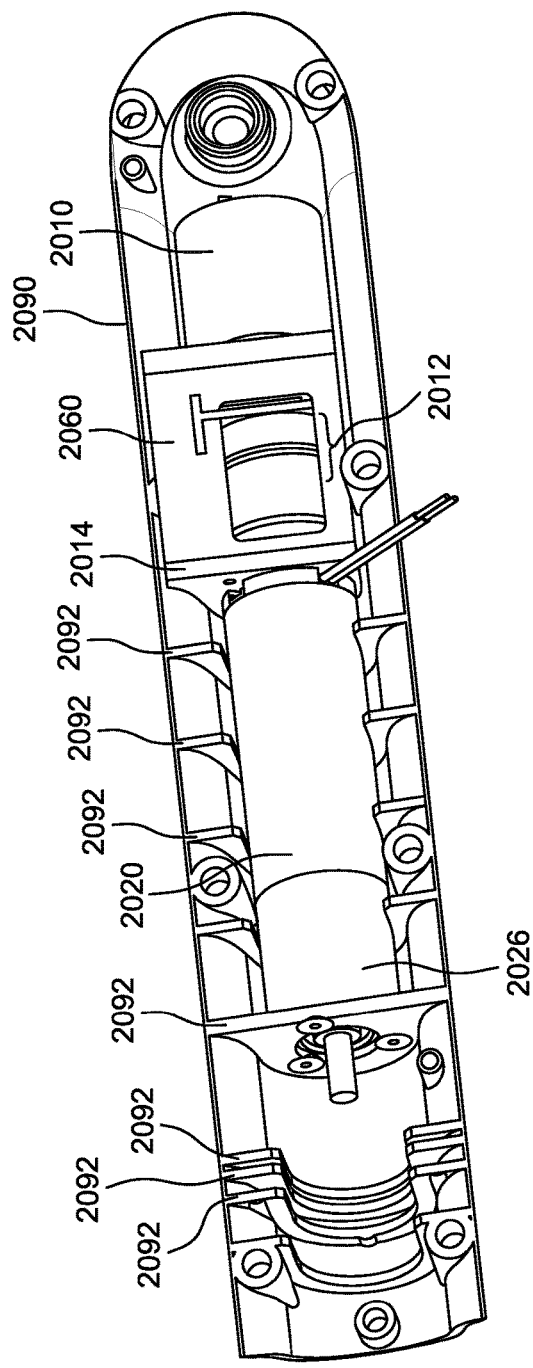
Figure 20D:
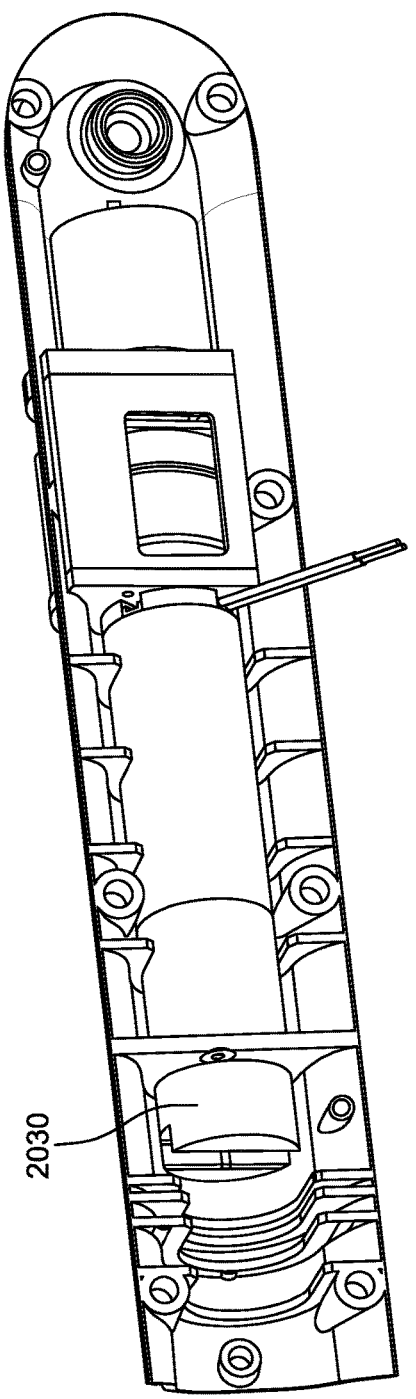
Figure 20E:
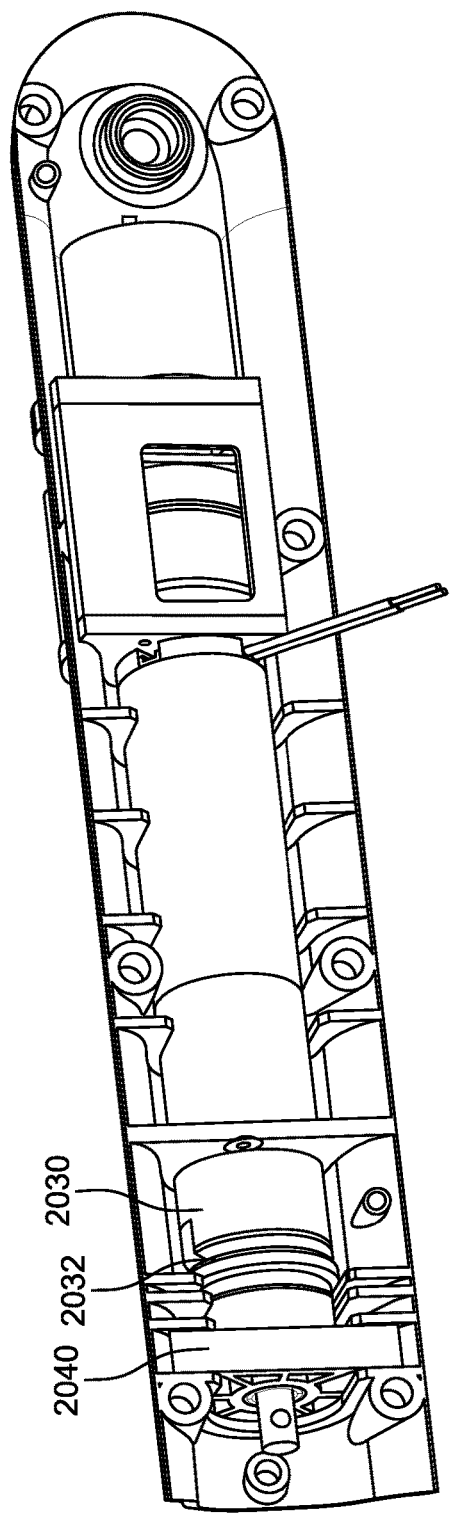
Figure 20F:
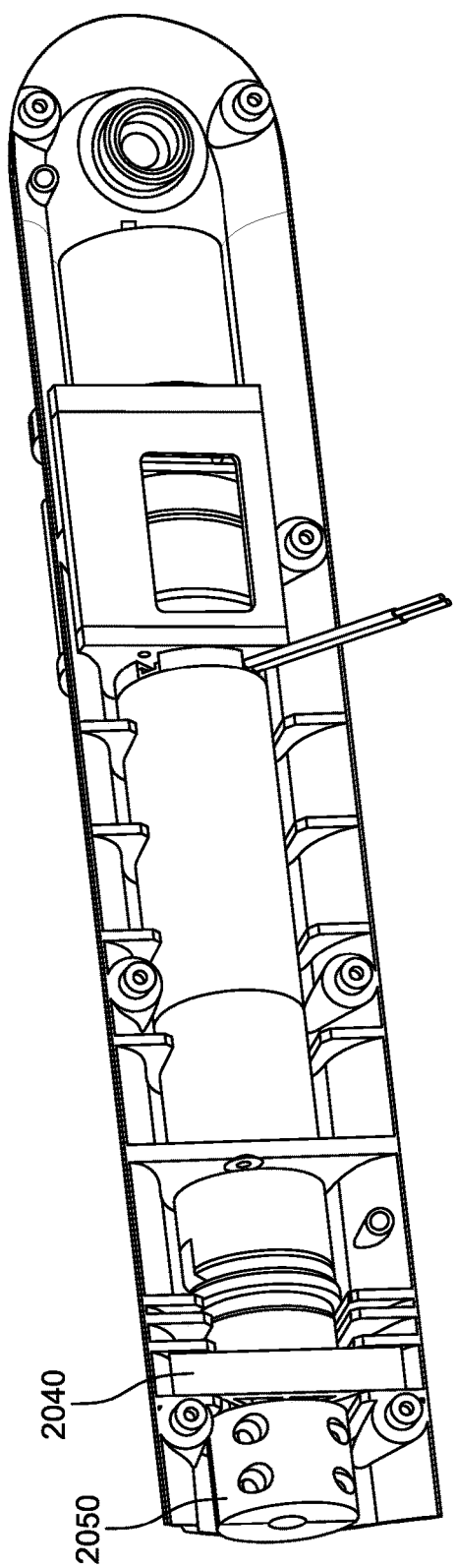

FIG. 20B shows base 2002, various components of module 2000 (such as lock motor 2010, lock mechanism 2012, encoder 2014, and drive motor 2020), and cover 2090. Cover 2090 may fit around the components of the flexdrive and be secured to base 2002. FIG. 20C shows flexdrive module 2000 with base 2002 removed. Cover 2090 can include ribs 2092 to support and register components of the flexdrive. FIG. 20D-20F also show flexdrive module 2000 in different stages of assembly. In particular, FIG. 20D shows addition of coupler 2030, FIG. 20E show addition coupler members 2032, sensor 2040, and FIG. 20F shows a string coupler 2050.

Figure 20G:
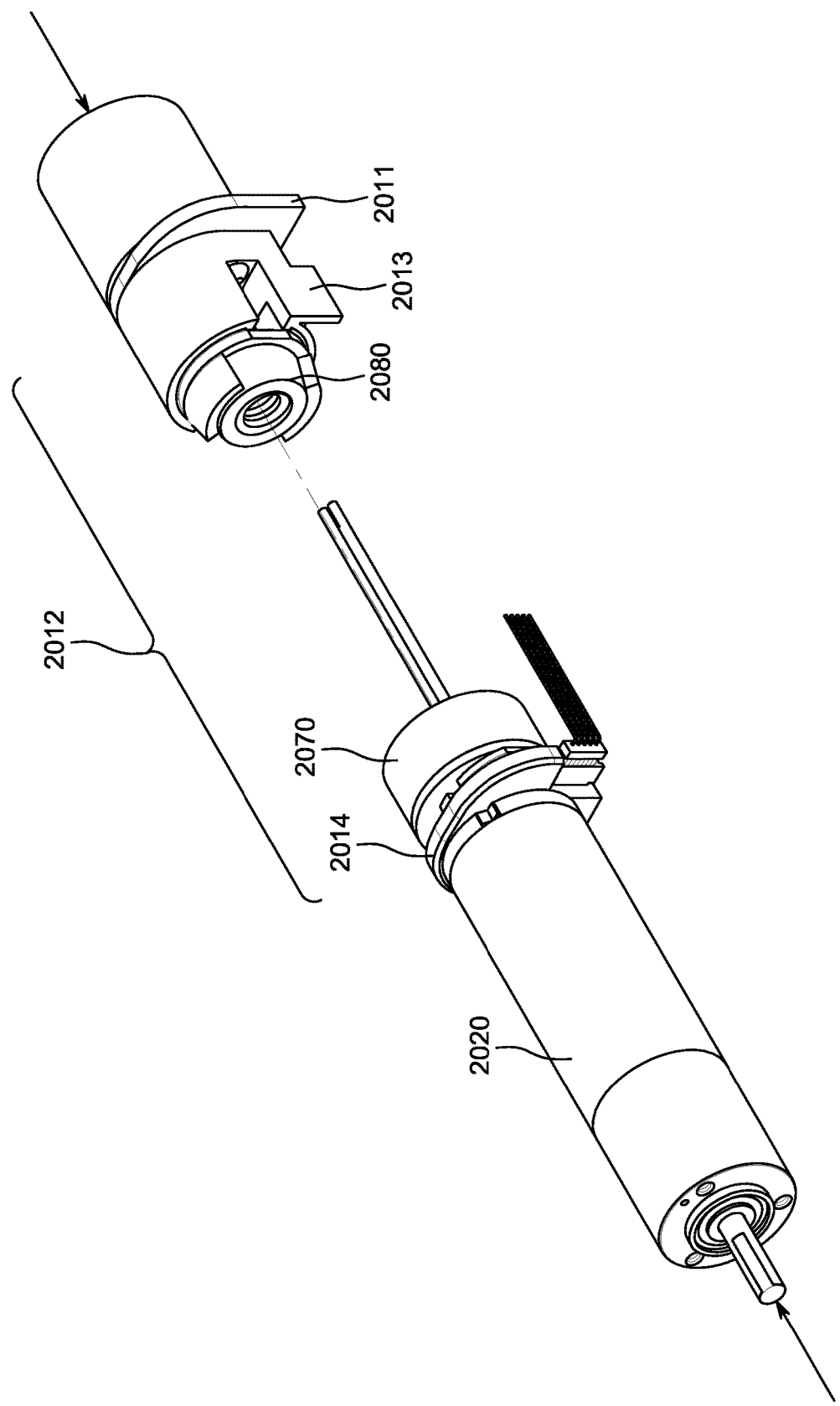

FIG. 20G shows a partial exploded view of a portion of flexdrive module 2000. In particular, FIG. 20G shows drive motor 2020 coupled to encoder 2014 and lock cone 2070 of lock mechanism 2012. FIG. 20G also shows lock motor 2010 coupled to locking plate 2011, which is coupled to block 2013. Nut 2072 (which is part of may be connected to locking motor 2011 via locking screw 2081 (shown in FIG. 20I).

Figure 20H:
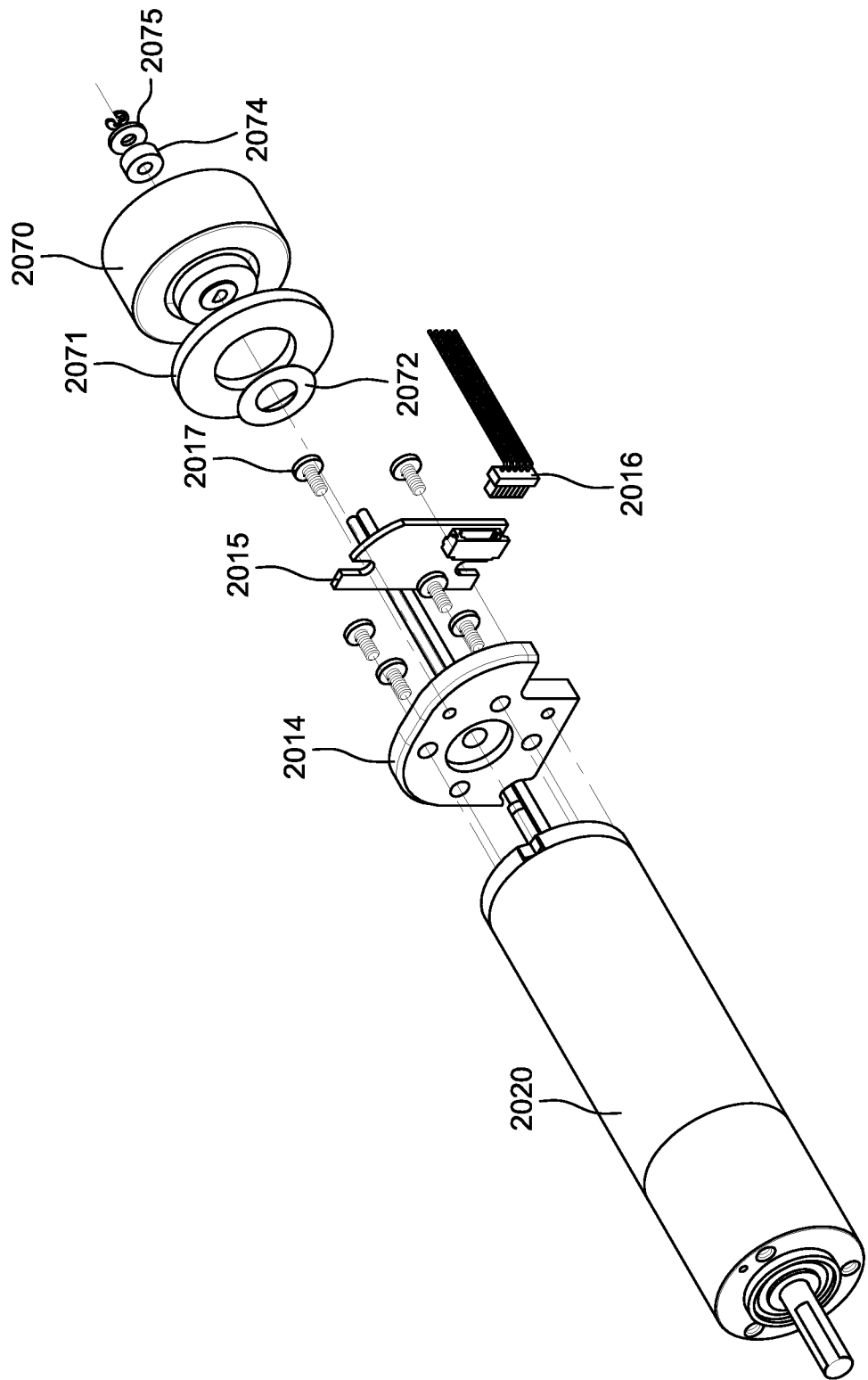

FIG. 20H shows an illustrative exploded view of drive motor 2020, encoder 2014, and lock cone 2070. The exploded view shows encoder PCB 2015, encoder power/data wires 2016, fasteners 2017 that couple PCB 2015 and encoder 2014 to drive motor 2020. Also shown in FIG. 20H is washer 2072, encoder magnet 2071, female lock cone 2070, retaining washer 2074, and retaining ring 2075. A shaft (not shown) extends from drive motor and passes through encoder 2014, washer, encoder magnet 2071, female lock cone 2070, retaining washer 2074, and is capped with retaining ring 2075. Lock cone 2070 may turn in concert with the drive shaft of drive motor 2020. Thus, when female lock cone 2070 is locked in place, the drive shaft of drive motor 2020 may not be permitted to rotate.

Figure 20I:
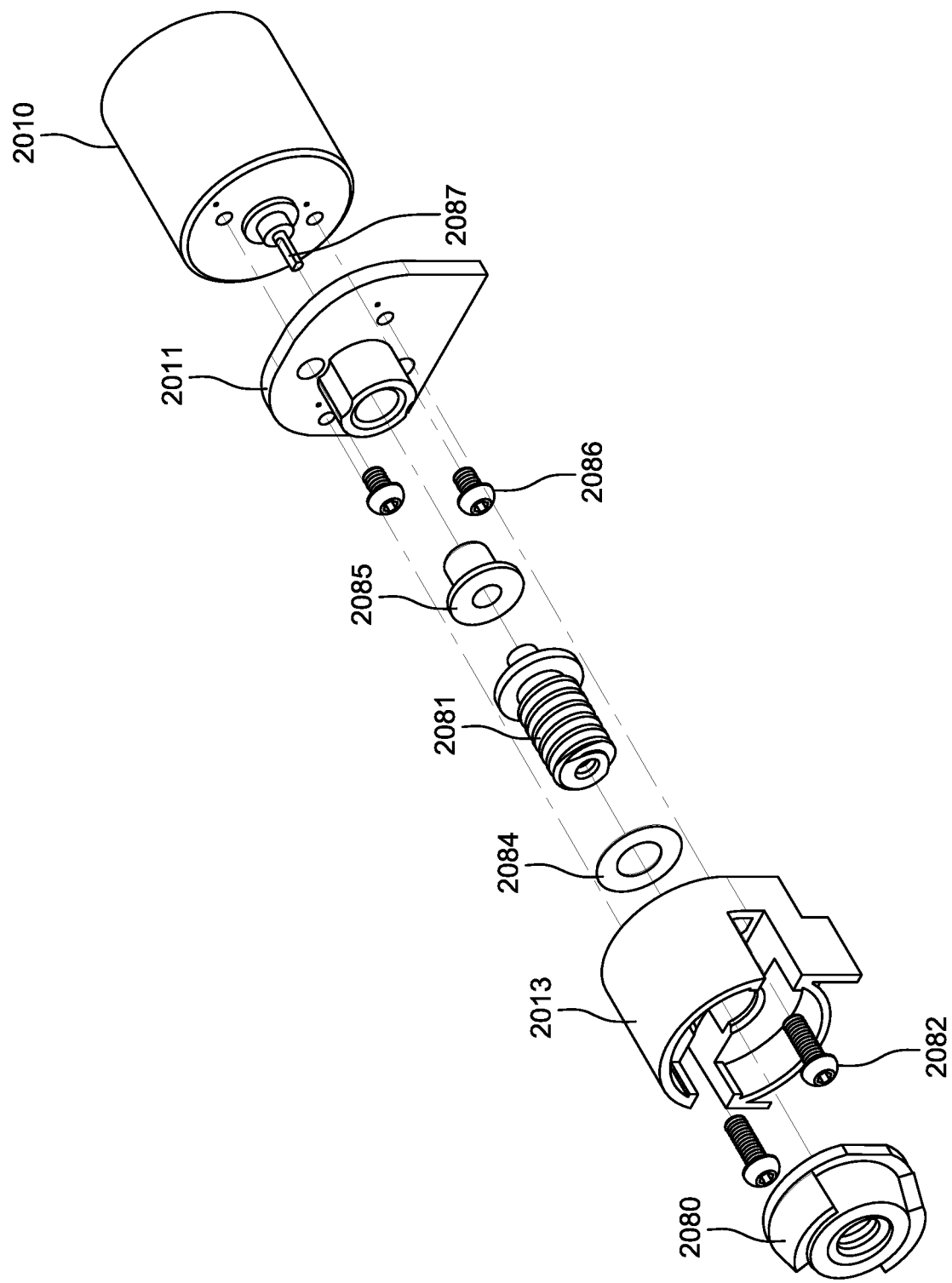

FIG. 20I shows an illustrative exploded view of lock motor 2010, locking plate 2011, block 2013, nut 2072, locking screw 2081, among other components. Fasteners 2086 secure locking plate 2011 to lock motor 2010. Lock motor shaft 2087 pass through bushing 2085 is secured to locking screw 2081. Locking screw 2081 may pass through washer 2084 and block 2013 and is secured to male lock cone 2080. Fasteners 2082 may secure block 2013 to locking plate 2011. When lock motor 2010 rotates in a locking direction, locking screw 2081 rotates and causes male locking cone 2080 to be driven axially into female locking cone 2070. When male locking cone 2080 is sufficiently seated within female locking cone, the shaft of drive motor 2020 is not permitted to rotate. When lock motor 2010 rotates in an unlocking direction, locking screw 2081 rotates and causes male locking cone 2080 to be pulled out of female locking cone 2070, thereby enabling the shaft of drive motor 2020 to rotate.

Figure 20J:
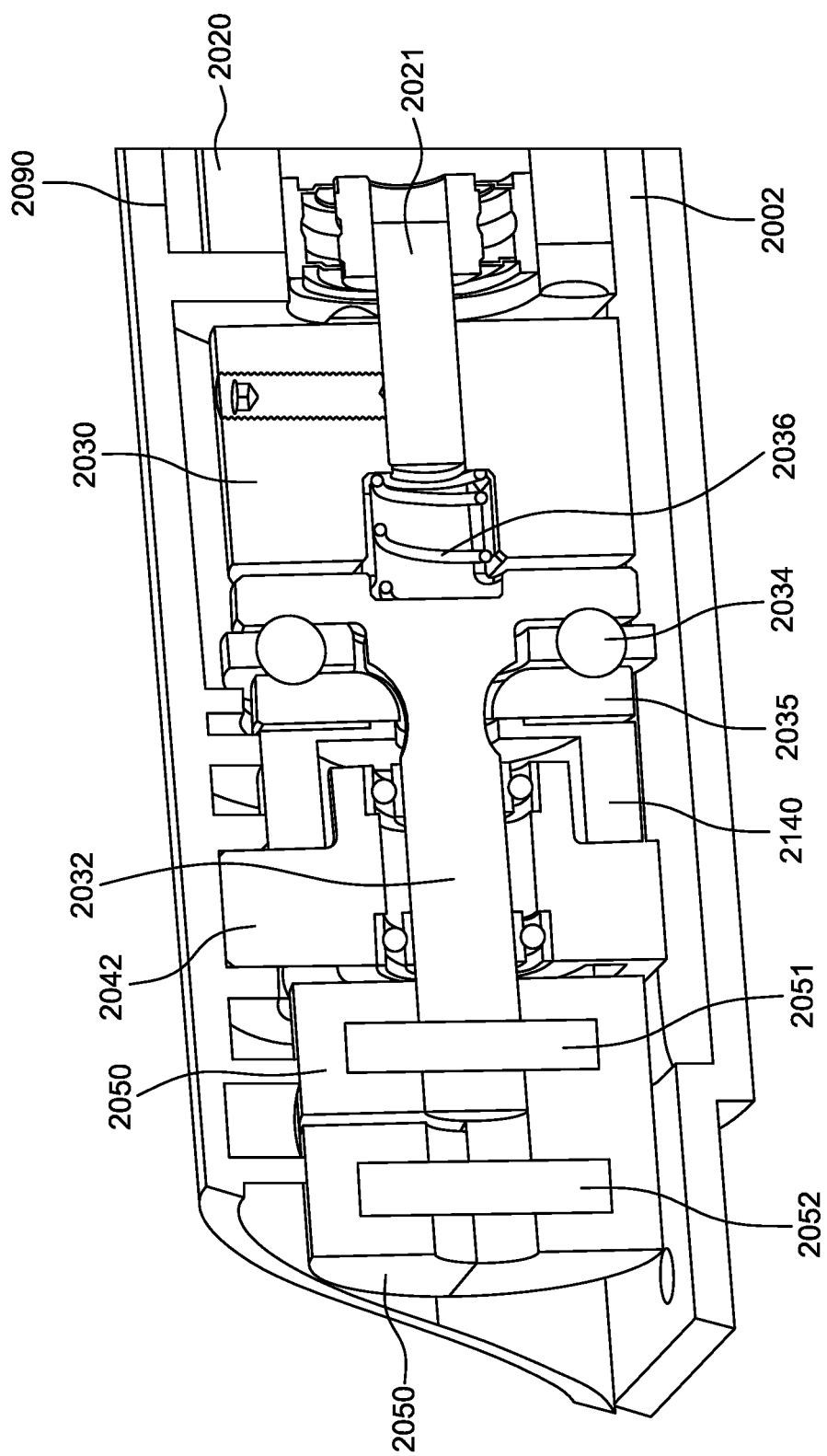

FIG. 20J shows an illustrative cross-sectional view base 2002, cover 2090, coupler 2030, sensor 2040, and string coupler 2050, among other features. String drive coupler member 2032 is shown connected to coupler 2030 and string coupler 2050, passing through bearings 2042, 2034 and 2035, and force sensor 2040. Compression spring 2036 may exist between coupler 2030 and coupler member 2032. Coupler 2030 is connected to drive shaft 2021 of driver motor 2020. Dowel 2051 may secure string coupler to coupler member 2032. Dowel 2052 may be secured to a twisted string (not shown).

Figure 20K:
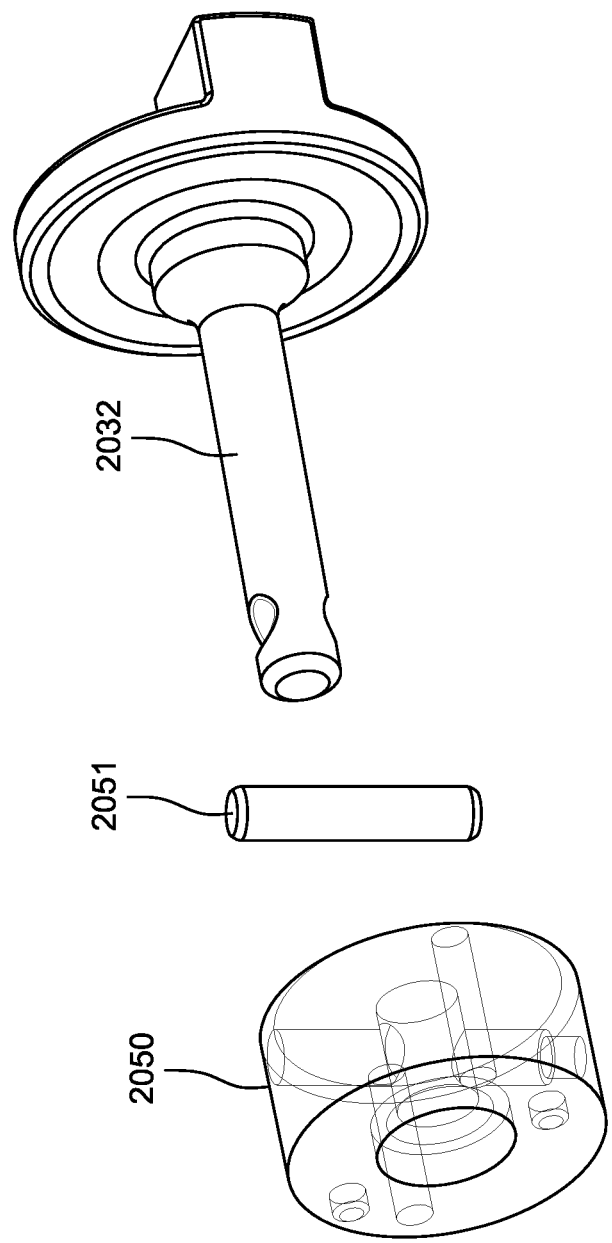

FIG. 20K shows illustrative exploded view of string drive coupler member 2032, string coupler 2050, and dowel 2051.

Figure 21A:
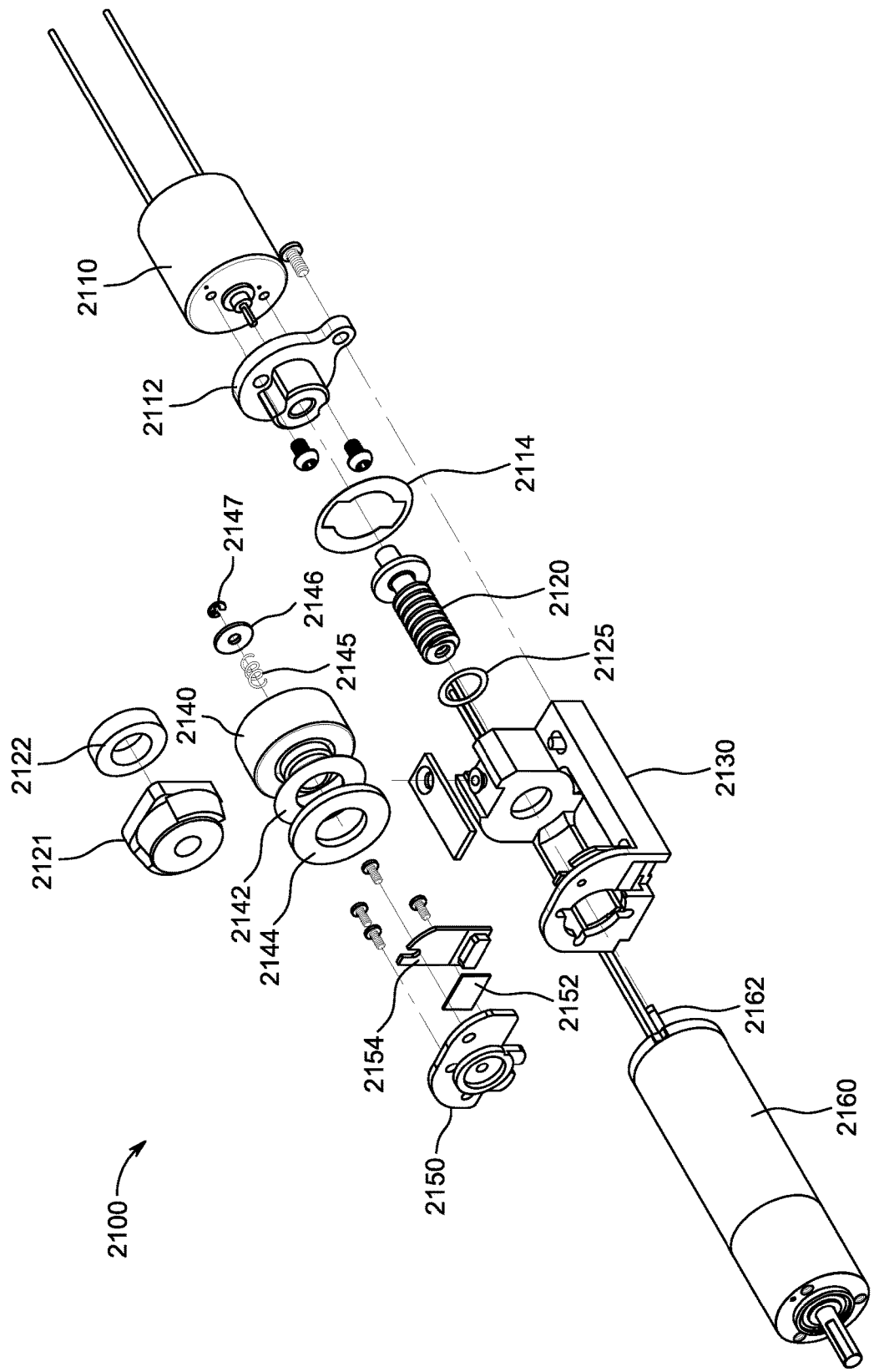
FIG. 21A shows an illustrative exploded view of a flexdrive module according to an embodiment.
Figure 21B:
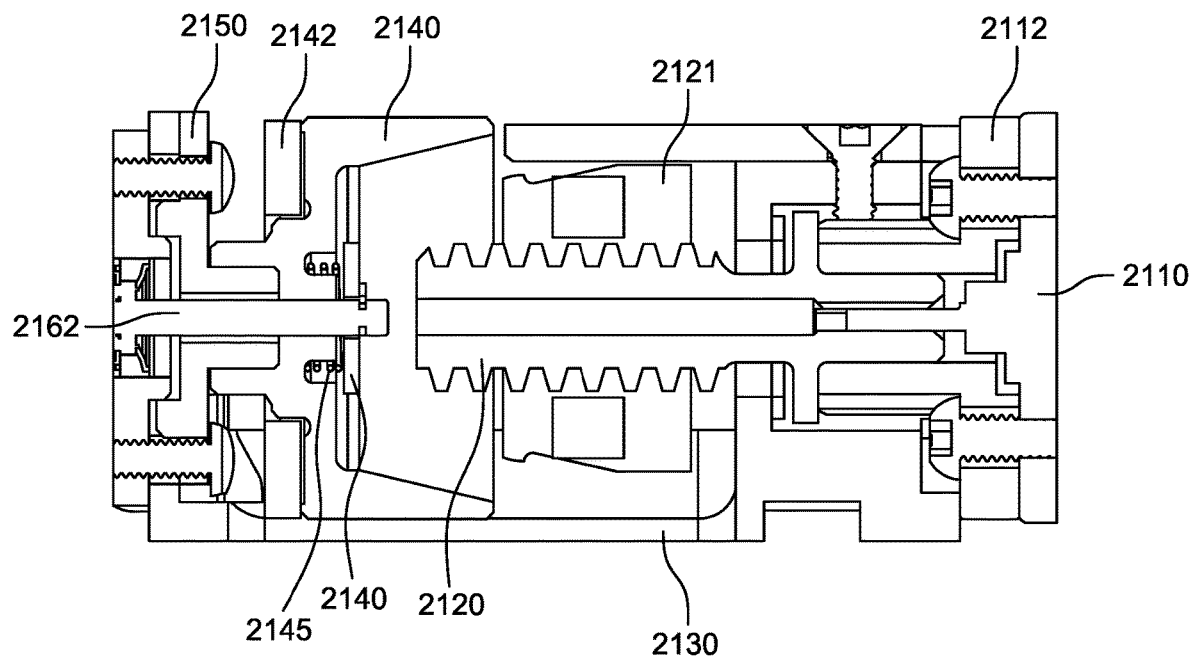
FIG. 21B shows an illustrative cross-sectional view of a flexdrive module according to an embodiment.
Figure 21C:
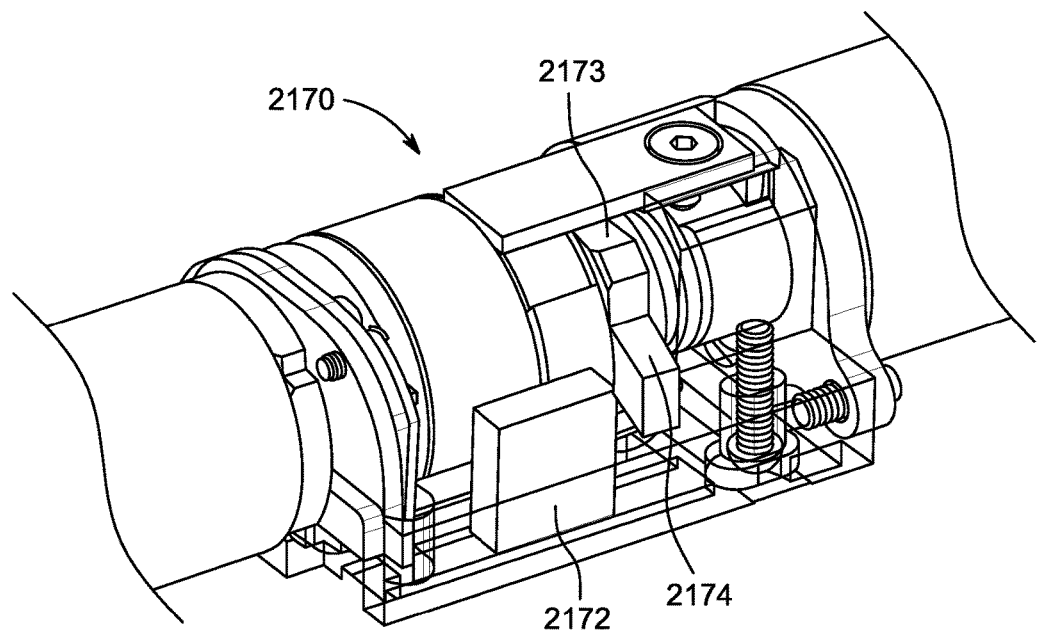
Figure 21D:
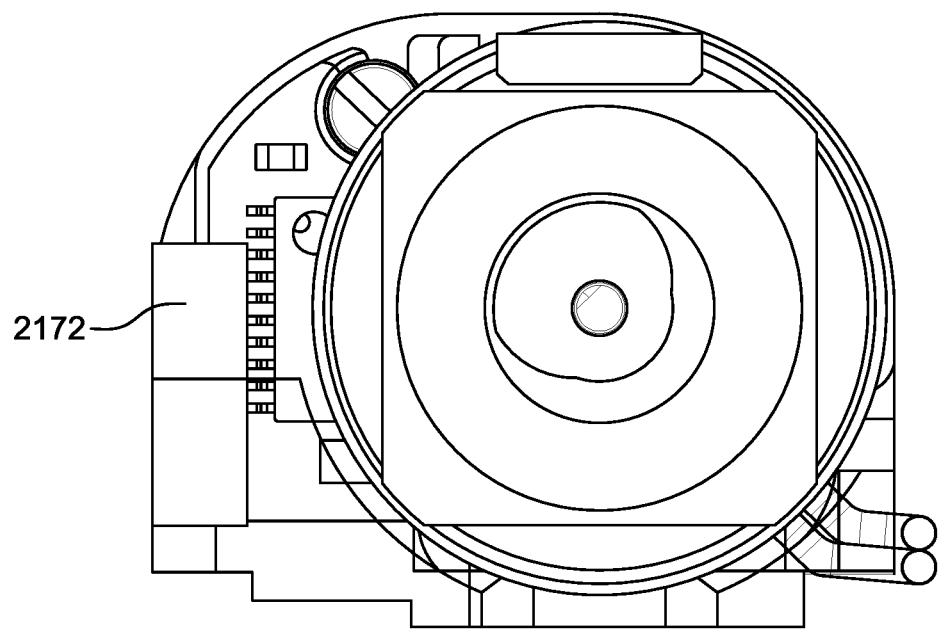
Figure 21E:
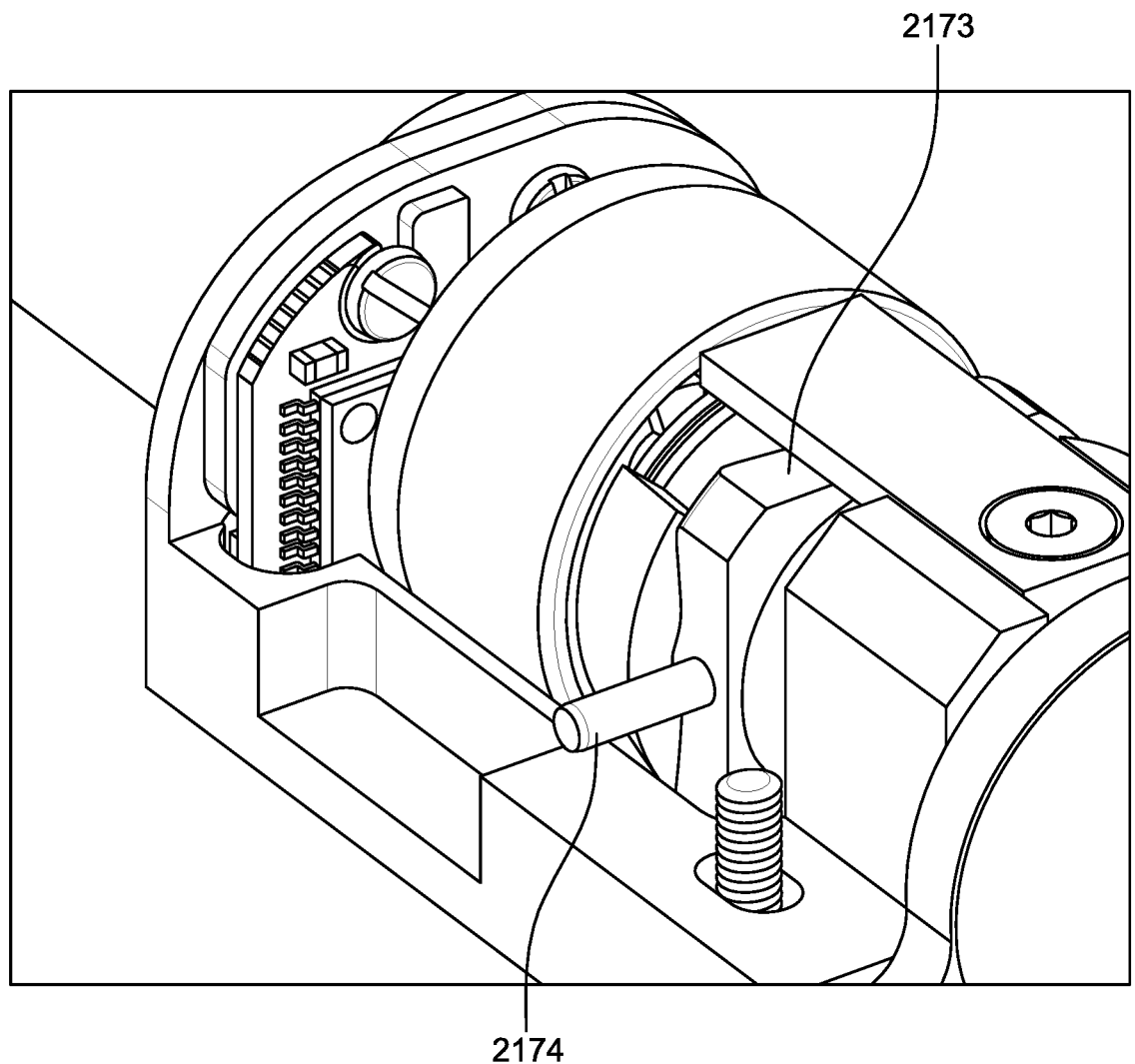
Figure 21G:
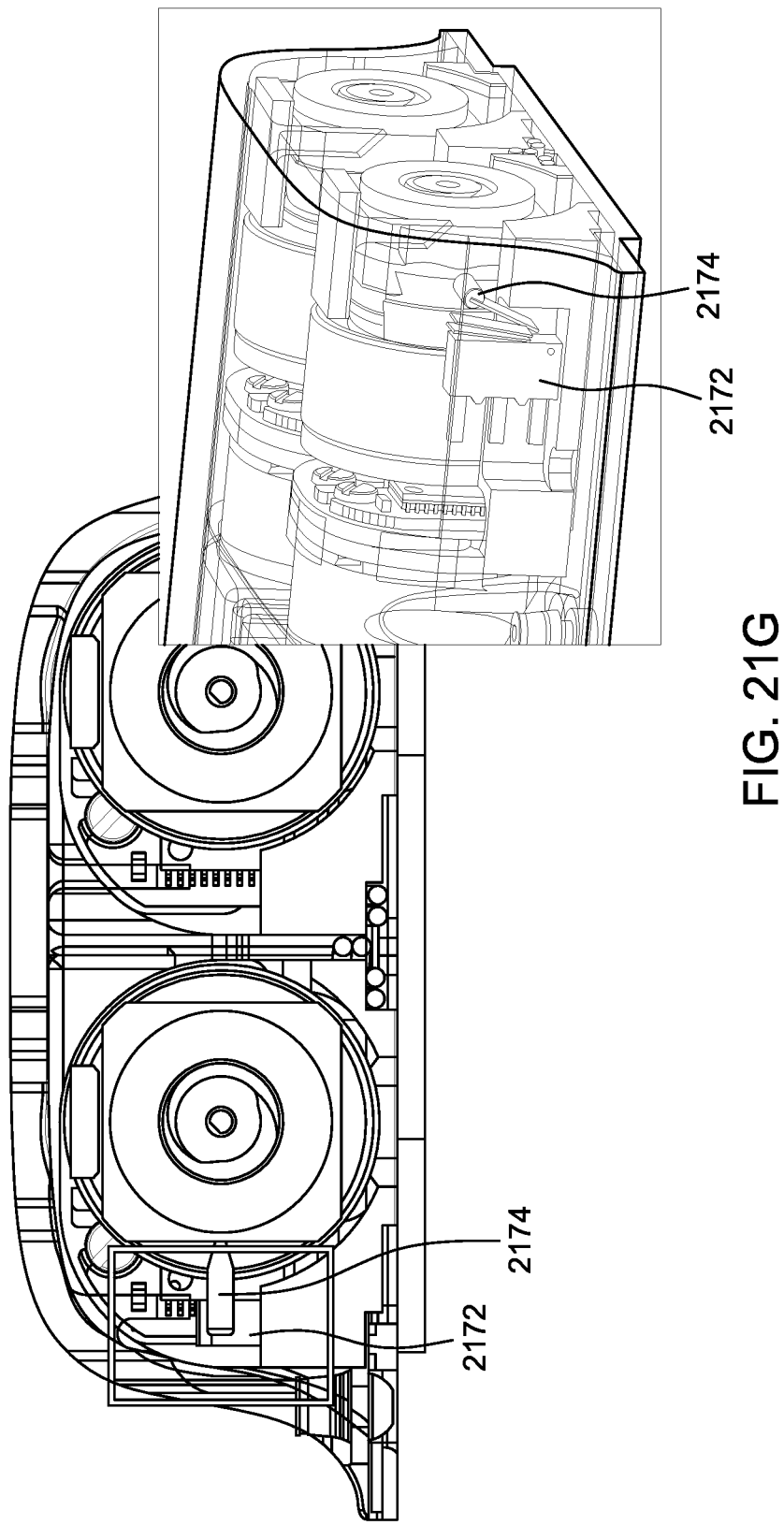
Figure 21H:
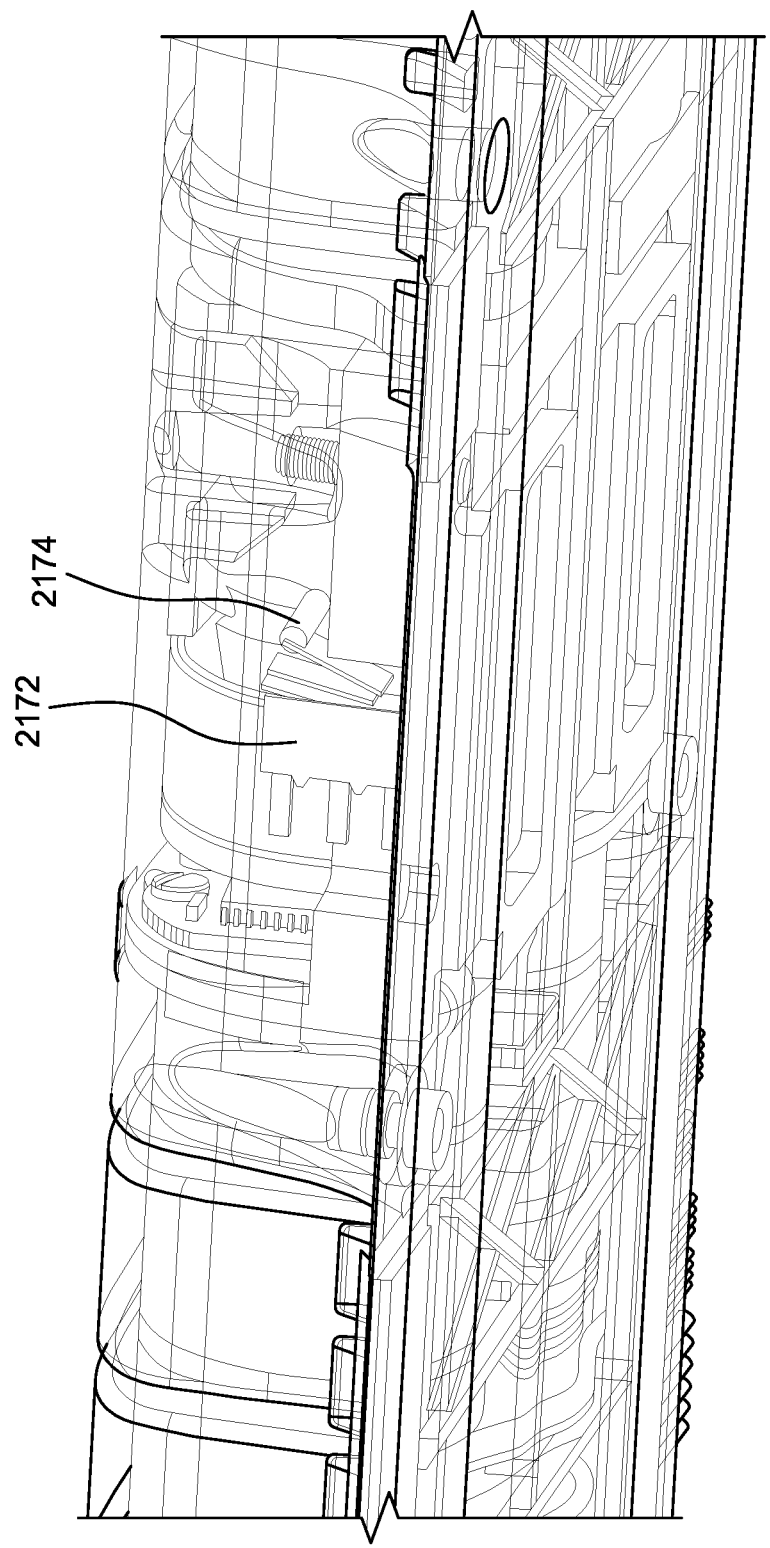

FIG. 21A shows an illustrative exploded view of flexdrive module 2100 according to an embodiment. FIG. 21B shows an illustrative cross-sectional view of flexdrive module 2100. Flexdrive module 2100 is similar to flexdrive 2000, but has additions to and a few modifications to various components. Flexdrive 2100 can include lock motor 2110, lock motor mount 2112, lock mount adhesive 2114, lock lead screw 2120, washer 2125, lead screw nut 2121, and foam pad 2122. Lock motor 2110 may be coupled to motor mount 2112, and lead screw 2120 may be coupled to lock motor 2010 via motor mount 2112. Lead screw may pass through washer 2125, through-hole 2132 of chassis 2130, and foam pad 2122 to be secured to lead screw nut 2121. Adhesive 2114 may be positioned between lock motor mount 2112 and chassis 2130. Lock motor mount 2112 may be coupled to chassis 2130 via one or more screws, for example. Shaft 2162 of drive motor 2160 passes through encoder 2150 and encoder magnet 2144 and is connected to lock cone 2140 via compression spring 2145, retaining washer 2146 and retaining ring 2147. PCB 2154 may be coupled to encoder 2150 via adhesive 2152 and one or more fasteners such as screws. Encoder 2150, lock cone 2140, lead screw nut 2121 may all be contained within chassis 2130.

Figure 21I:
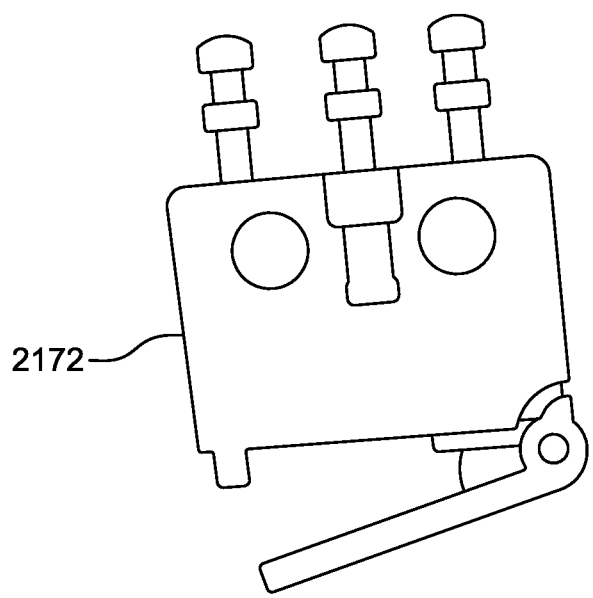
Figure 22:
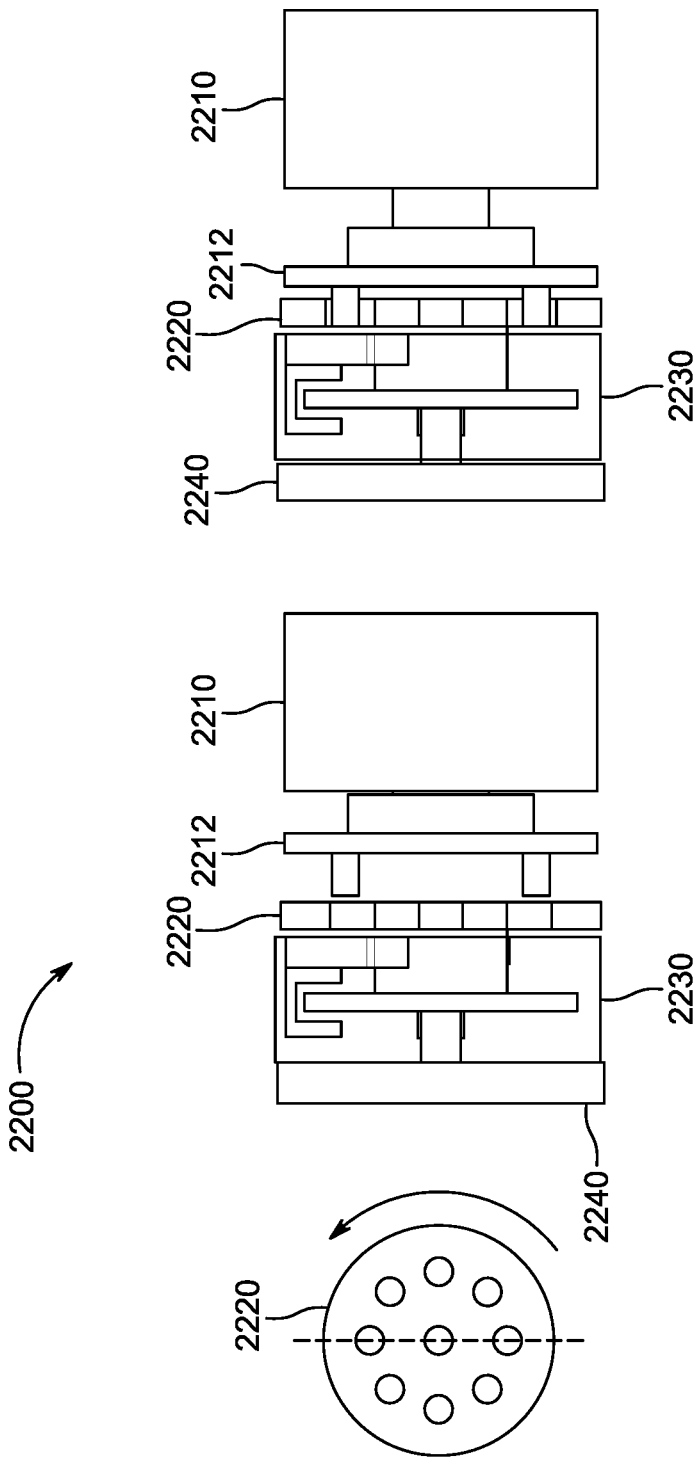
FIG. 22 shows a solenoid mechanical interlock assembly according to an embodiment.

FIGS. 21C-21J show views of an alternative flexdrive module 2170 according to an embodiment that includes switch 2172 and lead screw nut 2173. Lead screw lock 2173 replaces lead screw nut 2121 and has arm/pin 2174 that interfaces with switch 2172 depending on whether flexdrive module 2170 is locked or unlocked. In the arm embodiment, a protrusion may be injected molded as part of lead screw lock 2173. In the pin embodiment, a pin may be secured to lead screw lock 2173, and FIG. 21J shows illustrative views of lead screw lock 2173 capable of accepting the pin. Switch 2172, an illustrative detailed view of which is shown in FIG. 21I, is positioned within housing of flexdrive module 2170 and is operative to be closed when flexdrive module 2170 is in the locked position. Switch 2172 can be used to verify that flexdrive module 2170 is in the locked or unlocked position. In the locked position, arm/pin 2174 presses switch 2172 into a closed position. In the unlocked position, arm/pin 2174 does not engage switch 2172 and it reverts to an open position.

The flexdrives can be designed to lock in place to hold the twisted string in a fixed position without require the drive motor to expend energy to maintain that hold. FIGS. 22-27 show different locking mechanisms that may be used in flexdrives according to various embodiments. Starting with FIG. 22, views of a solenoid mechanical interlock assembly 2200 according to an embodiment is shown. Assembly 2200 can include push-pull solenoid 2210 that is attached to engagement member 2212. Engagement member 2212 is operative to interface with sectioned lock wheel 2220, which is coupled to encoder 2230 drive motor 2240. In the unlocked position, solenoid pulls engagement member 2212 back away from lock wheel 2220. In the locked position, solenoid pushes engagement member 2212 into lock wheel 2220 to lock drive motor 2040 in place.

Figure 23:
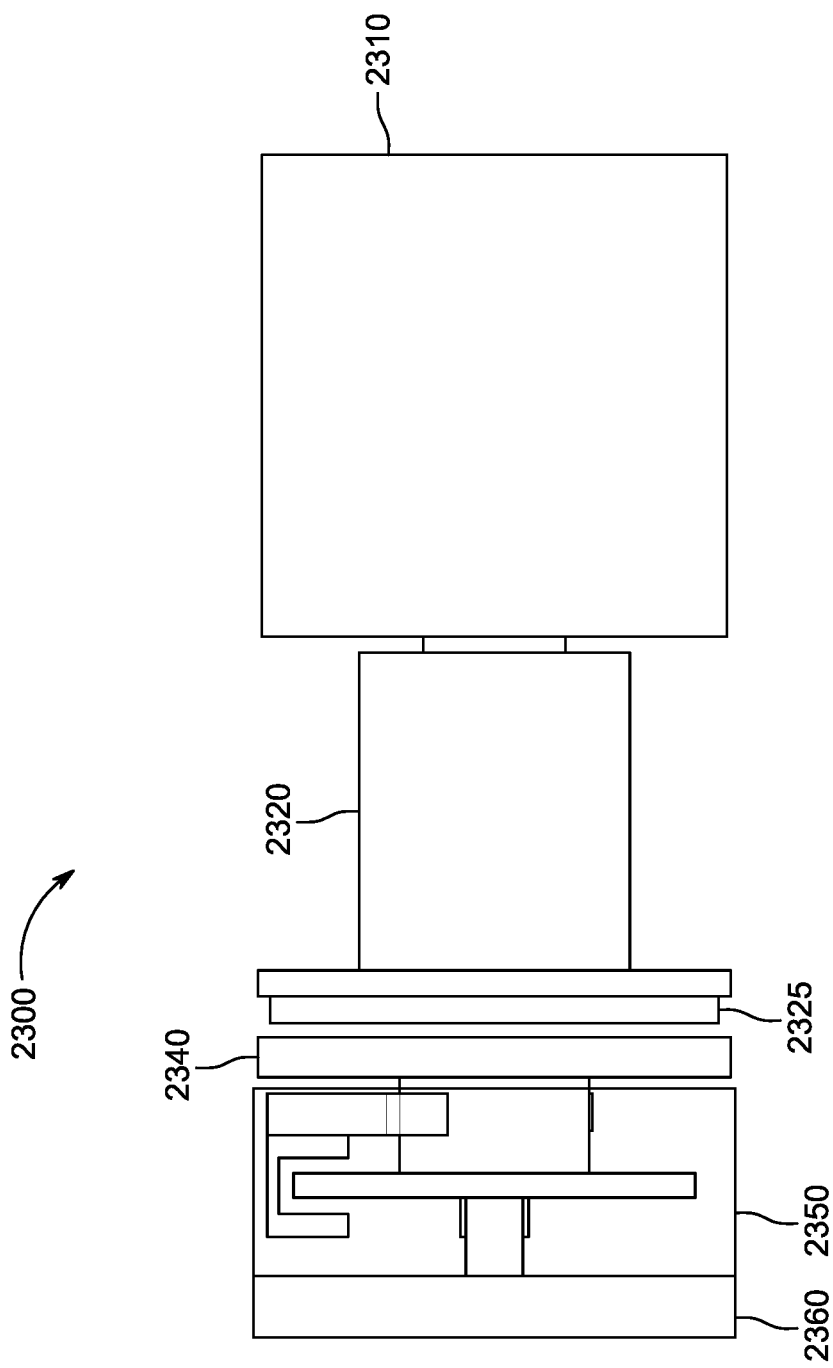
FIG. 23 shows a lead screw locking mechanism assembly according to an embodiment.

FIG. 23 shows a lead screw locking mechanism assembly 2300 according to an embodiment. Assembly 2300 can include motor 2310, nut 2320, friction pad 2325, and cone 2340. Cone 2340 may be coupled to encoder 2350, which is secured to drive motor 2360. To lock drive motor 2360, motor 2010 may cause nut 2320 (and by extension friction pad 2325) to press into cone 2340. When sufficient force is applied to cone 2340 by friction pad 2325, cone 2340 may be locked in place. To unlock drive motor 2360, motor 2310 can pull nut 2320 away from cone 2340 to decouple friction pad 2325 from cone 2340.

Figure 24:
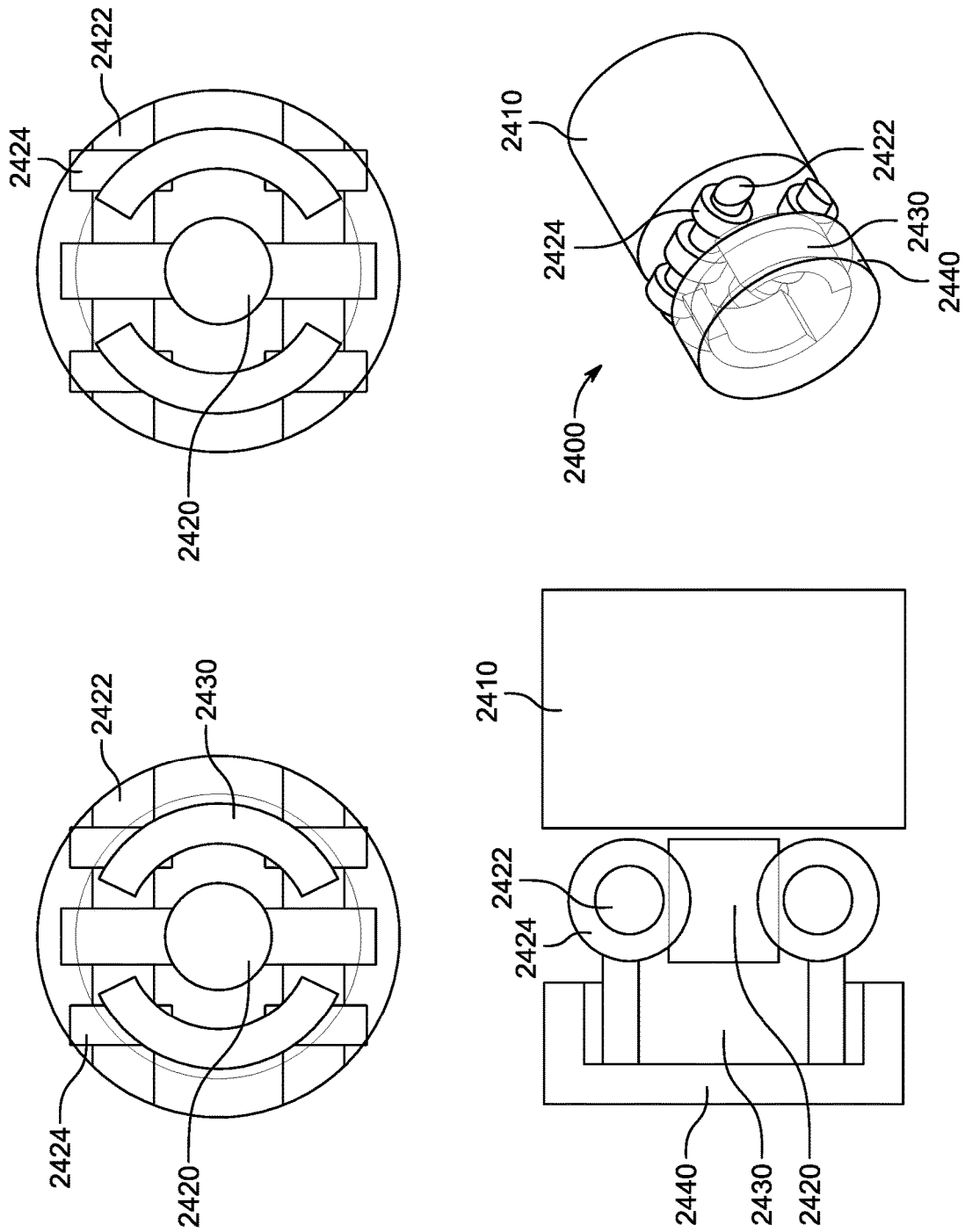
FIG. 24 shows a worm drive locking mechanism assembly according to an embodiment.

FIG. 24 shows a worm drive locking mechanism assembly 2400 according to an embodiment. Assembly 2400 can include motor 2410, worm 2420, lead screw 2422, worm gear 2424, friction shoe 2430, and drive motor attachment 2440. To lock the drive motor in place, motor 2410 may turn worm 2420 in a first direction to cause friction shoe 2430 to expand and engage motor attachment 2440. When worm 2420 turns, it engages worm gear 2424, which causes lead screw 2422 to move friction shoe 2430. to unlock the drive motor, motor 2410 may turn worm 2420 in the opposite direction to cause friction shoe 2430 to not engage motor attachment 2440.

Figure 25:
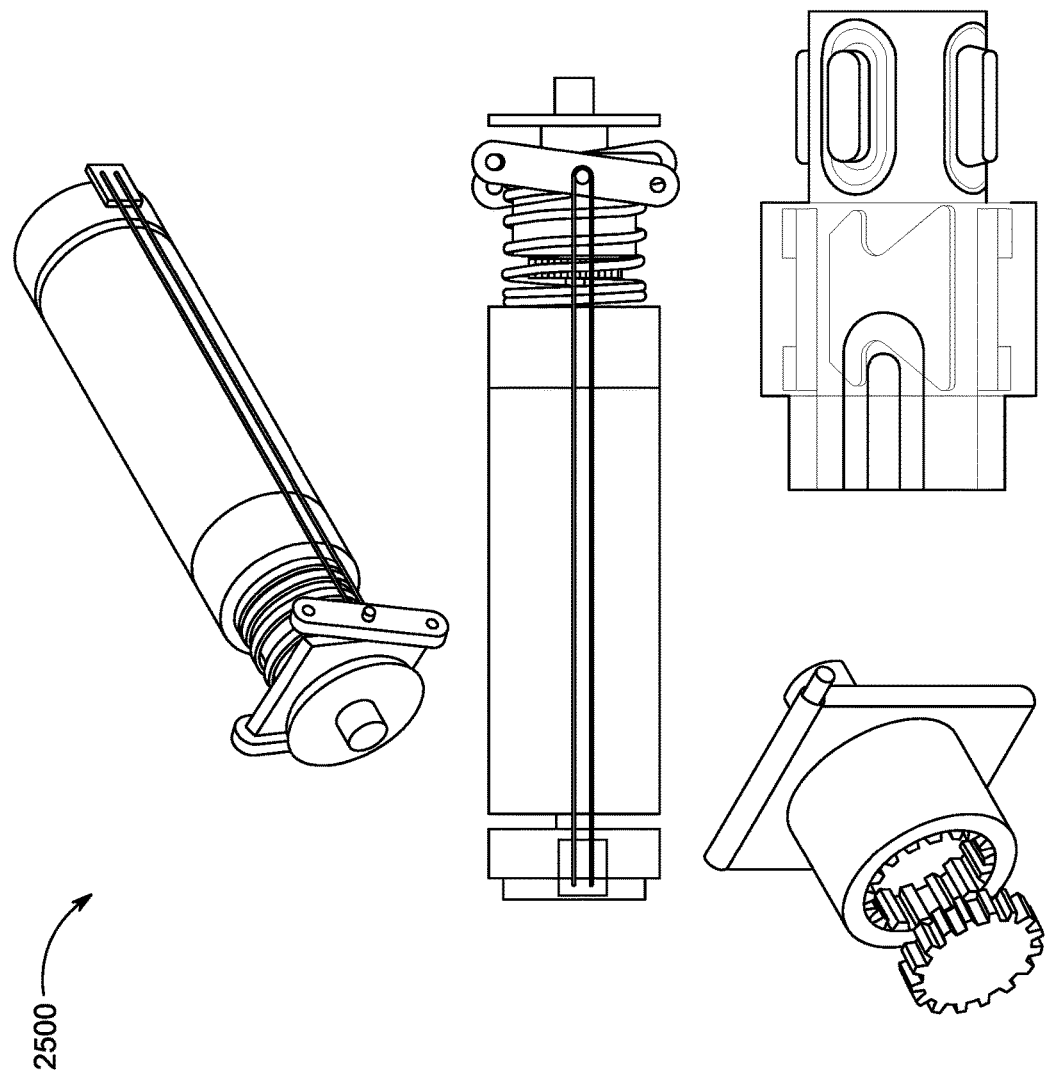
FIG. 25 shows a nitinol actuated push-push mechanism assembly according to an embodiment.

FIG. 25 shows a nitinol actuated push-push mechanism assembly 2500 according to an embodiment.

FIG. 26 shows a solenoid lock mechanism assembly 2600 according to an embodiment.

Figure 27:
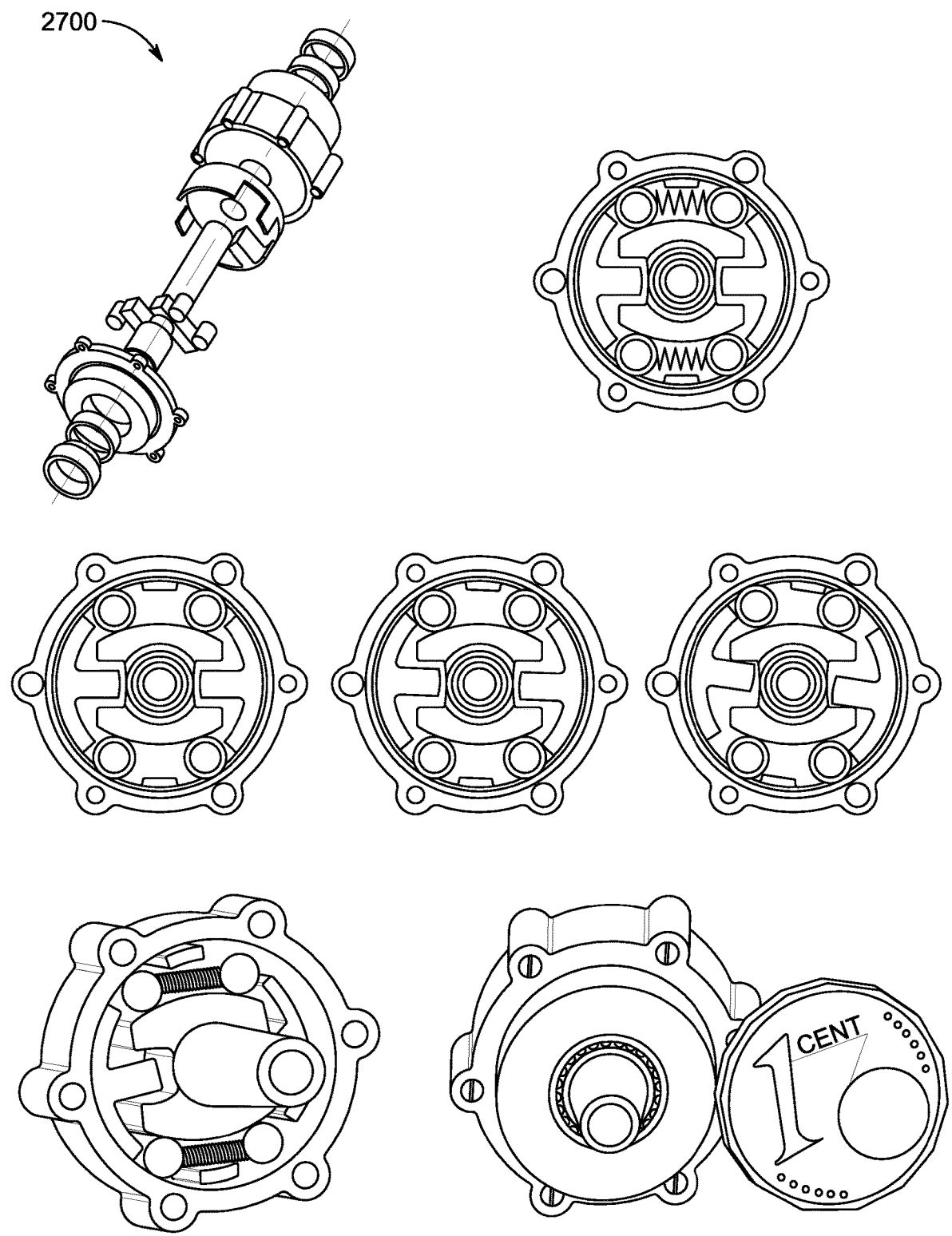
FIG. 27 shows a non-backdrivable lock mechanism assembly according to an embodiment.

FIG. 27 shows a non-backdrivable lock mechanism assembly 2700 according to an embodiment.

Users of the exosuit will have to use the toilet, and as such, appropriate regions of the user's body need to be exposed. The user may not or cannot doff the exosuit to toilet for at least the reason that is inconvenient to do so and that the user may require assistance from the exosuit while toileting (e.g., urinating into a toilet in a standing position) or standing up from the toilet after sitting thereon. Different toileting embodiments are now discussed.

Figure 30C:
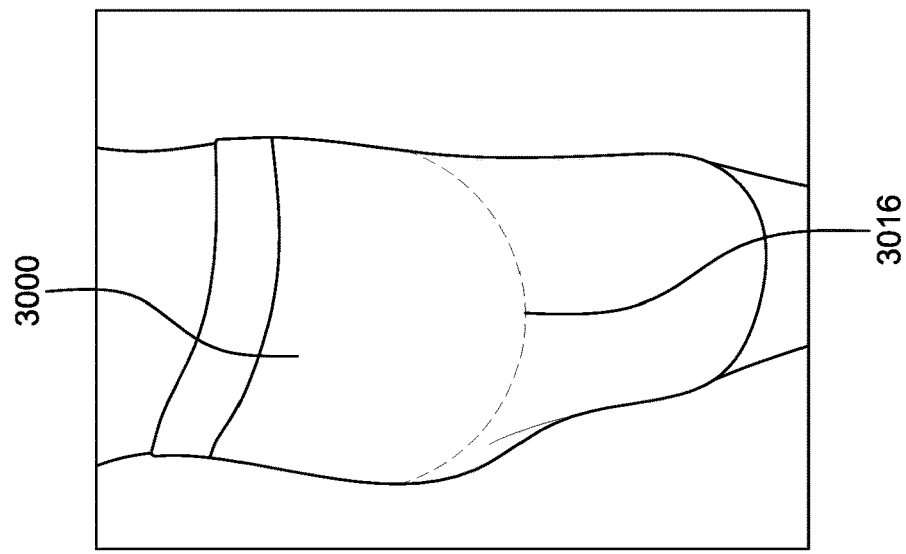
FIGS. 30A-30C show illustrative front, back, and side views of next to skin layer having toileting access according to an embodiment.
Figure 30B:
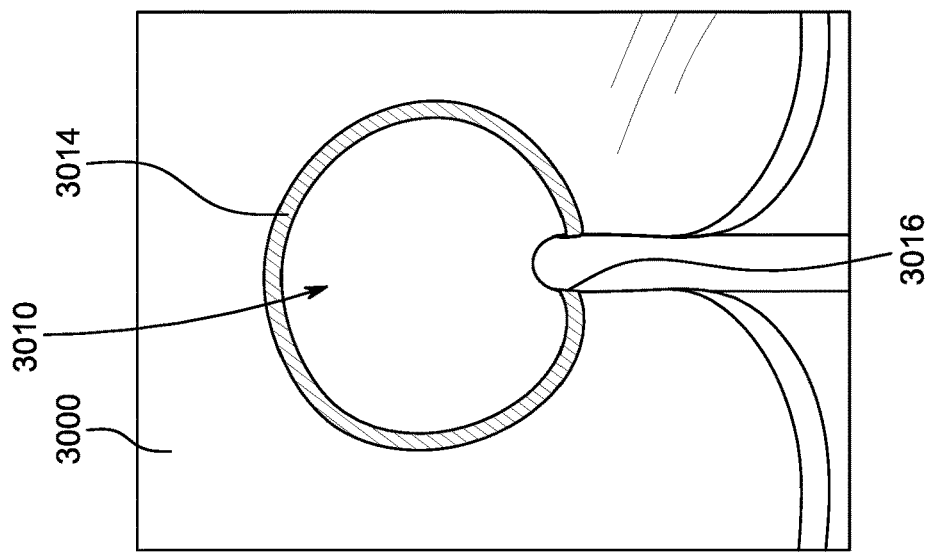
Figure 30A:
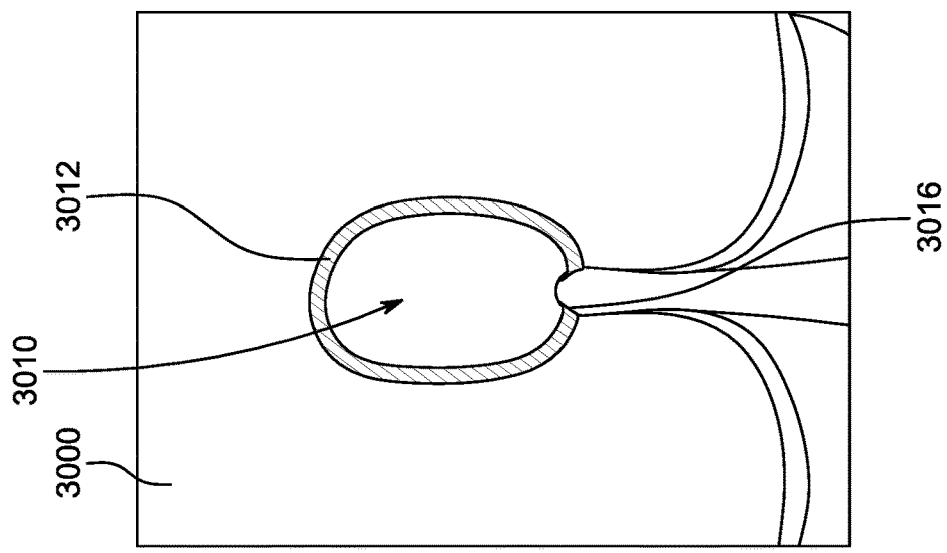

FIGS. 30A-30C show illustrative front, back, and side views of next to skin layer 3000 having toileting access 3010. Toileting access 3010 may be a cutout existing on the front and back sides of layer 3000. Access 3010 can include hole 3012 on the front side and hole 3014 on the back side. Channel gap 3016 may exist between holes 3012 and 3014. Hole 3012 may be smaller in size than hole 3014.

Figure 31C:
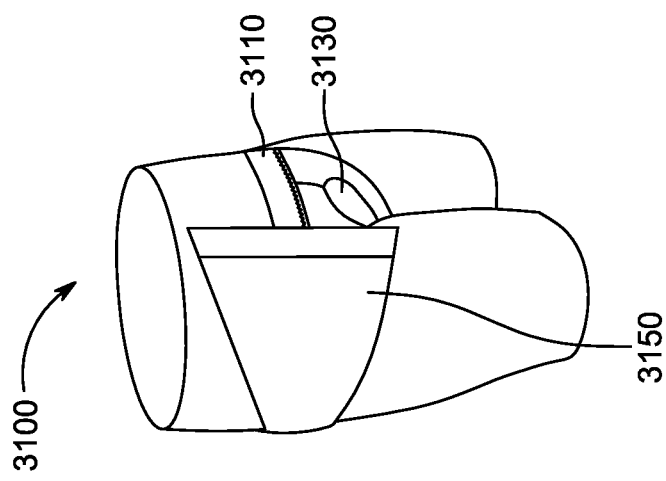
FIGS. 31A-31F show different views of next to skin layer having a removable flap according to various embodiments.
Figure 31B:
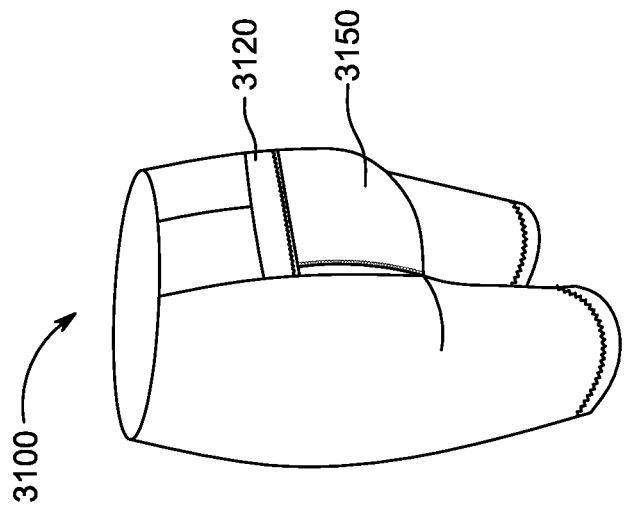
Figure 31A:
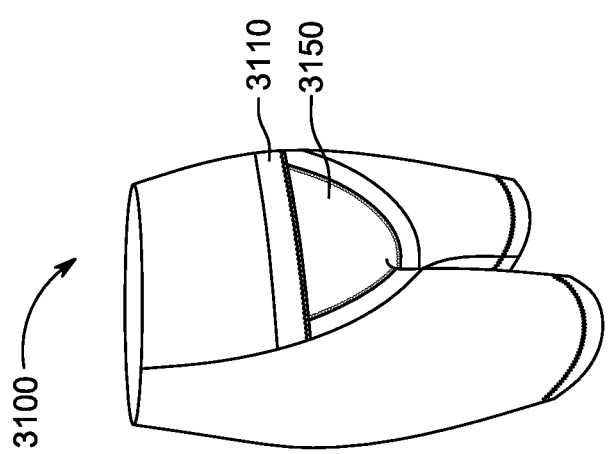
Figure 31F:
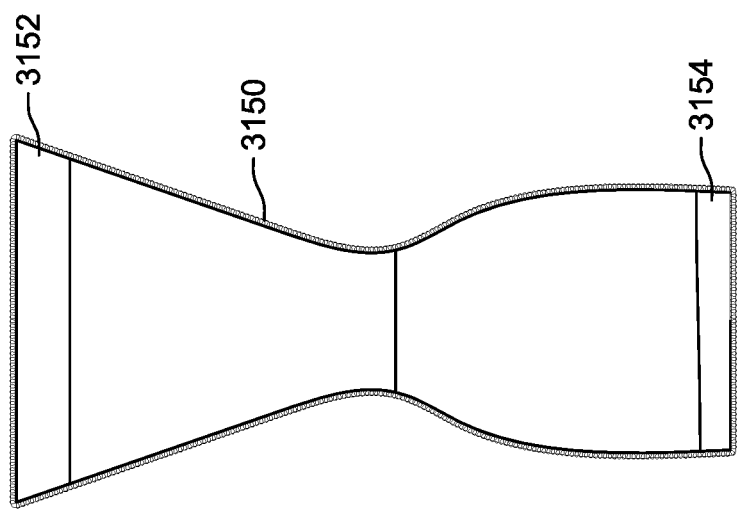

FIGS. 31A-31F show different views of next to skin layer 3100 having a removable flap 3150 according to various embodiments. FIGS. 31A and 32B show illustrative front quarter and back quarter views of skin layer 3100 with flap 3150 attached in place. Flap 3150 may be attached front attachment region 3110 and rear attachment region 3120. Flap 3150 may be attached to regions 3110 and 3120 via magnets, hook and loop (e.g., Velcro), button snaps, or a combination thereof. When the user wishes to use the toilet (as shown in FIG. 31C), he or she may decouple flap 3150 from regions 3110 and 3120 to expose cutout 3130 that exist under flap 3150. If desired, the user may wrap flap 3150 around his or her waist and secure flap 3150 to regions 3110 and 3120. Cutout 3130 may extend from the front to the back of layer 3100 to bridge the front and rear openings.

Figure 31E:
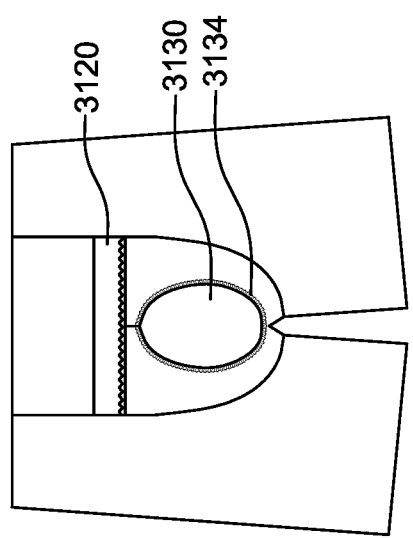
Figure 31D:
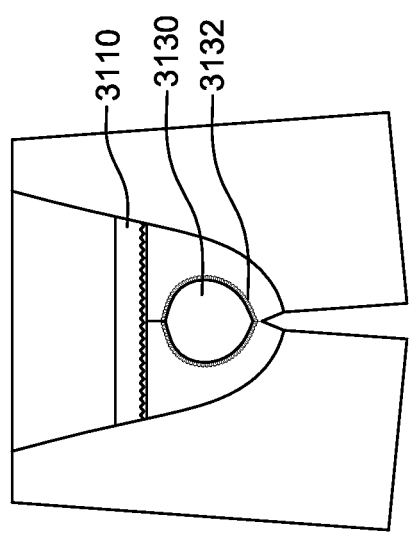

FIGS. 31D and 31E shows illustrative front and back views of layer 3100 with flap 3150 removed. Cutout 3130 can include first hole 3132 and second hole 3134 with open channel (not shown) connected to both holes 3132 and 3134. Front attachment region 3110 and rear attachment region 3120 may include overlap pockets into which ends of flap 3150 may be inserted. FIG. 31F shows an illustrative view of flap 3150 with end portions 3152 and 3154. Each of end portions 3152 and 3154 can include one of magnets, hook and loop (e.g., Velcro), button snaps for being secured to regions 3110 and 3120. In embodiments that use magnets, the magnets may be removable (to promote ease of washing). For example, the magnets may exist on a strip that can be removed from flap 3150 and regions 3110 and 3120. In some embodiments, a portion of flap 3150 may be lined with a water proof membrane to help with incontinence and provide structural support to flap 3150 to prevent twisting.

Figure 32C:
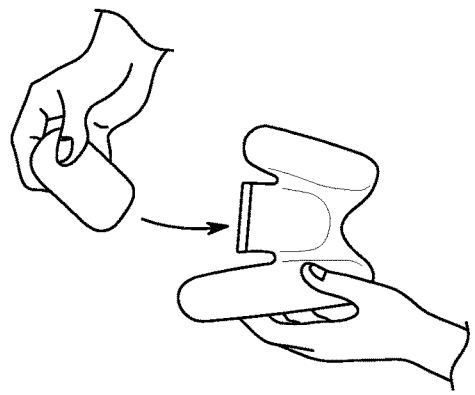
FIGS. 32A-32R show different steps in an exosuit donning process according to an embodiment.
Figure 32F:
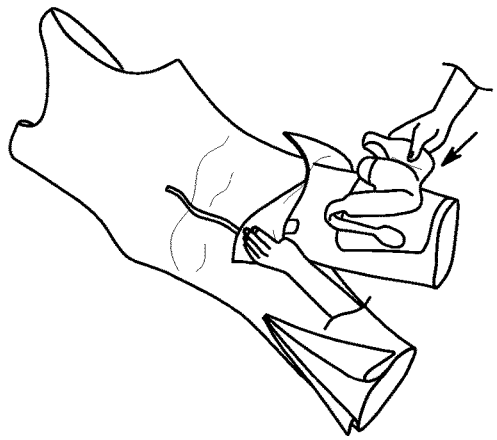
Figure 32B:
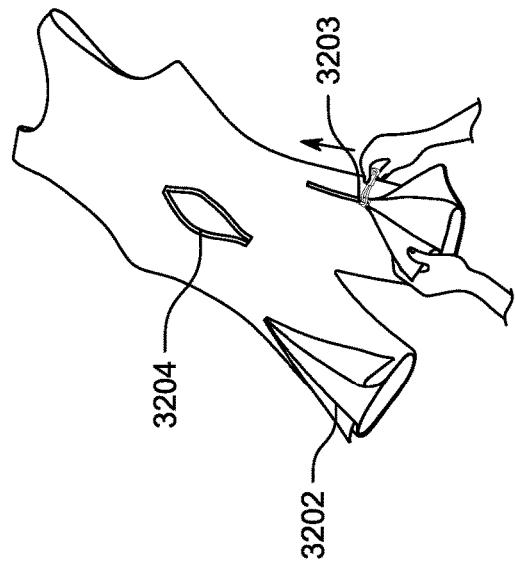
Figure 32E:
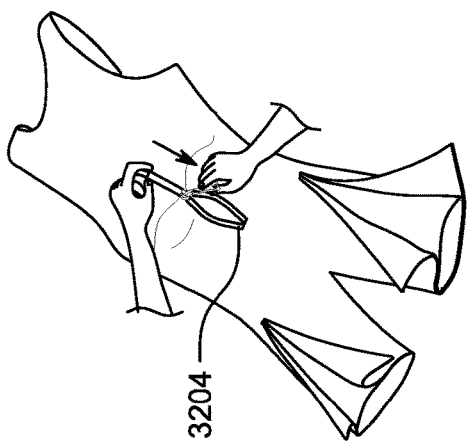
Figure 32A:
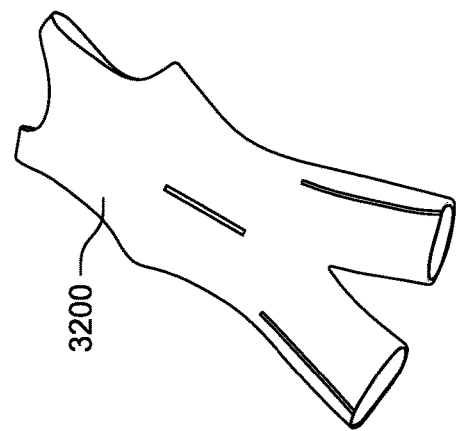
Figure 32D:
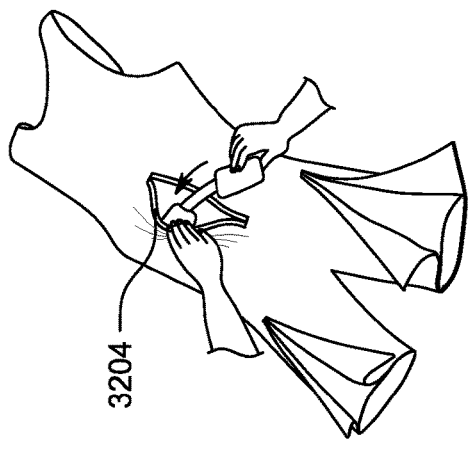
Figure 32I:
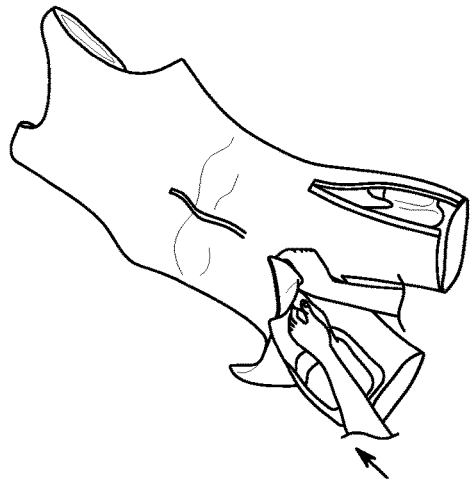
Figure 32L:
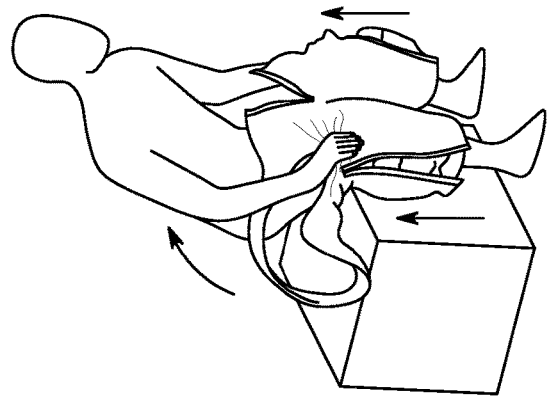
Figure 32H:
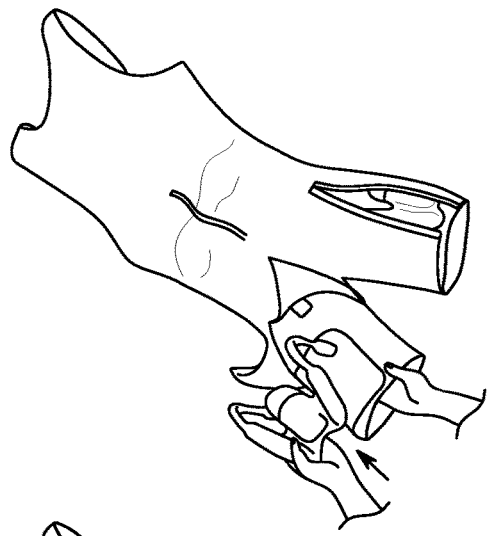
Figure 32K:
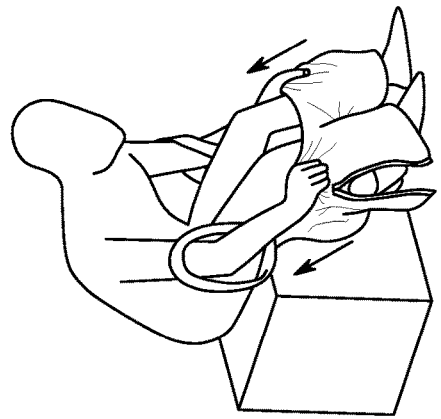
Figure 32G:
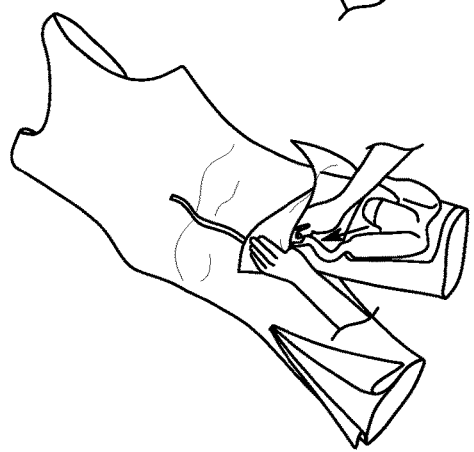
Figure 32J:
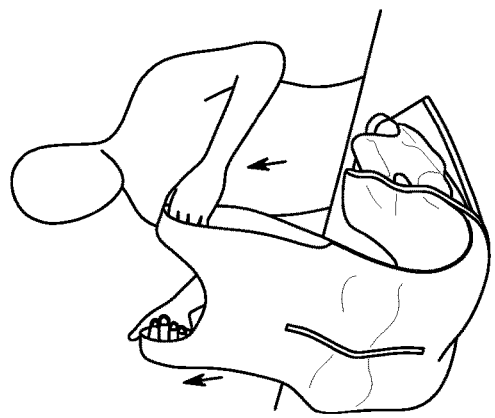
Figure 32O:
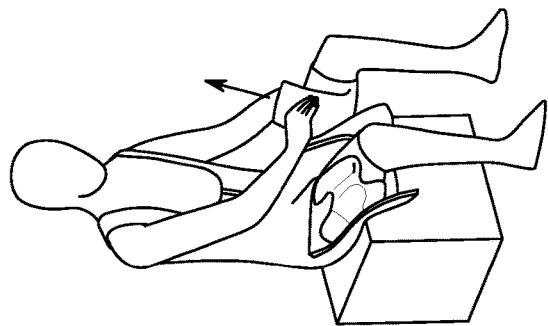
Figure 32R:
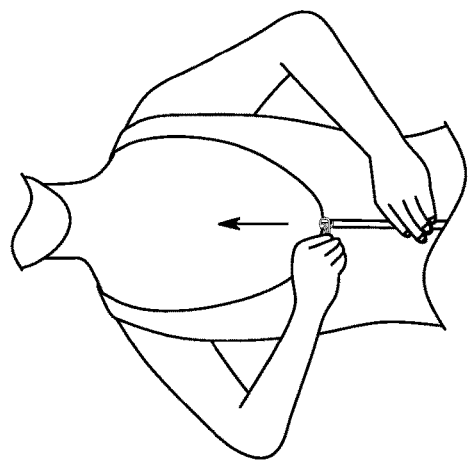
Figure 32N:
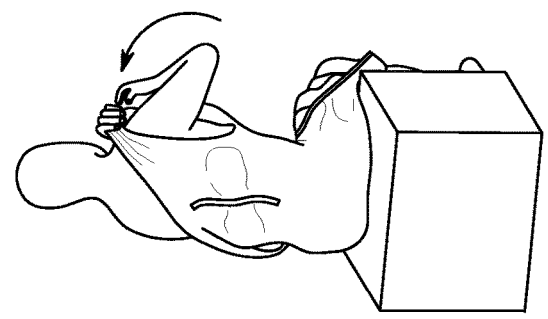
Figure 32Q:
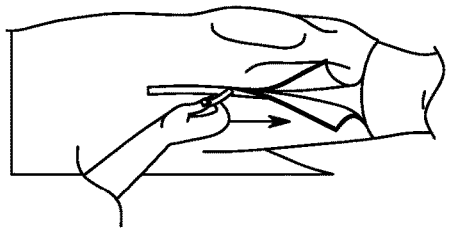
Figure 32M:
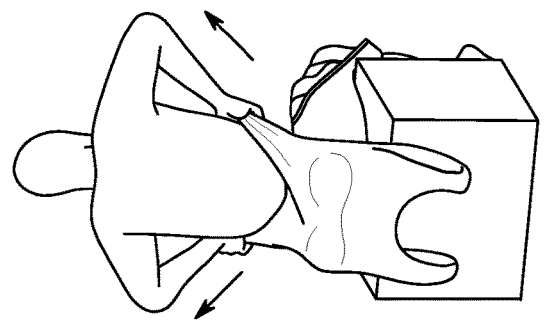
Figure 32P:
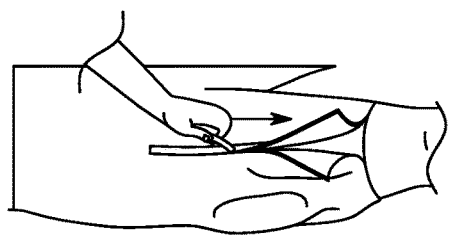

FIGS. 32A-32R show different steps in an exosuit donning process according to an embodiment. The exosuit may be that that includes a module patch design in which patches are attached to load bearing members that are attached to or integrated into the suit. The exosuit may include zippers, flaps, buttons, or other suitable open and closing mechanism that enables the user to access different portions of the suit. Starting with FIG. 32A, a user may place exosuit 3200 on a flat surface and open all access ports 3202-3204, as shown in FIG. 32B. In FIG. 32C, the user may prepare all patches (e.g., patches 1000, 1200, or 1800) for attachment to exosuit 3200. Preparation of patches can include installing battery packs and/or control modules. The patches can include, for example, thigh patches and a core patch. The user may install a core patch in core patch attachment area, as shown in FIG. 32D, and then the use may close access port 3204. The core patch may be connected to a lumbar load distribution member that applies transverse pressure to the lumbar region and the stomach of the user. The user may install a first thigh patch to a thigh distribution load member via access port 3203 and attach flex drive elements and/or electrical connections, as shown in FIGS. 32F and 32G. The user may install a second thigh patch to a thigh distribution load member via access port 3202 and attach flex drive elements and/or electrical connections, as shown in FIGS. 32H and 32I. In FIGS. 32J and 32K, the user may lift the suit off the surface, and then sit down and pull on the suit to mid thigh. The user may stand up and pull suit past mid thigh and up to waist, as shown in FIG. 32L, and then sit down again to pull suit up past hips, as shown in FIG. 32M. The user may pull shoulder straps onto shoulders (as shown in FIG. 32N). The user may tighten thigh grip load distribution members in FIG. 32O. The user may close access ports 3203-3204 as shown in FIGS. 32P-32Q, and close a zipper (FIG. 32R).

Figure 33C:
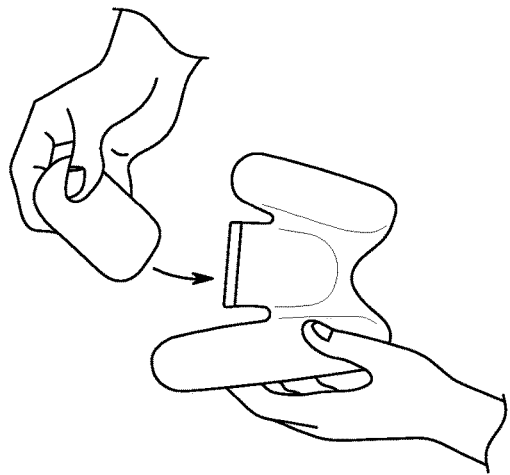
FIGS. 33A-33R show different steps in an exosuit donning process according to an embodiment.
Figure 33F:
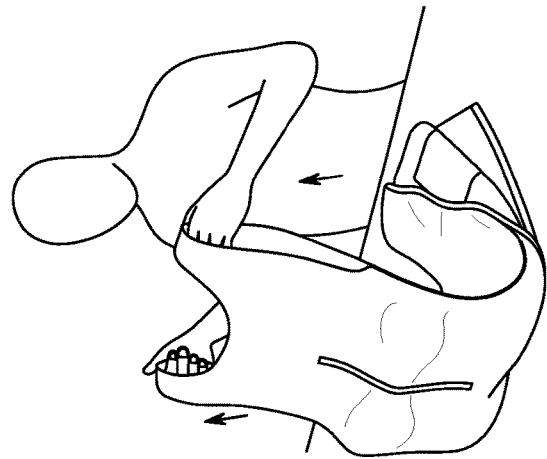
Figure 33B:
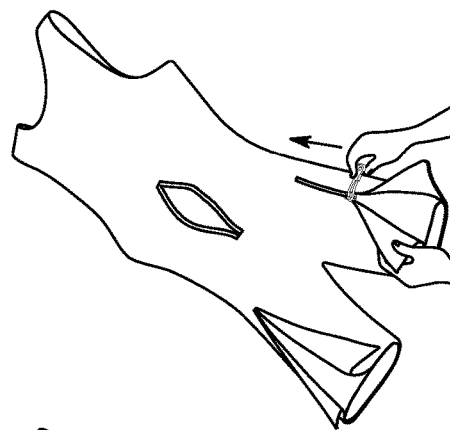
Figure 33E:
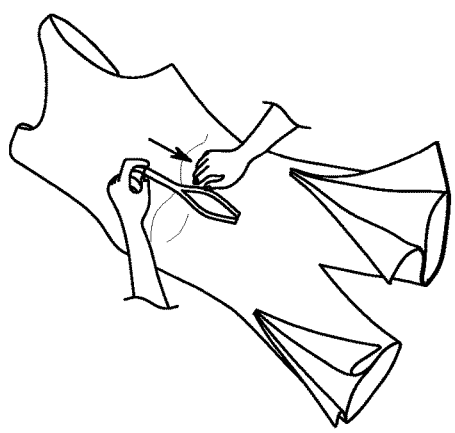
Figure 33A:
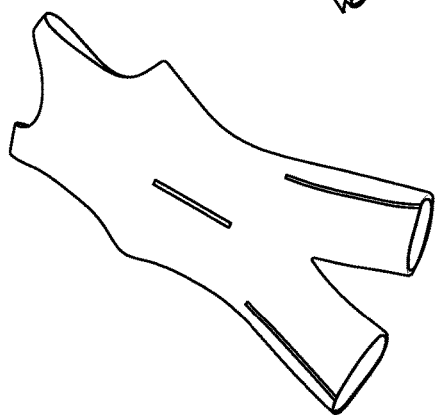
Figure 33D:
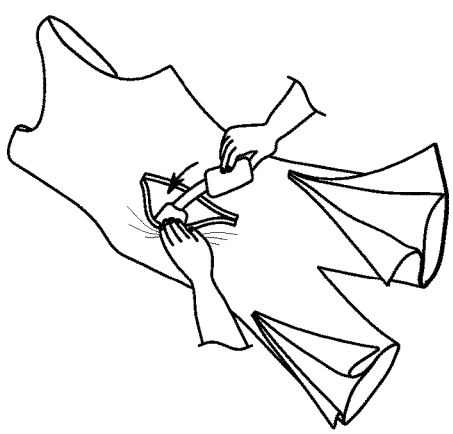
Figure 33I:
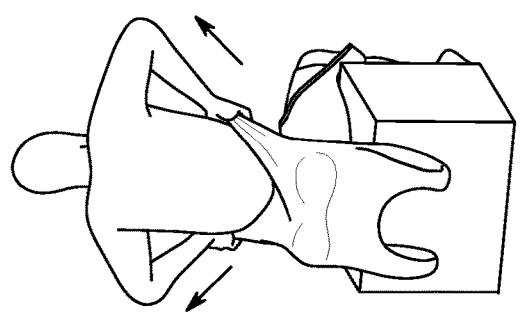
Figure 33L:
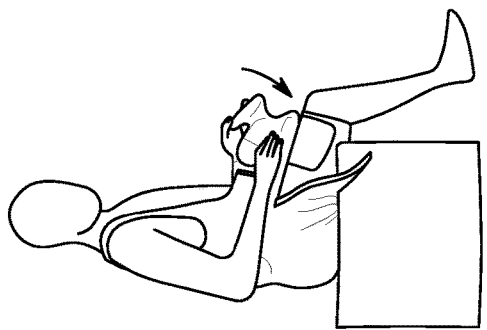
Figure 33H:
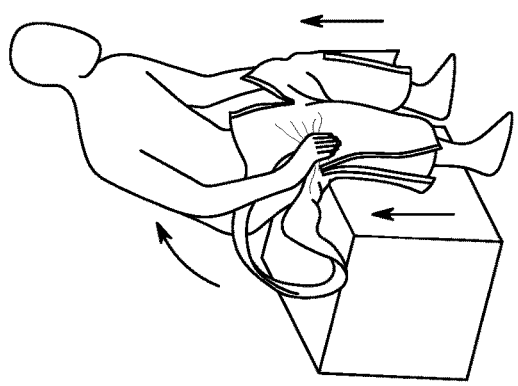
Figure 33K:
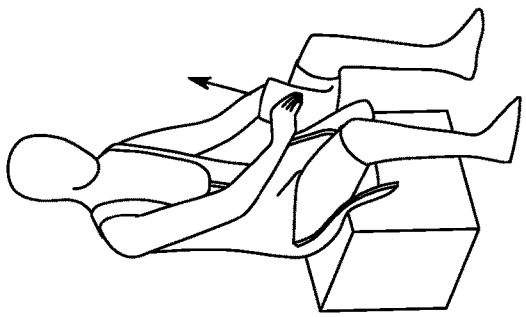
Figure 33G:
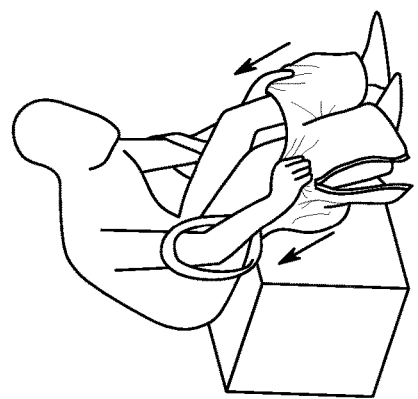
Figure 33J:
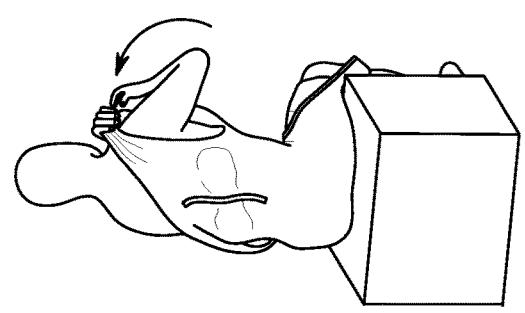
Figure 33O:
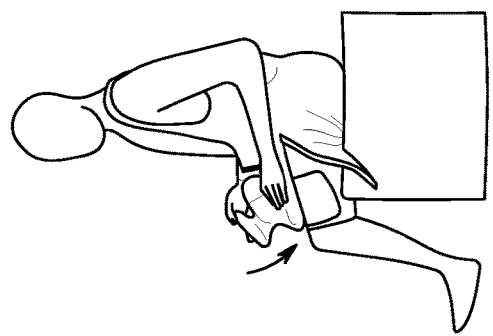
Figure 33R:
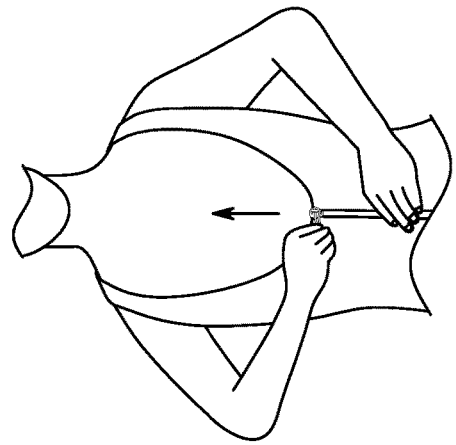
Figure 33N:
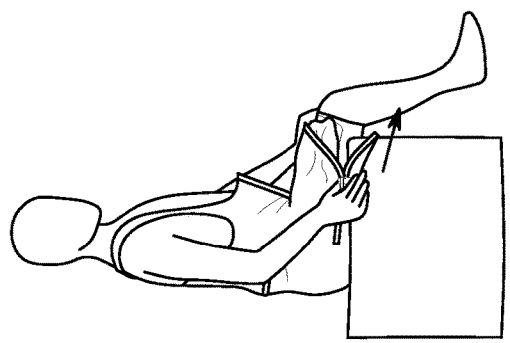
Figure 33Q:
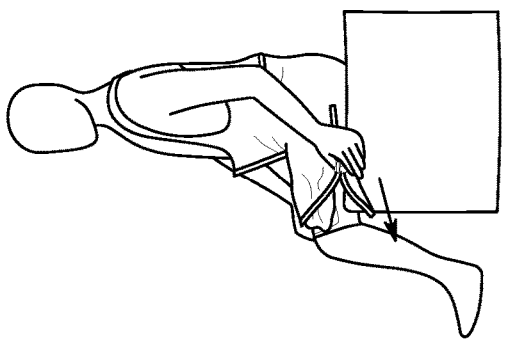
Figure 33M:
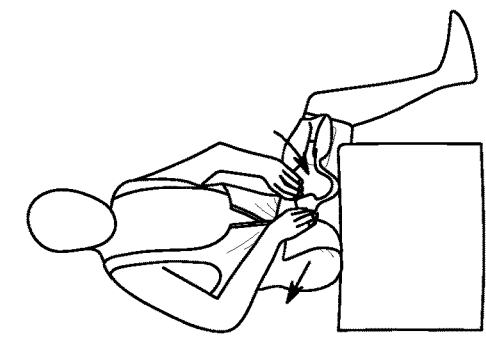
Figure 33P:
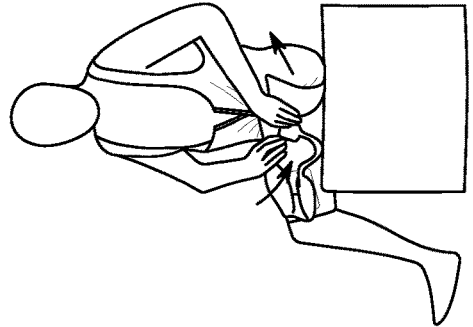

FIGS. 33A-33R show different steps in an exosuit donning process according to an embodiment. The donning process shown in FIGS. 33A-33R is similar to those in FIGS. 32A-32R but are performed in a different order. Starting with FIG. 33A, a user may place exosuit 3300 on a flat surface and open all access ports 3302-3304, as shown in FIG. 33B. In FIG. 33C, the user may prepare all patches (e.g., patches 1000, 1200, or 1800) for attachment to exosuit 3300. The user may install a core patch in core patch attachment area, as shown in FIG. 33D, and then the use may close access port 3204, as shown in FIG. 33E. In FIGS. 33F and 33G, the user may lift the suit off the surface, and then sit down and pull on the suit to mid thigh. The user may stand up and pull suit past mid thigh and up to waist, as shown in FIG. 33H, and then sit down again to pull suit up past hips, as shown in FIG. 33I. The user may pull shoulder straps onto shoulders (as shown in FIG. 33J). The user may adjust thigh load distribution member (FIG. 33K) and attach a first thigh patch, strings, and electronic connections (FIGS. 33L and 33M) and close the access port (FIG. 33N). The user may attach a second thigh patch, strings, and electronic connections (FIGS. 33O and 33P) and close the access port (FIG. 33Q). Finally, the use may close a zipper (FIG. 33R) to complete donning of exosuit 3300.

Figure 34C:
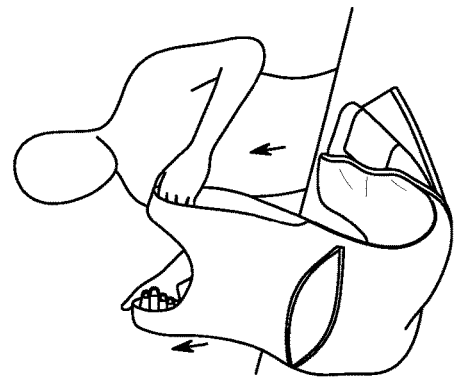
FIGS. 34A-34R show different steps in an exosuit donning process according to an embodiment.
Figure 34F:
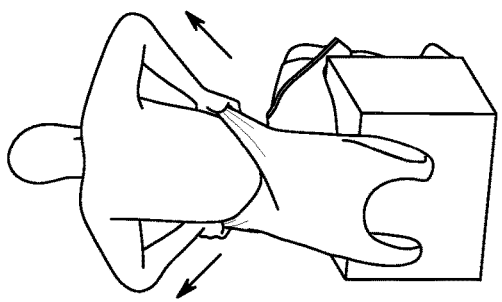
Figure 34B:
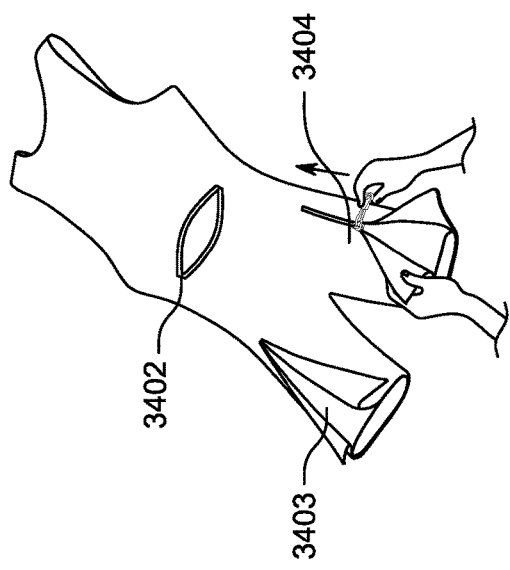
Figure 34E:
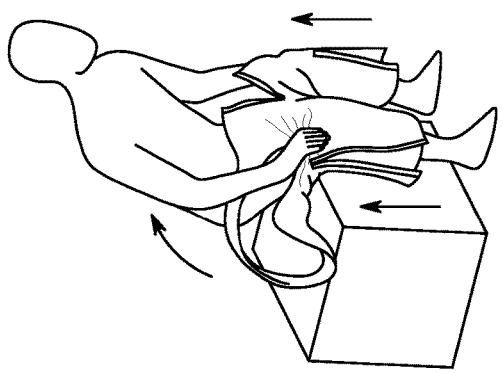
Figure 34A:
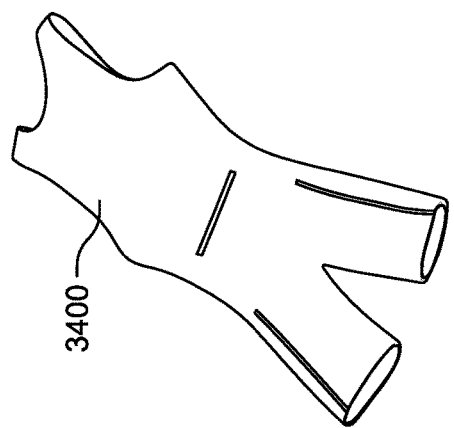
Figure 34D:
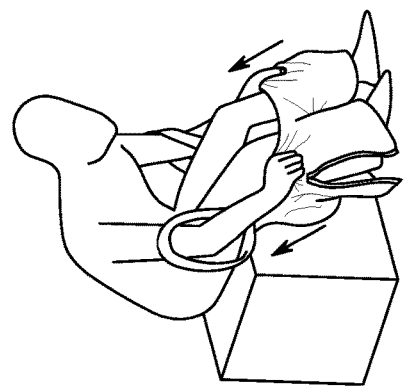
Figure 34I:
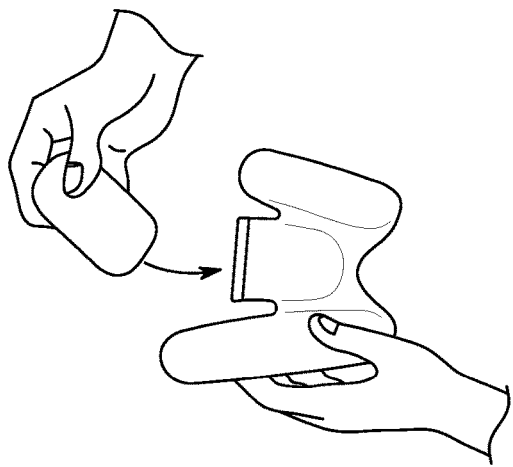
Figure 34L:
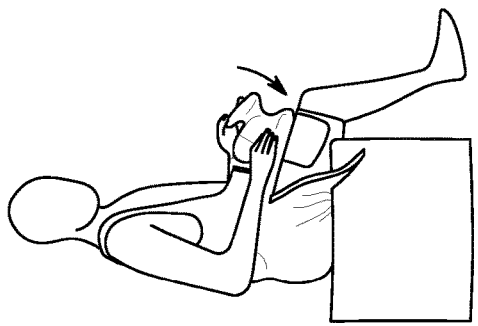
Figure 34H:
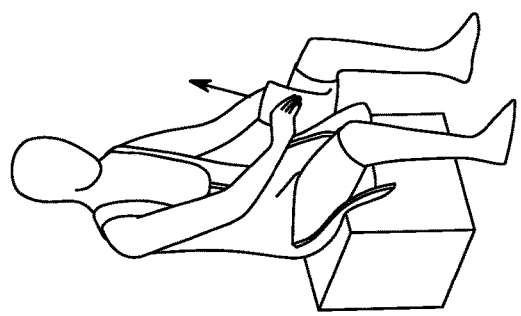
Figure 34K:
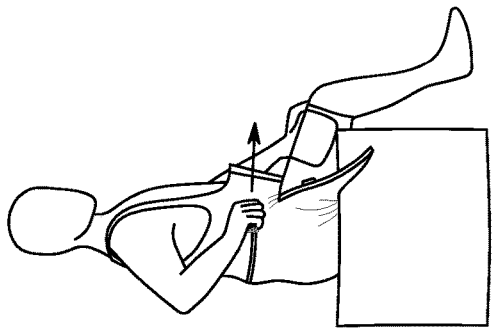
Figure 34G:
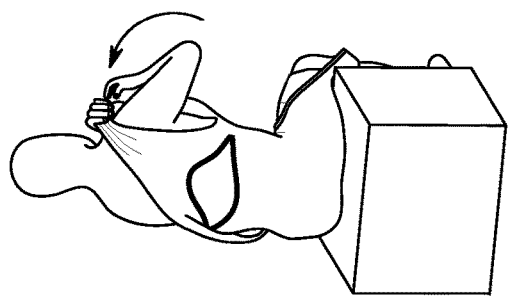
Figure 34J:
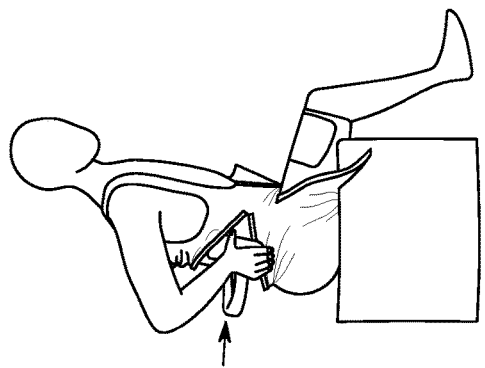
Figure 34M:
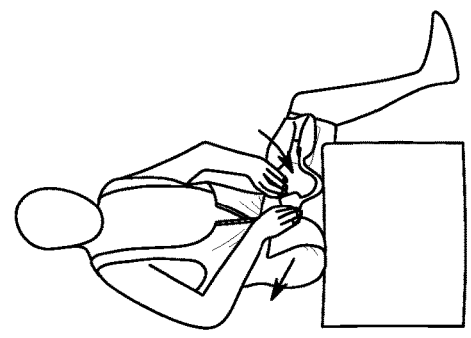
Figure 34N:
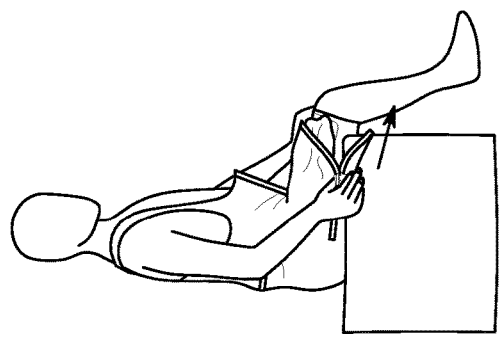
Figure 34O:
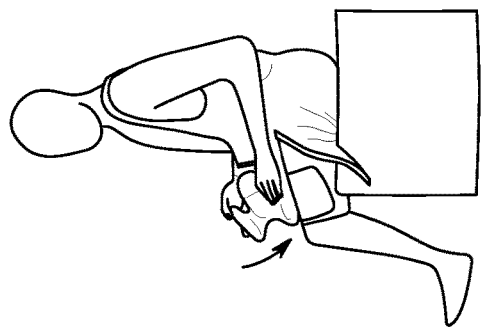
Figure 34P:
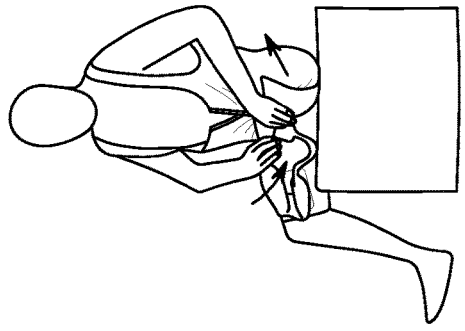
Figure 34Q:
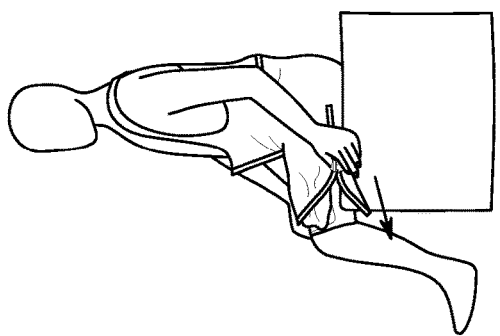
Figure 34R:
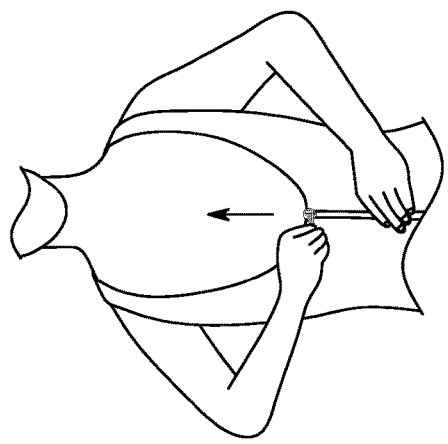

FIGS. 34A-34R show different steps in an exosuit donning process according to an embodiment. The donning process shown in FIGS. 34A-34R is similar to those in FIGS. 32A-32R but are performed in a different order. Starting with FIG. 33A, a user may place exosuit 3400 on a flat surface and open all access ports 3402-3404, as shown in FIG. 34B. In FIGS. 34C and 34D, the user may lift the suit off the surface, and then sit down and pull on the suit to mid thigh. The user may stand up and pull suit past mid thigh and up to waist, as shown in FIG. 34E, and then sit down again to pull suit up past hips, as shown in FIG. 34F. The user may pull shoulder straps onto shoulders (as shown in FIG. 34G). The user may adjust thigh load distribution member (FIG. 32H). In FIG. 34I, the user may prepare all patches (e.g., patches 1000, 1200, or 1800) for attachment to exosuit 3400. The user may install a core patch in core patch attachment area, as shown in FIG. 34J, and then the use may close access port 3204, as shown in FIG. 34K. The user may attach a first thigh patch, strings, and electronic connections (FIGS. 34L and 34M) and close the access port (FIG. 34N). The user may attach a second thigh patch, strings, and electronic connections (FIGS. 34O and 34P) and close the access port (FIG. 34Q). Finally, the use may close a zipper (FIG. 34R) to complete donning of exosuit 3400.

An exosuit can be operated by electronic controllers disposed on or within the exosuit or in wireless or wired communication with the exosuit. The electronic controllers can be configured in a variety of ways to operate the exosuit and to enable functions of the exosuit. The electronic controllers can access and execute computer-readable programs that are stored in elements of the exosuit or in other systems that are in direct or indirect communications with the exosuit. The computer-readable programs can describe methods for operating the exosuit or can describe other operations relating to a exosuit or to a wearer of a exosuit.

Figure 52:
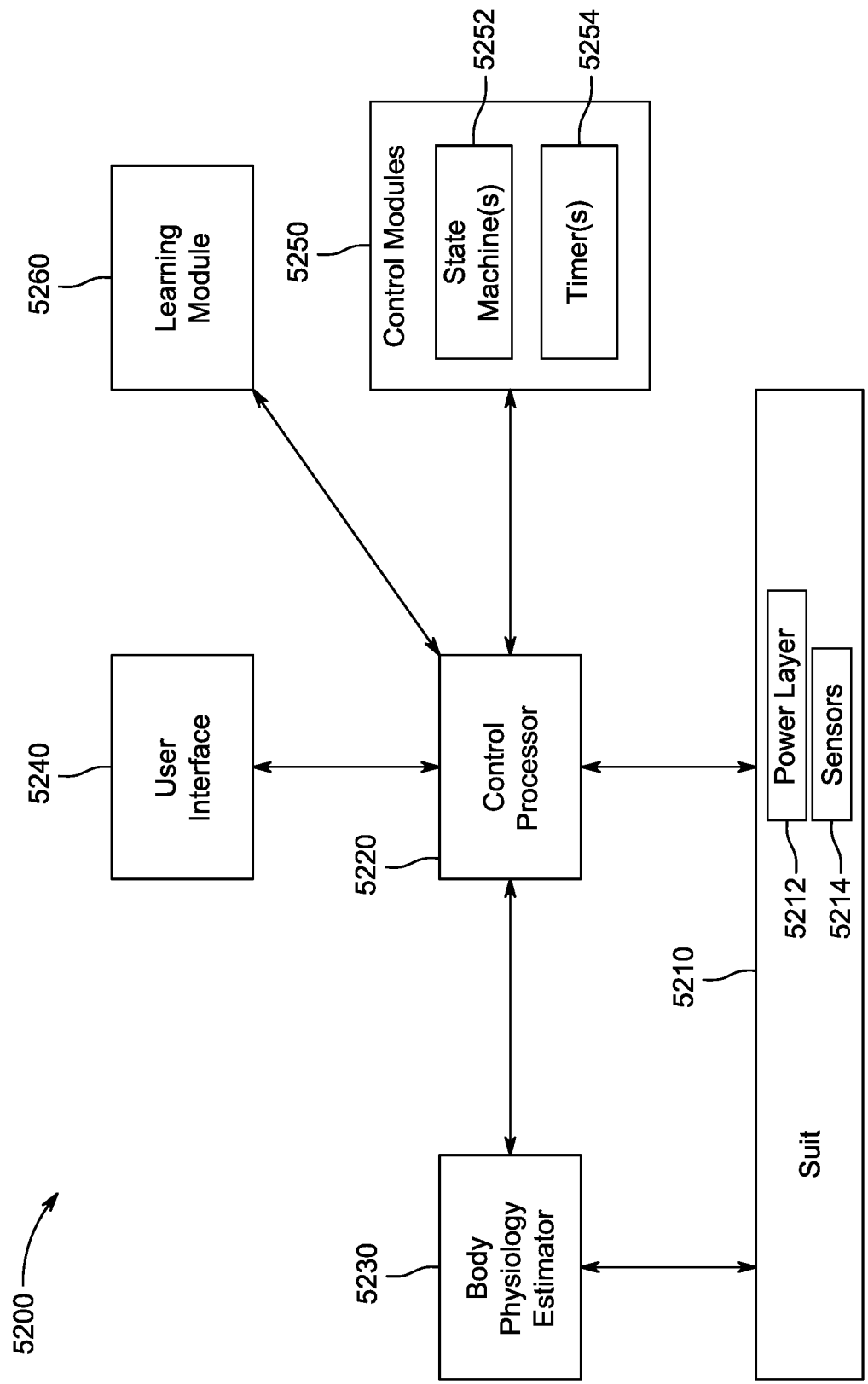
FIG. 52 shows an illustrative symbiosis exosuit system according to an embodiment.

FIG. 52 shows an illustrative symbiosis exosuit system 5200 according to an embodiment. The symbiosis enables the exosuit to serve as an autonomous exosuit nervous system that mimics or emulates the nervous system of a lifeform such as a human being. That is, a nervous system is responsible for basic life functions (e.g., breathing, converting food into energy, and maintaining muscle balance) that are performed automatically without requiring conscious thought or input. The autonomous exosuit nervous system enables the exosuit to automatically provide assistance to the user when and where the user needs it without requiring intervention by the user. Exosuit system 5200 can do this by tracking the user's body physiology and automatically controlling the suit to provide the anticipated or required support and/or assistance. For example, if a user has been standing for a prolonged period of time, one or more of the muscles being used to help the user stand may begin to tire, and a result, the user's body may exhibit signs of fatigue. Exosuit 5200 can observe this muscle fatigue (e.g., due to observed physiological signs) and can automatically cause exosuit 5200 to engage the appropriate power layers to compensate for the muscle fatigue.

Symbiosis of exosuit 5200 may be expressed in different autonomy levels, where each autonomy level represents a degree to which physiological factors are observed and a degree to which suit assistance or movement actions are performed based on the observed physiological factors. For example, the symbiosis levels can range from a zero level of autonomy to absolute full level of autonomy, with one or more intermediate levels of autonomy. As metaphorical example, autonomous cars operate according to different levels, where each level represents a different ability for the car to self-drive. The symbiosis levels of exosuit operation can be stratified in a similar manner. In a zero level of autonomy, exosuit 300 may not monitor for any physiological cues, nor automatically engage any suit assistance or movement actions. Thus, in a zero level, the user may be required to provide user input to instruct the suit to perform a desired movement or assistance. In an absolute full level of autonomy, exosuit 5200 may be able to observe and accurately analyze the observed physiological data (e.g., with 99 percent accuracy or more) and automatically execute the suit assistance or movement actions in a way expressly desired by the user. Thus, in the absolute full level, the exosuit seamlessly serves as an extension of the user's nervous system by automatically determining what the user needs and providing it.

The one or more intermediate levels of autonomy provide different observable physiological results that are accurate but do not represent the absolute nature of the absolute full level of autonomy. For example, the intermediate levels may represent that the exosuit is fully capable of autonomously performing certain actions (e.g., sit to stand) but not others. A corollary to this is ABS braking; the ABS braking system automatically figures out how best to stop the vehicle without requiring the user to pump the brakes or engage in any other activity other than stepping on the brake pedal. In the exosuit context, the exosuit knows when the user wishes to stand from a sitting position, the exosuit knows when the user wishes to perform the movement and engages the appropriate power layer segments to assist in the movement. The intermediate levels may also exist while the exosuit is learning about its user. Each user is different, and the physiological responses are therefore different and particular to each user. Therefore, the ability to discern the physiological cues and the assistance and movements made in response thereto may endure a learning curve before the suit is able to operate at the absolute full level.

FIG. 52 shows that exosuit system 5200 can include suit 5210, control processor 5220, body physiology estimator 5230, user interface 5240, control modules 5250, and learning module 5260. Suit 5210 can be any suitable exosuit (e.g., exosuit 200) and can include, among other things, power layer 5212 and sensors 5214. Control processor 5220 may process instructions, pass data, and control the suit. Control processor 5220 may be connected to suit 5210, body physiology estimator 5230, user interface 5240, control modules 5250, and learning module 5260. Control processor 5220 may provide signals to suit 5210 to control, for example, operation of power layer 5212.

Body physiology estimator 5230 may receive data inputs from sensor 5214, control processor 5220, and other components if desired. Estimator 5230 is operative to analyze the data to ascertain the physiology of the user. Estimator 5230 may apply data analytics and statistics to the data to resolve physiological conditions of the user's body. For example, estimator 5230 can determine whether the user is sitting, standing, leaning, laying down, laying down on a side, walking, running, jumping, performing exercise movements, playing sports, reaching, holding an object or objects, or performing any other static or active physiological event. The results may be provided to control modules 5250, for example, via control processor 5220.

Control modules 5250 can include various state machines 5252 and timers 5254 operative to control operation of suit 5210 based on outputs supplied by estimator 5230, inputs received via user interface 5240, and signals provided by control processor 5220. Multiple state machines 5252 may control operation of the suit. For example, a master state machine may be supported by multiple slave state machines. The slave state machines may be executed in response to a call from the master state machine. In addition, the slave state machines may execute specific assistance functions or movements. For example, each of a sit-to-stand assistance movement, stand-to sit movement, stretch movement, standing movement, walking movement, running movement, jumping movement, crouch movement, specific exercise movement, or any other movement may have its own slave state machine to control suit operation.

Learning module 5260 may be operative to learn preferences, peculiarities, or other unique features of a particular user and feedback the learnings to body physiology estimator 5230 and control module 5250. In some embodiments, learning module 5260 may use data analytics to learn about the user. For example, learning module 5260 may learn that a particular user walks with a particular gait and cadence. The gait and cadence learnings can be used to modify state machines 5252 that control walking for that user. In another embodiment, learning module 5260 may incorporate user feedback received via user interface 5240. For example, a user may go through an initial setup process whereby the user is instructed to perform a battery of movements and provide responses thereto so that state machines 5252 and timers 5254 are set to operate in accordance with the preferences of the user.

Figure 53:
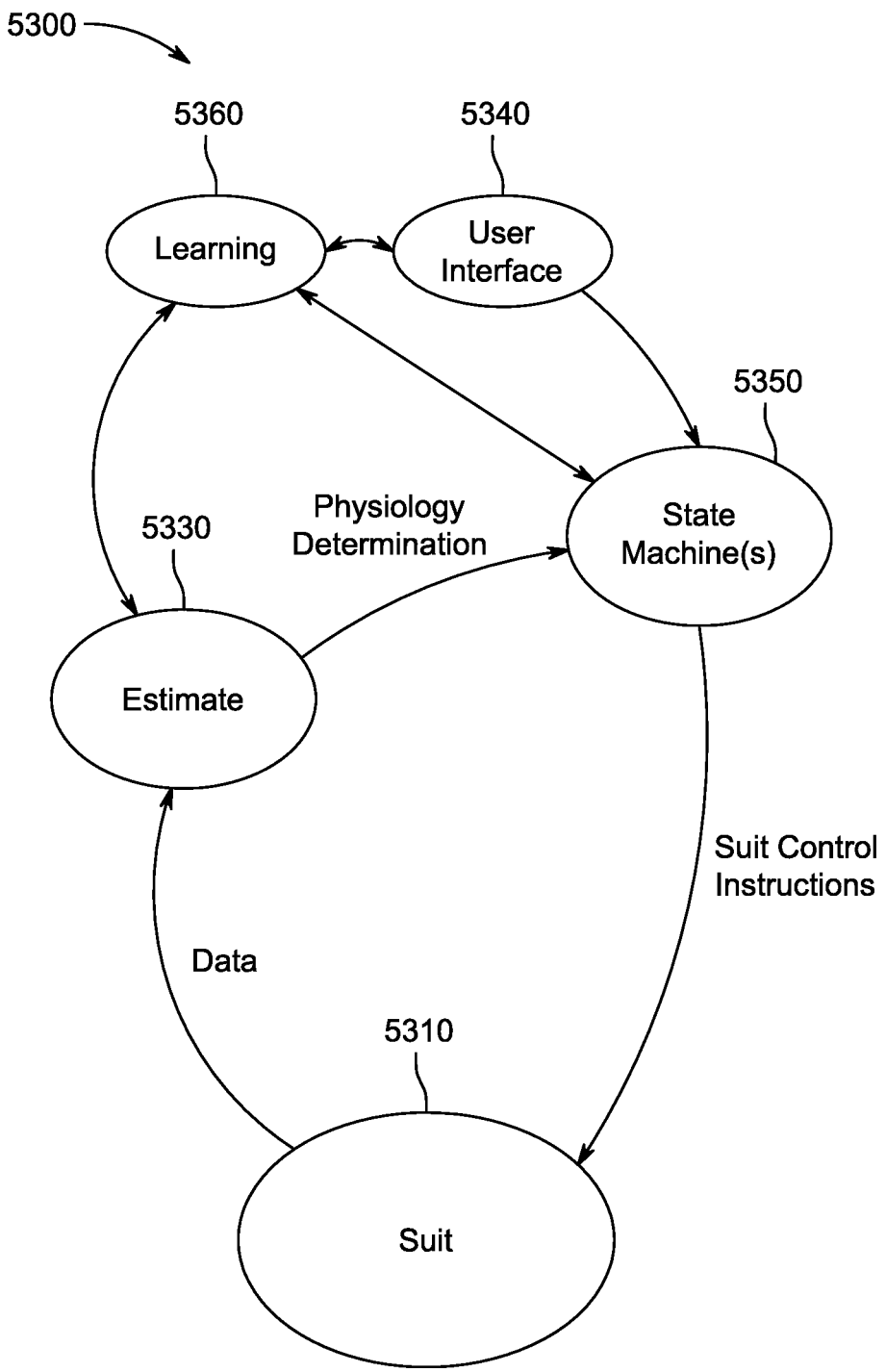
FIG. 53 shows illustrative process for implementing symbiosis exosuit system according to an embodiment.

FIG. 53 shows illustrative process 5300 for implementing symbiosis exosuit system 5200 according to an embodiment. Process 5300 includes suite 5310, estimator 5330, user interface 5340, and state machines 5350. Process 5300 can be represented by a continuous feedback loop in which data is supplied from suit 5310 to estimator 5330, which provides a physiology determination to state machines 5350, which uses the determination to generate suit control instructions that are provided to suit 5310. User inputs received via user interface 5340 may provide user specified controls that can instruct state machines 5350 to execute a particular movement. The autonomous exosuit nervous system is implemented through the continuous feedback loop. The continuous feedback loop enables the autonomous exosuit nervous system to provide rapid response and control of suit 5310. For example, if the user is sitting down, the estimator 5330 can determine that the sitting position is the current physiological determination. Assume that the user reaches for something on a table. Such a movement may result in a movement that appears to be a sit-to-stand. In response to this movement, estimator 5330 may register it as the start of a sit-to-stand physiological determination and instruct state machines 5350 to initiate a sit-to-stand movement. This way, regardless of whether the user actually stands or sits back down, suit 5310 is primed and ready to immediately perform the assistance movement. Further assume that the user sits back down (after having grabbed the item on the table). In response to initiation of the sit down movement, estimator 5330 can make this determination as it is happening and instruct state machines 5350 to cease the sit-to-stand operation. Thus, the continuous feedback loop provides real-time assessment and instantaneous suit controls in response to the user's immediate physiological needs, and not after.

In some embodiments, estimator 5330 may be able to determine that the user is was attempting to reach something on the table while also performing the motion that includes at least the start of a sit to stand movement. Estimator 5330 may be able to correlate the reaching motion with the sit-to-stand motion and decide that the user does not actually need to stand, but may require an appropriate amount of assist to reach the item. In this particular situation, state machine 5350 may activate a power layer segment (e.g., a particular one of the hip extensors) to provide the user with the reach assistance.

Learning 5360 can receive and provide data to estimator 5330, user interface 5340, and state machines 5350. Learning 5360 may be leveraged to update state machines 5350 and/or estimator 5330.

Figure 54:
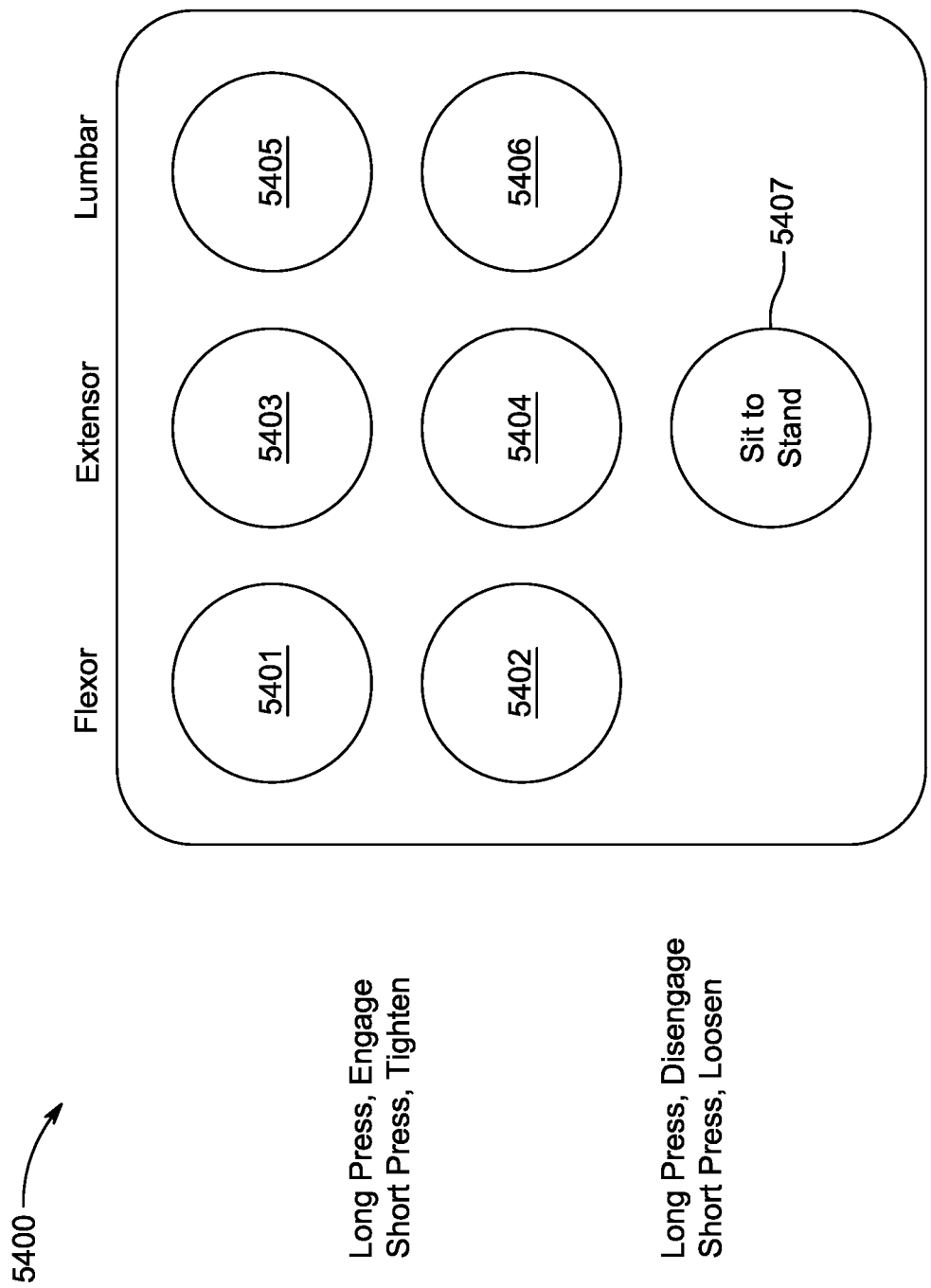
FIG. 54 shows illustrative user interface that may be incorporated into an exosuit according to an embodiment.

FIG. 54 shows illustrative user interface 5400 that may be incorporated into an exosuit according to an embodiment. User interface 5400 may include seven different buttons 5401-5407 arranged as shown. Buttons 5401 and 5402 may be associated with flexor activation and deactivation. A relatively long press of button 5401 may fully engage flexor flexdrives (such that they maximize their FLA contraction) and a relatively short press of button 5401 may tighten flexor FLAs (to a degree that is a stepwise increased contraction). A relatively long press of button 5402 may fully disengage flexor flexdrives (such that they minimize their FLA contraction) and a relatively short press of button 5402 may loosen flexor FLAs (to a degree that is a stepwise decrease in contraction). Buttons 5403 and 5404 may be associated with extensor activation and deactivation. A relatively long press of button 5403 may fully engage extensor flexdrives (such that they maximize their FLA contraction) and a relatively short press of button 5403 may tighten extensor FLAs (to a degree that is a stepwise increased contraction). A relatively long press of button 5404 may fully disengage extensor flexdrives (such that they minimize their FLA contraction) and a relatively short press of button 5404 may loosen extensor FLAs (to a degree that is a stepwise decrease in contraction). Buttons 5405 and 5406 may be associated with lumbar activation and deactivation. A relatively long press of button 5405 may fully engage lumbar flexdrives (such that they maximize their FLA contraction) and a relatively short press of button 5405 may tighten lumbar FLAs (to a degree that is a stepwise increased contraction). A relatively long press of button 5406 may fully disengage lumbar flexdrives (such that they minimize their FLA contraction) and a relatively short press of button 5406 may loosen lumbar FLAs (to a degree that is a stepwise decrease in contraction). Button 5417 may be associated with a functional movement (e.g., sit-to-stand). Selection of button 5417 may instruct the exosuit to perform the associated functional movement. It should be appreciated that user interface 5400 can include any number of buttons. For example, additional buttons may be added for other functional movements.

Figure 28:
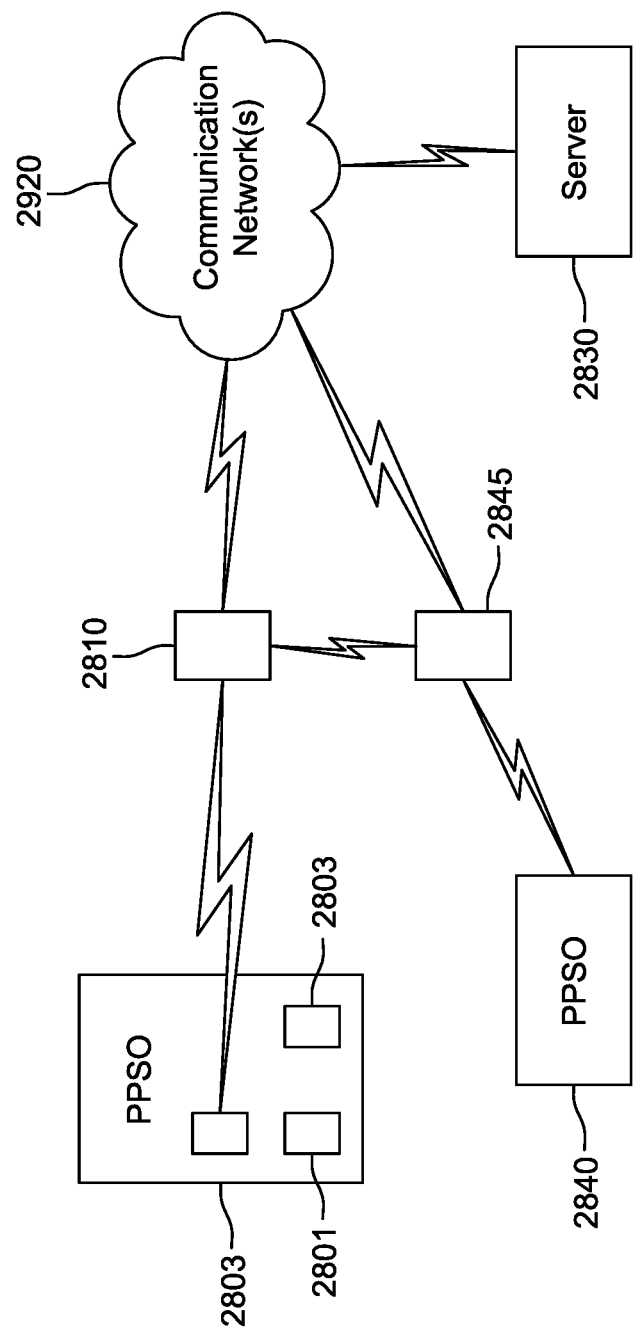
FIG. 28 illustrates an example exosuit according to an embodiment.

FIG. 28 illustrates an example exosuit 2800 that includes actuators 2801, sensors 2803, and a controller configured to operate elements of exosuit 2800 (e.g., 2801, 2803) to enable functions of the exosuit 2800. The controller 2805 is configured to communicate wirelessly with a user interface 2810. The user interface 2810 is configured to present information to a user (e.g., a wearer of the exosuit 2800) and to the controller 2805 of the flexible exosuit or to other systems. The user interface 2810 can be involved in controlling and/or accessing information from elements of the exosuit 2800. For example, an application being executed by the user interface 2810 can access data from the sensors 2803, calculate an operation (e.g., to apply dorsiflexion stretch) of the actuators 2801, and transmit the calculated operation to the exosuit 2800. The user interface 2810 can additionally be configured to enable other functions; for example, the user interface 2810 can be configured to be used as a cellular telephone, a portable computer, an entertainment device, or to operate according to other applications.

The user interface 2810 can be configured to be removably mounted to the exosuit 2800 (e.g., by straps, magnets, Velcro, charging and/or data cables). Alternatively, the user interface 2810 can be configured as a part of the exosuit 2800 and not to be removed during normal operation. In some examples, a user interface can be incorporated as part of the exosuit 2800 (e.g., a touchscreen integrated into a sleeve of the exosuit 2800) and can be used to control and/or access information about the exosuit 2800 in addition to using the user interface 2810 to control and/or access information about the exosuit 2800. In some examples, the controller 2805 or other elements of the exosuit 2800 are configured to enable wireless or wired communication according to a standard protocol (e.g., Bluetooth, ZigBee, WiFi, LTE or other cellular standards, IRdA, Ethernet) such that a variety of systems and devices can be made to operate as the user interface 2810 when configured with complementary communications elements and computer-readable programs to enable such functionality.

The exosuit 2800 can be configured as described in example embodiments herein or in other ways according to an application. The exosuit 2800 can be operated to enable a variety of applications. The exosuit 2800 can be operated to enhance the strength of a wearer by detecting motions of the wearer (e.g., using sensors 2803) and responsively applying torques and/or forces to the body of the wearer (e.g., using actuators 2801) to increase the forces the wearer is able to apply to his/her body and/or environment. The exosuit 2800 can be operated to train a wearer to perform certain physical activities. For example, the exosuit 2800 can be operated to enable rehabilitative therapy of a wearer. The exosuit 2800 can operate to amplify motions and/or forces produced by a wearer undergoing therapy in order to enable the wearer to successfully complete a program of rehabilitative therapy. Additionally or alternatively, the exosuit 2800 can be operated to prohibit disordered movements of the wearer and/or to use the actuators 2801 and/or other elements (e.g., haptic feedback elements) to indicate to the wearer a motion or action to perform and/or motions or actions that should not be performed or that should be terminated. Similarly, other programs of physical training (e.g., dancing, skating, other athletic activities, vocational training) can be enabled by operation of the exosuit 2800 to detect motions, torques, or forces generated by a wearer and/or to apply forces, torques, or other haptic feedback to the wearer. Other applications of the exosuit 2800 and/or user interface 2810 are anticipated.

The user interface 2810 can additionally communicate with communications network(s) 2820. For example, the user interface 2810 can include a WiFi radio, an LTE transceiver or other cellular communications equipment, a wired modem, or some other elements to enable the user interface 2810 and exosuit 2800 to communicate with the Internet. The user interface 2810 can communicate through the communications network 2820 with a server 2830.

Communication with the server 2830 can enable functions of the user interface 2810 and exosuit 2800. In some examples, the user interface 2810 can upload telemetry data (e.g., location, configuration of elements 2801, 2803 of the exosuit 2800, physiological data about a wearer of the exosuit 2800) to the server 2830.

In some examples, the server 2830 can be configured to control and/or access information from elements of the exosuit 2800 (e.g., 2801, 2803) to enable some application of the exosuit 2800. For example, the server 2830 can operate elements of the exosuit 2800 to move a wearer out of a dangerous situation if the wearer was injured, unconscious, or otherwise unable to move themselves and/or operate the exosuit 2800 and user interface 2810 to move themselves out of the dangerous situation. Other applications of a server in communications with a exosuit are anticipated.

The user interface 2810 can be configured to communicate with a second user interface 2845 in communication with and configured to operate a second flexible exosuit 2840. Such communication can be direct (e.g., using radio transceivers or other elements to transmit and receive information over a direct wireless or wired link between the user interface 2810 and the second user interface 2845). Additionally or alternatively, communication between the user interface 2810 and the second user interface 2845 can be facilitated by communications network(s) 2820 and/or a server 2830 configured to communicate with the user interface 2810 and the second user interface 2845 through the communications network(s) 2820.

Communication between the user interface 2810 and the second user interface 2845 can enable applications of the exosuit 2800 and second exosuit 2840. In some examples, actions of the exosuit 2800 and second flexible exosuit 2840 and/or of wearers of the exosuit 2800 and second exosuit 2840 can be coordinated. For example, the exosuit 2800 and second exosuit 2840 can be operated to coordinate the lifting of a heavy object by the wearers. The timing of the lift, and the degree of support provided by each of the wearers and/or the exosuit 2800 and second exosuit 2840 can be controlled to increase the stability with which the heavy object was carried, to reduce the risk of injury of the wearers, or according to some other consideration.

Coordination of actions of the exosuit 2800 and second exosuit 2840 and/or of wearers thereof can include applying coordinated (in time, amplitude, or other properties) forces and/or torques to the wearers and/or elements of the environment of the wearers and/or applying haptic feedback (though actuators of the exosuits 2800, 2840, through dedicated haptic feedback elements, or through other methods) to the wearers to guide the wearers toward acting in a coordinated manner.

Coordinated operation of the exosuit 2800 and second exosuit 2840 can be implemented in a variety of ways. In some examples, one exosuit (and the wearer thereof) can act as a master, providing commands or other information to the other exosuit such that operations of the exosuit 2800, 2840 are coordinated. For example, the exosuit 2800, 2840 can be operated to enable the wearers to dance (or to engage in some other athletic activity) in a coordinated manner. One of the exosuits can act as the 'lead', transmitting timing or other information about the actions performed by the 'lead' wearer to the other exosuit, enabling coordinated dancing motions to be executed by the other wearer. In some examples, a first wearer of a first exosuit can act as a trainer, modeling motions or other physical activities that a second wearer of a second exosuit can learn to perform. The first exosuit can detect motions, torques, forces, or other physical activities executed by the first wearer and can send information related to the detected activities to the second exosuit. The second exosuit can then apply forces, torques, haptic feedback, or other information to the body of the second wearer to enable the second wearer to learn the motions or other physical activities modeled by the first wearer. In some examples, the server 2830 can send commands or other information to the exosuits 2800, 2840 to enable coordinated operation of the exosuits 2800, 2840.

The exosuit 2800 can be operated to transmit and/or record information about the actions of a wearer, the environment of the wearer, or other information about a wearer of the exosuit 2800. In some examples, kinematics related to motions and actions of the wearer can be recorded and/or sent to the server 2830. These data can be collected for medical, scientific, entertainment, social media, or other applications. The data can be used to operate a system. For example, the exosuit 2800 can be configured to transmit motions, forces, and/or torques generated by a user to a robotic system (e.g., a robotic arm, leg, torso, humanoid body, or some other robotic system) and the robotic system can be configured to mimic the activity of the wearer and/or to map the activity of the wearer into motions, forces, or torques of elements of the robotic system. In another example, the data can be used to operate a virtual avatar of the wearer, such that the motions of the avatar mirrored or were somehow related to the motions of the wearer. The virtual avatar can be instantiated in a virtual environment, presented to an individual or system with which the wearer is communicating, or configured and operated according to some other application.

Conversely, the exosuit 2800 can be operated to present haptic or other data to the wearer. In some examples, the actuators 2801 (e.g., twisted string actuators, exotendons) and/or haptic feedback elements (e.g., EPAM haptic elements) can be operated to apply and/or modulate forces applied to the body of the wearer to indicate mechanical or other information to the wearer. For example, the activation in a certain pattern of a haptic element of the exosuit 2800 disposed in a certain location of the exosuit 2800 can indicate that the wearer had received a call, email, or other communications. In another example, a robotic system can be operated using motions, forces, and/or torques generated by the wearer and transmitted to the robotic system by the exosuit 2800. Forces, moments, and other aspects of the environment and operation of the robotic system can be transmitted to the exosuit 2800 and presented (using actuators 2801 or other haptic feedback elements) to the wearer to enable the wearer to experience force-feedback or other haptic sensations related to the wearer's operation of the robotic system. In another example, haptic data presented to a wearer can be generated by a virtual environment, e.g., an environment containing an avatar of the wearer that is being operated based on motions or other data related to the wearer that is being detected by the exosuit 2800.

Note that the exosuit 2800 illustrated in FIG. 28 is only one example of a exosuit that can be operated by control electronics, software, or algorithms described herein. Control electronics, software, or algorithms as described herein can be configured to control flexible exosuits or other mechatronic and/or robotic system having more, fewer, or different actuators, sensors or other elements. Further, control electronics, software, or algorithms as described herein can be configured to control exosuits configured similarly to or differently from the illustrated exosuit 2800. Further, control electronics, software, or algorithms as described herein can be configured to control flexible exosuits having reconfigurable hardware (i.e., exosuits that are able to have actuators, sensors, or other elements added or removed) and/or to detect a current hardware configuration of the flexible exosuits using a variety of methods.

A controller of a exosuit and/or computer-readable programs executed by the controller can be configured to provide encapsulation of functions and/or components of the flexible exosuit. That is, some elements of the controller (e.g., subroutines, drivers, services, daemons, functions) can be configured to operate specific elements of the exosuit (e.g., a twisted string actuator, a haptic feedback element) and to allow other elements of the controller (e.g., other programs) to operate the specific elements and/or to provide abstracted access to the specific elements (e.g., to translate a command to orient an actuator in a commanded direction into a set of commands sufficient to orient the actuator in the commanded direction). This encapsulation can allow a variety of services, drivers, daemons, or other computer-readable programs to be developed for a variety of applications of a flexible exosuits. Further, by providing encapsulation of functions of a flexible exosuit in a generic, accessible manner (e.g., by specifying and implementing an application programming interface (API) or other interface standard), computer-readable programs can be created to interface with the generic, encapsulated functions such that the computer-readable programs can enable operating modes or functions for a variety of differently-configured exosuit, rather than for a single type or model of flexible exosuit. For example, a virtual avatar communications program can access information about the posture of a wearer of a flexible exosuit by accessing a standard exosuit API. Differently-configured exosuits can include different sensors, actuators, and other elements, but can provide posture information in the same format according to the API. Other functions and features of a flexible exosuit, or other robotic, exoskeletal, assistive, haptic, or other mechatronic system, can be encapsulated by APIs or according to some other standardized computer access and control interface scheme.

Figure 29:
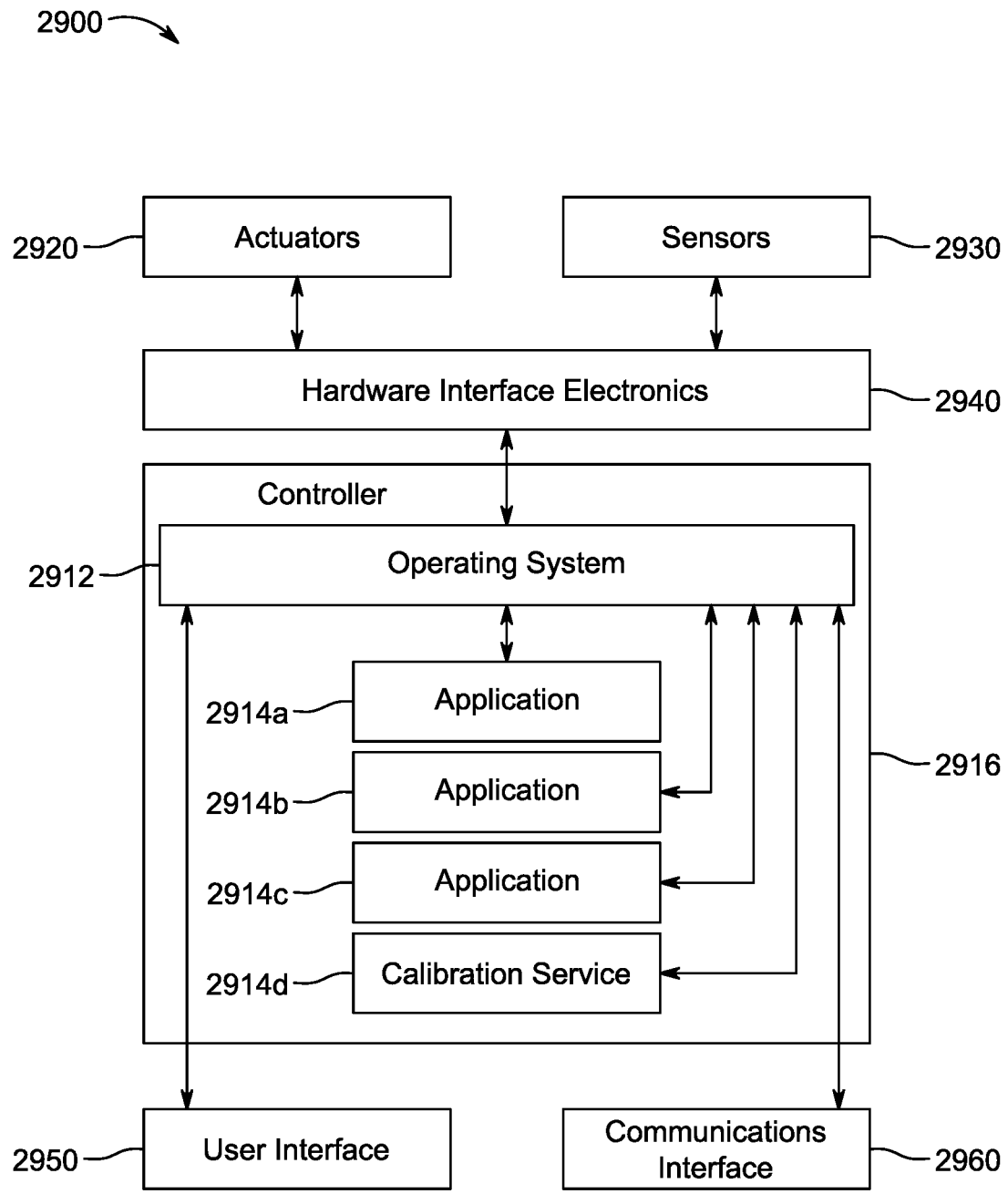
FIG. 29 is a schematic illustrating elements of a exosuit and a hierarchy of control or operating the exosuit according to an embodiment.

FIG. 29 is a schematic illustrating elements of a exosuit 2900 and a hierarchy of control or operating the exosuit 2900. The flexible exosuit includes actuators 2920 and sensors 2930 configured to apply forces and/or torques to and detect one or more properties of, respectively, the exosuit 2900, a wearer of the exosuit 2900, and/or the environment of the wearer. The exosuit 2900 additionally includes a controller 2910 configured to operate the actuators 2920 and sensors 2930 by using hardware interface electronics 2940. The hardware electronics interface 2940 includes electronics configured to interface signals from and to the controller 2910 with signals used to operate the actuators 2920 and sensors 2930. For example, the actuators 2920 can include exotendons, and the hardware interface electronics 2940 can include high-voltage generators, high-voltage switches, and high-voltage capacitance meters to clutch and un-clutch the exotendons and to report the length of the exotendons. The hardware interface electronics 2940 can include voltage regulators, high voltage generators, amplifiers, current detectors, encoders, magnetometers, switches, controlled-current sources, DACs, ADCs, feedback controllers, brushless motor controllers, or other electronic and mechatronic elements.

The controller 2910 additionally operates a user interface 2950 that is configured to present information to a user and/or wearer of the exosuit 2900 and a communications interface 2960 that is configured to facilitate the transfer of information between the controller 2910 and some other system (e.g., by transmitting a wireless signal). Additionally or alternatively, the user interface 2950 can be part of a separate system that is configured to transmit and receive user interface information to/from the controller 2910 using the communications interface 2960 (e.g., the user interface 2950 can be part of a cellphone).

The controller 2910 is configured to execute computer-readable programs describing functions of the flexible exosuit 2912. Among the computer-readable programs executed by the controller 2910 are an operating system 2912, applications 2914 *a*, 2914 *b*, 2914 *c*, and a calibration service 2916. The operating system 2912 manages hardware resources of the controller 2910 (e.g., I/O ports, registers, timers, interrupts, peripherals, memory management units, serial and/or parallel communications units) and, by extension, manages the hardware resources of the exosuit 2900. The operating system 2912 is the only computer-readable program executed by the controller 2910 that has direct access to the hardware interface electronics 2940 and, by extension, the actuators 2920 and sensors 2930 of the exosuit 2900.

The applications 2914 *a*, 2914 *b*, 2914 are computer-readable programs that describe some function, functions, operating mode, or operating modes of the exosuit 2900. For example, application 2914 *a* can describe a process for transmitting information about the wearer's posture to update a virtual avatar of the wearer that includes accessing information on a wearer's posture from the operating system 2912, maintaining communications with a remote system using the communications interface 2960, formatting the posture information, and sending the posture information to the remote system. The calibration service 2916 is a computer-readable program describing processes to store parameters describing properties of wearers, actuators 2920, and/or sensors 2930 of the exosuit 2900, to update those parameters based on operation of the actuators 2920, and/or sensors 2930 when a wearer is using the exosuit 2900, to make the parameters available to the operating system 2912 and/or applications 2914 *a*, 2914 *b*, 2914 *c*, and other functions relating to the parameters. Note that applications 2914 *a*, 2914 *b*, 2914 and calibration service 2916 are intended as examples of computer-readable programs that can be run by the operating system 2912 of the controller 2910 to enable functions or operating modes of a exosuit 2900.

The operating system 2912 can provide for low-level control and maintenance of the hardware (e.g., 2920, 2930, 2940). In some examples, the operating system 2912 and/or hardware interface electronics 1540 can detect information about the exosuit 2900, the wearer, and/or the wearer's environment from one or more sensors 2930 at a constant specified rate. The operating system 2912 can generate an estimate of one or more states or properties of the exosuit 2900 or components thereof using the detected information. The operating system 2912 can update the generated estimate at the same rate as the constant specified rate or at a lower rate.

The generated estimate can be generated from the detected information using a filter to remove noise, generate an estimate of an indirectly-detected property, or according to some other application. For example, the operating system 2912 can generate the estimate from the detected information using a Kalman filter to remove noise and to generate an estimate of a single directly or indirectly measured property of the exosuit 2900, the wearer, and/or the wearer's environment using more than one sensor. In some examples, the operating system can determine information about the wearer and/or exosuit 2900 based on detected information from multiple points in time. For example, the operating system 2900 can determine an eversion stretch and dorsiflexion stretch.

In some examples, the operating system 2912 and/or hardware interface electronics 2940 can operate and/or provide services related to operation of the actuators 2920. That is, in case where operation of the actuators 2920 requires the generation of control signals over a period of time, knowledge about a state or states of the actuators 2920, or other considerations, the operating system 2912 and/or hardware interface electronics 2940 can translate simple commands to operate the actuators 2920 (e.g., a command to generate a specified level of force using a twisted string actuator (TSA) of the actuators 2920) into the complex and/or state-based commands to the hardware interface electronics 2940 and/or actuators 2920 necessary to effect the simple command (e.g., a sequence of currents applied to windings of a motor of a TSA, based on a starting position of a rotor determined and stored by the operating system 2910, a relative position of the motor detected using an encoder, and a force generated by the TSA detected using a load cell).

In some examples, the operating system 2912 can further encapsulate the operation of the exosuit 2900 by translating a system-level simple command (e.g., a commanded level of force tension applied to the footplate) into commands for multiple actuators, according to the configuration of the exosuit 2900. This encapsulation can enable the creation of general-purpose applications that can effect a function of an exosuit (e.g., allowing a wearer of the exosuit to stretch his foot) without being configured to operate a specific model or type of exosuit (e.g., by being configured to generate a simple force production profile that the operating system 2912 and hardware interface electronics 2940 can translate into actuator commands sufficient to cause the actuators 2920 to apply the commanded force production profile to the footplate).

The operating system 2912 can act as a standard, multipurpose platform to enable the use of a variety of exosuits having a variety of different hardware configurations to enable a variety of mechatronic, biomedical, human interface, training, rehabilitative, communications, and other applications. The operating system 2912 can make sensors 2930, actuators 2920, or other elements or functions of the exosuit 2900 available to remote systems in communication with the exosuit 2900 (e.g., using the communications interface 2960) and/or a variety of applications, daemons, services, or other computer-readable programs being executed by operating system 2912. The operating system 2912 can make the actuators, sensors, or other elements or functions available in a standard way (e.g., through an API, communications protocol, or other programmatic interface) such that applications, daemons, services, or other computer-readable programs can be created to be installed on, executed by, and operated to enable functions or operating modes of a variety of flexible exosuits having a variety of different configurations. The API, communications protocol, or other programmatic interface made available by the operating system 2912 can encapsulate, translate, or otherwise abstract the operation of the exosuit 2900 to enable the creation of such computer-readable programs that are able to operate to enable functions of a wide variety of differently-configured flexible exosuits.

Additionally or alternatively, the operating system 2912 can be configured to operate a modular flexible exosuit system (i.e., a flexible exosuit system wherein actuators, sensors, or other elements can be added or subtracted from a flexible exosuit to enable operating modes or functions of the flexible exosuit). In some examples, the operating system 2912 can determine the hardware configuration of the exosuit 2900 dynamically and can adjust the operation of the exosuit 2900 relative to the determined current hardware configuration of the exosuit 2900. This operation can be performed in a way that was 'invisible' to computer-readable programs (e.g., 2914 a, 2914 b, 2914 c) accessing the functionality of the exosuit 2900 through a standardized programmatic interface presented by the operating system 2912. For example, the computer-readable program can indicate to the operating system 2912, through the standardized programmatic interface, that a specified level of torque was to be applied to an ankle of a wearer of the exosuit 2900. The operating system 2912 can responsively determine a pattern of operation of the actuators 2920, based on the determined hardware configuration of the exosuit 2900, sufficient to apply the specified level of torque to the ankle of the wearer.

In some examples, the operating system 2912 and/or hardware interface electronics 2940 can operate the actuators 2920 to ensure that the exosuit 2900 does not operate to directly cause the wearer to be injured and/or elements of the exosuit 2900 to be damaged. In some examples, this can include not operating the actuators 2920 to apply forces and/or torques to the body of the wearer that exceeded some maximum threshold. This can be implemented as a watchdog process or some other computer-readable program that can be configured (when executed by the controller 2910) to monitor the forces being applied by the actuators 2920 (e.g., by monitoring commands sent to the actuators 2920 and/or monitoring measurements of forces or other properties detected using the sensors 2930) and to disable and/or change the operation of the actuators 2920 to prevent injury of the wearer. Additionally or alternatively, the hardware interface electronics 2940 can be configured to include circuitry to prevent excessive forces and/or torques from being applied to the wearer (e.g., by channeling to a comparator the output of a load cell that is configured to measure the force generated by a TSA, and configuring the comparator to cut the power to the motor of the TSA when the force exceeded a specified level).

In some examples, operating the actuators 2920 to ensure that the exosuit 2900 does not damage itself can include a watchdog process or circuitry configured to prevent over-current, over-load, over-rotation, or other conditions from occurring that can result in damage to elements of the exosuit 2900. For example, the hardware interface electronics 2940 can include a metal oxide varistor, breaker, shunt diode, or other element configured to limit the voltage and/or current applied to a winding of a motor.

Note that the above functions described as being enabled by the operating system 2912 can additionally or alternatively be implemented by applications 2914 a, 2914 b, 2914 c, services, drivers, daemons, or other computer-readable programs executed by the controller 2900. The applications, drivers, services, daemons, or other computer-readable programs can have special security privileges or other properties to facilitate their use to enable the above functions.

The operating system 2912 can encapsulate the functions of the hardware interface electronics 2940, actuators 2920, and sensors 2930 for use by other computer-readable programs (e.g., applications 2914 a, 2914 b, 2914 c, calibration service 2916), by the user (through the user interface 2950), and/or by some other system (i.e., a system configured to communicate with the controller 2910 through the communications interface 2960). The encapsulation of functions of the exosuit 2900 can take the form of application programming interfaces (APIs), i.e., sets of function calls and procedures that an application running on the controller 2910 can use to access the functionality of elements of the exosuit 2900. In some examples, the operating system 2912 can make available a standard exosuit API' to applications being executed by the controller 2910. The exosuit API' can enable applications 2914 a, 2914 b, 2914 c to access functions of the exosuit 2900 without requiring those applications 2914 a, 2914 b, 2914 c to be configured to generate whatever complex, time-dependent signals are necessary to operate elements of the exosuit 2900 (e.g., actuators 2920, sensors 2930).

The exosuit API' can allow applications 2914 a, 2914 b, 2914 c to send simple commands to the operating system 2912 (e.g., 'begin storing mechanical energy from the ankle of the wearer when the foot of the wearer contacts the ground') in such that the operating system 2912 can interpret those commands and generate the command signals to the hardware interface electronics 2940 or other elements of the exosuit 2900 that are sufficient to effect the simple commands generated by the applications 2914 a, 2914 b, 2914 c (e.g., determining whether the foot of the wearer has contacted the ground based on information detected by the sensors 2930, responsively applying high voltage to an exotendon that crosses the user's ankle).

The exosuit API' can be an industry standard (e.g., an ISO standard), a proprietary standard, an open-source standard, or otherwise made available to individuals that can then produce applications for exosuits. The 'exosuit API' can allow applications, drivers, services, daemons, or other computer-readable programs to be created that are able to operate a variety of different types and configurations of exosuits by being configured to interface with the standard exosuit API' that is implemented by the variety of different types and configurations of exosuits. Additionally or alternatively, the 'exosuit API' can provide a standard encapsulation of individual exosuit-specific actuators (i.e., actuators that apply forces to specific body segments, where differently-configured exosuits may not include an actuator that applies forces to the same specific body segments) and can provide a standard interface for accessing information on the configuration of whatever exosuit is providing the exosuit API'. An application or other program that accesses the 'exosuit API' can access data about the configuration of the exosuit (e.g., locations and forces between body segments generated by actuators, specifications of actuators, locations and specifications of sensors) and can generate simple commands for individual actuators (e.g., generate a force of 30 newtons for 50 milliseconds) based on a model of the exosuit generated by the application and based on the information on the accessed data about the configuration of the exosuit. Additional or alternate functionality can be encapsulated by an exosuit API' according to an application.

Applications 2914 *a*, 2914 *b*, 2914 *c* can individually enable all or parts of the functions and operating modes of a flexible exosuit described herein. For example, an application can enable haptic control of a robotic system by transmitting postures, forces, torques, and other information about the activity of a wearer of the exosuit 2900 and by translating received forces and torques from the robotic system into haptic feedback applied to the wearer (i.e., forces and torques applied to the body of the wearer by actuators 2920 and/or haptic feedback elements). In another example, an application can enable a wearer to locomote more efficiently by submitting commands to and receiving data from the operating system 2912 (e.g., through an API) such that actuators 2920 of the exosuit 2900 assist the movement of the user, extract negative work from phases of the wearer's locomotion and inject the stored work to other phases of the wearer's locomotion, or other methods of operating the exosuit 2900. Applications can be installed on the controller 2910 and/or on a computer-readable storage medium included in the exosuit 2900 by a variety of methods. Applications can be installed from a removable computer-readable storage medium or from a system in communication with the controller 2910 through the communications interface 2960. In some examples, the applications can be installed from a web site, a repository of compiled or un-compiled programs on the Internet, an online store (e.g., Google Play, iTunes App Store), or some other source. Further, functions of the applications can be contingent upon the controller 2910 being in continuous or periodic communication with a remote system (e.g., to receive updates, authenticate the application, to provide information about current environmental conditions).

The exosuit 2900 illustrated in FIG. 29 is intended as an illustrative example. Other configurations of flexible exosuits and of operating systems, kernels, applications, drivers, services, daemons, or other computer-readable programs are anticipated. For example, an operating system configured to operate an exosuit can include a real-time operating system component configured to generate low-level commands to operate elements of the exosuit and a non-real-time component to enable less time-sensitive functions, like a clock on a user interface, updating computer-readable programs stored in the exosuit, or other functions. A exosuit can include more than one controller; further, some of those controllers can be configured to execute real-time applications, operating systems, drivers, or other computer-readable programs (e.g., those controllers were configured to have very short interrupt servicing routines, very fast thread switching, or other properties and functions relating to latency-sensitive computations) while other controllers are configured to enable less time-sensitive functions of a flexible exosuit. Additional configurations and operating modes of an exosuit are anticipated. Further, control systems configured as described herein can additionally or alternatively be configured to enable the operation of devices and systems other than exosuit; for example, control systems as described herein can be configured to operate robots, rigid exosuits or exoskeletons, assistive devices, prosthetics, or other mechatronic devices.

Control of actuators of an exosuit can be implemented in a variety of ways according to a variety of control schemes. Generally, one or more hardware and/or software controllers can receive information about the state of the flexible exosuit, a wearer of the exosuit, and/or the environment of the exosuit from sensors disposed on or within the exosuit and/or a remote system in communication with the exosuit. The one or more hardware and/or software controllers can then generate a control output that can be executed by actuators of the exosuit to affect a commanded state of the exosuit and/or to enable some other application. One or more software controllers can be implemented as part of an operating system, kernel, driver, application, service, daemon, or other computer-readable program executed by a processor included in the exosuit.

In some embodiments, a powered assistive exosuit intended primarily for assistive functions can also be adapted to perform exosuit functions. In one embodiment, an assistive exosuit similar to the embodiments described in U.S. Pat. No. 10,926,123, that is used for assistive functions may be adapted to perform exosuit functions. Embodiments of such an assistive exosuit typically include FLAs approximating muscle groups such as hip flexors, gluteal/hip extensors, spinal extensors, or abdominal muscles. In the assistive modes of these exosuits, these FLAs provide assistance for activities such as moving between standing and seated positions, walking, and postural stability. Actuation of specific FLAs within such an exosuit system may also provide stretching assistance. Typically, activation of one or more FLAs approximating a muscle group can stretch the antagonist muscles. For example, activation of one or more FLAs approximating the abdominal muscles might stretch the spinal extensors, or activation of one or more FLAs approximating gluteal/hip extensor muscles can stretch the hip flexors. The exosuit may be adapted to detect when the wearer is ready to initiate a stretch and perform an automated stretching regimen; or the wearer may indicate to the suit to initiate a stretching regimen.

It can be appreciated that assistive exosuits may have multiple applications. Assistive exosuits may be prescribed for medical applications. These may include therapeutic applications, such as assistance with exercise or stretching regimens for rehabilitation, disease mitigation or other therapeutic purposes. Mobility-assistance devices such as wheelchairs, walkers, crutches and scooters are often prescribed for individuals with mobility impairments.

Likewise, an assistive exosuit may be prescribed for mobility assistance for patients with mobility impairments. Compared with mobility assistance devices such as wheelchairs, walkers, crutches and scooters, an assistive exosuit may be less bulky, more visually appealing, and conform with activities of daily living such as riding in vehicles, attending community or social functions, using the toilet, and common household activities.

An assistive exosuit may additionally function as primary apparel, fashion items or accessories. The exosuit may be stylized for desired visual appearance. The stylized design may reinforce visual perception of the assistance that the exosuit is intended to provide. For example, an assistive exosuit intended to assist with torso and upper body activities may present a visual appearance of a muscular torso and upper body. Alternatively, the stylized design may be intended to mask or camouflage the functionality of the assistive exosuit through design of the base layer, electro/mechanical integration or other design factors.

Similarly to assistive exosuits intended for medically prescribed mobility assistance, assistive exosuits may be developed and utilized for non-medical mobility assistance, performance enhancement and support. For many, independent aging is associated with greater quality of life, however activities may become more limited with time due to normal aging processes. An assistive exosuit may enable aging individuals living independently to electively enhance their abilities and activities. For example, gait or walking assistance could enable individuals to maintain routines such as social walking or golf. Postural assistance may render social situations more comfortable, with less fatigue. Assistance with transitioning between seated and standing positions may reduce fatigue, increase confidence, and reduce the risk of falls. These types of assistance, while not explicitly medical in nature, may enable more fulfilling, independent living during aging processes.

Athletic applications for an assistive exosuit are also envisioned. In one example, an exosuit may be optimized to assist with a particular activity, such as cycling. In the cycling example, FLAs approximating gluteal or hip extensor muscles may be integrated into bicycle clothing, providing assistance with pedaling. The assistance could be varied based on terrain, fatigue level or strength of the wearer, or other factors. The assistance provided may enable increased performance, injury avoidance, or maintenance of performance in the case of injury or aging. It can be appreciated that assistive exosuits could be optimized to assist with the demands of other sports such as running, jumping, swimming, skiing, or other activities. An athletic assistive exosuit may also be optimized for training in a particular sport or activity. Assistive exosuits may guide the wearer in proper form or technique, such as a golf swing, running stride, skiing form, swimming stroke, or other components of sports or activities. Assistive exosuits may also provide resistance for strength or endurance training. The provided resistance may be according to a regimen, such as high intensity intervals.

Assistive exosuit systems as described above may also be used in gaming applications. Motions of the wearer, detected by the suit, may be incorporated as a game controller system. For example, the suit may sense wearer's motions that simulate running, jumping, throwing, dancing, fighting, or other motions appropriate to a particular game. The suit may provide haptic feedback to the wearer, including resistance or assistance with the motions performed or other haptic feedback to the wearer.

Assistive exosuits as described above may be used for military or first responder applications. Military and first responder personnel are often to be required to perform arduous work where safety or even life may be at stake. An assistive exosuit may provide additional strength or endurance as required for these occupations. An assistive exosuit may connect to one or more communication networks to provide communication services for the wearer, as well as remote monitoring of the suit or wearer.

Assistive exosuits as described above may be used for industrial or occupational safety applications. Exosuits may provide more strength or endurance for specific physical tasks such as lifting or carrying or repetitive tasks such as assembly line work. By providing physical assistance, assistive exosuits may also help avoid or prevent occupational injury due overexertion or repetitive stress.

Assistive exosuits as described above may also be configured as home accessories. Home accessory assistive exosuits may assist with household tasks such as cleaning or yard work, or may be used for recreational or exercise purposes. The communication capabilities of an assistive exosuit may connect to a home network for communication, entertainment or safety monitoring purposes.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art can appreciate that the conception, upon which this disclosure is based, may readily be utilized as a basis for the designing of other structures, systems, methods and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. A lumbar tensioning system for use with an exosuit worn by a human being having a core region, the lumbar tensioning system comprising:
    first and second belt segments;
    a buckle coupled to the first and second belt segments;
    a pouch system coupled to the first and second belt segments, the pouch system comprising:
        a motor;
        a slide track;
        a slide member coupled to the first belt segment and operative to move back and forth along the slide track; and
        a tensioning member coupled to the motor and the slide member, the tensioning member comprising a circumferential loop mounted substantially in line with the slide track;
        wherein the lumbar tensioning system is configured to increase pressure applied to the core region when the motor causes the circumferential loop of the tensioning member to pull the first belt segment, via the slide member, towards the second belt segment.

2. The lumbar system of claim 1, wherein the pouch system comprises a battery and control electronics.

3. The lumbar system of claim 1, wherein the slide member is the only slide member in the pouch system.

4. A lumbar system for use with an exosuit worn by a human being having a core region, the lumbar system comprising:
    first and second belt segments;
    a buckle coupled to the first and second belt segments;
    a pouch system coupled to the first and second belt segments, the pouch system comprising:
        a motor;
        a slide rail;
        a first slide member coupled to the first belt segment and operative to move back and forth along the slide rail;
        a second slide member coupled to the second belt segment and operative to move back and forth along the slide rail; and
        a tensioning member coupled to the motor and the first and second slide members, wherein the tensioning member comprises a circumferential loop mounted substantially in line with the slide rail is operative to increase pressure applied to the core region by pulling the first and second slide members together.

5. The lumbar system of claim 4, wherein the pouch system comprises a battery and control electronics.

6. The lumbar system of claim 4, wherein the first and second slide members pull respective first and second belt segments together when the tensioning member is operative to increase pressure applied to the core region.

7. The lumbar system of claim 4, wherein the tensioning member is operative to decrease pressure applied to the core region by enabling the first and second slide members to be pulled apart.

8. The lumbar system of claim 4, wherein the tensioning member comprises:
   the motor being mounted to the second sliding member such that the motor slides along the slide rail in conjunction with the second sliding member; and
   a tensioning member coupled to the motor and the first sliding member.

9. The lumbar system of claim 4, wherein the tensioning member comprises a pulley tensioning system comprising a plurality of pullies and a plurality of pulley lines, wherein the plurality of pully lines move in response to operation of the motor.

\* \* \* \* \*